(12) United States Patent
Silverman et al.

(10) Patent No.: US 9,783,500 B2
(45) Date of Patent: *Oct. 10, 2017

(54) 2-AMINOQUINOLINE-BASED COMPOUNDS FOR POTENT AND SELECTIVE NEURONAL NITRIC OXIDE SYNTHASE INHIBITION

(71) Applicant: Northwestern University, Evanston, IL (US)

(72) Inventors: Richard B. Silverman, Winnetka, IL (US); Maris A. Cinelli, Evanston, IL (US); Anthony V. Pensa, Arlington Heights, IL (US)

(73) Assignee: Northwestern University, Evanston, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/252,754

(22) Filed: Aug. 31, 2016

(65) Prior Publication Data

US 2016/0368877 A1   Dec. 22, 2016

Related U.S. Application Data

(63) Continuation-in-part of application No. 14/967,806, filed on Dec. 14, 2015, which is a continuation-in-part of application No. 14/594,925, filed on Jan. 12, 2015, now Pat. No. 9,212,144.

(60) Provisional application No. 61/964,645, filed on Jan. 10, 2014.

(51) Int. Cl.
*C07D 215/38* (2006.01)
*C07D 401/12* (2006.01)
*C12N 9/02* (2006.01)

(52) U.S. Cl.
CPC ......... *C07D 215/38* (2013.01); *C07D 401/12* (2013.01); *C12N 9/0075* (2013.01); *C12Y 114/13039* (2013.01)

(58) Field of Classification Search
CPC .... C07D 215/38; C07D 401/12; A61K 31/47; C12N 9/0075; C12Y 114/13039
See application file for complete search history.

(56) References Cited

U.S. PATENT DOCUMENTS 9,212,144 B2 * 12/2015 Silverman ............ C07D 215/38
2016/0096806 A1 * 4/2016 Silverman ............ C07D 215/38
514/313

* cited by examiner

*Primary Examiner* — D M Seaman
(74) *Attorney, Agent, or Firm* — Andrus Intellectual Property Law, LLP

(57) ABSTRACT

Various 2-aminoquinoline compounds as can be used, in vivo or in vitro, for selective inhibition of neuronal nitric oxide synthase.

36 Claims, 12 Drawing Sheets

1

2
First Generation

3

4
Second Generation

2-AMINOQUINOLINE-BASED COMPOUNDS FOR POTENT AND SELECTIVE NEURONAL NITRIC OXIDE SYNTHASE INHIBITION

This application is a continuation in part of and claims priority to and the benefit of application Ser. No. 14/967,806 filed Dec. 14, 2015, which is a continuation in part of and claimed priority to and the benefit of application Ser. No. 14/594,925 filed Jan. 12, 2015 and issued as U.S. Pat. No. 9,212,144 on Dec. 15, 2015, which claimed priority to and the benefit of Application Ser. No. 61/964,645, filed Jan. 10, 2014—each of which is incorporated herein by reference in its entirety.

This invention was made with government support under R01 GM049725 awarded by the National Institutes of Health. The government has certain rights in the invention.

BACKGROUND OF THE INVENTION

The term neurodegenerative disorder is used to describe diseases characterized by the progressive breakdown of neuronal function and structure. This term encompasses disorders such as Alzheimer's, Parkinson's, and Huntington's diseases, as well as amyotrophic lateral sclerosis (ALS), among others, although neuronal damage is also associated with stroke and ischemic events, cerebral palsy, and head trauma. Although the human and economic cost of neurodegeneration continues to be astronomical, treatment is largely limited to palliative care and prevention of symptom progression. Therefore, there is a constant demand for novel and effective approaches to slow or prevent the progression of these diseases.

One target under investigation is neuronal nitric oxide synthase (nNOS). Nitric oxide (NO) is an important second messenger in the human body, and dysregulation of its production is implicated in many pathologies. NO is produced by the nitric oxide synthase enzymes, of which there are three isoforms: endothelial nitric oxide synthase (eNOS), which regulates blood pressure and flow, inducible nitric oxide synthase (iNOS), involved in immune system activation, and nNOS, which is required for normal neuronal signaling. Nonetheless, over-expression of nNOS in neural tissue and increased levels of NO can result in protein nitration and oxidative damage to neurons, especially if peroxynitrite is formed from excess NO. Indeed, overexpression of nNOS or excess NO has been implicated in or associated with many neurodegenerative disorders. The inhibition of nNOS is, therefore, a viable therapeutic strategy for preventing or treating neuronal damage.

All NOS enzymes are active only as homodimers. Each monomer consists of both a reductase domain with FAD, FMN, and NADPH binding sites, and a heme-containing oxygenase domain, where the substrate (L-arginine) and cofactor (6R)-5,6,7,8-tetrahydrobiopterin ($H_4B$) bind. Activated and regulated by calmodulin binding, electron flow proceeds from one monomer's reductase domain to the other's oxygenase domain, catalyzing the oxidation of arginine to citrulline with concomitant production of NO. (See, Rosen, G. M.; Tsai, P.; and Pou, S. Mechanism of free-radical generation by nitric oxide synthase. *Chem. Rev.* 2002, 102 (4), 1191-1199.)

Not unexpectedly, most investigated nNOS inhibitors are mimetics of arginine and act as competitive inhibitors. One major challenge in designing nNOS inhibitors is that eNOS and iNOS share high sequence similarity and an identical overall architecture with nNOS, especially in their substrate-binding sites. Lack of isoform selectivity could have deleterious effects; inhibition of eNOS can cause severe hypertension, and iNOS inhibition could impair immune system activation. Previously, fragment hopping and subsequent structure-based optimization afforded compounds 1 and 2 (representative nNOS inhibitors are shown in FIG. 1). These compounds are highly potent and selective nNOS inhibitors, and compound 1 reverses a hypoxic-ischemic brain damage phenotype in newborn rabbit kits when administered intravenously to the dam. (See, Ji, H.; Tan, S.; Igarashi, J.; Li, H.; Derrick, M.; Martásek, P.; Roman, L. J.; Vasquez-Vivar, J.; Poulos, T. L.; and Silverman, R. B. Selective Neuronal Nitric Oxide Synthase Inhibitors and the Prevention of Cerebral Palsy. *Ann. Neurol.* 2009. 65, 209-217.)

Although effective, compounds 1 and 2 suffer from several drawbacks. Like most arginine mimics, they are very polar and hydrophilic and contain numerous basic moieties and hydrogen-bond donors, as well as many rotatable bonds and a high total polar surface area (tPSA), all properties that hamper both GI absorption and blood-brain barrier permeation. Many attempts to improve the bioavailability of these compounds have been made, including alkylation, fluorination, introduction of lipophilic tails, and replacement of amine moieties—most of these strategies either diminished potency or selectivity or were synthetically challenging. The chiral scaffolds of 1 and 2 are also difficult (>12 steps) to prepare, making them less desirable, from a clinical standpoint, than simpler scaffolds such as that of a compound 3 and commercial candidate 4; (potencies and selectivities given in FIG. 1). Nonetheless, these simplified molecules are not without fault; their isoform selectivities are lower, 3 suffers from poor Caco-2 permeability, and 4 is much less potent in cell-based assays than against isolated enzymes—both likely the result, in part, of the amidine moiety, which will be charged at physiological pH.

Accordingly, the design of NOS inhibitors remains an on-going concern in the art. In particular, the search continues for compounds providing good bioavailability without compromising potency and/or selectivity, while offering the advantages and benefits associated with ease of preparation and molecular variation.

SUMMARY OF THE INVENTION

In light of the foregoing, it is an object of the present invention to provide selective nNOS inhibitor compounds and/or methods for their use, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all of its respects, to every aspect of this invention. As such, the following objects can be viewed in the alternative with respect to any one aspect of this invention.

It can be an object of the present invention to provide compounds which, in comparison with the prior art, can be prepared using relatively simple, straight-forward synthetic techniques with inexpensive and/or commercially-available starting materials.

It can also be an object of the present invention to provide such compounds exhibiting improved oral bioavailability and blood-brain barrier penetration.

It can be another object of the present invention, alone or in conjunction with one or more of the preceding objectives, to provide a structural scaffold for the development of a range of compounds for selective inhibition of nNOS.

Other objects, features, benefits and advantages of the present invention will be apparent from the summary and the following descriptions of certain embodiments and will be readily apparent to those skilled in the art having knowledge of synthetic techniques of the sort described herein. Such objects, features, benefits and advantages will be apparent from the above as taken into conjunction with the accompanying examples, data, figures and all reasonable inferences to be drawn therefrom alone or with consideration of the references incorporated herein.

In part, the present invention can be directed to compounds of a formula

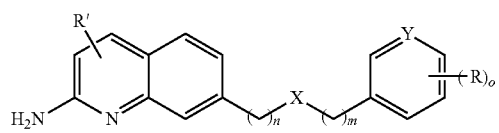

wherein X can be selected from O and NH; Y can be selected from CH and N; n can be an integer selected from 1-2; m can be an integer selected from 0-4; o can be an integer selected from 0-3; each R can be independently selected from halo, cyano, alkyl, alkoxy, amino, alkylamino, aminealkyl and N-substituted (—NH—) and oxa-substituted (—O—) aminealkyl moieties; and R' can be selected from H, halo, alkyl, haloalkyl and cyano moieties, and salts thereof. Independent of the foregoing, and as illustrated below, such a quinoline moiety can be substituted at either the 6-position or 7-position (as shown above), with a linking moiety of the sort described above.

In certain embodiments, as discussed above, X can be NH and Y can be CH. In certain such embodiments, n can be 1, and m can be 0-3. Alternatively, X can be NH and Y can be N; and, in certain such embodiments, m can be 2-3. Regardless, R' can be methyl; and R can be selected from fluoro, cyano, methoxy, N-methylamino, N, N-dimethylamino, alkyl, aminealkyl, and N-methyl- and N, N-dimethylaminealkyl moieties or a combination thereof.

In certain other embodiments, X can be O and Y can be CH. In certain such embodiments, n can be 1, m can be 0, and R can be selected from one or a combination of moieties of the sort discussed above or elsewhere herein. Alternatively, Y can be NH and, without limitation, o can be 1 and R can be an N-methylaminealkyl moiety.

In part, the present invention can also be directed to compounds of a formula

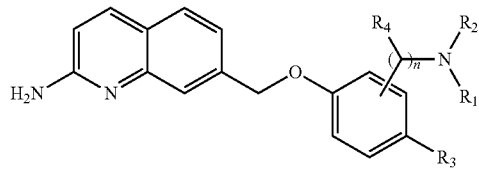

wherein, $R_1$ and $R_2$ can be independently selected from H and methyl moieties; $R_3$ can be selected from R moieties of the sort discussed above and illustrated elsewhere herein (e.g., without limitation halo, cyano, etc.); n can be an integer selected from 0-3; and each $R_4$ can be independently selected from H and methyl moieties, and salts thereof.

In part, the present invention can also be directed to compounds of a formula

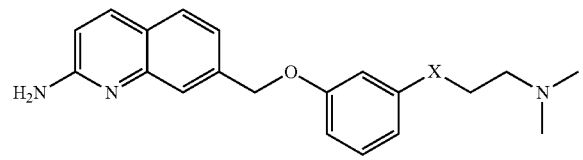

wherein X can be selected from CH and O (e.g., without limitation, providing an oxa-substituted N,N-dimethylaminealkyl moiety), and salts thereof.

In part, the present invention can be directed to compounds of a formula

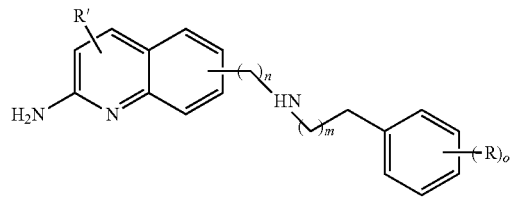

wherein n can be an integer selected from 1-2; m can be an integer selected from 0-2; each R can be independently selected from halo, cyano, alkyl, alkoxy, amino, alkylamino, aminealkyl and N-substituted (—NH—) and oxa-substituted (—O—) aminealkyl moieties; and R' can be selected from H, halo, alkyl, haloalkyl and cyano combinations thereof o can be an integer selected from 0-3; and R' can be selected from H, halo, alkyl, haloalkyl and cyano moieties, and salts thereof. In certain embodiments, m can be 1-3. In certain such embodiments, the sum of n and m can be 1-4. Regardless, in certain embodiments, o can be 1-2 and R can be selected from one or a combination of halo, alkyl and cyano moieties, optionally with a para and/or a meta-relationship to the alkyleneamine linker moiety. Independent of the foregoing and other structural considerations, such a quinoline moiety can be substituted at either the 6- or 7-positions thereof with such an arylalkyleneaminealkylene moiety.

Accordingly, in part, the present invention can be directed to compounds of a formula

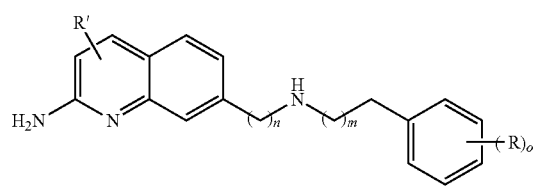

and salts thereof, wherein n, m, o, R' and R can be as described above or illustrated elsewhere herein.

Alternatively, in part, the present invention can be directed to compounds of a formula

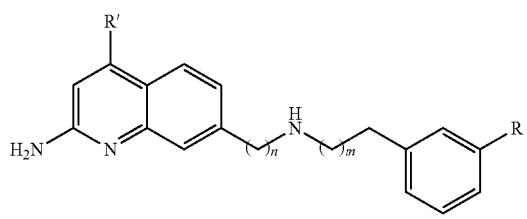

wherein n can be an integer selected from 1-2; m can be an integer selected from 2-3, providing where m is 3, n can be 1; each of $R_1$ and $R_2$ can be independently selected from H, halo, alkyl and cyano moieties; and R' can be selected from H and methyl moieties, and salts thereof. In certain embodiments, the sum of n and m can be 2-4. Regardless, one of $R_1$ and $R_2$ can be cyano and the other can be H, fluoro, chloro or methyl.

It will be understood by those skilled in the art that compounds of this invention can comprise an acid salt, hydrate and/or solvate of any such compound. Without limitation, certain embodiments can be partially or fully protonated, comprising a primary, secondary and/or tertiary amine, whereby the counter ion(s) of such an ammonium salt can be a conjugate base of a protic acid. Further, as may pertain to certain embodiments, the present compounds are without stereochemical limitation. Where such compounds and/or their intermediates are available as racemic mixtures, the respective isomers can be resolved. Likewise, where such compounds are diastereomers, the corresponding enantiomers can be separated. Accordingly, any such stereocenter can be (S) or (R) with respect to any other stereocenter(s), whether such a compound is present as a salt, hydrate and/or solvate. Regardless, any such compound(s) can be provided as part of a pharmaceutical composition comprising a pharmaceutically-acceptable carrier component for use in conjunction with a method or medicament of this invention.

In part, the present invention can also be directed to a method of affecting, inhibiting and/or otherwise modulating nitric oxide synthase activity. Such a method can comprise contacting, whether in vitro or in vivo, a nitric oxide synthase with an effective amount of any one or more of the present compounds or compositions, including but not limited to those compounds illustrated or inferred by the following examples, figures, accompanying synthetic schemes and/or incorporated references. More specifically, as discussed below, the present invention can provide a method for selective inhibition of neuronal nitric oxide synthase. Regardless, such methods can comprise providing a compound or corresponding pharmaceutical composition of this invention; and contacting a nitric oxide synthase with an effective amount of such a compound/composition, to reduce nitric oxide production. In certain embodiments, as demonstrated below, such contact or administration can selectively inhibit neuronal nitric oxide synthase over inducible and endothelial isoforms.

In part, the present invention can also be directed to compounds of a formula

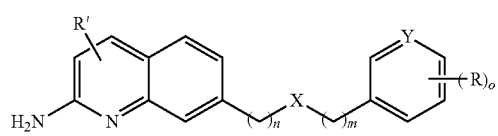

wherein X can be selected from O and $CH_2$; Y can be selected from CH and N; n can be an integer selected from 1-2; m can be an integer selected from 0-2; o can be an integer selected from 0-3; each R can be independently selected from H, halo, alkyl, haloalkyl, alkoxy, cyano, amino, N-alkylamino, N,N-dialkylamino, aminealkyl, N-alkylaminealkyl, and N,N-dialkylaminealkyl; and R' can be selected from H, halo, alkyl, haloalkyl and cyano moieties, or a salt of such a compound.

In certain, non-limiting embodiments, X can be O and Y can be CH. In certain such embodiments, n can be 1 and m can be 0. In certain other embodiments, o can be 1-3 and each R can be independently select from H, halo, cyano and N-alkylaminealkyl moieties. Without limitation, one R can be cyano and such a phenyl moiety can be substituted at the 5-position thereof. As a separate consideration, R' can be methyl and such a quinoline moiety can be substituted at the 4-position thereof.

In certain other non-limiting embodiments, X can be $CH_2$ and Y can be CH. In certain such embodiments, n, m and o can be described above, and each R can be independently selected from H, halo, cyano and N-alkylaminealkyl moieties. Without limitation, one R can be cyano and such a phenyl moiety can be substituted at the 5-position thereof. Regardless, such compound can be an ammonium salt, and such a salt can have a counter ion that is the conjugate base of a protic acid.

In part, the present invention can also be directed to compounds of a formula

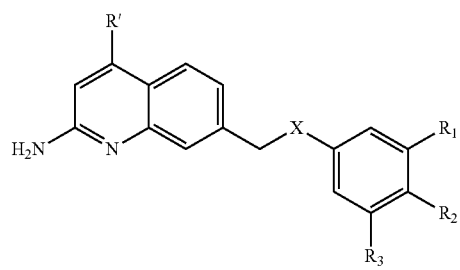

wherein X can be selected from O and $CH_2$; each of $R_1$-$R_3$ can be independently selected from H, halo, alkyl, haloalkyl, alkoxy, cyano and N-alkylaminealkyl moieties and R' can be selected from H, alkyl and haloalkyl moieties, or a salt of such a compound. In certain non-limiting embodiments, X can be O and $R_1$ can be an N-methylaminealkyl moiety. In certain such embodiments $R_2$ can be selected from H and a halo moiety; and $R_3$ can be selected from H and a cyano moiety. Without limitation, $R_2$ can be H and $R_3$ can be cyano. Regardless, independently, R' can be methyl, such a compound can be an ammonium salt and a counter ion thereof can be the conjugate base of a protic acid.

In part, the present invention can also be directed to a compound of a formula

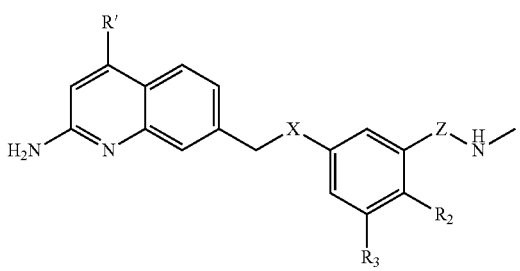

wherein X can be selected from O and CH$_2$; Z can be select from methylene, ethylene and methyl-substituted ethylene moieties; each of R$_2$-R$_3$ can be independently selected from H, halo, alkyl and cyano moieties and R' can be selected from H and a methyl moiety, or a salt of such a compound. In certain non-limiting embodiments, X can be O and Z can be a methyl-substituted ethylene moiety. In certain such embodiments, such a phenyl moiety can be substituted with a 2-(methylamino) propyl moiety and, optionally, have an (S)-configuration. Without limitation, R$_2$ can be selected from H and a halo moiety; and R$_3$ can be selected from H and a cyano moiety. In one such embodiment, R$_2$ can be H and R$_3$ can be cyano. Regardless, such a compound can be an ammonium salt, with a counter ion that can be the conjugate base of a protic acid.

In part, the present invention can also be directed to a method of affecting, inhibiting or otherwise modulating nitric oxide synthase activity. Such a method can comprise contacting a nitric oxide synthase with an effective amount of a compound of this invention. With respect to the preceding, the sum of n and m can be 1. In certain, non-limiting embodiments, o can be 2-3, and R can be selected from a combination of halo, alkyl, cyano and N-alkylaminealkyl moieties. In certain such embodiments, o can be 2, and such a phenyl moiety can be substituted at the 3-position with an N-alkylaminealkyl moiety and at the 5-position with a cyano moiety.

In part, the present invention can also be directed to a method of inhibiting a nitric oxide synthase. Such a method can comprise providing a compound of this invention; and contacting such a compound with a nitric oxide synthase, such a compound in an amount effective to inhibit nitric oxide synthase activity, thereby reducing nitric oxide production. In certain embodiments, X can be O and such a method can be selective for inhibition of neuronal nitric oxide synthase. In particular, such a method can be selective for inhibition of human neuronal nitric oxide synthase. Regardless, such a compound can be provided in a pharmaceutical composition.

DETAILED DESCRIPTION OF CERTAIN EMBODIMENTS

Figure 1:
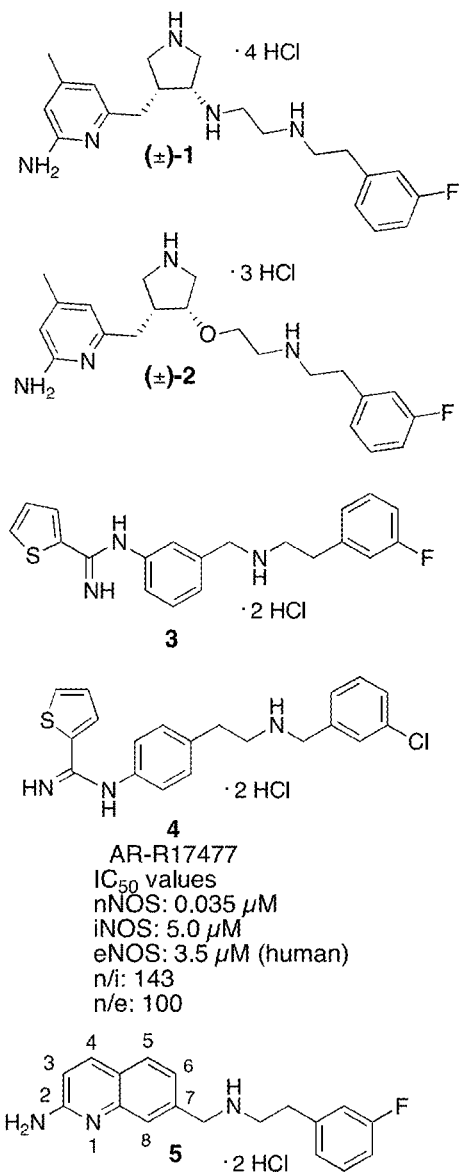
FIG. 1. Prior art compounds 1-4 and a representative nNOS inhibitor compound 5 discussed in this study. Chemical properties were calculated using ChemBioDraw version 12.3.

As relates to certain non-limiting embodiments of this invention, the generation of more structurally-simple and synthetically-available nNOS inhibitor scaffolds was undertaken, in one respect, to replace the amidine group of prior art molecule 3. For suitable amidine replacement, such a group should be stable, weakly basic (e.g., pKa between 6 and 8) and possess as few hydrogen-bond donors as possible. One such moiety is the 2-aminoquinoline group, with a pK$_a$ of 7.3, and a considerably higher C Log P than the amino-pyridine group of prior art compounds 1 and 2. With such considerations, aminoquinoline compound 5 was prepared.

Assaying compound 5 against purified nNOS, eNOS, and iNOS revealed potent inhibition of nNOS (74 nM) and good selectivity for nNOS over iNOS, but the selectivity for nNOS over eNOS was only approximately 6-fold. There is a hydrophobic pocket at the far end of the substrate access channel of nNOS; contact between an inhibitor and the residues lining this pocket is implicated in high selectivity for nNOS over the other two isoforms. In the case of 5, it was hypothesized that the low selectivity resulted from the lack of contact between residues in this pocket and the fluorophenyl ring. Preliminary docking studies and crystallography indicated that elongation of the chain between the aminoquinoline system and the distal fluorophenyl ring, moving the position of the secondary amine, or a combination of both, might provide the right length and orientation to reach this hydrophobic pocket, and a series of analogues investigating chain length (6-9) and nitrogen position was, therefore, prepared. Additionally, on the basis of computer modeling, it was hypothesized that placement of the "tail" of the inhibitor at position 6 of the aminoquinoline system (instead of position 7) could also be effective; to this end, compounds 10-13 were prepared. Finally, it was thought that the use of other halogens and substitution patterns on the non-coordinating aryl ring could be beneficial for enhancing potency and selectivity, so a small series of 7-substituted compounds (14-16) with different halogens and substitution patterns was prepared. All compounds were assayed against purified rat nNOS, and select compounds were assayed against eNOS, iNOS, and human nNOS, and for cellular permeability in a Caco-2 model.

6- and 7-Substituted 2-aminoquinolines were prepared by variations of methods reported in the literature. In the present study, 7-substituted aminoquinolines (5-9 and 14-16) were prepared by a versatile, late-divergent route that began with the preparation of 3'-methylcinnamanilide (17) from m-toluidine and cinnamoyl chloride, by literature procedures. Compound 17 was subsequently treated with an excess of aluminum chloride in chlorobenzene to affect cyclization (with concomitant cleavage of the C-aryl bond) to yield the carbostyril 18 as a mixture of the 7-isomer 18a (major) and 5-isomer 18b (minor). The isomers were not separated at this stage, but were converted into the 2-chloroquinolines 19a and 19b by treatment with POCl₃; unwanted 5-isomer 19b was removed by fractional crystallization from isopropanol. Pure 19a was converted into 2-acetamidoquinoline 20, and free-radical bromination afforded versatile intermediate 21 (Scheme 1).

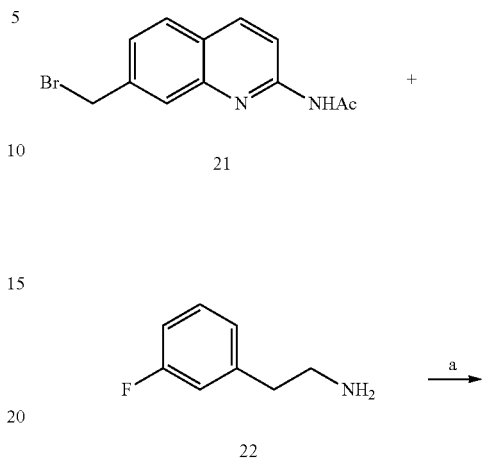

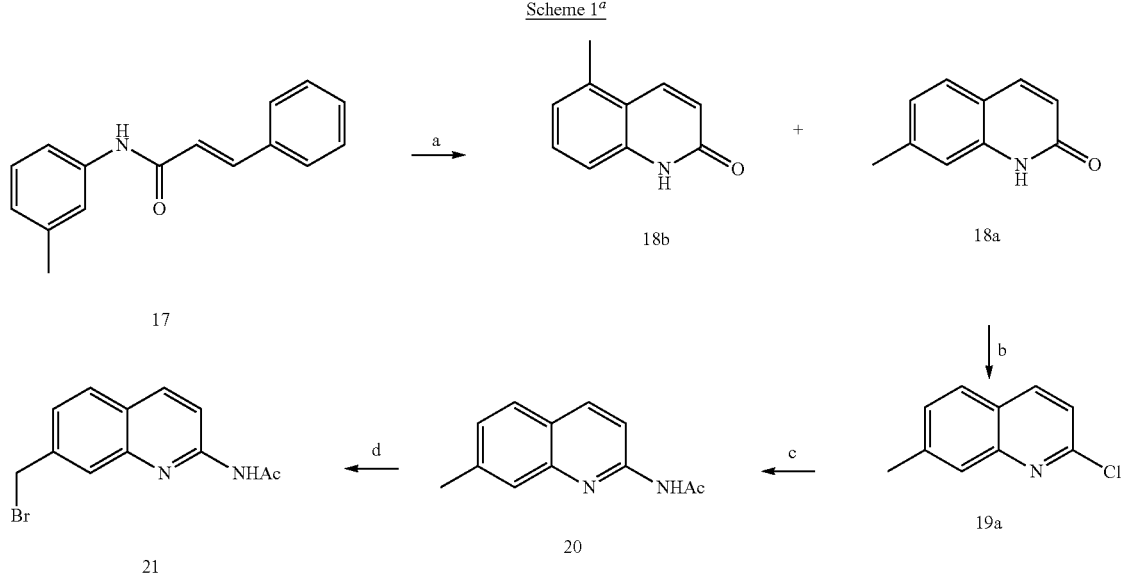

$^a$Reagents and conditions: (a) AlCl₃, PhCl, 90° C.; (b) i. POCl₃, reflux, ii. fractional crystallization from i-PrOH after isolation; (c) AcNH₂, K₂CO₃, reflux (~230° C.); (d) NBS, (PhCO₂)₂, benzene, reflux.

For those aminoquinoline analogues possessing one methylene unit between the quinoline system and the secondary amine (5 and 9, Schemes 2 and 3) the bromide was treated with a slight excess of 3-fluorophenethylamine (22) or 3-fluoro-1-phenylpropanamine (25, prepared by hydrogenation of 3-fluorophenethyl cyanide [24, prepared from 23]) under basic S$_N$2 conditions, to afford amines 26 and 27, respectively (the former was characterized, while the latter was simply carried on to the last step). Deacetylation of these compounds in refluxing methanolic K₂CO₃ afforded the final analogues as their syrupy free-bases, which were readily converted to water-soluble dihydrochloride salts 5 and 9 by treatment with methanolic HCl.

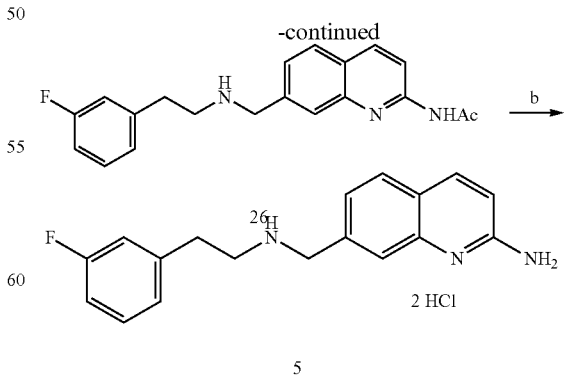

$^a$Reagents and conditions: (a) Cs₂CO₃, DMF, r.t.; (d) i. K₂CO₃, MeOH, reflux, ii. MeOH/HCl, r.t. (after isolation).

Scheme 3[a]

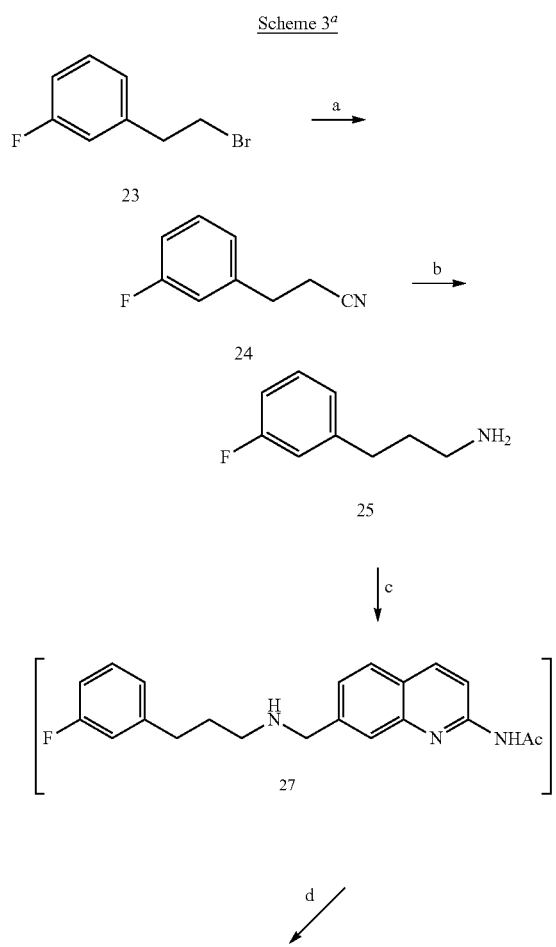

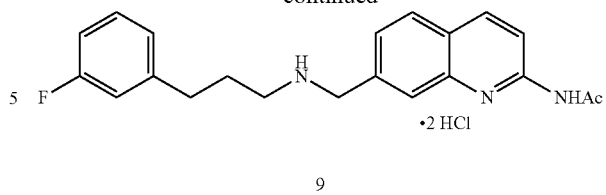

[a]Reagents and conditions: (a) NaCN, DMF, 60° C.; (b) H₂, Raney Ni, NH₃/MeOH/EtOH,
r.t.; (c) 21, Cs₂CO₃, DMF, r.t.; (d) i. K₂CO₃, MeOH, reflux, ii. MeOH/HCl, r.t. (after isolation).

Various other compounds of this invention can be prepared, analogously. For instance, reaction of bromide 21, with a substituted aniline, phenylmethylamine, phenyethylamine or an unsubstituted pyridinylpropylamine compound, under basic substitution conditions, can afford the corresponding N-linked compounds. (See, e.g., the representative compounds of FIG. 2.)

Aminoquinolines possessing two methylene units between the quinoline system and secondary amine (6, 7, 8, and 14-16) were likewise prepared from bromide 21 by homologation with cyanide ion to afford nitrile 28. (See, Scheme 4, below.) This compound was reduced to a very polar quinolinyl-ethanamine (29) using hydrogen and Raney nickel in an ethanol/methanolic ammonia solution; 29 was used crude in the next step (confirmed by TLC and MS). Benzyl analogue 6 was prepared by an "indirect" reductive amination, where 29 was treated with 3-fluorobenzaldehyde (30) under mildly acidic, dehydrating conditions. When the aldehyde was consumed (as measured by TLC), the dehydrating agent was filtered, and the resulting aldimine was reduced by NaBH₄. Subsequent deacetylation, workup, and acidification afforded 6.

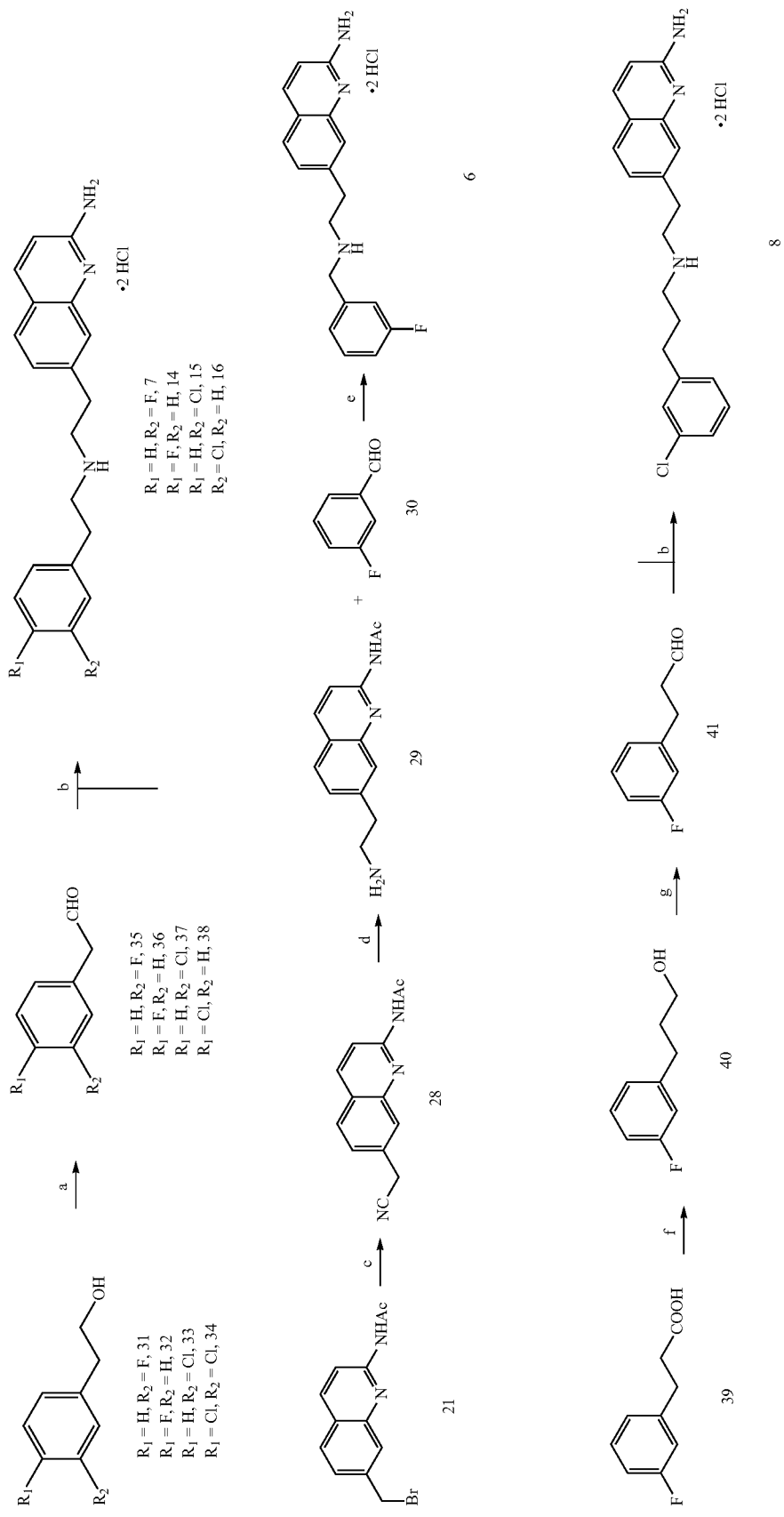

To prepare phenethyl analogues 7, 14, 15, and 16 (Scheme 4), requisite phenylacetaldehydes 35-38 were prepared by Dess-Martin oxidation of commercially available phenethyl alcohols 31-34, respectively. A "direct" reductive amination using 29, the desired aldehyde, sodium triacetoxyborohydride, MgSO$_4$, and catalytic AcOH was used to assemble the cores of the final analogues. Yields were low because of dialkylation and aldehyde condensation by-products; the use of other solvents, dehydrating agents, and reductants failed to alleviate these problems; the aldehydes may be light- and acid-sensitive as well. For these analogues, the intermediate acetamides were not characterized after isolation, but were immediately deprotected (because of some concerns about their stability) to yield 7, 14, 15, and 16, and converted into dihydrochloride salts, which could be easily purified by crystallization, trituration, or preparative HPLC. Finally, the preparation of propyl analogue 8 began with 3-fluorophenylpropionic acid (39). Reduction to phenylpropanol 40, followed by Swern oxidation, afforded sensitive aldehyde 41. Reductive amination using amine 29, deacetylation, workup, and acidification afforded 8.

6-Substituted 2-aminoquinolines were prepared by a similar means to those described above, beginning instead with 4'-methylcinnamanilide (42, Scheme 5). Using the cyclization-dearylation procedure, 43 was prepared and immediately chlorinated (to 44) using POCl$_3$. Amidation (to yield 45) and bromination afforded 46. Compound 46 was treated with 22, and the resulting acetamide was deacetylated, isolated, and acidified as before to yield 10.

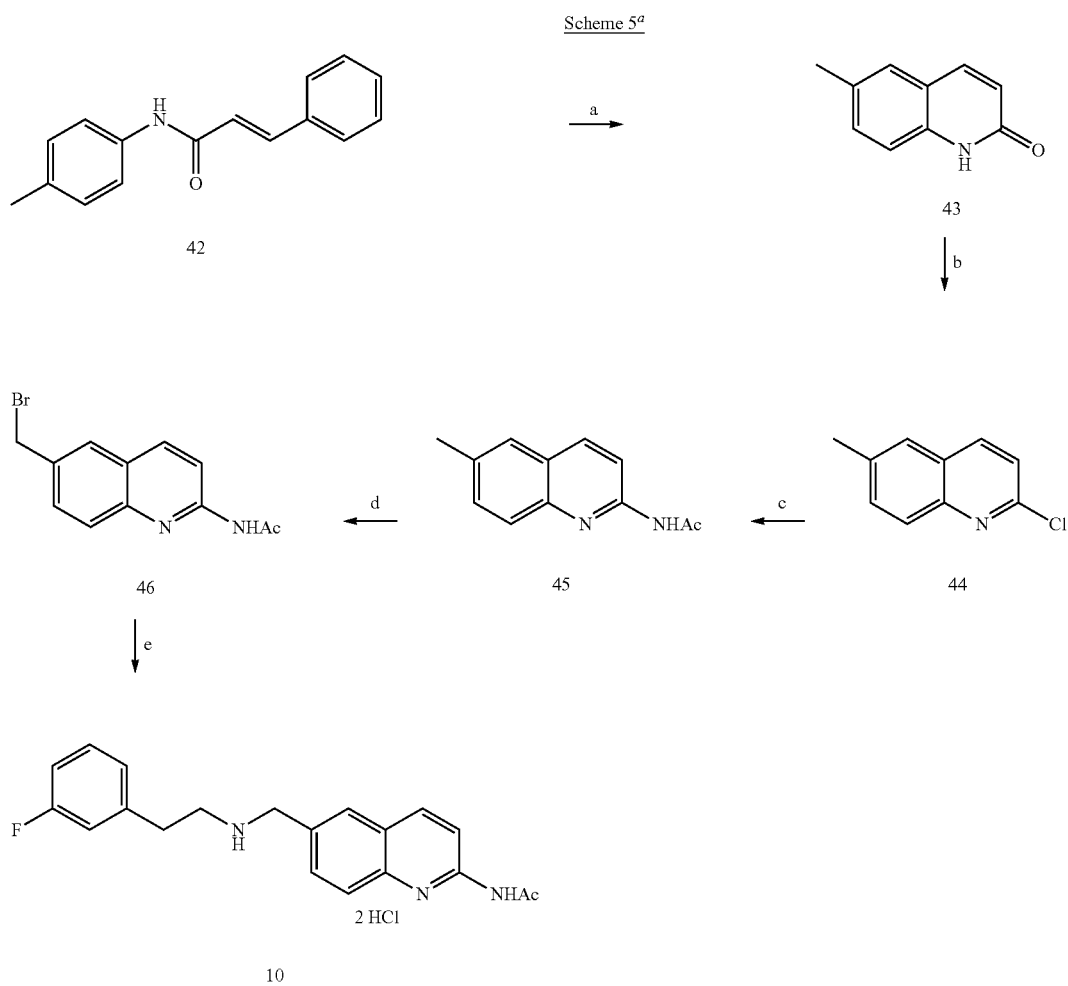

Scheme 5$^a$ $^a$Reagents and conditions: (a) AlCl$_3$, PhCl, 90° C.; (b) POCl$_3$, reflux; (c) AcNH$_2$, K$_2$CO$_3$, reflux (~230° C.); (d) NBS, (PhCO$_2$)$_2$, benzene, reflux; (e) i. 22, Cs$_2$CO$_3$, DMF, r.t., ii. K$_2$CO$_3$, MeOH, reflux (after isolation), iii. MeOH, HCl, r.t. (after isolation).

Likewise, homologation of 46 with cyanide ion afforded 47, which was readily reduced to ethanamine 48 (see, Scheme 6; confirmed by TLC, MS and $^1$H-NMR). The indirect reductive amination procedure (using 30) afforded 11 after deacetylation, isolation, and acidification. The direct reductive amination employing Na(OAc)$_3$BH (with aldehyde 35) similarly afforded 12 after deacetylation/acidification, while the same procedure using 41 instead yielded 13 after deprotection and salt formation.

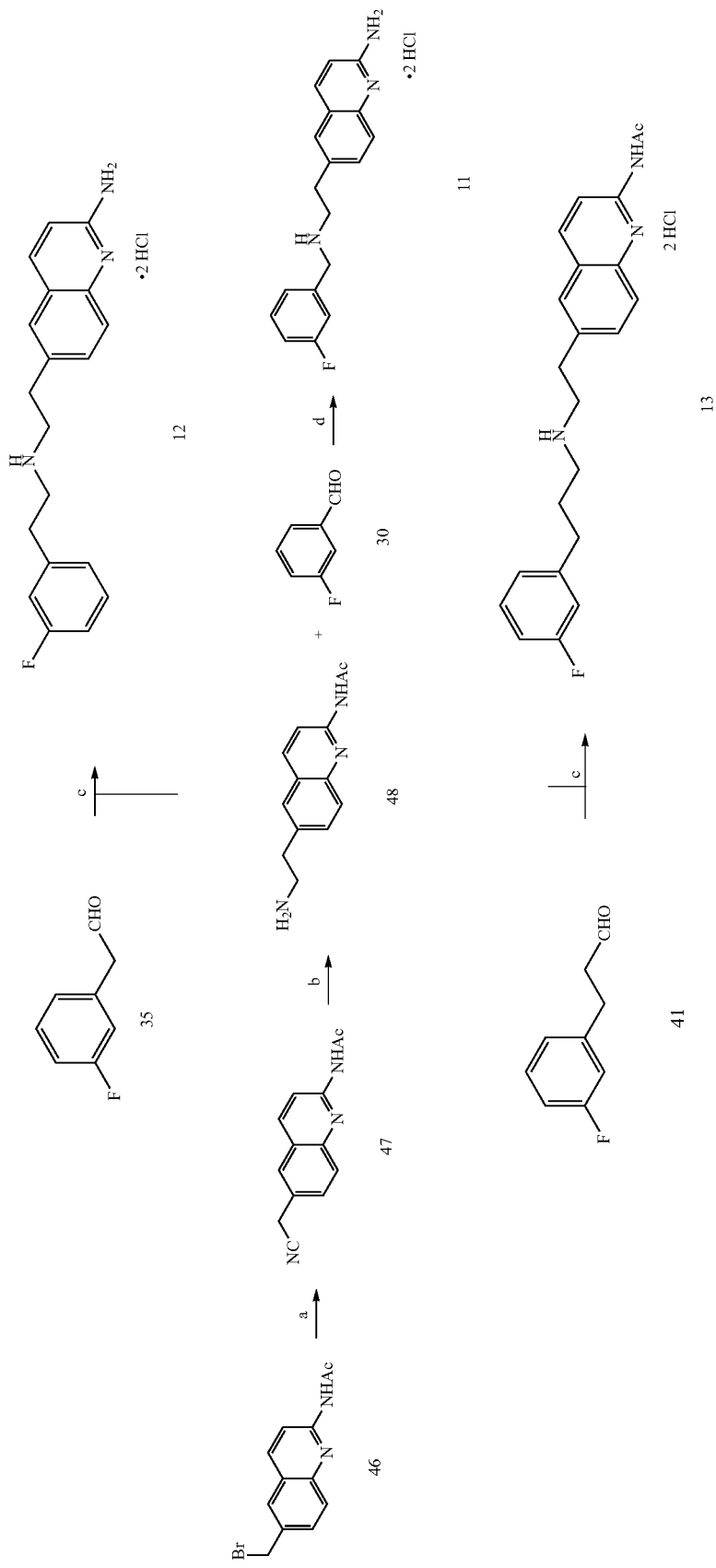

Figure 3:
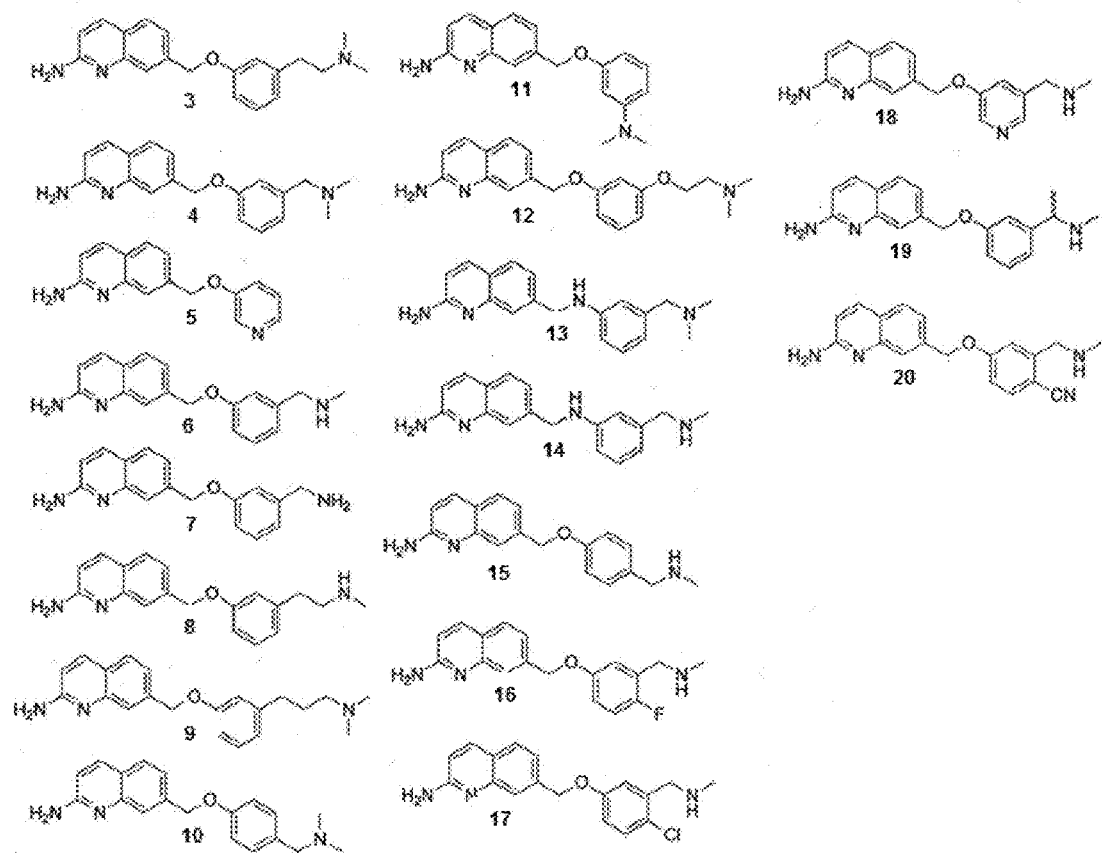

Representative O-linked compounds are illustrated in FIG. 3 and prepared as provided with reference to Schemes 7-14. As discussed above, 7-substituted-2-aminoquinolines were prepared via the readily accessible chloroquinoline 19a, by performing a Kóródi amidation (treatment with an excess of $K_2CO_3$ in neat acetamide at reflux to produce the 2-acetamidoquinoline 20). As an alternative approach (Scheme 7), amination of 2-chloroquinolines was achieved using LHMDS as both an ammonia surrogate and base; applying this procedure to 24 afforded the 2-aminoquinoline 25 in nearly quantitative yields, even on multigram scale. Treatment with N-acetylimidazole in refluxing THF afforded 26, and free-radical bromination, as previously reported, yielded the versatile bromide 27. (Notwithstanding the foregoing Schemes 1-6, Examples 1-30 and FIG. 1, Schemes 7-14 and FIG. 3 employ independent numerical references for the respective aminoquinoline compounds and corresponding intermediate and starting materials.)

Scheme 7[a]

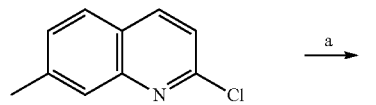

24

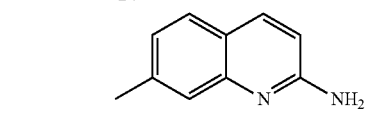

25

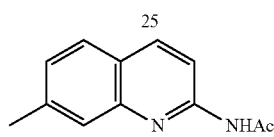

26

27

[a]Reagents and conditions: (a) LHMDS, $Pd_2(dba)_3$, DavePhos, THF/dioxane, 100° C.; (b) N-acetylimidazole, THF, reflux; (c) NBS, $(PhCO_2)_2$, benzene, reflux.

Figure 2:
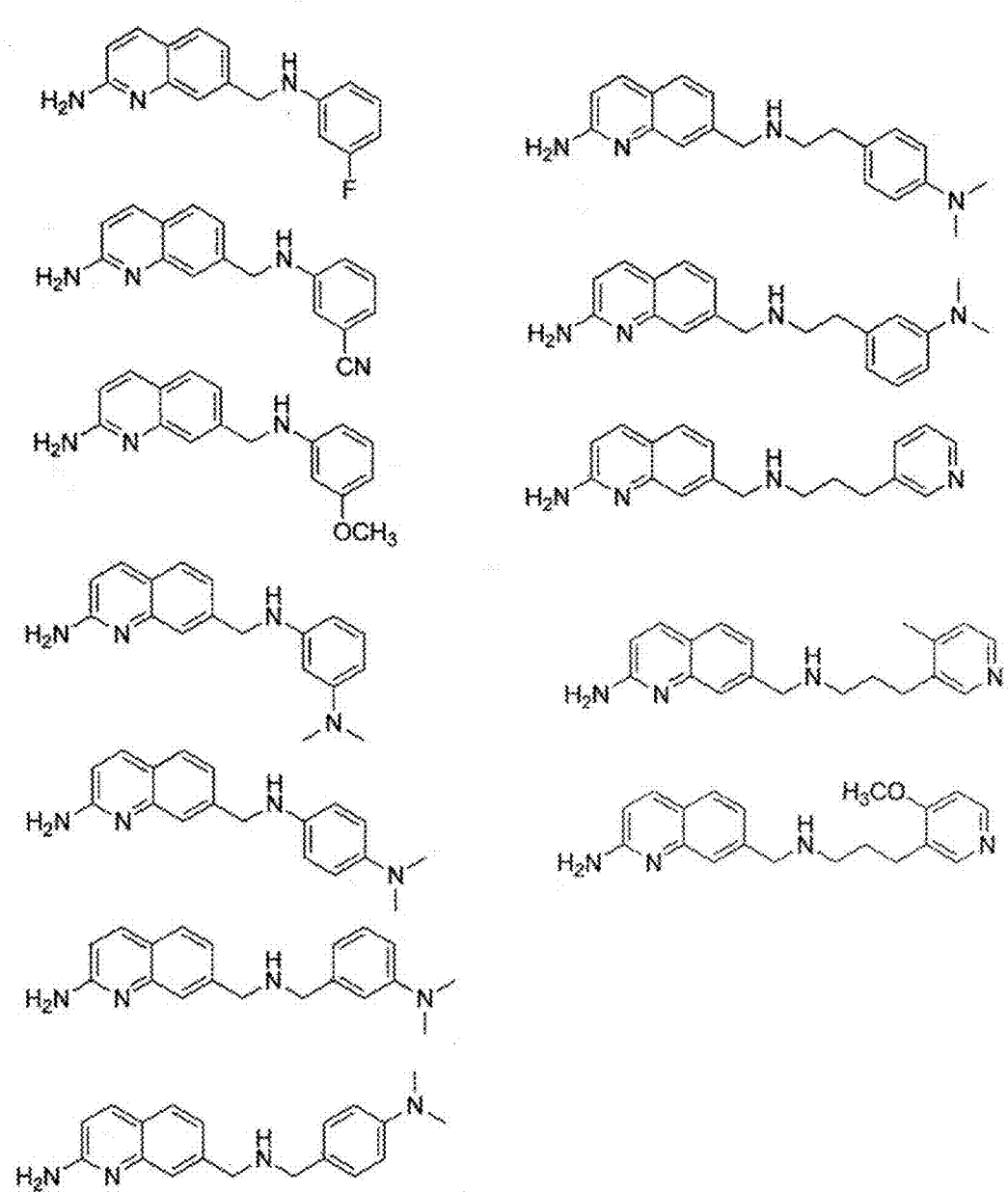
FIGS. 2-3. Chemical structures of representative compounds of this invention, in accordance with various non-limiting embodiments thereof.

With bromide 27 in hand, the phenol (and aniline) intermediate materials were then prepared prior to the final assembly of the corresponding phenyl ether or aniline compounds (FIGS. 2-3). To prepare phenyl ether 3 (Scheme 8A), 3-methoxyphenethylamine (28) was dimethylated, and the methyl group of 29 was removed to yield phenol 30. The monomethylated phenol 33 (for compound 8) was prepared from 3-methoxyphenethyl bromide (31, Scheme 8B) and excess methylamine solution, followed by demethylation of 32 and immediate Boc-protection, to aid in purification and prevent later interference by the free secondary amine. For the benzylic amine of compound 4, the phenol 35 (Scheme 8C) was prepared by reductive amination of commercially available 3-hydroxybenzaldehyde 34 with N,N-dimethylamine. Similarly, exchanging N,N-dimethylamine for methylamine (as needed for compound 6) yielded the an amine, which was immediately Boc-protected as 36. Phenol 38 (Scheme 8D) was prepared for the synthesis of compound 7 by Boc-protecting 3-hydroxybenzylamine (37).

Scheme 8[a]

A

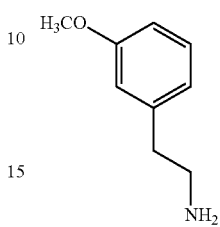

28

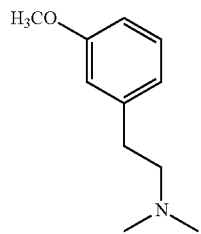

29

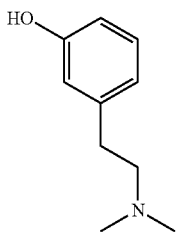

30

B

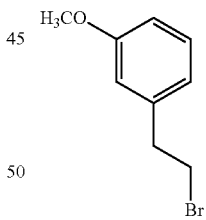

31

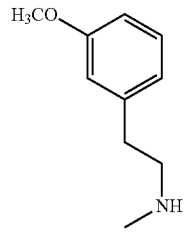

32

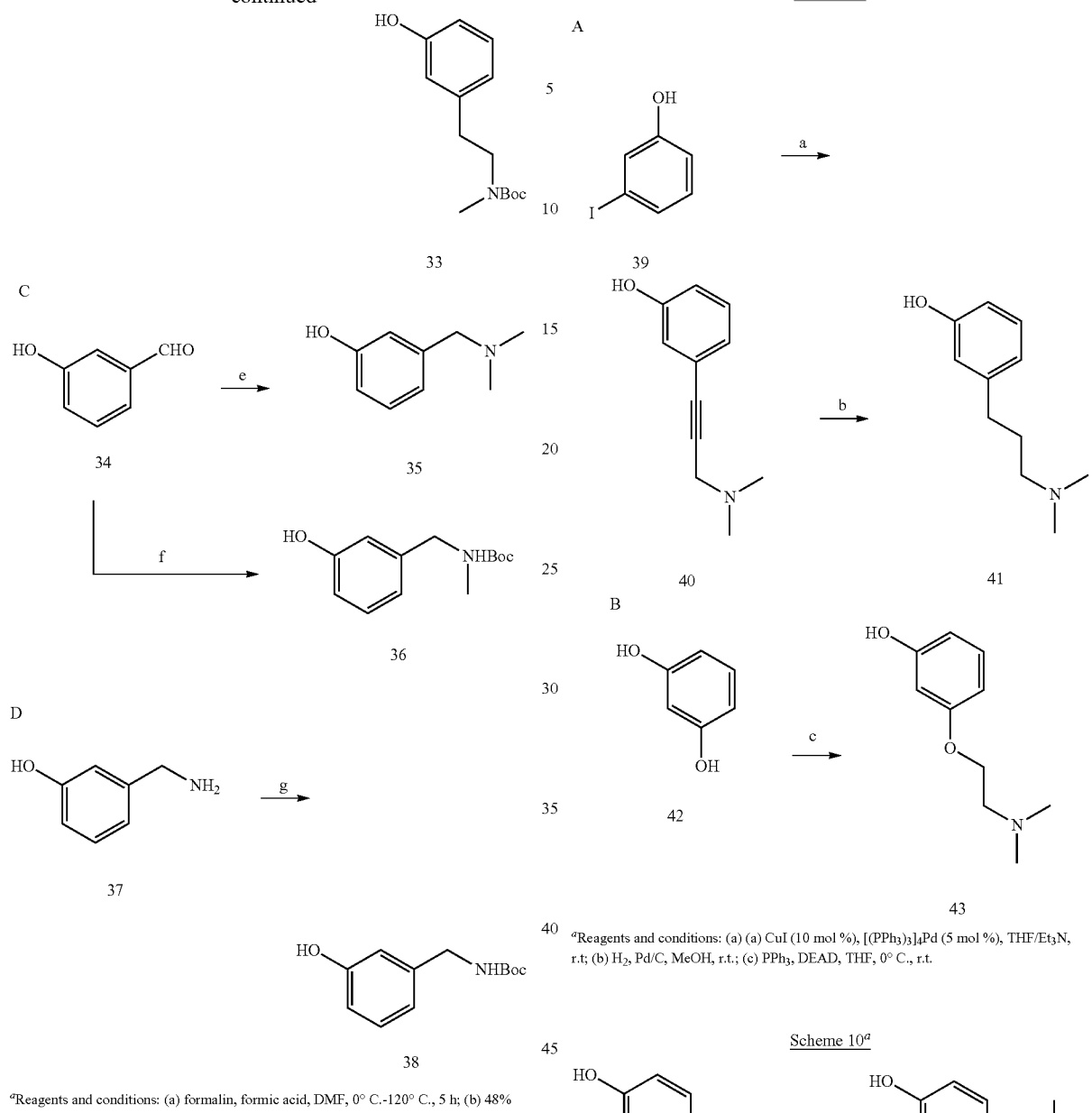

*Reagents and conditions: (a) (a) CuI (10 mol %), [(PPh₃)₃]₄Pd (5 mol %), THF/Et₃N, r.t; (b) H₂, Pd/C, MeOH, r.t.; (c) PPh₃, DEAD, THF, 0° C., r.t.

*Reagents and conditions: (a) formalin, formic acid, DMF, 0° C.-120° C., 5 h; (b) 48% HBr, AcOH, reflux; (c) 40% MeNH₂ in H₂O, THF/H₂O, r.t.; (d) i. 48% HBr, HOAc, reflux, ii. Boc₂O, Et₃N, THF, r.t.; (e) i. Me₂NH·HCl, Et₃N, CHCl₃/MeOH, Na₂SO₄, r.t.; ii. Na(OAc)₃BH, r.t.; (f) i. MeNH₂ in THF, cat. AcOH, CHCl₃/MeOH, Na₂SO₄, r.t.; ii. NaBH₄, MeOH, 0° C. - r.t., iii. Boc₂O, THF, r.t.; (g) Boc₂O, THF, 0° C.- r.t.

With reference to Scheme 9, the longer linker of 9, via phenol 41, was prepared by the Sonogashira coupling of 3-iodophenol (39) with N,N-dimethylpropargylamine, followed by reduction of the triple bond of 40 (Scheme 9A). For compound 12, the intermediate 43 was prepared by a Mitsunobu reaction between resorcinol (42) and 3-(N,N-dimethylamino)ethanol (Scheme 9B). With reference to Scheme 10, as performed for the meta-analogues, the intermediate phenols 45 and 46 (for para-analogues 10 and 15, respectively) were prepared from 4-hydroxybenzaldehyde (44), and either methylamine (for 46) or N,N-dimethylamine (for 45).

*Reagents and conditions: (a) i. Me₂NH·HCl, Et₃N, Na₂SO₄, CHCl₃/MeOH, r.t.; ii. Na(OAc)₃BH, r.t.(b) i. MeNH₂ in THF, CHCl₃/MeOH, Na₂SO₄, AcOH, r.t.; ii. NaBH₄, MeOH, 0° C. - r.t., iii. Boc₂O, THF, r.t.

With reference to Scheme 11, the aniline materials for preparation of compounds 13 and 14 were both prepared from 3-nitrobenzyl bromide (47) upon treatment with either dimethylamine (48) or methylamine (followed by Boc-protection to yield 50). Reduction of the nitro group with Raney nickel afforded 49 (for 13) and 51 (for 14).

Scheme 11[a]

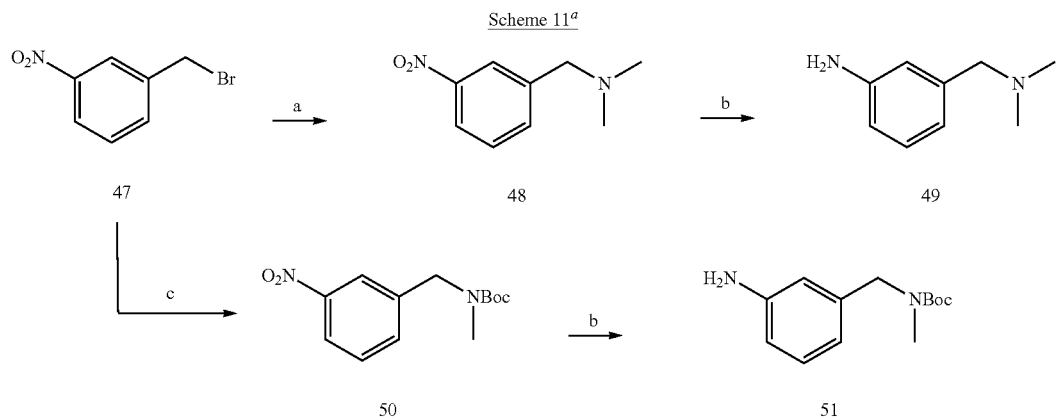

[a]Reagents and conditions: (a) Me$_2$NH-HCl, Et$_3$N, CH$_2$Cl and MeOH, r.t.; (b) H$_2$, Raney Ni, MeOH, r.t.; (c) i. MeNH$_2$ in THF, CH$_2$Cl$_2$, r.t., ii. Boc$_2$O, CH$_2$Cl$_2$, r.t With reference to Scheme 12A, the substituted phenols (for compounds 16-17 and 19-20) can be prepared by employing reductive amination/Boc protection to commercially available aldehydes (52, 53) or acetophenones (54) to yield protected amines 56-58. To prepare cyanophenol 60 (for compound 20), the brominated precursor phenol 59 (prepared from 55) was subjected to a palladium-catalyzed cyanation. Lastly, the pyridinol 63 (for compound 18, Scheme 12B) was prepared by reductive amination of nicotinaldehyde 61, and cleavage of the methyl group and protection furnished 63.

Scheme 12[a]

A

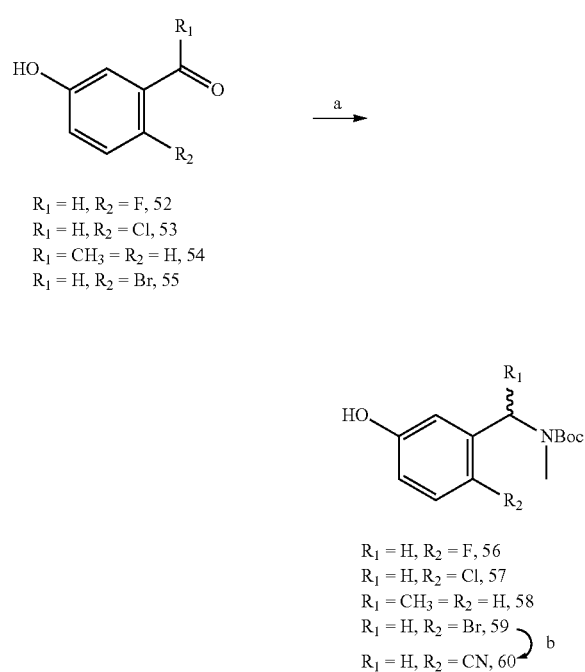

B

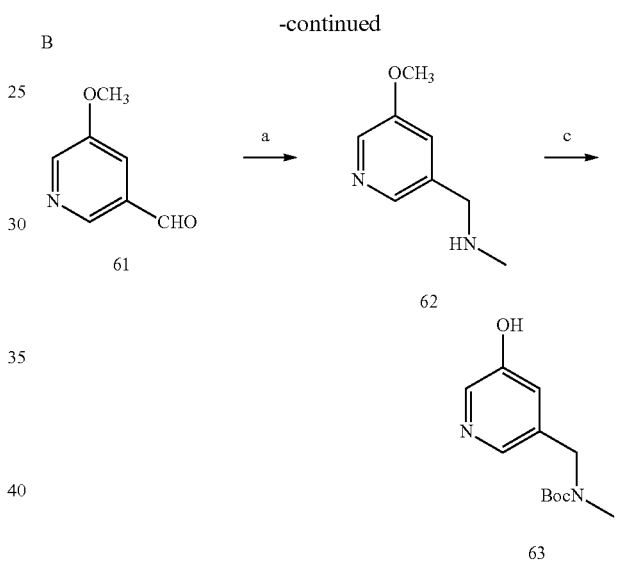

[a]Reagents and conditions: (a) i. MeNH$_2$ in THF, cat. AcOH, CHCl$_3$/MeOH, Na$_2$SO$_4$,, r.t.; ii. NaBH$_4$, MeOH, 0° C.-r.t., iii. Boc$_2$O, THF, r.t.; (b) ZnCN$_2$, Pd(OAc)$_2$, PPh$_3$, DMF, 100° C.; (c) i. HBr/H$_2$O, HOAc, 130° C.; ii, Et$_3$N, Boc$_2$O, THF/MeOH, r.t.

With the components of the phenyl ether-substituted quinolines in hand, assembly of the final compounds of FIG. 3 (Scheme 13) was completed by first treating the desired phenol (30, 33, 35, 36, 38, 41, 43, 45, 46, 56-58, 60, 63, or commercially available 3-hydroxypyridine or 3-(N,N-dimethylamino)phenol, in the case of compounds 5 and 18, respectively) with sodium hydride in DMF at 0° C. A solution of 27 was then added, and the reaction was typically complete within 1 h. The intermediate acetamides (64-79) were not characterized and were purified and deprotected immediately: the acetyl group was first removed by K$_2$CO$_3$ in refluxing methanol, and after isolation, the free aminoquinolines were treated with methanolic HCl in ether to produce water-soluble hydrochloride salts. Compounds without a Boc group present were isolated after 5-15 min; those with a Boc group were stirred overnight to ensure complete deprotection. In the case of 76, HCl induced unfavorable side-reactions, so TFA was instead used for deprotection.

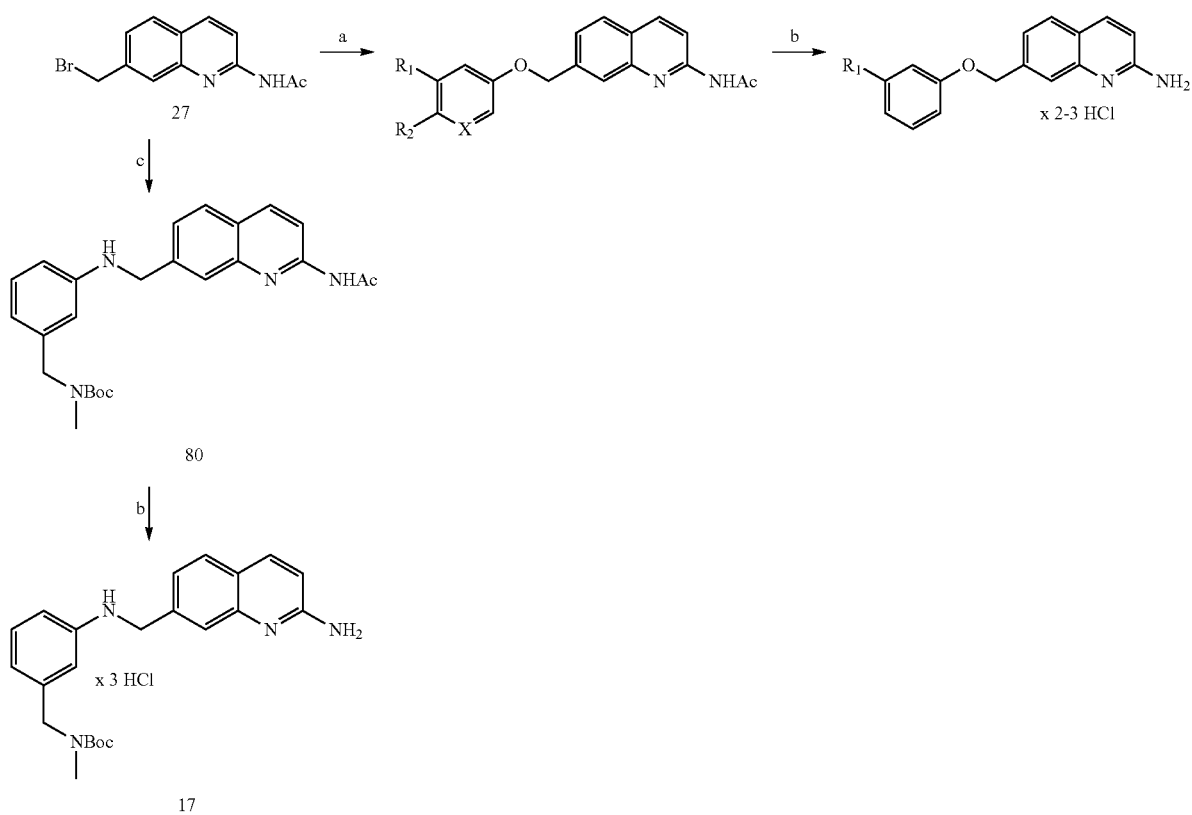

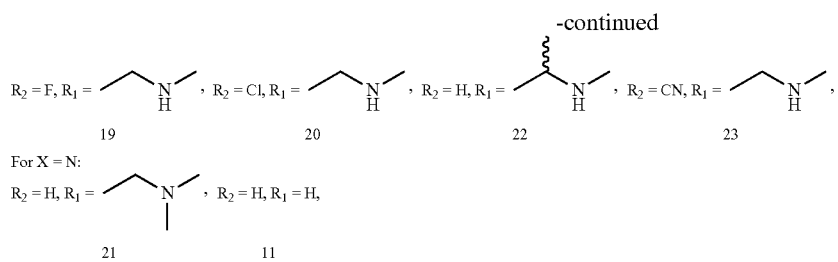

19    20    22    23

For X = N:

21    11

[a]Reagents and conditions: (a) i. Phenols 30, 33, 35, 36, 38, 41, 43, 45, 46, 56-58, 60, 63, 3-(N-N-dimethylamino)phenol, or 3-hydroxypyridine, NaH, DMF, 0° C., ii. 27 (in DMF), 0° C.; (b) i. $K_2CO_3$, MeOH, reflux, ii, HCl/MeOH, ether, R.T., or TFA/DCM (for 76), after isolation, 5 min-overnight; (c) 51 (2.5 eq.) cat. KI, μwave, MeCN, 110° C.

The microwave alkylation procedure of Romero et al. was employed to synthesize the aniline 17 (Scheme 13) Compound 27, excess 51, and catalytic potassium iodide were heated in acetonitrile under microwave radiation to furnish intermediate 80, which was deprotected as described above. However, the low acidity and reactivity of aniline 49 produced only water-soluble quaternization by-products upon reaction with 27. It was proposed that the two halves of the N-linked compound 13 could be joined via reductive amination as previously reported, beginning with the quinolinecarboxaldehyde 86 (Scheme 14). After unsuccessful attempts to prepare 86 from 26 and 27, the aldehyde was prepared in five steps (Scheme 14), starting with a Wittig cyanovinylation of commercially available aldehyde 81. The desired trans-isomer 82 was obtained in 80% yield and was readily purified. Reductive cyclization in the presence of iron yielded aminoquinoline 83; and acetylation of the non-nucleophilic amine proceeded in good yield using N-acetylimidazole. Ester 84 was reduced to alcohol 85, and the oxidation to 86 was performed using Dess-Martin periodinane. An indirect reductive amination with 49 was effective at elevated temperatures, and the crude acetamide was deprotected to yield final compound 13 in low yield but very high purity.

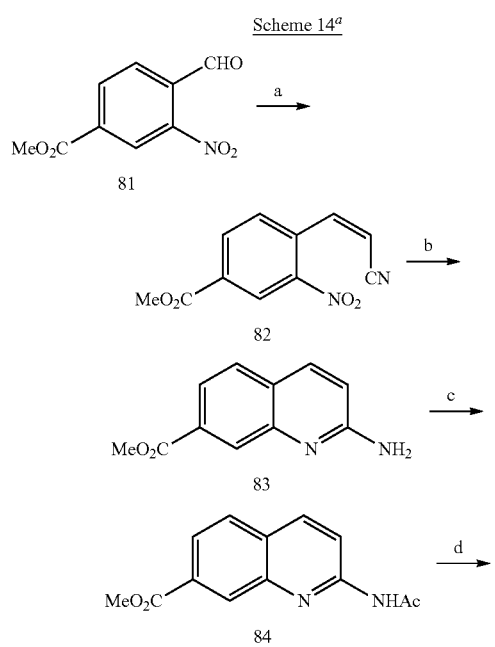

Scheme 14[a]

[a]Reagents and conditions: (a) (Triphenylphosphoranylidene)acetonitrile (slow addition), $CH_2Cl_2$, -10° C.; (b) Fe powder, DMF/AcOH, 100° C.; (c) N-acetylimidazole, cat., DMAP, dioxane, 100° C.; (d) $LiAlH_4$ (1.5 eq.), THF, -10° C.-0° C.; (e) $PPh_3$, $CBr_4$, THF, 0° C.-r.t.; (e) Dess-Martin periodinane, $CH_2Cl_2$,r.t.; (f) i. EtOH, AcOH, $Na_2SO_4$, 60° C., ii., $NaBH_4$, r.t., (g) i. $K_2CO_3$, MeOH, reflux; ii. HCl/MeOH, ether, r.t. (after isolation).

Compounds 5-16 were assayed against purified rat nNOS, bovine eNOS, and murine macrophage iNOS (there is large active-site homology among species), using the hemoglobin capture assay, as previously described. (Labby, K. J.; Xue, F.; Kraus, J. M.; Ji, H.; Mataka, J.; Li, H.; Martásek, P.; Roman, L. J.; Poulos, T. L.; and Silverman, R. B. Intramolecular hydrogen bonding: A potential strategy for more bioavailable inhibitors of neuronal nitric oxide synthase. Bioorg. Med. Chem. 2012, 20, 2435-2443; Hevel, J. M. and Marletta, M. A. "Nitric-Oxide Synthase assays" in Methods in Enzymology, 1994, 233, 250-258.) The apparent $K_i$ values and isoform selectivities are summarized in Table 1, and values for compounds 1, 2, and 3 are included for comparative purposes; the $IC_{50}$ values for 4 are given in FIG. 1. (Likewise, various compounds of FIGS. 2-3 were similarly assayed, with data available, but not reported herein.)

TABLE 1

Inhibition of NOS enzymes by compounds 5-16.

| Compound | $K_i$ (μM)[a] | | | Selectivity | |
| --- | --- | --- | --- | --- | --- |
| | nNOS | iNOS | eNOS | n/i | n/e |
| 1 | 0.014 | 4.1 | 28 | 293 | 2000 |
| 2 | 0.007 | 5.8 | 19.2 | 807 | 2676 |
| 3 | 0.011 | 1.6 | 0.9 | 149 | 82 |

TABLE 1-continued

Inhibition of NOS enzymes by compounds 5-16.

| Compound | $K_i$ (μM)[a] | | | Selectivity | |
|---|---|---|---|---|---|
| | nNOS | iNOS | eNOS | n/i | n/e |
| 5 (Ex. 8) | 0.075 | 9.14 | 0.485 | 124 | 6.2 |
| 6 (Ex. 12) | 0.254 | 24.5 | 7.77 | 97 | 30 |
| 7 (Ex. 13) | 0.049 | 44.0 | 11.16 | 899 | 228 |
| 8 (Ex. 21) | 0.164 | 31.9 | 7.25 | 194 | 44 |
| 9 (Ex. 9) | 0.060 | 32.3 | 3.69 | 538 | 62 |
| 10 (Ex. 25) | >5.7 | NT | NT | ND | ND |
| 11 (Ex. 28) | >5.7 | NT | NT | ND | ND |
| 12 (Ex. 29) | >5.7 | NT | NT | ND | ND |
| 13 (Ex. 30) | 4.37 | NT | NT | ND | ND |
| 14 (Ex. 16) | 0.183 | 51.2 | 8.86 | 280 | 37 |
| 15 (Ex. 17) | 0.066 | 28.4 | 7.24 | 431 | 110 |
| 16 (Ex. 18) | 0.212 | 19.2 | 9.89 | 91 | 47 |

[a]The compounds were assayed for in vitro inhibition against three purified NOS isoforms: rat nNOS, bovine eNOS and murine iNOS, using known literature methods (see experimental section for details), and $K_i$ values, calculated directly from $IC_{50}$ values, are the average of at least two replicates; selectivity values are ratios of respective $K_i$ values. NT=not tested, ND=not determined.

The lead 7-substituted 2-aminoquinoline, compound 5, has potent nNOS inhibitory activity and high n/i selectivity, yet it is only weakly selective for nNOS over eNOS. It was hypothesized that this low selectivity arose from the lack of contact between the fluorophenyl tail of the inhibitor and a hydrophobic pocket consisting of Tyr706, Leu337, and Met336 (the last of which is present in nNOS and iNOS, but is a valine in eNOS). Contact with these residues is implicated for high potency and isoform selectivity, and in the case of 5, it was predicted that the short fluorophenethyl group would instead sit out in the substrate access channel, where it could fit just as easily into the larger, looser hydrophobic pocket of eNOS (Tyr477, Leu107, and Val106). Indeed, the crystal structures of 5 bound to both nNOS and eNOS (FIGS. 4A and 4B, respectively) indicate that the bound conformation of 5 is virtually identical in both isoforms, a result that easily explains the low selectivity. In both cases, without restriction to any one theory or mode of operation, the aminoquinoline moiety can act as an arginine mimic and interacts with the active site glutamate (Glu 592 in nNOS; Glu363 in eNOS). The secondary amine sits between the heme propionates and could form hydrogen bonds with both carboxylates, while the fluorophenethyl moiety, as predicted, does not quite reach the hydrophobic pocket except for slight contact between the fluorine atom and Leu337; this is similar to the crystal structure of 3. To establish hydrogen bonds between both the amine group and heme propionates and between the aminoquinoline and Glu592, the rigid quinoline plane must tilt significantly from the heme plane.

Because of the low n/e selectivity of 5, improved potency and n/e selectivity were sought by elongating the chain between the aminoquinoline and the non-coordinating aryl ring. To this end, extra methylene groups were inserted between the secondary amine and fluorophenyl group (9), or between the quinoline and the secondary amine (7, 8). It was reasoned that moving the amine farther from the quinoline could also have the advantage of relaxing the constraints on the quinoline ring orientation but still allow the amine to interact with the heme propionates, thus, in turn, anchoring the tail in a favorable orientation to make hydrophobic contacts. Following that same rationale, compound 6 was also prepared.

Without limitation, there are two factors that can affect the comparative inhibitor potency in this series of aminoquinoline compounds: the linker length and the position of the amine group. Contrary to the prediction regarding amine position, the structure of nNOS with 6 bound (FIG. 5A) reveals that placing two carbons between the quinoline and the amine actually diminishes the interaction with the heme propionates (more than 3.6 Å distance), leading to increased flexibility as evidenced by the disordered fluorophenethyl tail in the structure and decreased potency relative to 5. Superimposition of these two nNOS structures (5 and 6, FIG. 5B) reveals that the loose interaction between the amine of 6 and the heme propionates (because of the more flexible chain) allows the quinoline to assume a more parallel orientation (relative to the heme) than observed in the structure of 5. However, as the 4-atom linker (of 5 and 6) is not long enough to bring the fluorophenyl ring in contact with the aforementioned hydrophobic pocket, the majority of the stabilization results from the hydrogen bonds from the aminoquinoline and the linker amine. Therefore, 5, with an extra hydrogen bond, is a stronger inhibitor than 6.

Figure 6A:
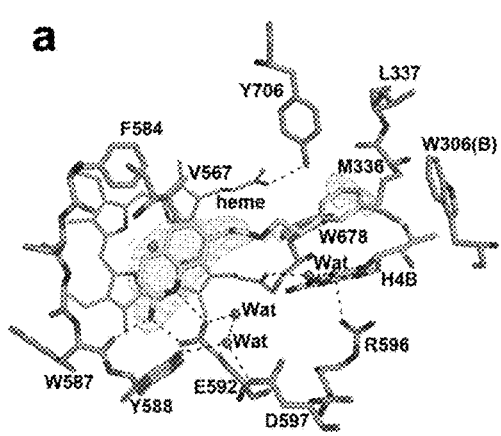
FIGS. 6A-B. Active site structure of 7 (A) or 9 (B) bound to nNOS. The omit Fo-Fc density map for the inhibitor is shown at 2.5 σ contour level. The fluorophenethyl tail of 7 shows weaker density indicative of disordering. Major hydrogen bonds are shown as dashed lines.

The influence of the linker amine is weakened in inhibitors with longer linker lengths. A general trend in linker length is evidenced by compounds with shorter linkers (5 and 6) having lower nNOS inhibitory activity than compounds with longer linkers (7 and 9, Table 1). The ideal chain length thus appears to be five atoms between the quinoline and fluorophenyl groups. nNOS inhibitory activity is similar between 7 and 9 (FIGS. 6A and 6B), with the nitrogen placement not drastically affecting potency, whereas compound 8 (FIG. 7A), which has six atoms between the fluorophenyl group and aminoquinoline, is less potent. The omit electron density map reveals that 7 (FIG. 6A), which does not have a strong secondary amine-heme propionate interaction, appears to be more flexible/disordered in the fluorophenyl tail region relative to the structure of 9, (which does show the amine-propionate interaction and an ordered fluorophenyl tail, like 5), yet their potencies are very similar, indicating that the nitrogen position may not be as crucial for these compounds with longer linkers. Indeed, the structure of 9 (FIG. 6B) shows numerous favorable hydrophobic contacts between the fluorophenyl group and the nonpolar residues at the far end of the substrate access channel (Tyr706, Leu337, Met336, and Trp306 of chain B). Although the crystal structure shows that the tail of 7 is more disordered than that of 9, these hydrophobic contacts exist with 7 as well. When the linker is long enough to allow contact between the fluorophenyl ring and the hydrophobic pocket, the combined stabilization from both the hydrophobic interactions and the aminoquinoline-Glu592 interaction may effectively outweigh any lack of interaction between the secondary amines and heme propionates.

Figure 6B:
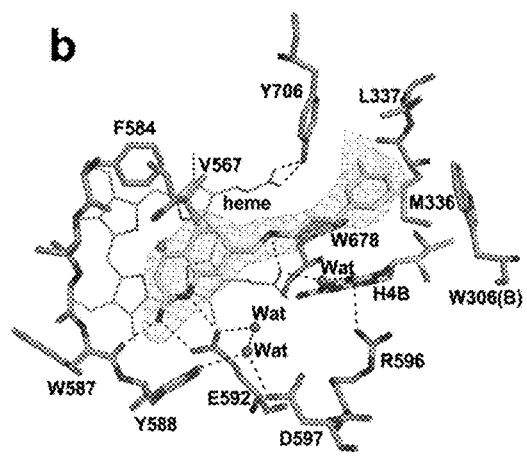
Figure 7A:
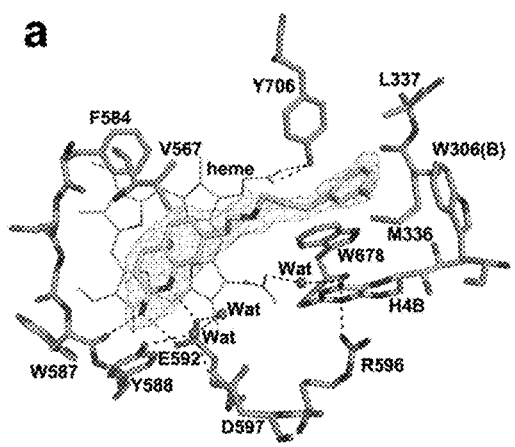
FIGS. 7A-B. Active site structure of 8 (A) or 15 (B) bound to nNOS. The omit Fo-Fc density map for inhibitor is shown at 2.5 σ contour level. The chlorophenethyl tail of 15 is partially disordered with weaker density. Major hydrogen bonds are shown as dashed lines.
Figure 7B:
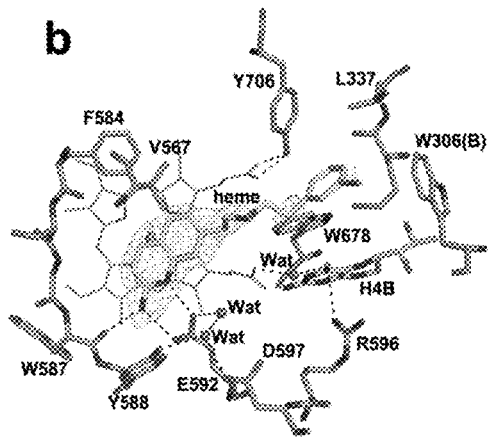

Chain lengths that are longer than the ideal (e.g., compound 8) result in a drop in potency when compared with 7 or 9. The crystal structure (FIG. 7A) shows that the fluorophenyl ring of 8 makes the same hydrophobic contacts as 7 and 9. Nonetheless, to make these contacts, the flexible chain has to assume a "kinked" conformation, in contrast to the fully extended linker conformation seen in 9 (FIG. 6B). The kinked conformation of 8 may result in unfavorable torsional strain in the linker region upon binding.

Compounds 7, 9, and 15 have $K_i$ values of 44 μM, 32.3 μM, and 51.2 μM, respectively, and 7 has nearly 900-fold selectivity for nNOS over iNOS, a value which is significantly higher than those of 1-4, and is among the highest selectivity reported for nNOS over iNOS for non-peptidic inhibitors. Any contact with the substrate-channel hydrophobic pocket (vide supra) could improve n/i selectivity. Murine iNOS contains a polar asparagine residue (Asn115) in this pocket (at the position of Leu337 of nNOS) that would strongly disfavor binding by a hydrophobic group. Nonetheless, even the short-chain inhibitors (5 and 6) still possess good n/i selectivity, despite not reaching this distal pocket, indicating that interactions with residues at this end of the binding site are not the full determinant of this poor iNOS inhibition.

It is reported that the heme-binding sites themselves differ between iNOS and nNOS isoforms, with the former possessing a smaller active site that may not tolerate the bulky and rigid aminoquinoline as well. Interestingly, the selectivity patterns (higher n/i selectivity) contrast with many aminopyridine-based inhibitors, which have higher n/e selectivity. In some cases (such as the R,R-enantiomer of 1), this high n/e selectivity can be explained by water-mediated contacts made between the center pyrrolidine ring and Asp597, a residue that exists in both nNOS and iNOS but is Asn369 in eNOS. This aspartate residue can provide considerable electrostatic or hydrogen-bonding stabilization in nNOS versus eNOS; this stabilization also manifests itself in the high n/e selectivity of dipeptide-based inhibitors but no contacts with Asp597 are observed in the aminoquinoline crystal structures.

Figure 8:
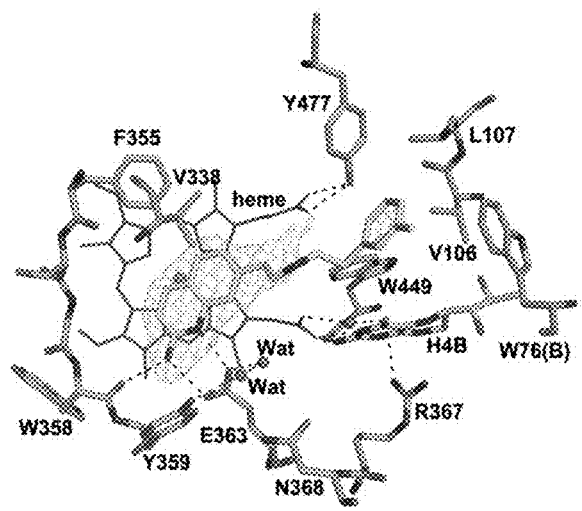
FIG. 8. Active site structure of 7 bound to eNOS. The omit Fo-Fc density map for the inhibitor is shown at 2.5 σ contour level. The fluorophenethyl tail of 7 shows weaker density indicative of partial disordering. Major hydrogen bonds are shown as dashed lines.

In other cases, high n/e selectivity is rationalized by the tighter pi-stacking with Tyr706 of nNOS than with the analogous Tyr477 of eNOS, leading to greater nonbonded contacts and better desolvation. While no clear pi-stacking interactions are visible in the nNOS crystal structures of 6, 7, 8, or 9, hydrophobic contacts and desolvation may still play a substantial role in n/e selectivity for aminoquinolines. The binding mode of the aminoquinoline portion is identical in the structure of 7 bound to nNOS (FIG. 6A) or eNOS (FIG. 8) and does not contribute to isoform selectivity. However, the length of the linker in 7 enables the fluorophenyl ring to make good hydrophobic contacts with the residues Met336, Leu337, Tyr706, and Trp306 from the other subunit. The bulky and flexible Met336 side chain makes extensive contacts with the fluorophenyl group of 7, whereas the analogous residue, Val106 in eNOS, with a smaller surface area, cannot make these contacts. Additionally, the side chain of Tyr706 in nNOS rotates by about 60° in order to make better contacts with the tail of 7, while in the eNOS structure (FIG. 8) Tyr477 remains in its original side chain orientation. Overall, these differences are fairly subtle but still contribute to the slightly tighter binding of 7 to nNOS over eNOS. Small changes in these hydrophobic contacts could also explain why 7 is more selective than 9.

Figure 5A:
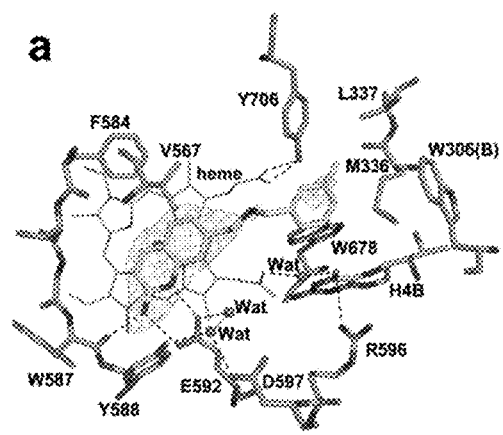
FIGS. 5A-B. (A) Active site structure of 6 bound to nNOS. The omit Fo-Fc density map for the inhibitor is shown at 2.5 σ contour level. The fluorophenethyl tail is partially disordered with weaker density. (B) Overlay of 5 (yellow) and 6 (cyan) showing the different tilt angles of the aminoquinoline ring relative to the heme plane in cases where a hydrogen-bond (dashed line) from the heme propionate to the linker amine is present (compound 5) or absent (compound 6).
Figure 5B:
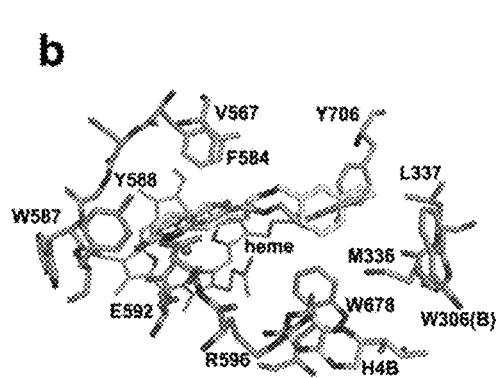

While 7-substituted aminoquinolines (5-9, 14-16) are all highly potent against nNOS, the analogous 6-substituted aminoquinolines 10-13 have low potency, regardless of chain length or nitrogen position. This disparity is also explained by the crystal structures of the bound 2-aminoquinolines. In the heme-binding pocket, the aminoquinoline system does not stack parallel to the heme, but rather tilts down slightly toward the "back wall" of this pocket (FIGS. 5A and 5B). In cases where a H-bond is formed between the secondary amine and heme propionates, the angle between the planes of the aminoquinoline and heme can be as large as 45°, held in this conformation by the H-bond. Even when no hydrogen bond is present, the aminoquinoline still tilts to avoid unfavorable contact with Val567 and Phe584, bulky residues that project downward from the roof of this pocket. A large or flexible substituent located at position 6, in any case, would clash directly with these bulky residues or the heme propionates, or force the rigid aminoquinoline system into a position where it can no longer be accommodated in the heme-binding pocket. This also explains why 4, a flexible ligand, has very potent nNOS inhibitory activity, despite sharing a similar overall structure with the rigid 6-substituted aminoquinoline 12. It also was reported in the literature that rigid fused 2-aminodihydroquinoline-based nNOS inhibitors show a similar SAR regarding substituent placement; large amine-containing tails can be easily placed in the region analogous to the 7-position, whereas the area occupied by the "6-position" can only fit small substituents, such as fluorine.

Figure 4A:
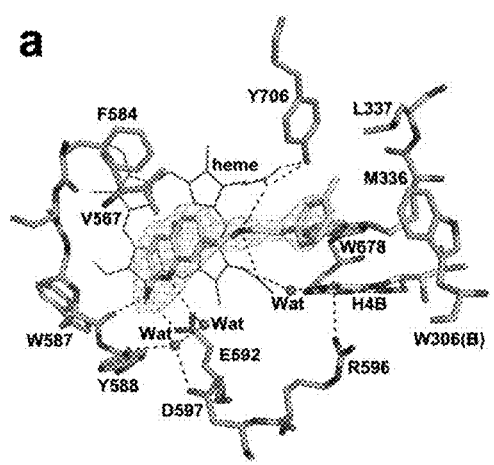
FIGS. 4A-B. Active site structures of lead 5 (FIG. 1) bound to rat nNOS (A) and bovine eNOS (B). The omit Fo-Fc density map for the inhibitor is shown at 2.5 σ contour level. Major hydrogen bonds are shown as dashed lines.
Figure 4B:
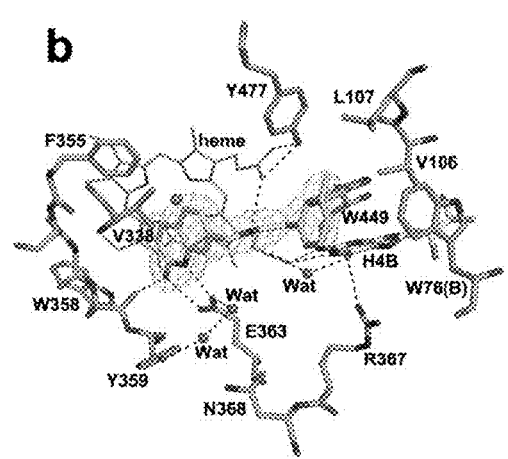

Interestingly, the replacement of the fluorine in the 3-fluorophenyl group of 7 with a bulkier chlorine (compound 15) does not significantly decrease nNOS inhibitory potency of 15 and is only modestly detrimental to isoform selectivity, which remains 431-fold and 110-fold for iNOS and eNOS, respectively. As shown in FIG. 5b, 15 binds to nNOS in a manner very similar to 7 (FIG. 4a). Without a strong interaction between the amine and the heme propionates, the chlorophenethyl tail is partially disordered, but can still be located based on the partial density contoured at 0.5 σ. In this model, the chlorine atom is not pointing directly into the hydrophobic pocket, so the switch between chlorine and fluorine should not significantly alter contacts with the enzyme. Placement of the fluorine (or chlorine) at the 4-position, however, is a disfavored modification (compare 7 to 14 or 15 to 16). This drop in potency could arise from unfavorable steric clashes between the 4-position substituent (which would face directly toward the back of the hydrophobic pocket) and any hydrophobic pocket residue, especially Met336 and Leu337.

Encouraged by the high potency and selectivity of 7 and 15, these compounds (and lead 5) were assayed against purified human nNOS (Table 2). The human isoform has an active site that is nearly identical to that in the rat enzyme, with the exception of the hydrophobic pocket, where Leu337 is replaced by a histidine (His341). This pocket is smaller and more polar, and may prefer to bind inhibitors with less bulky and more hydrophilic tails. Previously, aminopyridine-based inhibitors showed lower potency against the human enzyme when compared to the rat enzyme, and the same trend is observed for the aminoquinolines, although 5, 7, and 15 still display good nNOS inhibition. Because of the very similar selectivities ($K_i$-human/$K_i$-rat) among these three compounds, it can be concluded that the modifications that are well tolerated by the rat isoform (chain elongation and replacement of fluorine with chlorine) are likewise tolerated similarly by human nNOS, including the introduction of the bulkier chlorine.

TABLE 2

Inhibition of rat and human nNOS by compounds 5, 7, and 15.

| | $K_i$ (μM) | | |
|---|---|---|---|
| Compound | Rat nNOS | Human nNOS | Selectivity (Rat/Human) |
| 5 | 0.074 | 0.493 | 6.7 |
| 7 | 0.049 | 0.318 | 6.5 |
| 15 | 0.066 | 0.440 | 6.7 |

[a]See Table 1 and experimental section for details of assay. $K_i$ values, calculated directly from $IC_{50}$ values, are the average of at least two replicates; selectivity values are ratios of respective $K_i$ values.

Finally, compounds 7 and 15 were assayed in a Caco-2 monolayer permeability assay (Table 3). This assay is an approximation of both a compound's ability to penetrate the epithelium of the GI tract as well as the blood-brain barrier; ideally an orally bioavailable nNOS inhibitor should show high permeability in this assay. An efflux ratio (ratio of membrane permeability (A→B) to efflux (B→A))<3 is considered favorable. Pleasingly, both 7 and 15 display good membrane permeability in the apical to basolateral direction and high compound recovery values. Compound 15 even shows improved membrane permeation relative to compound 4, and both 7 and 15 display relatively low efflux ratios, diminishing the possibility that P-gp or other active transport mechanisms are significantly acting on these compounds (especially on 15). Interestingly, compound 15 is more membrane-permeable than 7 despite their nearly identical structures; this could be the result of the higher c Log P of 15 (3.8) relative to 7 (3.2) or to variability in the assay.

TABLE 3

Caco-2 permeability summary for select compounds.

| | Apparent Permeability $(P_{app}, 10^{-6}\ cm\ s^{-1})^b$ | | | Recovery | |
|---|---|---|---|---|---|
| Compound | Mean A-->B | Mean B-->A | Efflux ratio | A-->B | B-->A |
| 4 | 27.3 | 34.2 | 1.3 | 113% | 78% |
| 7 | 16.9 | 41.9 | 2.5 | 63% | 103% |
| 15 | 30.3 | 24.5 | 0.8 | 98% | 67% |
| Warfarin[c] | 46.8 | 15.7 | 0.3 | — | — |
| Ranitidine[d] | 0.5 | 3.8 | 7.2 | — | — |
| Talinolol[e] | 0.1 | 10.2 | 77.7 | — | — |

[a]All assays were performed over 2 h at a concentration of 10 μM. See experimental section for details.
[b]Apparent permeability value.
[c]High permeability control;
[d]low permeability control;
[e]high efflux control.

Figure 9:
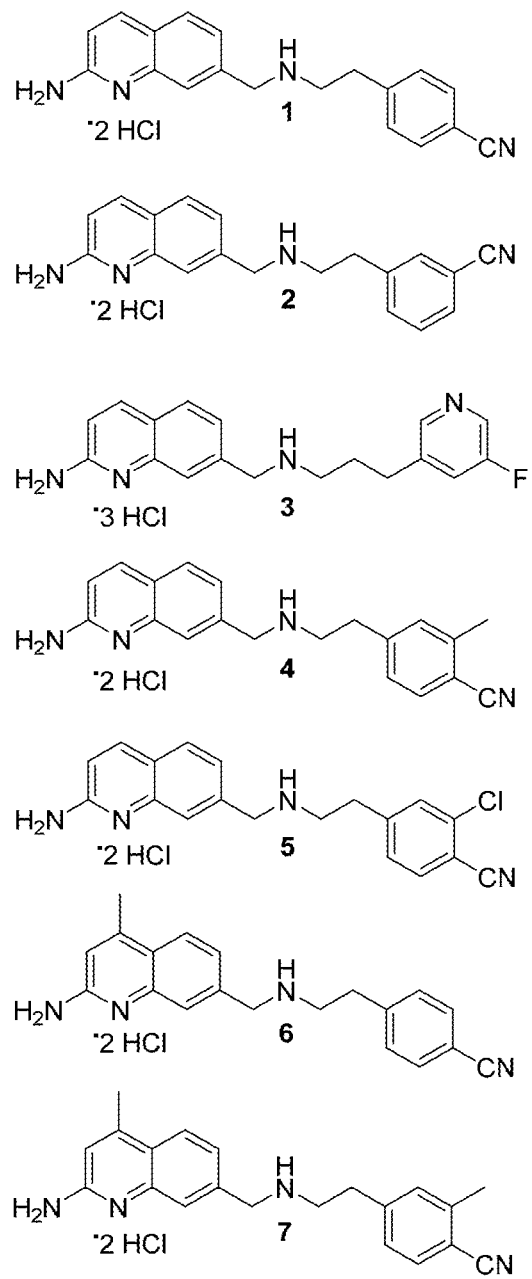
FIG. 9. Chemical structures of representative compounds of this invention, in accordance with various non-limiting embodiments thereof.

In accordance with this invention, additional non-limiting 2-aminoquinoline compounds are shown in FIG. 9, prepared as described, below in Examples 31-50 and Schemes 15-19 and characterized in Tables 4-6, with assays conducted as described in Example 51. (Independent numerical references for the respective aminoquinoline compounds, corresponding starting materials and intermediates are employed.)

Various other 2-aminoquinoline compounds can be prepared as would be understood by those skilled in the art and made aware of this invention, such compounds as are available through the synthetic procedures of the sort described herein or straight-forward modifications thereof, as would also be understood by those skilled in the art, such procedures and modifications thereof limited only by commercial or synthetic availability of corresponding starting materials and reagents.

Figure 10:
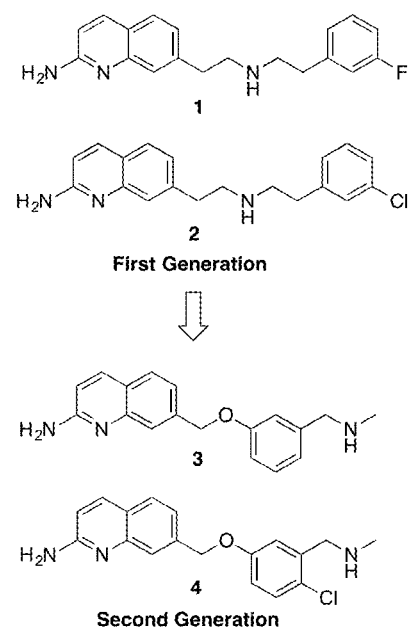
FIG. 10. Use of 2-aminoquinolines as nNOS inhibitors.
Figure 11:
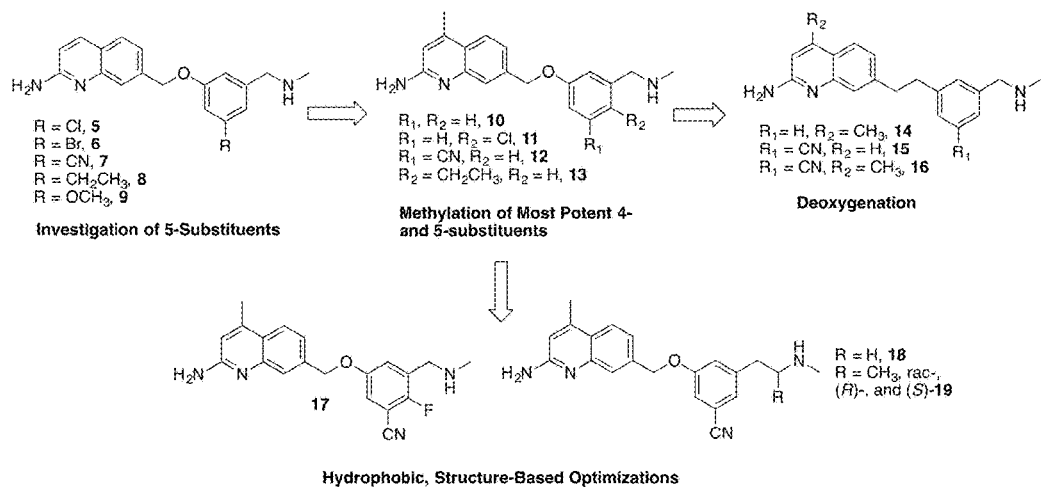
FIG. 11. Design strategy utilized and compounds synthesized in accordance with various non-limiting embodiments of this invention.
Figure 12:
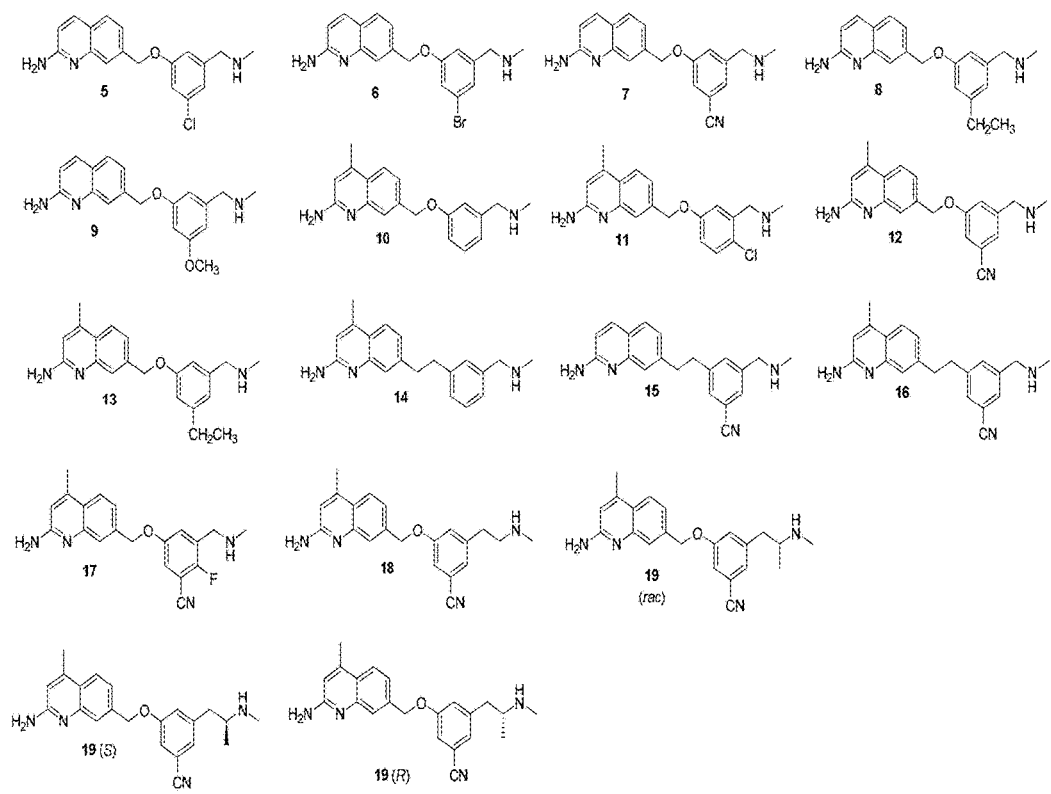
FIG. 12. Representative compounds of this invention, in accordance with non-limiting embodiments thereof.

Further, in accordance with various other embodiments of this invention, additional non-limiting 2-aminoquinoline compounds are discussed with reference to FIGS. 10-11, shown in FIG. 12, prepared as described, below, in Examples 55-126 and Schemes 20-27 and characterized in Tables 7-8, with assays, crystal preparation and x-ray defraction data collected as described in Examples 127-130. (Independent numerical references for the respective aminoquinoline compounds, corresponding starting materials and intermediates are employed.)

As discussed above, a first generation of inhibitors, such as 1 and 2 (FIG. 10) are potent and selective, and possess excellent cellular and in vivo pharmacokinetics. A second-generation, rearranged phenyl ether 4, optimized from compound 3, preserves the potency and selectivity of 1 and 2 and drastically decreases the off-target binding. It had significantly decreased Caco-2 permeability, but was still selective for rat nNOS over human nNOS, and still had low heNOS/hnNOS selectivity.

Accordingly, investigation continued on a potent, cleaner-binding phenyl ether scaffold, in attempt to improve n/e selectivity, human nNOS inhibitory potency, and cellular permeability. First, the 5-position of the phenyl ring (FIG. 11) was substituted with a variety of groups, leading to analogues 5-9. It was anticipated that such substituents on the phenyl ether scaffold could reach nNOS-specific regions that could improve hnNOS potency, such as the hnNOS-specific residue His342.

Second, it was previously reported that for 2-aminopyridines, installation of a methyl group at the 4-position of the pyridine could drastically improve potency, and in some cases, selectivity. A fragment screen then showed that 2-amino-4-methylquinoline (2-aminolepidine) bound nearly 7-fold tighter ($K_i$=94 nM) to rat nNOS than the unmethylated 2-aminoquinoline (630 nM). X-ray crystallography indicated that 2-aminolepidine acted exclusively as a competitive L-arginine antagonist. To this end, several lepidine derivatives were prepared—the methylated analogues of compounds 8 and 9 (11 and 13) and of the original phenyl ether leads 3 and 4 (10 and 12, respectively).

Removal of the oxygen from the ether linkage entirely was also investigated, as the phenyl ether could serve as a potential site of metabolism, and removal of the oxygen would lower the total polar surface area (tPSA). Therefore, analogues 14 and 16, and desmethyl analogue 15 (deoxygenated analogues of active compounds 8, 10, and 11) were synthesized.

Finally, several more specific efforts to optimize the most potent and selective scaffold (the 5-cyanophenyl ether, as in 8 and 11) were made, all centered on improving n/e selectivity and overall hydrophobicity. The short methylamine tail of 11 was replaced with the ethylamine of 18 and the chiral alpha-methyl ethylamine of 19, to point an extra alkyl region in the area of the nNOS-specific hydrophobic residue, Met336/Met341 (rnNOS/hnNOS). Van der Waals contact between inhibitors and this residue has been implicated in improved n/e selectivity, as this residue is replaced by a smaller valine in eNOS isoforms. Similarly, compound 17 makes an effort to combine an effective 4-substitution pattern (as in 4) with the 5-cyano group. The 4-fluoro was incorporated to both face toward the nNOS-specific methionine (As the chlorine of 4 does) and to possibly decrease the electron density of the aryl ring and favor its interaction with a nearby tyrosine, Tyr706/Tyr711 (rnNOS/hnNOS).

All compounds were assayed against rnNOS, and select compounds were also assayed against hnNOS. To shift structure-activity relationship (SAR) efforts toward increasingly "humanized" systems, human eNOS (heNOS) was employed instead of previously used bovine eNOS. Murine iNOS (miNOS) was used, and n/i selectivity is reported as the ratio of miNOS/rnNOS. Finally, potent and selective compounds were assayed in a Caco-2 assay to approximate their cellular permeability.

To prepare the initial set of 5-substituted quinoline analogues 5-9, a series of 3,5-disubstituted phenols was first synthesized (Scheme 20). Commercially available aldehydes 20-22 were reductively aminated and Boc-protected to afford the phenols 23-25, respectively. Brominated compound 24 was converted, via palladium-catalyzed cyanation, into cyanophenol 26 Sonogashira coupling between 24 and TMS-acetylene yielded 27, which was desilylated (to give 28) and reduced to give ethylphenol 29. With reference to Scheme 21, the requisite phenols were then treated with quinolinemethyl bromide 30 (prepared as described in Example 4) under basic conditions to afford the phenyl ether cores 31-35. Compounds 31-35 were first deacetylated using $K_2CO_3$ in hot methanol, and the Boc groups were then cleaved using HCl (31, 32, and 34) or TFA (33 and 35), to yield the pure final compounds 5-9 as water-soluble hydrochloride or trifluoroacetate salts.

Because of the reactivity and acidity of 4-methylquinolines, the analogous bromide 43 could not be prepared by a previous synthetic route (which utilized both free-radical bromination of a 7-methylquinoline and basic conditions that are incompatible with the 4-methyl group.) A new synthetic route was devised, as described elsewhere herein, providing a readily derivatizable handle at position 7 then functionalizing the 2-position. To this end, the 7-bromolepidine 37 was prepared by the Doebner-Miller condensation of 7-bromoaniline (36) with methyl vinyl ketone (Scheme 22). Treatment with m-CPBA afforded N-oxide 38, which readily underwent deoxygenative amination upon treatment with $Ts_2O$ and $t-BuNH_2$. Heating with TFA removed the t-butyl group to yield the free aminoquinoline 39 in good yield (even on multigram scale) following neutralization and column chromatography. The obtained aminoquinoline was then protected as the acetamidoquinoline (40) as previously described. To further functionalize 40, the bromide was converted into the aldehyde 41 using Ueda et al.'s palladium-catalyzed hydrocarbonylation, which employs N-formylsaccharin as the CO donor and $Et_3SiH$ as the reductant. Reduction of the aldehyde afforded 42, which could be brominated (Appel conditions or chlorinated ($SOCl_2$) to yield the bromide (43) or chloride (42), respectively. Bromide 43 was treated with phenols 26 and 29, as well as 45 and 46 (prepared according to Scheme 12), to yield the assembled cores 47-50, which were deprotected as described above to yield the 4-methylated analogues 10-13.

To prepare the deoxygenated analogues 14-16, bromide 40 was employed (to prepare 4-methyl analogues), and compound 51, via aminoquinoline 52, was converted into the desmethyl 7-bromoquinoline 53 (Scheme 23A). (See, Inglis, S.; Jones, R.; Fritz, D.; Stojkoski, C.; Booker, G.; and Pyke, S. Synthesis of 5-, 6- and 7-substituted-2-aminoquinolines as SH3 domain ligands. *Org. Biomol. Chem.* 2005, 3, 2543-2557.) Next, suitable Sonogashira coupling partners were prepared. To prepare 14, 3-iodobenzyl bromide (54, Scheme 23B) was converted into carbamate 55, and coupling with TMS-acetylene afforded 56 in excellent yield, which was then desilylated to yield 57. Synthesis of cyanated analogues 15 and 16 began with bromination of commercially available cyanotoluene 58 (Scheme 23C); bromide 59 was subsequently aminated and protected to yield 60. As described above, Sonogashira coupling and desilylation of 61 yielded 62. Phenylacetylene 62 is sensitive and polymerizes at room temperature, so it must be kept cold until use.

With the quinolines and phenylacetylenes in hand, copper-free Sonogashira conditions were used to join the halves (Scheme 24). The quinolinyl-acetylenes 63-65 were readily identifiable by TLC because of their bright blue fluorescence. After purification, the triple bonds were hydrogenated to the alkanes 66-68. For 63, this was readily accomplished with palladium on carbon (to yield 66), but these conditions also reduced the nitriles of 64 and 65. For these compounds, a Pd/C-ethylenediamine complex was used to reduce the alkyne, which showed excellent chemoselectivity, yielding 67 and 68 despite of requiring extended reaction times or higher pressures. Finally, 66-68 were deprotected to afford the final analogues 14-16.

Preparing the phenols required for analogues 17-19 proved more challenging, as phenolic (or other) precursors with these particular 1,3,5-substitution patterns are not commercially available or readily synthesized. Nonetheless, the meta-borylation/oxidation strategy has been employed to prepare similar 3,5-disubstituted phenols. In this case, to prepare a borylation substrate, commercially available toluene 69 (Scheme 25) was brominated (to give 70) and converted into the protected amine 71. Cyanation afforded 72. To prepare the phenol, iridium-catalyzed borylation with $Pin_2B_2$ afforded an intermediate boronic ester (not isolated), which was then treated with Oxone in aqueous acetone to yield the phenol 73 in moderate yield. The phenoxide of 73 was then treated with chloride 44. Due to 44's lower reactivity, the etherification reaction was performed at 50° C. (instead of 0° C. as for 43), and deprotection of 74 afforded analogue 17.

Similarly, phenethylamine analogues 18 and 19 (racemic) were also prepared via meta-borylation (Scheme 26). The substrates (unsubstituted 79 and alpha-methylated (RS)-80) were prepared by Boc-protection and methylation of 75 (to yield 77) or reductive amination and Boc-protection of 76 (to yield (RS)-78). Cyanation (as described above) afforded the benzonitriles 79 and (RS)-80, and the borylation-oxidation strategy produced, respectively, 81 and (RS)-82. These phenols were treated with 44, and deprotection of 83 and (RS)-84 afforded the final compounds 18 and (RS)-19, respectively.

As derivatives of 78 proved difficult to resolve into their enantiomers, an asymmetric synthesis of the two enantiomers of 19 (Scheme 27) was developed. Commercially available (R)- or (S)-t-butylsulfinamides (R and S-85) were condensed with 76. Low-temperature reduction of the imine with $NaBH_4$ afforded the expected (R,R)-diastereomer (R,R)-86, when (R)-85 was used) and (S,S)-diastereomer (S,S-86, when S-85 was used) in satisfactory (>7:1) diasteromeric ratios. Cleavage of the sulfinamide auxiliaries and Boc-protection of the free amines yielded (R)- and (S)-87, which were both methylated to yield (R)- and (S)-78. The remainder of the synthesis proceeded as with the racemic material: cyanation afforded (R)- and (S)-80, which were borylated and treated with oxone to yield the phenols (R)- and (S)-82. Enantiomeric purity of these phenols (as assessed by chiral HPLC) was very high (>99%). Subsequent phenyl ether formation and deprotection of (R)- and (S)-84 afforded (R)- and (S)-19.

Compounds 5-19 were assayed against purified rat nNOS (rnNOS) and murine iNOS (miNOS), and also against human nNOS (hnNOS) and human eNOS (heNOS). With recent advances, it is now possible to obtain and crystallize both human nNOS and human eNOS. (See, e.g., the preceding discussion, the following examples and Li, H.; Jamal, J.; Plaza, C.; Pineda, S. H.; Chreifi, G.; Jing, Q.; Cinelli, M. A.; Silverman, R. B.; Poulos, T. L. Crystal structures of human constitutive nitric oxide synthases. *Acta Crystallogr., Sect. D: Biol. Crystallogr.* 2014, D70, 2667-2674.) These enzymes were used as part of a shift to obtain more "humanized" SAR data. Rat nNOS and murine iNOS were also used, as historically, they are the easiest to express, purify, and utilize in X-ray crystallographic experiments, and for clinical purposes, it is desirable to prove efficacy and selectivity in lower animals. These data are summarized in Table 7, where iNOS (n/i) selectivity is reported as the ratio of the $K_i$ values obtained for miNOS/rnNOS, whereas eNOS (n/e) selectivity is for heNOS/hnNOS. Values for compounds 1-4 are included for comparison.

Compared to the unsubstituted compound 3, the 5-substituted phenyl ethers 5-9 all have considerably greater potency against rnNOS. The standout among this series is the 5-cyano compound 8, which is approximately four times more potent than 3 and 1.6 times more potent than previous phenyl ether lead 4. The X-ray crystal structure of 8 bound to rnNOS was examined to determine what causes this dramatic effect. As observed for similar phenyl-ether linked aminoquinoline-containing compounds the 2-aminoquinoline moiety of 8 acts as a competitive arginine mimic, strongly coordinating the catalytic glutamate residue (Glu592). As also previously observed, the phenyl ring extends beyond the heme-binding pocket, where the methylamine tail H-bonds the water bridging a heme propionate and the cofactor $H_4B$. In most nNOS-phenyl ether-linked structures (such as with 3), the phenyl ring region is flexible, as evidenced by choppy electron density in many crystal structures. The electron density of 8, by contrast, is intact throughout the inhibitor, indicating greatly reduced flexibility. This stabilization comes from the cyano group of 8, which fits into a narrow cleft formed by Tyr706, Met570, and the alkyl side chain of Gln707. The amide of Gln707 and backbone carbonyl of Asn569 also facing toward its interior, while the side-chain of Asn569 forms a "roof". While other nNOS inhibitors contain a 1,3,5-trisubstituted cyanophenyl motif, those portions of those inhibitors occupy entirely different spaces within the enzyme; this "auxiliary pocket" has never been previously reported to interact with any nNOS inhibitor. It is possible that the increased stabilization caused by the nitrile (and by proxy, improved potency) is a result of several factors. First, without limitation to any one theory or mode of operation, the effect may also be partially electrostatic in nature: a result of the nitrile fitting into this pocket is that the electron-poor benzonitrile ring is now anchored in very close proximity to the electron-rich Tyr706, enhancing pi-stacking interactions with this residue.

This "nitrile effect" also extends to human nNOS. In the hnNOS-8 structure, the Leu337 residue of rat nNOS is replaced by His342, but the small pocket is still present (bounded by Met575, Tyr711, and Gln712), which similarly accommodates the nitrile of 8—the binding modes of 8 between the two isozymes are virtually identical, and as expected, 8 is equipotent against rat and human nNOS. This represents a remarkable improvement in hnNOS potency over leads 1-4, all compounds that are highly selective (5-7-fold) for rnNOS over hnNOS. Interestingly, in the hnNOS-8 structure, a water molecule is visible inside the auxiliary pocket, forming a bridging H-bond between the nitrile and both the carbonyl of Asn574 and amide of Gln712 (Asn569 and Gln707 in rnNOS). It is likely this water molecule is structural, as it has been observed even in nNOS crystal structures with L-arginine and similar molecules. It should be present in the rnNOS-8 structure, but is not observed in the refinement due to experimental error. This indicates that the effects of the nitrile may be multifaceted—electrostatic enhancer and H-bond acceptor.

In addition to the improvements in potency, the nitrile-auxiliary pocket interaction may also enhance n/e selectivity. Compound 8 is over 300-fold selective for hnNOS over heNOS—high selectivity in a human-based system. The chief differences between hnNOS and heNOS are that the Asp602, His342, and Met341 residues of the former isoform are replaced with Asn366, Phe105, and Val104 in the latter. As previously discussed, the Asp/Asn difference does not appear to play any role in n/e selectivity for these phenyl ether-linked compounds, whereas the Met/Val difference can cause dramatic changes in $K_i$ value. In the heNOS-8 structure, the smaller Val104 residue causes the methylamine tail to assume an alternate rotamer where it is accommodated in next to Phe105, breaking the H-bond present between the amine and $H_4B$-site water in hnNOS. Although the small auxiliary pocket (which the nitrile fits into) is conserved between hnNOS and heNOS, the stabilization that the nitrile offers appears to be less pronounced in eNOS, as evidenced by the incomplete electron density. Additionally, Tyr475 in heNOS may be more rigid than the analogous Tyr711 in hnNOS (this tyrosine in eNOS isoforms tends to be less mobile than in nNOS isoforms), and its interaction with the benzonitrile ring may be weaker.

While the nitrile confers the highest potency, there is a general trend of 5-substituted compounds having greater activity than 3; the 5-ethylated analogue 9 shows the second-highest potency after 8. Although the density near the ethyl group is choppy, the rnNOS-9 structure suggests that the 5-ethyl group does not bind in the small auxiliary pocket, likely due to its large bulk. Instead, the phenyl ring swings over toward the $H_4B$ site, and the ethyl group reaches the nNOS-specific hydrophobic pocket, where it likely makes favorable Van der Waals contact with Met336, Tyr706, and Leu337, although the phenyl-Tyr706pi-stack is broken. It is likely that the bulky 5-substituents of 5, 6, and 7 (which have considerably lower potency than 8) also fit into this region of the enzyme, which would reflect the requirement for a small and linear substituent for auxiliary pocket access.

Compared to 8, 9 is a less effective human nNOS inhibitor. In the hnNOS-9 structure, there is a possible clash between the hydrophobic ethyl group and the side chain of His342. Indeed, an alternate rotamer of His342 can be modeled in this structure, where the bulky, polar imidazole ring faces away from the ethyl group. Interestingly, Compound 9 (and to a lesser degree, the structurally similar compound 7) are extremely selective for rnNOS over miNOS. Murine iNOS has a polar asparagine residue (Asn115, instead of Leu337 in rat nNOS) next to the conserved substrate access channel tyrosine, and it is likely that large, hydrophobic groups (such as methoxyl or ethyl) would disfavor binding near Asn115.

With respect to compounds 10-13, a methyl group was installed at position 4 of the 2-aminoquinoline. Previous work with 2-aminopyridines indicated that 4-methylation improved nNOS inhibitory potency (and in some cases, n/e selectivity). Computer modeling with these pyridines predicted that the 4-methyl would be accommodated in a sterically small, hydrophobic region (termed the "S pocket") located along the "back wall" of the heme-binding site. X-ray structures later confirmed the interaction of the 4-methyl with the hydrophobic residues of the S-pocket, explaining the increases in potency.

Originally, it was believed that the 2-aminoquinoline group may have been too bulky for this positive modification to be successfully translated to this scaffold, but this hypothesis appears disproven, both from fragment screening results (vide supra) and the from observation that the 4-methyl group in these phenyl ether analogues has positive effects on potency for both rat nNOS and human nNOS (cf. 3 and 10 and 4 and 12) when compared to their unmethylated congeners. As expected, the rnNOS-10 and hnNOS-10 crystal structures show that, as for the aminopyridines, the methyl group fits into the S-pocket, bounded by Phe584, Val567, and the backbone of Ser585 (rnNOS). The bulk of the aminoquinoline is still reflected in the binding mode: 4-methylation forces the 2-aminoquinoline into a more parallel orientation above the heme, instead of the tilted conformation assumed by unmethylated compounds to avoid steric clashes with Phe584 and Val567.

The enhancing effects that the 4-methyl group has on these 5-unsubstituted compounds (>2-fold for both isozymes) are greater than the effects observed for methylating the 5-substituted compounds (the effect for 11 and 13, while still present, is much less pronounced when compared to 10 and 12), which indicates that the combination of the 4-methyl and 5-substituent is not additive, and, in fact, may even be slightly antagonistic, although the crystal structures do not indicate a site of obvious antagonism. Nonetheless, compound 11, with its combination of S-pocket and nitrile-auxiliary pocket interactions, is a very potent dual rnNOS/hnNOS inhibitor. As with 8 and 10, the combination of these two interactions is identical in the rnNOS-11 and hnNOS-11 crystal structures, with clear electron density throughout, and the bridging structural water molecule is present in the structures with both rat and human nNOS.

The effects of methylation on eNOS selectivity are more complicated. It was previously reported that 4-methylation of 2-aminopyridine inhibitors can considerably improve n/e selectivity, but this is not consistently observed with 2-aminoquinolines. Compounds 10 and 12 have higher selectivity, due to the greatly improved hnNOS activities relative to 3 and 4 (respectively), but for the substituted compounds 11 and 13, the n/e selectivity decreases upon methylation. In all cases, the heNOS $K_i$ for the methylated analogue is lower than the desmethyl. This probably reflects a nonspecific increase in inhibitor binding (the S-pocket is conserved among all isoforms, although that region of the enzyme is smaller/tighter in iNOS enzymes), and the universal decrease in iNOS selectivity seems to indicate the nonspecific binding may also occur to some degree in miNOS. Additionally, the enzymes reported for the aminopyridines (rnNOS and bovine eNOS) could bind methylated compounds somewhat differently than hnNOS and heNOS do as well.

To examine the binding mode (and the requirements for the nitrile to reach the auxiliary pocket) further, deoxygenated derivatives 14-16 were prepared. These compounds are also desirable due to their high c Log P and lack of the polar oxygen, which increases tPSA and could also serve as a potential site of metabolism in vivo. Interestingly, compound 14 behaves similarly to compound 10—the $K_i$ values for rnNOS, miNOS, or heNOS for 14 are very close to those for 10, suggesting that the oxygen is not a crucial requirement for selectivity for this compound. Contrarily, the hnNOS activity has decreased somewhat. The rnNOS-14 structure indicates that removal of the oxygen changes the binding mode. While the 4-methylaminoquinoline is fixed in the same position as it is in 10, the larger ethylene linker of 14 (compared to the oxygen) prefers an "upward" position away from Met570 and Val567 (whereas the phenyl ether linker abuts these two residues), and the phenyl ring swings over toward the $H_4B$ site, where the methylamine tail displaces the $H_4B$-site water, instead of H-bonding it. As the rnNOS $K_i$ value is close to 10's, this is obviously a favorable conformation.

Like in the phenyl ether scaffold, methylation of the quinoline in the alkyl scaffold (15 to 16) also improves potency. However, the rnNOS-16 structure indicates 16 is less stable when bound than 11. The nitrile is not bound in the auxiliary pocket, and the electron density indicates higher flexibility. This reflects that the geometric and steric requirements to place a substituent into the auxiliary pocket are quite strict: the methylene bridge again assumes the "upward" position observed in the nNOS-14 structure to avoid steric clashes with Val567.

Despite the hypothesis that fluorine could improve potency, compound 17 has diminished hnNOS activity, and the selectivity values are lower. As discussed above, fluorine directly facing the nNOS-specific hydrophobic pocket was deleterious to n/i selectivity. This decrease is also observed here. Compound 18 represents an interesting example where cyanation and methylation can be used to "rescue" a substitution pattern with low activity. (An uncyanated and unmethylated version of this compound, compound 8 in FIG. 3, has a rat nNOS $K_i$ value of 332 nM—the methyl and cyano substituents together increase its potency nearly eight-fold, to 42 nM.) The rnNOS-18 structure shows the longer phenethylamine group displacing the $H_4B$-site water, whereas the hnNOS-18 structure indicates more flexibility in the tail region, and the amine only weakly H-bonds the $H_4B$ site water, a likely reason for the slightly lower hnNOS potency compared to rnNOS.

Compound 19, assayed initially as its racemate (RS)-19, is also very close in rnNOS and hnNOS potency to 18. Interestingly, when rnNOS and hnNOS crystals were soaked with (RS)-19, the electron density of the resulting crystal structures was consistent with both enantiomers being bound, suggesting that the two enantiomers are similar in potency, which was confirmed by assaying the two enantiomers separately. (R)-19 is 61 nM against rnNOS and 65 nM against hnNOS, whereas (S)-19 is 50 and 46 nM, respectively.

Compounds 18 and 19 (and its isomers) were designed to place extra hydrophobic groups in the vicinity of Met336/Met341 (rnNOS/hnNOS). As these residues are not present in eNOS enzymes (replaced instead by valines), extra contact with these methionine residues should, in theory, greatly improve eNOS selectivity, as less contact is possible with valines. As predicted, the heNOS/hnNOS selectivity for these bulkier compounds considerably exceeds that of 11. The rnNOS-18 structure indicates that contact with Met336 is so favorable, that this residue adopts an alternate rotamer to contact the tail portion of 18. Despite the similar potencies, there is a dramatic difference in selectivity between (R)- and (S)-19; the n/e selectivity for (S)-19 is nearly twice that of (R)-19. This is the highest n/e selectivity ever observed for a 2-aminoquinoline-based inhibitor. These results suggest that even very simple chiral groups such as the tail of 19 can impart excellent n/e selectivity for 2-aminoquinolines.

Finally, three of the most potent dual rnNOS/hnNOS inhibitors with different structural motifs and high n/e selectivity (8, 10, and 14) were assayed for permeability in a Caco-2 assay. In this assay, the permeability of a compound through a monolayer of cells resembling the intestinal epithelium is measured. Caco-2 assays have been used to approximate the potential for both oral bioavailability and blood-brain barrier permeation, although the latter is generally less accurate. Although compounds 1 and 2 were unfavorably promiscuous binders, they were highly permeable in this assay (2, for example, had an apical to basolateral (A→B) mean $P_{app}$ of $16.9 \times 10^{-6}$ cm s$^{-1}$). Compound 4, despite its significantly cleaner off-target profile, was much less permeable (A→B mean $P_{app}$ of $2.3 \times 10^{-6}$ cm s$^{-1}$) and had higher efflux (5.5 for 4 vs. 2.5 for 2) indicating that the structural rearrangement had detrimental effects on cellular pharmacokinetics. Pleasingly, compared to 4, both 8 and 10 have considerably increased permeability, lower efflux, and higher recovery values, suggesting that 4-methylation and 5-cyanation could be favored modifications for improving bioavailability.

It was thought that modification of a "cleaner-binding" phenyl ether-linked aminoquinoline scaffold could improve human nNOS inhibition, hnNOS/heNOS selectivity, and cellular permeability of this promising class of compounds. It was discovered that 5-substitution of the phenyl ring results in greatly improved hnNOS activity and hnNOS/heNOS selectivity, especially when the substituent is cyano. X-ray crystallographic studies revealed that the 5-cyano group fits into a small, previously unreported auxiliary pocket located next to the heme-binding sites of both rnNOS and hnNOS, resulting in good potency against both isoforms. The nitrile H-bonds to a deep structural water within this pocket and anchors an electron-deficient aryl ring next to an electron-rich tyrosine, an interaction which is weaker in heNOS. Additionally, the short methylamine tails of 8 and 11 favor a water-mediated H-bond to $H_4B$ and a heme propionate in nNOS, an interaction that is missing in heNOS. These combined interactions resulted in the first 2-aminoquinolines with high selectivity for human nNOS over human eNOS. Additionally, it was found that methylation of the 4-position of the aminoquinoline could greatly improve rnNOS and hnNOS potency further, although it decreased hnNOS/heNOS selectivity in some cases. In spite of the decrease, further modification of the cyanoaryl-containing tail (elongation to 18, or introduction of a stereocenter, such as 19) could also be used to disfavor binding to heNOS, and one compound, (S)-19, had nearly 500-fold selectivity for both eNOS and iNOS. Both cyanation and 4-methylation show ability to considerably improve the Caco-2 permeability of the phenyl ether scaffold. These results, taken together, highlight the promise of this new auxiliary pocket in nNOS as a novel "hot spot" for further structure-based design of nNOS inhibitors.

The present invention can also, as would be understood by those skilled in the art, be extended to or include methods using or in conjunction with a pharmaceutical composition comprising an inhibitor compound of the sort described herein in a physiologically or otherwise suitable formulation. In some embodiments, the present invention includes one or more such inhibitors, as outlined above or discussed more fully below, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or non-aqueous solutions, dispersions, suspensions or emulsions. The resulting compositions can be, in conjunction with the various methods described herein, for administration or contact with a human/animal enzyme expressed or otherwise present therein. Whether or not in conjunction with a pharmaceutical composition, "contacting" means that a nitric oxide synthase and one or more inhibitor compounds are brought together for purpose of binding and/or complexing such an inhibitor compound to the enzyme. Amounts of a compound effective to affect or otherwise inhibit a nitric oxide synthase may be determined empirically, and making such determinations is within the skill in the art. Inhibition, affecting or otherwise modulating nitric oxide synthase activity includes both reduction and/or mitigation, as well as elimination of NOS activity and/or nitric oxide production.

It is understood by those skilled in the art that dosage amount will vary with the activity of a particular inhibitor compound, disease state, route of administration, duration of treatment and like factors well-known in the medical and pharmaceutical arts. In general, a suitable dose will be an amount which is the lowest dose effective to produce a therapeutic or prophylactic effect. If desired, an effective dose of such a compound, pharmaceutically acceptable salt thereof or related composition may be administered in two or more sub-doses, administered separately over an appropriate period of time.

Methods of preparing pharmaceutical formulations or compositions include the step of bringing an inhibitor compound into association with a carrier and, optionally, one or more additional adjuvants or ingredients. For example, standard pharmaceutical formulation techniques can be employed, such as those described in Remington's Pharmaceutical Sciences, Mac Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more inhibitor compounds for the manufacture of a medicament for therapeutic use in the treatment or prevention of disease states indicated by high nitric oxide production and/or associated neuronal damage and degeneration.

As discussed above, the present invention provides a series of simplified 2-aminoquinoline compounds based on the rationale that they might bind to and inhibit nNOS in a manner similar to aminopyridines, while being less polar, less basic, more lipophilic, and, therefore, more bioavailable. Compounds were assayed with purified NOS enzymes, and it was revealed that, in particular, 7-substituted 2-aminoquinolines are highly potent inhibitors of nNOS, and that subtle modifications can enhance potency and greatly improve isoform selectivity over both iNOS and eNOS. These results indicate that these compounds have high potential for oral bioavailability and brain penetration, and that the 7-substituted 2-aminoquinoline cores offer very promising leads for further nNOS inhibitor development.

EXAMPLES OF THE INVENTION

The following non-limiting examples and data illustrate various aspects and features relating to the compounds and/or methods of the present invention, including the preparation of various nitric oxide synthase inhibitor compounds, as are available through the synthetic methodologies described herein. In comparison with the prior art, the present compounds and/or methods provide results and data which are surprising, unexpected and contrary thereto. While the utility of this invention is illustrated through the use of several compounds and moieties/groups which can be used therewith, it will be understood by those skilled in the art that comparable results are obtainable with various other compounds, moieties and/or groups, as are commensurate with the scope of this invention.

General Procedures.

Anhydrous solvents (THF, $CH_2Cl_2$, and DMF) were distilled prior to use. The remaining solvents, reactants, and reagents were purchased from commercial vendors and were used without further purification, with the exception of acetamide, which was heated to 80° C. and dried under vacuum before use. Melting points were determined in capillary tubes using a Buchi Melting Point B-540 apparatus, and are uncorrected. $^1H$ NMR spectra were recorded at 500 MHz, using a Bruker Avance III 500 (direct cryoprobe), and $^{13}$C NMR spectra were obtained at 126 MHz using the same instrument. Low-resolution ESIMS was performed using a Thermo Finnigan LCQ system. High-resolution mass spectral data were obtained at the Integrated Molecular Structure Education and Research Facility (Northwestern University) on an Agilent 6210A TOF mass spectrometer in positive ion mode using electrospray ionization, with an Agilent G1312A HPLC pump and an Agilent G1367B autoinjector. Data were processed using MassHunter software version B.02.00. Flash column chromatography was performed using an Agilent 971-FP automated flash purification system, using a Varian column station with SiliCycle cartridges (8-80 g), or manually in glass columns using SiliCycle SiliaFlash P60 40-63 µM silica gel. Analytical HPLC was performed either using a Beckman System Gold 125 solvent module and 166 Detector, or an Agilent Infinity 1260 system and an injection volume of 10 µL. A Phenomenex Gemini C18 5µ 110 Å reverse-phase column, Gemini NX 5µ 100 Å column (both with dimensions of 250 mm×4.6 mm), or Phenomenex Synergi 5µ polar RP column (4.6×50 mm) was used for all HPLC experiments. The purity of all target compounds was found to be ≥95% by HPLC, using either isocratic elution at 70% MeOH in $H_2O$ (with 0.1% TFA), or a gradient of 65-95% MeOH in $H_2O$ (with 0.1% TFA), at 0.8 mL/min. When the polar RP column was used, elution was isocratic at either 50% acetonitrile in $H_2O$ or 35% acetonitrile in $H_2O$, at 1.5 mL/min. Preparative HPLC was performed at the Northwestern University Center for Molecular Innovation and Drug Discovery ChemCore lab, using an Agilent 1200 Series HPLC and Agilent 6120 Quadrupole Mass Spectrometer (API-MS mode) and a Phenomenex Gemini-NX 5 µm C18 column (150×21.2 mm). Analytical thin-layer chromatography was performed on Silicycle extra hard 250 µM TLC plates. Compounds were visualized with short-wavelength UV light, ninhydrin, and $KMnO_4$ stain, where relevant. Compounds 17, 35, 36, and 42 were prepared by literature procedures, and their spectral data are consistent with those data reported for the same.

Example 1

7-Methylquinolin-2(1H)-one (18a) and 5-Methylquinolin-2(1H)-one (18b)

Compound 17 (4.26 g, 18.0 mmol) was diluted in chlorobenzene (45 mL) and anhydrous $AlCl_3$ (12.0 g, 5.00 mmol) was added. The mixture was heated to 90° C. for 2 h, upon which the solution became black. The solution was cooled and poured into ice-$H_2O$ (300 mL), which was extracted with EtOAc (2×300 mL). The organic phase was washed with $H_2O$ (200 mL), and the aqueous layer was extracted with EtOAc (100 mL). The combined organic layers were washed with sat. aq. NaCl (200 mL) and dried over anhydrous sodium sulfate. The orange solution was filtered through Celite and concentrated to afford the mixture of products as a beige solid (2.53 g, 88%) after washing with hexanes and drying. $^1$H NMR spectra indicated that 18a and 18b were present as a 70:30 mixture (consistent with prior reports), which was used without any further purification.

Example 2

2-Chloro-7-methylquinoline (19a)

A mixture of 18a and 18b (2.53 g, 15.9 mmol) was diluted in $POCl_3$ (~35 mL), and the mixture was heated at reflux for 70 min, before the clear orange solution was cooled to room temperature and poured into ice-$H_2O$ (300 mL) in a large beaker. The beaker was immersed in ice and cooled to 0° C. with stirring, and solid NaOH was added until the pH of the mixture was approximately 7. The resultant cloudy suspension was extracted with EtOAc (300 mL) and the organic layers were washed with $H_2O$ (100 mL) and sat. aq. NaCl (100 mL). The organic layer was dried over anhydrous sodium sulfate, concentrated, and the residue was purified by flash column chromatography ($SiO_2$), eluting with a gradient of hexanes to 12% ethyl acetate in hexanes to afford orange crystals. Fractional crystallization from hot isopropanol yielded pure 19a (0.850 g, 30%) as light orange iridescent crystals; the analytical data for this compound is identical to prior literature reports. H-NMR (500 MHz; $CDCl_3$): δ 8.05 (d, J=8.5 Hz, 1H), 8.00 (m, 1H), 7.71 (d, J=8.3 Hz, 1H), 7.39 (dd, J=8.3, 1.5 Hz, 1H), 7.32 (d, J=8.5 Hz, 1H), 2.56 (s, 3H).

Example 3

2-(Acetamido)-7-methylquinoline (20)

Chloride 19a (0.300 g, 1.69 mmol) was diluted with molten anhydrous acetamide (8 g, 135 mmol) and $K_2CO_3$ (1.17 g, 8.45 mmol) was added. The mixture was heated in a sand bath, at reflux (~230° C.) for 17 h. The mixture was cooled, poured into $H_2O$ (120 mL) and extracted with EtOAc (4×30 mL). The organic layers were washed with $H_2O$ (3×100 mL) and sat. aq. NaCl (50 mL), dried over anhydrous sodium sulfate, and concentrated. Purification of the residue by flash column chromatography ($SiO_2$, 15% EtOAc in $CH_2Cl_2$) afforded the desired compound as a white solid (0.265 g, 78%). $^1$H-NMR chemical shifts for this compound are consistent with those reported in the literature for the 7-isomer. H-NMR (500 MHz; $CDCl_3$): δ 9.89-9.88 (br s, 1H), 8.40 (d, J=8.9 Hz, 1H), 8.15 (d, J=9.0 Hz, 1H), 7.67 (d, J=8.3 Hz, 1H), 7.58 (d, J=0.6 Hz, 1H), 7.29 (dd, J=8.3, 1.4 Hz, 1H), 2.54 (s, 3H), 2.27 (s, 3H).

Example 4

2-(Acetamido)-7-(bromomethyl)quinoline (21)

Compound 20 (0.265 g, 1.32 mmol) was diluted in anhydrous benzene (10 mL). N-Bromosuccinimide (0.247 g, 1.39 mmol) and a catalytic amount (~0.020 g) of benzoyl peroxide were added, and the mixture was heated to reflux under argon until an orange tint was no longer visible in the solution refluxing in the condenser (typically 4 h). The mixture was cooled, concentrated, and purified by flash column chromatography ($SiO_2$), eluting with a gradient of 7% to 14% EtOAc in $CH_2Cl_2$, to yield the product (0.236 g, 64%) as a flocculent yellow solid. $^1$H NMR chemical shifts for this compound are consistent with those reported in the literature for the 7-isomer. $^1$H-NMR (500 MHz; $CDCl_3$): δ 8.43-8.41 (m, 2H), 8.16 (d, J=8.9 Hz, 1H), 7.79-7.77 (m, 2H), 7.49 (dd, J=8.4, 1.7 Hz, 1H), 4.65 (s, 2H), 2.27 (s, 3H).

Example 5

3-Fluorophenethyl Cyanide (24)

3-Fluorophenethyl bromide (23, 1.00 g, 12.3 mmol) was diluted in dry DMF (25 mL). Sodium cyanide (1.06 g, 61.6 mmol) was added in one portion, and the mixture was heated to 60° C. under argon for 16 h. The mixture was cooled and concentrated, and the residue was partitioned between EtOAc and H$_2$O (50 mL each). The layers were separated, and the aqueous phase was extracted with EtOAc (2×20 mL). The organic layers were washed with H$_2$O and sat. aq. NaCl (50 mL each), dried over anhydrous sodium sulfate, and concentrated. The resulting oil was purified by flash column chromatography (SiO$_2$), eluting with a gradient of 5% EtOAc in hexanes to 30% EtOAc in hexanes to yield the desired product as a colorless oil (0.638 g, 87%). $^1$H-NMR (500 MHz; CDCl$_3$): δ 7.31 (td, J=7.9, 6.0 Hz, 1H), 7.03-6.93 (m, 3H), 2.96 (t, J=7.4 Hz, 2H), 2.63 (t, J=7.4 Hz, 2H).

Example 6

3-(3-Fluorophenyl)-propan-1-amine (25)

Compound 24 (0.180 g, 1.21 mmol) was diluted in EtOH (3 mL) and methanolic ammonia (7 M, 6 mL) and Raney nickel (~1 g) were added. The mixture was degassed and hydrogenated with a H$_2$-filled balloon for 30 minutes. The mixture was filtered through a Pall 0.2 μm syringe filter and concentrated to yield a sticky green syrup (0.083 g, 45%). The presence of amine was confirmed by $^1$H NMR spectrometry, TLC, and ninhydrin staining, and this material was used crude without any further purification.

Example 7

2-Acetamido-7-[(3-fluorophenethylamino)methyl] quinoline (26)

Anhydrous Cs$_2$CO$_3$ (0.295 g, 0.906 mmol) was diluted in anhydrous DMF (10 mL). 3-Fluorophenethylamine (22, 0.126 g, 0.906 mmol) was added, and the mixture was stirred at room temperature for 30 min before a solution of 21 (0.220 g, 0.788 mmol) in DMF (4 mL) was added slowly over 5 min. The cloudy yellow mixture was stirred at room temperature for 16 h and concentrated. The residue was diluted with EtOAc (50 mL) and washed with H$_2$O (2×50 mL) and sat. aq. NaCl (50 mL). The organic phase was dried over anhydrous sodium sulfate, concentrated, and purified by flash column chromatography (SiO$_2$) eluting with 10% MeOH in EtOAc to yield the product as a clear yellow oil (0.187 g, 70%). $^1$H-NMR (500 MHz; CDCl$_3$): δ 8.95 (s, 1H), 8.40 (br d, J=8.2 Hz, 1H), 8.15 (d, J=8.9 Hz, 1H), 7.74 (d, J=8.3 Hz, 1H), 7.72 (s, 1H), 7.41 (dd, J=8.3, 1.5 Hz, 1H), 7.26-7.22 (m, 1H), 6.98 (d, J=7.7 Hz, 1H), 6.93-6.88 (m, 2H), 4.00 (s, 2H), 2.95 (t, J=7.0 Hz, 2H), 2.85 (t, J=7.0 Hz, 2H), 2.23 (s, 3H); $^{13}$C NMR (126 MHz; CDCl$_3$): δ 169.3 (1C), (163.9+162.0, 1C), 151.3 (1C), 146.5 (1C), (142.47+142.41, 1C), 142.37 (1C), 138.5 (1C), (129.95+129.88, 1C), 127.8 (1C), 125.76 (1C), 125.71 (1C), 125.4 (1C), (124.42+124.40, 1C), (115.63+115.46, 1C), 114.0 (1C), (113.23+113.06, 1C), 53.7 (1C), 50.1 (1C), 36.1 (1C), 24.9 (1C); ESIMS m/z (rel. intensity) 338 (MH$^+$, 80).

Example 8

7-[(3-Fluorophenethylamino)methyl]quinolin-2-amine Dihydrochloride (5)

Compound 26 (0.187 g, 0.554 mmol) was diluted in MeOH (8 mL) and K$_2$CO$_3$ (0.077 g, 0.554 mmol) was added. The mixture was heated at 50° C. for 2 h, and then at reflux for an additional 1 h. The mixture was cooled and concentrated, and the residue was diluted in EtOAc (50 mL), washed with H$_2$O (2×50 mL), and dried over anhydrous sodium sulfate. The solution was concentrated and the residue was diluted in methanolic HCl (~1.4 M, 12 mL), and the mixture was heated for 3 h at 50° C., upon which a white crystalline precipitate formed. The mixture was cooled and filtered, and additional product was obtained upon concentration of the filtrate and recrystallization of the residue from MeOH. A total of 0.140 g of product (69%) was obtained: mp 283-285° C. (dec.); $^1$H-NMR (500 MHz; DMSO-d$_6$): δ 14.47 (s, 1H), 9.65 (br s, 2H), 9.31 (br m, 1H), 8.39 (d, J=9.3 Hz, 1H), 8.30 (br s, 1H), 7.99 (d, J=8.2 Hz, 1H), 7.87 (s, 1H), 7.68 (d, J=8.5 Hz, 1H), 7.40 (td, J=7.8, 6.4 Hz, 1H), 7.16-7.09 (m, 4H), 4.36-4.35 (m, 2H), 3.23-3.22 (m, 2H), 3.06 (t, J=8.1 Hz, 2H); $^{13}$C-NMR (126 MHz; DMSO-d$_6$): δ (163.2+161.3, 1C), 154.7 (1C), 142.6 (1C), (140.09+140.03, 1C), 136.5 (1C), 135.5 (1C), (130.60+130.53, 1C), 129.1 (1C), 126.5 (1C), (124.82+124.81, 1C), 120.9 (1C), 118.8 (1C), (115.53+115.36, 1C), 114.5 (1C), (113.70+113.54, 1C), 49.5 (1C), 47.3 (1C), 31.0 (1C); ESIMS m/z (rel. intensity) 296 (MH$^+$, 100); HRMS calcd for C$_{18}$H$_{18}$FN$_3$: 295.1485. found: 295.1487.

Example 9

7-{2-[3-(3-Fluorophenyl(propylamino)methyl]}quinolin-2-amine Dihydrochloride (9)

Anhydrous Cs$_2$CO$_3$ (0.105 g, 0.322 mmol) was diluted with anhydrous DMF (3 mL), 25 (0.050 g, 0.322 mmol) was added as a solution in DMF (~2 mL), and the mixture was stirred for 30 min at room temperature. Compound 21 (0.075 g, 0.269 mmol) was then added as a solution in DMF (1.3 mL) over several minutes. The mixture was stirred at room temperature for 16 h and then concentrated. The residue was partitioned between EtOAc and H$_2$O (10 mL each), the layers were separated, and the aqueous layer was saturated with NaCl and extracted with EtOAc (2×5 mL). The combined organic layers were washed with sat. aq. NaCl (10 mL), dried over anhydrous sodium sulfate, and concentrated. The residue was purified by flash column chromatography (SiO$_2$), eluting with a gradient of EtOAc to 15% MeOH in EtOAc to yield 27 as a yellow syrup (0.039 g, 41%), which was used without further characterization. This compound was diluted with anhydrous MeOH (6 mL), and anhydrous K$_2$CO$_3$ (0.031 g, 0.022 mmol) was added. The mixture was heated at reflux for 2 h 15 min, cooled, and concentrated. The residue was diluted with EtOAc (10 mL), and 3 mL each of H$_2$O and sat. aq. NaCl were added. The layers were separated, the aqueous layer was extracted with EtOAc (3×4 mL), and the combined organic layers were washed with sat. aq. NaCl (4 mL), dried over anhydrous sodium sulfate, and concentrated. The residue was diluted with CH$_2$Cl$_2$ (5 mL), filtered to remove particulate matter, and re-concentrated. Methanolic HCl (~1.4 M, 3 mL) was added, the mixture was stirred for 5 min, and ether (30 mL) was added slowly until a white precipitate formed. This solid was collected and dried to afford the title compound as a white microcrystalline solid (0.029 g, 28% based on 21) after drying in vacuo: mp 250-252° C. (dec). $^1$H-NMR (500 MHz; DMSO-d$_6$): δ 14.44 (s, 1H), 9.50 (s, 2H), 9.30 (br s, 1H), 8.39 (d, J=9.2 Hz, 1H), 8.30 (br s, 1H), 7.98 (d, J=8.2 Hz, 1H), 7.86 (s, 1H), 7.66 (d, J=8.3 Hz, 1H), 7.35 (td, J=8.0, 6.4 Hz, 1H), 7.15 (d, J=9.3 Hz, 1H), 7.10-7.02 (m, 3H), 4.32 (t, J=5.5 Hz, 2H), 2.95-2.90 (m, 2H), 2.70 (t, J=7.6 Hz, 2H), 2.00 (quintet, J=7.7 Hz, 2H); $^{13}$C-NMR (126 MHz; DMSO-d$_6$): δ (163.2+161.3, 1C), 154.6 (1C), (143.67+143.61, 1C), 142.6 (1C), 136.6 (1C), (130.32+130.25, 1C), 129.0 (1C), 126.4 (1C), (124.47+124.45, 1C), 120.9 (1C), 118.7 (1C), (115.08+114.91, 1C), 114.5 (1C), (112.95+112.78, 1C), 49.3 (1C), 46.0 (1C), 31.5 (1C), 26.7 (1C), one of the aminoquinoline carbons is not visible due to baseline broadening; ESIMS m/z (rel. intensity) 310 (MH$^+$, 100); HRMS calcd for $C_{19}H_{20}FN_3$: 309.1641. found: 309.1645.

Example 10

2-(Acetamido)-7-(cyanomethyl)quinoline (28)

Compound 21 (0.216 g, 0.773 mmol) was diluted with anhydrous DMF (10 mL), and NaCN (0.190 g, 3.87 mmol) was added. The orange mixture was stirred at room temperature for 17 h. The mixture was concentrated and partitioned between EtOAc and $H_2O$ (50 mL each), and the layers were separated. The aqueous phase was extracted with EtOAc (2×50 mL), the combined organic layers were washed with $H_2O$ (2×80 mL) and sat aq. NaCl (50 mL) and dried over anhydrous sodium sulfate and concentrated. The residue was purified by flash column chromatography ($SiO_2$), eluting with a gradient of 15% EtOAc in $CH_2Cl_2$ to 25% EtOAc in $CH_2Cl_2$ to yield the title compound as a white solid (0.109 g, 63%): mp 180-182° C. $^1$H-NMR (500 MHz; $CDCl_3$): δ 8.44 (dd, J=8.3, 0.4 Hz, 1H), 8.27-8.22 (m, 1H), 8.18 (d, J=9.0 Hz, 1H), 7.81 (d, J=8.4 Hz, 1H), 7.79 (s, 1H), 7.40 (dd, J=8.3, 1.7 Hz, 1H), 3.94 (s, 2H), 2.28 (s, 3H); $^{13}$C-NMR (126 MHz; $CDCl_3$): δ 169.2 (1C), 151.5 (1C), 138.8 (1C), 132.1 (1C), 128.7 (1C), 126.2 (1C), 125.6 (1C), 124.9 (1C), 117.3 (1C), 114.7 (1C), 25.1 (1C), 24.0 (1C); ESIMS m/z (rel. intensity) 473 (2M+Na$^+$, 100).

Example 11

2-(Acetamido)-7-[2-aminoethyl)]quinoline (29)

Compound 28 (0.060 g, 0.266 mmol) was diluted in absolute EtOH (7 mL), and methanolic ammonia (7 N, 7 mL) was added. Raney nickel (~1.5 g, washed with $H_2O$ and MeOH) was added, and the mixture was degassed and hydrogenated with a $H_2$-filled balloon at room temperature for 30 min while stirring rapidly. The clear solution was decanted from the nickel and was filtered through a Pall 0.2 μm syringe filter to remove fine particulate matter. The solution was concentrated and dried in vacuo to yield an off-white semisolid (0.062 g, 100%). Conversion to this amine was confirmed by TLC and ninhydrin staining and was used crude without any further characterization or purification.

Example 12

7-[2-(3-Fluorobenzylamino)ethyl]quinolin-2-amine Dihydrochloride (6)

To a solution of 29 (0.062 g, 0.266 mmol) in 5:1 $CHCl_3$/MeOH (6 mL) was added aldehyde 30 (0.033 g, 0.319 mmol) and anhydrous sodium sulfate (approximately 0.5 g). The mixture was stirred rapidly for 90 min, and additional $Na_2SO_4$ (~0.3 g) and a catalytic amount of glacial AcOH (approximately 10 μL) was added. After a total of 3 h, extra $Na_2SO_4$ (~0.3 g) was added. After 4 h, TLC indicated consumption of amine 29, and the mixture was filtered to remove the $Na_2SO_4$ and the filter cake was washed with 10 mL of $CHCl_3$. The mixture was concentrated and the oily residue was diluted in MeOH (5 mL), then $NaBH_4$ (~0.015 g, 0.4 mmol) was added. After being stirred for 20 min at room temperature, the solution was concentrated, and the residue was partitioned between EtOAc and $H_2O$ (20 mL each). The layers were separated, and the aqueous layer was extracted with EtOAc (20 mL). The combined organic layers were washed with sat. aq. NaCl and dried over anhydrous sodium sulfate. Concentration afforded an oily residue that was purified by flash column chromatography ($SiO_2$), eluting with a gradient of EtOAc to 10% MeOH in EtOAc to yield the intermediate acetamide (0.055 g, 75%, confirmed by MS), which was immediately dissolved in MeOH (6 mL). $K_2CO_3$ (0.023 g, 0.167 mmol) was added, and the mixture was heated to vigorous reflux for 1 h 45 min. The mixture was cooled, concentrated, and the residue was partitioned between EtOAc and 1:1 $H_2O$/sat. aq. NaCl (15 mL:5 mL). The layers were separated, and the aqueous layer was extracted with EtOAc (5 mL). The combined organic layers were dried over anhydrous sodium sulfate and concentrated to yield a sticky residue that was diluted with $CH_2Cl_2$ (5 mL), and filtered to remove particulate matter. Methanolic HCl (~1.4 M, 2 mL) was added, the mixture was stirred for 10 min, and ether (25 mL) was added slowly until a whitish precipitate formed. This solid was collected and dried to afford the title compound as a cream-colored amorphous solid (0.052 g, 65% based on 29): mp 278-279° C. $^1$H-NMR (500 MHz; DMSO-$d_6$): δ 14.36 (s, 1H), 9.65 (s, 2H), 9.20 (br s, 1H), 8.36 (d, J=9.3 Hz, 1H), 8.25 (br s, 1H), 7.91 (d, J=8.2 Hz, 1H), 7.59 (s, 1H), 7.51 (m, J=5.0 Hz, 2H), 7.44-7.39 (m, 2H), 7.30-7.26 (m, 1H), 7.09 (d, J=9.3 Hz, 1H), 4.22 (s, 2H), 3.22 (br s, 4H); $^{13}$C-NMR (126 MHz; DMSO-$d_6$): δ (162.9+160.9, 1C), 154.3 (1C), 142.8 (1C), 142.4 (1C), 135.9 (1C), (134.63+134.57, 1C), (130.76+130.70, 1C), 129.1 (1C), (126.24+126.22, 1C), 125.8 (1C), 119.8 (1C), 117 (1C), (116.96+116.79, 1C), (115.90+115.73, 1C), 113.4 (1C), 49.2 (1C), 47.1 (1C), 31.6 (1C); ESIMS m/z (rel. intensity) 296 (MH$^+$, 100); HRMS calcd for $C_{18}H_{18}FN_3$: 295.1485. found: 295.1487.

Example 13

7-[(3-Fluorophenethylamino)ethyl]quinolin-2-amine Dihydrochloride (7)

To a solution of 29 (0.74 g, 0.321 mmol) in 7:1 $CHCl_3$/MeOH (8 mL), aldehyde 35 (0.052 g, 0.375 mmol) was added, followed by glacial AcOH (7 μL) and anhydrous $MgSO_4$ (approx. 0.5 g). The mixture was stirred at room temperature for 30 min and then cooled to 0° C. Sodium triacetoxyborohydride (0.079 g, 0.375 mmol) was added in one portion, and the mixture was slowly warmed to room temperature over 45 min, stirred 15 min at room temperature, and diluted with $CHCl_3$ (30 mL). The mixture was filtered, the filtrate was washed with sat. aq. $NaHCO_3$ (10 mL), and the aqueous layer was extracted with $CHCl_3$ (5 mL). The combined organic layers were washed with sat aq. NaCl (10 mL) and dried over anhydrous sodium sulfate. The solution was concentrated and the residue was purified by flash column chromatography ($SiO_2$), eluting with a gradient of EtOAc to 18% MeOH in EtOAc to yield the intermediate acetamide as a sticky syrup (0.030 g, 25%), which was immediately dissolved in MeOH (4 mL). $K_2CO_3$ (0.023 g, 0.163 mmol) was added, and the mixture was heated to vigorous reflux for 2 h. The mixture was cooled, concentrated, and the residue was partitioned between EtOAc and 3:2 $H_2O$/sat. aq. NaCl (10 mL: 5 mL). The layers were separated, and the aqueous layer was extracted with EtOAc (2 mL). The combined organic layers were washed with sat. NaCl (4 mL), dried over anhydrous sodium sulfate, and concentrated to yield a sticky residue that was diluted with CH$_2$Cl$_2$ (4 mL), and filtered to remove particulate matter. Methanolic HCl (~1.4 M, 2 mL) was added, the mixture was stirred for 10 min, and ether (20 mL) was added slowly and the mixture was sonicated until a whitish precipitate formed. This solid was collected and dried to afford the title compound as a hygroscopic, cream-colored amorphous solid (0.023 g, 18% based on 29): mp 247-249° C. (dec). $^1$H-NMR (500 MHz; DMSO-d$_6$): δ 14.34 (s, 1H), 9.21 (br s, 3H), 8.37 (d, J=9.3 Hz, 1H), 8.27 (br s, 1H), 7.92 (d, J=8.2 Hz, 1H), 7.60 (s, 1H), 7.43-7.38 (m, 2H), 7.18-7.08 (m, 4H), 3.25-3.16 (m, 6H), 3.02 (t, J=8.1 Hz, 2H). $^{13}$C-NMR (126 MHz; DMSO-d$_6$): δ (163.7+161.8, 1C), 154.8 (1C), 143.3 (1C), 142.9 (1C), (140.55+140.49, 1C), 136.4 (1C), (131.07+131.00, 1C), 129.6 (1C), 126.3 (1C), (125.35+125.33, 1C), 120.2 (1C), 117.5 (1C), (116.03+115.86 1C), (114.19+114.02, 1C), 113.86 (1C), 47.7 (1C), 32.1 (1C), 31.6 (1C); ESIMS m/z (rel. intensity) 310 (MH$^+$, 65); HRMS calcd for C$_{19}$H$_{20}$FN$_3$: 309.1641. found: 309.1645.

Example 14

3-Chlorophenylacetaldehyde (37)

Dess-Martin periodinane (1.02 g, 2.4 mmol) was diluted in anhydrous CH$_2$Cl$_2$ (25 mL) under argon, and when solution was affected, 3-chlorophenethyl alcohol (33, 0.313 g, 2.00 mmol) was added dropwise. The mixture was stirred for 2 h and 15 min at room temperature, and was then quenched by addition of 20 mL sat. aq. Na$_2$S$_2$O$_3$. After stirring at room temperature for 15 min, the layers were separated, and the aqueous layer was extracted with CH$_2$Cl$_2$ (2×50 mL). The organic layer was washed with H$_2$O and sat. aq. NaCl (50 mL each) and was dried over anhydrous sodium sulfate and concentrated. The resulting semisolid residue was triturated with 10% EtOAc in hexanes, and the solid was filtered out and discarded. The filtrate was concentrated, and the oily residue was purified by flash column chromatography (SiO$_2$), eluting with a gradient of hexanes to 10% EtOAc in hexanes to afford the title compound as a clear yellow volatile oil (0.241 g, 78%). $^1$H-NMR (500 MHz; CDCl$_3$): δ 9.75 (t, J=2.1 Hz, 1H), 7.31-7.23 (m, 3H), 7.11-7.09 (m, 1H), 3.69 (d, J=2.1 Hz, 2H).

Example 15

4-Chlorophenylacetaldehyde (38)

Dess-Martin periodinane (1.02 g, 2.4 mmol) was diluted in anhydrous CH$_2$Cl$_2$ (25 mL) under argon, and when solution was affected, 4-chlorophenethyl alcohol (33, 0.313 g, 2 mmol) was added dropwise. The mixture was stirred for 2 h and 15 min at room temperature, and was then quenched by addition of 20 mL sat. aq. Na$_2$S$_2$O$_3$. After stirring at room temperature for 15 min, the layers were separated, and the aqueous layer was extracted with CH$_2$Cl$_2$ (2×50 mL). The organic layer was washed with H$_2$O and sat. aq. NaCl (50 mL each) and was dried over anhydrous sodium sulfate and concentrated. The resulting semisolid residue was triturated with 10% EtOAc in hexanes, and the solid was filtered and discarded. The filtrate was concentrated, and the oily residue was purified by flash column chromatography (SiO$_2$), eluting with a gradient of hexanes to 15% EtOAc in hexanes to afford the title compound as a clear yellow volatile oil (0.211 g, 88%). $^1$H-NMR (500 MHz; CDCl$_3$): δ 9.75 (t, J=2.1 Hz, 1H), 7.34 (d, J=8.3 Hz, 2H), 7.15 (d, J=8.2 Hz, 2H), 3.69 (d, J=2.0 Hz, 2H).

Example 16

7-[(4-Fluorophenethylamino)ethyl]quinolin-2-amine Dihydrochloride (14)

Compound 29 (0.076 g, 0.333 mmol) was diluted in 7:1 CHCl$_3$:MeOH (7 mL), and aldehyde 36 (0.045 g, 0.327 mmol) was added as a solution in 1 mL CHCl$_3$, followed by glacial acetic acid (7 µL) and anhydrous MgSO$_4$ (~0.5 g). The flask was sheathed with aluminum foil, and the mixture was stirred for 45 min, cooled to 0° C., and sodium triacetoxyborohydride (0.085 g, 0.401 mmol) was added in one portion. The mixture was allowed to warm to room temperature slowly over 1 h and 15 min and was diluted with CHCl$_3$ (to a volume of approximately 50 mL) and filtered. The yellow filtrate was washed with sat. aq. NaHCO$_3$ (10 mL) and the aqueous layer was extracted with CHCl$_3$ (2×5 mL). The organic phase was washed with sat. aq. NaCl (20 mL), dried over anhydrous sodium sulfate, and concentrated. The resulting residue was purified by flash column chromatography (SiO$_2$) eluting with a gradient of EtOAc to 14% MeOH in EtOAc to yield the intermediate acetamide (0.051 g, 44%) as an oil that began to solidify on standing. This substance was immediately diluted with anhydrous MeOH (8 mL), and K$_2$CO$_3$ (0.030 g, 0.217 mmol) was added. The mixture was heated at reflux for 2 h, cooled, and concentrated. The residue was diluted with EtOAc (10 mL) and the solution was washed with H$_2$O:sat. aq. NaCl (1:1, 6 mL). The aqueous layer was extracted with EtOAc (3×6 mL), and the combined organic layers were washed with sat. aq. NaCl (6 mL), dried over anhydrous sodium sulfate, and concentrated. The resulting syrup was diluted in CH$_2$Cl$_2$ (5 mL) filtered to remove particulate matter, and reconcentrated. To the residue was added methanolic HCl (~1.4 M, 1 mL), and the mixture was stirred at room temperature for 1 h, upon which a white crystalline solid formed. The mixture was cooled to −30° C. and filtered to yield the title compound as white flocculent crystals (0.021 g, 16% from 29): mp 279-281° C. $^1$H-NMR (500 MHz; DMSO-d$_6$): δ 14.34 (s, 1H), 9.20 (s, 3H), 8.37 (d, J=9.3 Hz, 1H), 8.26-8.24 (br s, 1H), 7.92 (d, J=8.2 Hz, 1H), 7.60 (s, 1H), 7.42 (dd, J=8.2, 1.2 Hz, 1H), 7.33 (td, J=6.1, 2.5 Hz, 2H), 7.21-7.17 (m, 2H), 7.09 (d, J=9.3 Hz, 1H), 3.26-3.16 (m, 6H), 2.98 (t, J=8.1 Hz, 2H); $^{13}$C-NMR (126 MHz; DMSO-d$_6$): δ (162.1+160.2 1C), 154.3 (1C), 142.8 (1C), 142.4 (1C), 135.9 (1C), (133.34+133.32, 1C), (130.59+130.53, 1C), 129.1 (1C), 125.8 (1C), 119.7 (1C), 117.0 (1C), (115.45+115.28, 1C), 113.4 (1C), 47.7 (1C), 47.2 (1C), 31.7 (1C), 30.7 (1C); ESIMS m/z (rel. intensity) 310 (MH$^+$, 100); HRMS calcd for C$_{19}$H$_{20}$FN$_3$: 309.1641. found: 309.1644.

Example 17

7-[(3-Chlorophenethylamino)ethyl]quinolin-2-amine Dihydrochloride (15)

Compound 29 (0.076 g, 0.333 mmol) was diluted in 8:1 CHCl$_3$:MeOH (7 mL), and aldehyde 37 (0.051 g, 0.330 mmol) was added as a solution in 1 mL CHCl$_3$, followed by glacial acetic acid (7 µL) and anhydrous MgSO$_4$ (~0.5 g). The mixture was stirred for 30 min, cooled to 0° C., and sodium triacetoxyborohydride (0.085 g, 0.401 mmol) was added in one portion. The mixture was allowed to warm to room temperature slowly over 1 h and was diluted with CHCl$_3$ (to a volume of approximately 50 mL) and filtered. The yellow filtrate was washed with sat. aq. NaHCO$_3$ (10 mL) and the aqueous layer was extracted with CHCl$_3$ (10 mL). The organic phase was washed with sat. aq. NaCl (20 mL), dried over anhydrous sodium sulfate, and concentrated. The resulting residue was purified by flash column chromatography (SiO$_2$) eluting with a gradient of EtOAc to 13% MeOH in EtOAc to yield the intermediate acetamide (0.039 g, 32%) as a semisolid. This substance was diluted with anhydrous MeOH (6 mL) and K$_2$CO$_3$ (0.029 g, 0.210 mmol) was added. The mixture was heated at reflux for 2 h, cooled, and concentrated. The residue was immediately diluted with EtOAc (10 mL) and the solution was washed with H$_2$O:sat. aq. NaCl (3:5, 8 mL). The organic layers were washed with sat. aq. NaCl (5 mL), dried over anhydrous sodium sulfate, and concentrated. The resulting syrup was diluted in CH$_2$Cl$_2$ (5 mL) filtered to remove particulate matter, and reconcentrated. To the residue was added methanolic HCl (~1.4 M, 3 mL) and the mixture was stirred at room temperature for 5 min, and ether (20 mL) was added, upon which an off-white solid (0.030 g, 23%) was collected. An analytically pure sample for assay was prepared by preparative LC-MS, using the instrument and column detailed in the General Procedures section, eluting with a gradient of 95% H$_2$O+0.1%/formic acid 5% MeCN+0.1% formic acid for 2 min, to 70% H$_2$O at 27 min, then to 0% H$_2$O at 32 min. Evaporation and re-treatment of the residue with methanolic HCl (1 mL) and ether (1 mL) afforded the pure compound as a white flocculent solid (0.014 g, 11% from 29): mp 281-282° C. $^1$H-NMR (500 MHz; DMSO-d$_6$): δ 14.29 (s, 1H), 9.17 (br s, 3H), 8.37 (d, J=9.3 Hz, 1H), 8.25 (br s, 1H), 7.92 (d, J=8.2 Hz, 1H), 7.60 (s, 1H), 7.44-7.34 (m, 4H), 7.27 (d, J=7.4 Hz, 1H), 7.09 (d, J=9.3 Hz, 1H), 3.25-3.20 (m, 4H), 3.20-3.16 (m, 2H), 3.00 (t, J=8.1 Hz, 2H); $^{13}$C-NMR (126 MHz; DMSO-d$_6$): δ 154.3 (1C), 142.8 (1C), 142.5 (1C), 139.8 (1C), 135.8 (1C), 133.2 (1C), 130.5 (1C), 129.1 (1C), 128.6 (1C), 127.5 (1C), 126.8 (1C), 125.8 (1C), 119.7 (1C), 116.9 (1C), 113.4 (1C), 47.2 (1C), 31.6 (1C), 31.0 (1C); ESIMS m/z (rel. intensity) 326 (MH$^+$, 100); HRMS calcd for C$_{19}$H$_{20}$ClN$_3$: 325.1346. found: 325.1352.

Example 18

7-[(4-Chlorophenethylamino)ethyl]quinolin-2-amine Dihydrochloride (16)

Compound 29 (0.076 g, 0.333 mmol) was diluted in 7:1 CHCl$_3$:MeOH (7 mL), and aldehyde 38 (0.051 g, 0.330 mmol) was added as a solution in 1 mL CHCl$_3$, followed by glacial acetic acid (7 μL) and anhydrous MgSO$_4$ (~0.5 g). The mixture was stirred for 30 min, cooled to 0° C., and sodium triacetoxyborohydride (0.085 g, 0.401 mmol) was added in one portion. The mixture was allowed to warm to room temperature slowly over 1 h 15 min, and was diluted with CHCl$_3$ (to a volume of approximately 50 mL) and filtered. The yellow filtrate was washed with sat. aq. NaHCO$_3$ (10 mL), and the aqueous layer was extracted with CHCl$_3$ (2×5 mL). The organic phase was washed with sat. aq. NaCl (20 mL), dried over anhydrous sodium sulfate, and concentrated. The resulting residue was purified by flash column chromatography (SiO$_2$) eluting with a gradient of EtOAc to 13% MeOH in EtOAc) to yield the intermediate acetamide (0.032 g, 26%) as a white semisolid. This substance was immediately diluted with anhydrous MeOH (7 mL), and K$_2$CO$_3$ (0.024 g, 0.174 mmol) was added. The mixture was heated at reflux for 2 h, cooled, and concentrated. The residue was diluted with EtOAc (10 mL), and the solution was washed with H$_2$O:sat. aq. NaCl (3:5, 8 mL). The organic layers were washed with sat. aq. NaCl (5 mL), dried over anhydrous sodium sulfate, and concentrated. The resulting syrup was diluted in CH$_2$Cl$_2$ (5 mL) filtered to remove particulate matter, and reconcentrated. To the residue was added methanolic HCl (~1.4 M, 3 mL), the mixture was stirred at room temperature for 5 min, and ether (20 ml) was added, upon which an off-white solid (0.027 g, 20%) was collected. An analytically pure sample for assay was prepared by preparative LC-MS, using the instrument and column detailed in the General Procedures section, eluting with a gradient of 95% H$_2$O+0.1% formic acid/5% MeCN+ 0.1% formic acid for 5 min, to 93% H$_2$O in 30 min, then to 0% H$_2$O at 32 min. Evaporation and re-treatment of the residue with methanolic HCl (1 mL) and ether (1 mL) afforded the pure compound as a white flocculent solid (0.0094 g, 7.4% from 29): mp 288-290° C. (dec). $^1$H-NMR (500 MHz; DMSO-d$_6$): δ 14.20 (s, 1H), 9.07 (s, 3H), 8.36 (dd, J=9.2, 0.5 Hz, 1H), 8.22 (br s, 1H), 7.91 (d, J=8.1 Hz, 1H), 7.58 (s, 1H), 7.44-7.41 (m, 3H), 7.32 (d, J=8.4 Hz, 2H), 7.07 (d, J=9.2 Hz, 1H), 3.28-3.14 (m, 6H), 2.97 (t, J=8.1 Hz, 2H); $^{13}$C-NMR (126 MHz; DMSO-d$_6$): δ 154.4 (1C), 142.8 (1C), 142.4 (1C), 136. (1C), 131.4 (1C), 130.6 (1C), 129.1 (1C), 128.6 (1C), 125.8 (1C), 119.8 (1C), 117.0 (1C), 113.4 (1C), 47.40 (1C), 47.22 (1C), 31.7 (1C), 30.8 (1C); one of the aminoquinoline carbons is not visible due to linebroadening. ESIMS m/z (rel. intensity) 326 (MH$^+$, 30); HRMS calcd for C$_{19}$H$_{20}$ClN$_3$: 325.1346. found: 325.1353.

Example 19

3-Fluorophenyl-1-propanol (40)

3-Fluorophenylpropionic acid (39, 0.500 g, 2.97 mmol) was diluted in anhydrous THF (2 mL) under argon, and cooled to 0° C. Borane-THF (1 M, 4.16 mL, 4.16 mmol) was added dropwise, and the mixture was allowed to warm to room temperature and stirred for 18 h. The reaction was quenched by the addition of 1:1 THF/H$_2$O (5 mL). When gas evolution ceased, solid K$_2$CO$_3$ was added until the mixture separated into two layers, which were separated. The aqueous layer was extracted with EtOAc (2×5 mL), and the combined organic layers were washed with H$_2$O (15 mL) and sat. aq. NaCl (15 mL), dried over anhydrous sodium sulfate, and concentrated to yield the product as a clear oil (0.446 g, 97%) after drying in vacuo. $^1$H-NMR (500 MHz; CDCl$_3$): δ 7.29-7.25 (m, 1H), 7.00 (d, J=7.6 Hz, 1H), 6.95-6.89 (m, 2H), 3.71 (t, J=6.4 Hz, 2H), 2.74 (t, J=7.7 Hz, 2H), 1.95-1.89 (m, 2H), 1.39 (s, 1H).

Example 20

3-Fluorophenyl-1-propanal (41)

Anhydrous CH$_2$Cl$_2$ (10 mL) was cooled to −78° C., and anhydrous DMSO (0.546 g, 7.00 mmol) was added, followed, dropwise, by oxalyl chloride (0.380 g, 3.00 mmol). Once gas evolution ceased, compound 40 (0.308 g, 2 mmol) was added dropwise and the resulting milky solution was stirred for 15 min. Et$_3$N (1.17 mL, 8.4 mmol) was added slowly and the mixture was stirred for 15 min at −78° C. and then warmed to room temperature and stirred for 1 h. The yellow mixture was diluted with H$_2$O (30 mL) and the layers were separated. The aqueous layer was extracted with CH$_2$Cl$_2$ (2×15 mL), and the organic layers were washed with H$_2$O and sat. aq. NaCl (15 mL each). The solution was dried over anhydrous sodium sulfate, concentrated, and the resulting residue was purified by flash column chromatography (SiO$_2$), eluting with a gradient of hexanes to 10% EtOAc in hexanes to yield the title aldehyde as a colorless volatile oil (0.220 g, 72%). $^1$H-NMR (500 MHz; CDCl$_3$): δ 9.82 (s, 1H), 7.27-7.23 (m, 1H), 6.97 (d, J=7.6 Hz, 1H), 6.92-6.89 (m, 2H), 2.96 (t, J=7.5 Hz, 2H), 2.81-2.78 (m, 2H).

Example 21

7-{2-[3-(3-Fluorophenyl(propylamino)ethyl]}quinolin-2-amine Dihydrochloride (8)

Compound 29 (0.064 g, 0.280 mmol) was diluted in 7:1 CHCl$_3$: MeOH (7 mL), and aldehyde 41 (0.049 g, 0.322 mmol) was added, followed by glacial acetic acid (6 µL) and anhydrous MgSO$_4$ (~0.5 g). The mixture was stirred for 30 min, cooled to 0° C., and sodium triacetoxyborohydride (~0.070 g, 0.333 mmol) was added in one portion. The mixture was allowed to warm to room temperature slowly over 50 min and was diluted with CHCl$_3$ (to a volume of approximately 50 mL) and filtered. The yellow filtrate was washed with sat. aq. NaHCO$_3$ (8 mL) and the aqueous layer was extracted with CHCl$_3$ (5 mL). The organic phase was washed with sat. aq. NaCl (10 mL), dried over anhydrous sodium sulfate, and concentrated. The resulting residue was purified by flash column chromatography (SiO$_2$) eluting with a gradient of EtOAc to 17% MeOH in EtOAc to yield the intermediate acetamide (0.045 g, 44%) as a sticky semisolid. This substance was immediately diluted with anhydrous MeOH (6 mL) and K$_2$CO$_3$ (0.034 g, 0.246 mmol) was added. The mixture was heated at reflux for 1 h 50 min, cooled, and concentrated. The residue was diluted with EtOAc (10 mL), and the solution was washed with H$_2$O:sat. aq. NaCl (1:1, 6 mL). The organic layers were washed with sat. aq. NaCl (5 mL), dried over anhydrous sodium sulfate, and concentrated. The resulting syrup was diluted in CH$_2$Cl$_2$ (3 mL), filtered to remove particulate matter, methanolic HCl added (~1.4 M, 3 mL), and the mixture stirred at room temperature for 10 min. Ether (30 mL) was added, and the mixture was sonicated, concentrated, and the residue was washed twice with ether (2 mL each) to afford the product as a cream-colored hygroscopic solid (0.042 g, 37% from 29): mp 81-83° C. (softens), 210° C. (dec). $^1$H-NMR (500 MHz; DMSO-d$_6$): δ 14.31 (s, 1H), 9.21-9.13 (m, 3H), 8.37 (d, J=9.3 Hz, 1H), 8.25 (br s, 1H), 7.91 (d, J=8.2 Hz, 1H), 7.59 (s, 1H), 7.42 (dd, J=8.2, 1.3 Hz, 1H), 7.38-7.34 (m, 1H), 7.12-7.03 (m, 4H), 3.21-3.14 (m, 4H), 2.95-2.90 (m, 2H), 2.71 (t, J=7.6 Hz, 2H), 1.96 (dt, J=15.3, 7.7 Hz, 2H); $^{13}$C-NMR (126 MHz; DMSO-d$_6$): δ (163.2+161.3, 1C), 154.3 (1C), (143.71+143.65, 1C), 142.8 (1C), 142.5 (1C), 135.8 (1C), (130.32+130.25, 1C), 129.1 (1C), 125.8 (1C), (124.47+124.45, 1C), 119.7 (1C), 117.0 (1C), (115.09+114.92, 1C), 113.4 (1C), (112.95+112.79, 1C), 47.1 (1C), 46.1 (1C), 31.73 (1C), 31.54 (1C), 26.8 (1C); ESIMS m/z (rel. intensity) 324 (MH$^+$, 28); HRMS calcd for C$_{20}$H$_{22}$FN$_3$: 323.1798. found: 323.1800.

Example 22

2-Chloro-6-Methylquinoline (44)

Compound 42 (3.75 g, 15.8 mmol) was diluted in chlorobenzene (40 mL), and aluminum chloride (10.5 g, 75.0 mmol) was added. The mixture was heated to 90° C. under nitrogen for 2 h, upon which the mixture became black, was subsequently cooled, and poured into ice-H$_2$O (300 g). The resulting suspension was extracted with EtOAc (700 mL), and the organic layer was washed with H$_2$O (300 mL) and dried over anhydrous sodium sulfate. Concentration afforded an orange solid that was recrystallized from hot MeOH (60 mL) to yield an orange iridescent solid (1.95 g, 77%). This was not characterized, but was instead diluted in POCl$_3$ (30 mL) and heated at reflux for 70 min before cooling and pouring into ice-H$_2$O (400 mL) in a large beaker. The beaker was immersed in a cooler of ice, with stirring, and solid NaOH was added until the pH was approximately 7. The oily suspension was extracted with EtOAc (400 mL), washed with sat. aq. NaCl (300 mL), and the organic layer was dried over anhydrous sodium sulfate. The solution was concentrated to yield a solid that was purified by flash column chromatography (SiO$_2$), eluting with a gradient of hexanes to 40% EtOAc in hexanes to yield the product as an orange crystalline solid (1.79 g, 64% from 42). The $^1$H NMR chemical shifts for this compound are identical to those previously reported by Inglis et al. $^1$H-NMR (500 MHz; CDCl$_3$): δ 8.01 (d, J=8.6 Hz, 1H), 7.91 (d, J=9.2 Hz, 1H), 7.57-7.55 (m, 2H), 7.34 (d, J=8.6 Hz, 1H), 2.53 (s, 3H).

Example 23

2-(Acetamido)-6-methylquinoline (45)

Chloride 44 (0.300 g, 1.69 mmol) was diluted with molten anhydrous acetamide (8 g, 135 mmol), and K$_2$CO$_3$ (1.17 g, 8.45 mmol) was added. The mixture was heated in a sand bath, at reflux (~230° C.) for 16 h. The mixture was cooled, poured into H$_2$O (120 mL) and extracted with EtOAc (4×30 mL). The organic layers were washed with H$_2$O (3×100 mL) and sat. aq. NaCl (50 mL) and dried over anhydrous sodium sulfate and concentrated. Purification of the residue by flash column chromatography (SiO$_2$), eluting with a gradient of 10% EtOAc in CH$_2$Cl$_2$ to 30% EtOAc in CH$_2$Cl$_2$ afforded the desired compound as a white solid (0.250 g, 74%). $^1$H NMR chemical shifts for this compound are consistent with those reported in the literature. $^1$H-NMR (500 MHz; CDCl$_3$): δ 8.36 (br d, J=8.6 Hz, 1H), 8.27 (br s, 1H), 8.09 (d, J=8.9 Hz, 1H), 7.70 (d, J=8.6 Hz, 1H), 7.55 (s, 1H), 7.50 (dd, J=8.6, 1.9 Hz, 1H), 2.51 (s, 3H), 2.24 (s, 3H).

Example 24

2-(Acetamido)-6-(bromomethyl)quinoline (46)

Compound 45 (0.300 g, 1.50 mmol) was diluted in anhydrous benzene (10 mL). N-Bromosuccinimide (0.280 g, 1.57 mmol) and a catalytic amount (~0.020 g) of benzoyl peroxide were added, and the mixture was heated to reflux under nitrogen until an orange tint was no longer visible in the solution refluxing in the condenser (around 2 h 40 min). The mixture was cooled, concentrated, and purified by flash column chromatography (SiO$_2$), eluting with a gradient of 10% to 12% EtOAc in CH$_2$Cl$_2$ to yield the product (0.262 g, 63%) as a flocculent yellow solid. The $^1$H NMR chemical shifts for this compound are identical to those previously reported in the literature. $^1$H-NMR (500 MHz; CDCl$_3$): δ 8.44 (br d, J=8.6 Hz, 1H), 8.30 (br s, 1H), 8.17 (d, J=9.0 Hz, 1H), 7.82 (m, J=9.1 Hz, 2H), 7.72 (dd, J=8.6, 2.1 Hz, 1H), 4.67 (s, 2H), 2.29 (s, 3H).

Example 25

6-[(3-Fluorophenethylamino)methyl]quinolin-2-amine Dihydrochloride (10)

Anhydrous Cs$_2$CO$_3$ (0.090 g, 0.288 mmol) was diluted in anhydrous DMF (5 mL), and amine 22 (0.040 g, 0.288 mmol) was added. The mixture was stirred for 30 min at room temperature before compound 46 (0.070 g, 0.250 mmol) was added dropwise as a solution in anhydrous DMF (2 mL). The resultant suspension was stirred for 16 h at room temperature and concentrated, and the residue was partitioned between EtOAc and $H_2O$ (5 mL each), and the layers were separated. The aqueous layer was extracted with EtOAc (2×5 mL), and the organic layers were washed with sat. aq. NaCl (5 mL), dried over anhydrous sodium sulfate, and concentrated. The residue was purified by flash column chromatography ($SiO_2$), eluting with a gradient of EtOAc to 10% MeOH in EtOAc to yield the intermediate acetamide as a yellow syrup (0.040 g, 47%, confirmed by MS). This syrup was dissolved in MeOH (5 mL), and $K_2CO_3$ (0.026 g, 0.148 mmol) was added. The mixture was heated at reflux for 2 h, cooled to room temperature, and concentrated. The residue was partitioned between EtOAc (5 mL) and sat. aq. NaCl: $H_2O$ (4:1, 5 mL). The layers were separated and the aqueous layer was extracted with EtOAc (2×5 mL). The combined organic phase was washed with sat aq. NaCl (4 mL), dried over anhydrous sodium sulfate, and concentrated. The resulting residue was diluted in $CH_2Cl_2$ (5 mL), filtered to remove particulate matter, and methanolic HCl (~1.4 M, 3 mL) was added. After 10 min, ether (20 mL) was added, and a precipitate formed. This was collected and dried to yield the title compound as a cream-colored powder (0.036 g, 38% from 46: mp 277-278° C. $^1$H-NMR (500 MHz; DMSO-$d_6$): δ 14.35 (s, 1H), 9.58 (s, 2H), 9.28 (br s, 1H), 8.37 (d, J=9.5 Hz, 1H), 8.32 (br s, 1H), 8.05 (s, 1H), 7.96 (d, J=8.6 Hz, 1H), 7.78 (d, J=8.5 Hz, 1H), 7.39 (td, J=7.8, 6.4 Hz, 1H), 7.16-7.09 (m, 4H), 4.29 (s, 2H), 3.20-3.19 (m, 2H), 3.05 (t, J=8.1 Hz, 2H); $^{13}$C-NMR (126 MHz; DMSO-$d_6$): δ (163.2+ 161.2, 1C), 154.4 (1C), 142.8 (1C), (140.11+140.05, 1C), 135.9 (1C), 134.2 (1C), 130.59 (1C), (130.58+130.52, 1C), 128.6 (1C), (124.83+124.81, 1C), 120.5 (1C), 117.6 (1C), (115.53+115.36, 1C) 114.5 (1C), (113.69+113.52, 1C), 49.2 (1C), 47.0 (1C), 31.0 (1C); ESIMS m/z (rel. intensity) 296 ($MH^+$, 100); HRMS calcd for $C_{18}H_{18}FN_3$: 295.1485. found: 295.1490.

Example 26

2-(Acetamido)-6-(cyanomethyl)quinoline (47)

Compound 46 (0.254 g, 0.91 mmol) was diluted with anhydrous DMF (10 mL), and NaCN (0.230 g, 4.55 mmol) was added. The orange mixture was stirred at room temperature for 17 h. The mixture was concentrated and partitioned between EtOAc and $H_2O$ (50 mL each) and the layers were separated. The aqueous phase was extracted with EtOAc (2×50 mL) and the combined organic layers were washed with $H_2O$ (2×80 mL) and sat aq. NaCl (50 mL), and dried over anhydrous sodium sulfate and concentrated. The residue was purified by flash column chromatography ($SiO_2$), eluting with a gradient of 15% EtOAc in $CH_2Cl_2$ to 25% EtOAc in $CH_2Cl_2$ to yield the title compound as a white solid (0.170 g, 83%): mp 154-155° C.; $^1$H-NMR (500 MHz; $CDCl_3$): δ 8.48 (d, J=8.6 Hz, 1H), 8.22 (br s, 1H), 8.20 (d, J=9.0 Hz, 1H), 7.85 (d, J=8.7 Hz, 1H), 7.81 (d, J=1.0 Hz, 1H), 7.61 (dd, J=8.7, 2.1 Hz, 1H), 3.96 (s, 2H), 2.30 (s, 3H); $^{13}$C-NMR (126 MHz; $CDCl_3$): δ 169.1 (1C), 151.3 (1C), 145.8 (1C), 138.6 (1C), 129.8 (1C), 128.3 (1C), 126.74 (1C), 126.64 (1C), 126.2 (1C), 117.6 (1C), 114.9 (1C), 25.0 (1C), 23.7 (1C); ESIMS m/z (rel. intensity) 472 ($2M+Na^+$, 100).

Example 27

2-(Acetamido)-6-(2-aminoethyl)quinoline (48)

Compound 47 (0.060 g, 0.266 mmol) was diluted in absolute EtOH (7 mL) and methanolic ammonia (7 N, 7 mL) was added. Raney nickel (~1.5 g, washed with $H_2O$ and MeOH) was added, and the mixture was degassed and hydrogenated with a balloon at room temperature for 30 min while stirring rapidly. The clear solution was decanted away from the nickel and was filtered through a Pall 0.2 μm syringe filter to remove fine particulate matter. The solution was concentrated and dried in vacuo to yield a colorless gum that became a white semisolid upon standing (0.050 g, 82%). Conversion to this amine was confirmed by $^1$H NMR spectrometry, TLC, MS, and ninhydrin staining, and it was used crude without any further characterization or purification.

Example 28

6-[2-(3-Fluorobenzylamino)ethyl]quinolin-2-amine Dihydrochloride (11)

Amine 48 (0.050 g, 0.218 mmol) was dissolved in anhydrous $CHCl_3$ (3 mL), and aldehyde 30 (0.034 g, 0.274 mmol) was added, followed by 3 mL of a 2:1 mixture of $CHCl_3$:MeOH and anhydrous sodium sulfate (~0.5 g). The mixture was stirred rapidly at room temperature for 90 min, after which glacial acetic acid (10 μL) was added. After a total of 4 h, the amine appeared consumed by TLC, and the mixture was filtered to remove the sodium sulfate. The filtrate was concentrated, and the oily residue was diluted in MeOH (5 mL). $NaBH_4$ (0.020 g, 0.523 mmol) was added and the mixture was stirred for 40 minutes at room temperature. The mixture was concentrated and partitioned between EtOAc and $H_2O$ (10 mL of each). The layers were separated, and the aqueous layer was extracted with EtOAc (10 mL). The organic layer was washed with $H_2O$ and sat aq. NaCl (20 mL each), dried over anhydrous sodium sulfate, and concentrated. The residue was purified by flash column chromatography ($SiO_2$), eluting with a gradient of EtOAc to 20% MeOH in EtOAc to yield the intermediate acetamide as a yellow syrup (0.052 g, 72%, confirmed by MS). This compound was immediately diluted in MeOH (5 mL), and $K_2CO_3$ (0.021 g, 0.154 mmol) was added. The mixture was heated at vigorous reflux for 2 h, cooled, concentrated, and the resulting residue was diluted with EtOAc (20 mL) and washed with $H_2O$ (10 mL). The aqueous layer was extracted with EtOAc (2×10 mL), and the combined organic layers were washed with sat. aq. NaCl (10 mL) and dried over anhydrous sodium sulfate. Concentration afforded a white solid, which was diluted with methanolic HCl (~1.4 M, 3 mL) and stirred for 10 min. The addition of ether (50 mL) resulted in the precipitation of a solid that was collected, washed with ether (20 mL) and dried in vacuo to yield the title compound as a white solid (0.043 g, 54% from 48): mp 282-284° C. $^1$H-NMR (500 MHz; DMSO-$d_6$): δ 14.24 (s, 1H), 9.62 (s, 2H), 9.16 (br s, 1H), 8.35 (d, J=9.4 Hz, 1H), 8.19 (br s, 1H), 7.80 (d, J=0.7 Hz, 1H), 7.71-7.67 (m, 2H), 7.52-7.48 (m, 2H), 7.42 (d, J=7.7 Hz, 1H), 7.30-7.26 (m, 1H), 7.12 (d, J=9.3 Hz, 1H), 4.22 (s, 2H), 3.17-3.14 (m, 4H); $^{13}$C-NMR (126 MHz; DMSO-$d_6$): δ (162.9+160.9, 1C), 154.0 (1C), 142.8 (1C), (134.62+134.56, 1C), 134.0 (1C), 133.3 (1C), (130.76+130.70, 1C), 128.3 (1C), (126.24+126.22, 1C), 121.0 (1C), 117.7 (1C), (116.96+116.79, 1C), (115.90+115.74, 1C), 114.0 (1C), 49.2 (1C), 47.2 (1C), 30.8

(1C); one of the aminoquinoline carbons is not visible because of baseline broadening; ESIMS m/z (rel. intensity) 296 (MH$^+$, 100); HRMS calcd for $C_{18}H_{18}FN_3$: 295.1485. found: 295.1486.

Example 29

6-[(3-Fluorophenethylamino)ethyl]quinolin-2-amine Dihydrochloride (12)

To a solution of 48 (0.074 g, 0.321 mmol) in 7:1 $CHCl_3$/MeOH (8 mL), aldehyde 35 (0.049 g, 0.353 mmol) was added, followed by glacial AcOH (7 μL) and anhydrous $MgSO_4$ (approx 0.5 g). The mixture was stirred at room temperature for 20 min and then cooled to 0° C. Sodium triacetoxyborohydride (0.082 g, 0.385 mmol) was added in one portion, and the mixture was slowly warmed to room temperature over 50 min, then diluted with $CH_2Cl_2$ (10 mL). The mixture was filtered, the filtrate was washed with sat. aq. $NaHCO_3$ (2×20 mL), and the aqueous layer was extracted with $CH_2Cl_2$ (2×10 mL). The combined organic layers were washed with sat. aq. NaCl (10 mL) and dried over anhydrous sodium sulfate. The solution was concentrated, and the residue was purified by flash column chromatography ($SiO_2$), eluting with a gradient of EtOAc to 20% MeOH in EtOAc to yield the intermediate acetamide as a sticky syrup (0.039 g, 34%) that was immediately dissolved in MeOH (3 mL). $K_2CO_3$ (0.023 g, 0.167 mmol) was added, and the mixture was heated to vigorous reflux for 1 h 50 min. The mixture was cooled, concentrated, and the residue was partitioned between EtOAc (10 mL) and 1:1 $H_2O$/sat. aq. NaCl (4 mL). The layers were separated, and the aqueous layer was extracted with EtOAc (2×4 mL). The combined organic layers were washed with sat. aq. NaCl (4 mL), dried over anhydrous sodium sulfate, and concentrated to yield a sticky residue that was diluted with $CH_2Cl_2$ (3 mL), and filtered to remove particulate matter. Methanolic HCl (~1.4 M, 2 mL) was added, the mixture was stirred for 10 min and concentrated, and the residue was recrystallized from 1:1 MeOH/ether (1 mL) to yield the product as a pale tan hygroscopic solid (0.025 g, 21% based on 48): mp 223-226° C. (dec). $^1$H-NMR (500 MHz; DMSO-d$_6$): δ 14.37 (s, 1H), 9.35-9.23 (m, 3H), 8.36 (d, J=9.4 Hz, 1H), 8.30 (br s, 1H), 7.83 (s, 1H), 7.73-7.69 (m, 2H), 7.42-7.38 (m, 1H), 7.18-7.09 (m, 4H), 3.22-3.19 (m, 4H), 3.14 (t, J=7.9 Hz, 2H), 3.04 (t, J=8.1 Hz, 2H); $^{13}$C-NMR (126 MHz; DMSO-d$_6$): δ (163.2+161.3, 1C), 154.0 (1C), 142.8 (1C), (140.14+140.08, 1C), 134.6 (1C), 134.1 (1C), 133.3 (1C), (130.58+130.51, 1C), 128.3 (1C), (124.86+124.84, 1C), 120.9 (1C), 117.5 (1C), (115.54+115.37, 1C), 114.0 (1C), (113.68+113.52, 1C), 47.35 (1C), 47.20 (1C), 31.0 (1C), 30.8 (1C); ESIMS m/z (rel. intensity) 310 (MH$^+$, 100); HRMS calcd for $C_{19}H_{20}FN_3$: 309.1641. found: 309.1647.

Example 30

6-{2-[3-(3-Fluorophenyl(propylamino)ethyl]}quinolin-2-amine Dihydrochloride (13)

To a solution of 48 (0.060 g, 0.261 mmol) in 10:1 $CHCl_3$/MeOH (5 mL), aldehyde 41 (0.047 g, 0.313 mmol) was added, followed by glacial AcOH (6 μL) and anhydrous $MgSO_4$ (approx 0.5 g). The mixture was stirred at room temperature for 25 min and then cooled to 0° C. Sodium triacetoxyborohydride (0.070 g, 0.332 mmol) was added in one portion, and the mixture was slowly warmed to room temperature over 30 min, filtered, and concentrated. The residue was purified by flash column chromatography ($SiO_2$), eluting with a gradient of EtOAc to 20% MeOH in EtOAc to yield a sticky yellow solid (0.036 g, 27%). This substance was immediately dissolved in MeOH (3 mL), $K_2CO_3$ (0.030 g, 0.217 mmol) was added, and the mixture was heated to vigorous reflux for 2 h. The mixture was cooled, concentrated, and the residue was partitioned between EtOAc (6 mL) and 1:1 $H_2O$/sat. aq. NaCl (2 mL). The layers were separated, and the aqueous layer was extracted with EtOAc (2×3 mL). The combined organic layers were washed with sat. aq. NaCl (3 mL), dried over anhydrous sodium sulfate, and concentrated to yield a sticky residue that was diluted with $CH_2Cl_2$ (3 mL), and filtered to remove particulate matter. Methanolic HCl (~1.4 M, 2 mL) was added, the mixture was stirred for 10 min, concentrated, and the residue was washed with 1:1 $CH_2Cl_2$/ether (3 mL) to yield the product as a yellow-green hygroscopic solid (0.033 g, 32% based on 48): mp 70° C. (softens), 211-213° C. (dec). $^1$H-NMR (500 MHz; DMSO-d$_6$): δ 14.31 (s, 1H), 9.20 (br s, 3H), 8.34 (d, J=9.4 Hz, 1H), 8.22 (br s, 1H), 7.82 (s, 1H), 7.70 (s, 2H), 7.38-7.33 (m, 1H), 7.14-7.03 (m, 4H), 3.23-3.17 (m, 2H), 3.11 (t, J=7.8 Hz, 2H), 2.94-2.89 (m, 2H), 2.71 (t, J=7.6 Hz, 2H), 1.97 (quintet, J=7.6 Hz, 2H); $^{13}$C NMR (126 MHz; DMSO-d$_6$): δ (163.2+161.3, 1C), 154.0 (1C), (143.72+143.66, 1C), 142.8 (1C), 134.6 (1C), 134.1 (1C), 133.3 (1C), (130.31+130.25, 1C), 128.2 (1C), (124.47+124.45, 1C), 120.9 (1C), 117.5 (1C), (115.09+114.93, 1C), 114.0, (112.95+112.78, 1C), 47.3 (1C), 46.1 (1C), 31.5 (1C), 30.9 (1C), 26.8 (1C); ESIMS m/z (rel. intensity) 325 (MH$^+$, 100); HRMS calcd for $C_{20}H_{22}FN_3$: 323.1798. found: 323.1803.

With reference to Schemes 15-19, Tables 4-6 and FIG. 9, below, various other 2-aminoquinoline compounds can be prepared in accordance with procedures provided in Examples 31-50.

Example 31

General Procedure: Synthesis of 2-Aminoquinolines Containing a Phenethylamine or Propylamine-Derived Tail Step 1. Intermediate 8 (1 eq.) or 36 (1 eq.) and the requisite phenethylamine or propylamine (1.1-1.2 eq.) were diluted with anhydrous $CHCl_3$ (6-9 mL). Anhydrous sodium sulfate (~1 g) was added to the reaction mixture and the resulting suspension was stirred at room temperature for 1 h. Acetic acid (~4-8 μL) was added and the reaction solution was stirred at room temperature for 16 h. The resulting solution was filtered and concentrated to give the crude imine, which was diluted with MeOH (4-7 mL) and cooled to 0° C. Sodium borohydride (1.5 eq.) was added while stirring and the resulting solution was warmed to room temperature and stirred for 20 min. Concentration afforded a solid, which was diluted with EtOAc (30 mL) and washed with sat. aq. $NaHCO_3$ (25 mL), $H_2O$ (25 mL), and sat. aq. NaCl (25 mL). The resulting organics were dried with anhydrous sodium sulfate and concentrated to give the crude amine. Step 2. The amine was diluted with anhydrous THF (5-7 mL) and Boc$_2$O (1.1-1.2 eq.) was added. The resulting solution was stirred at room temperature for 4-18 h, concentrated and purified by flash column chromatography ($SiO_2$; the gradient is described below for individual compounds) to yield the protected amine. Step 3. This intermediate was not characterized, but was instead diluted with MeOH (5-8 mL) and $K_2CO_3$ (2 eq.) was added. The resulting suspension was stirred and heated at 75° C. for 2-2.5 h, concentrated, and stirred at room temperature with EtOAc (10 mL), $H_2O$ (5 mL) and sat. aq. NaCl (5 mL) for 10 min.

The organic phase was removed, the aqueous phase was extracted with EtOAc (3×20 mL), and the organics were combined, washed with sat. aq. NaCl (20 mL), and dried with anhydrous sodium sulfate. Step 4. The resulting unprotected aminoquinoline was treated with methanolic HCl (~3 M, 1.5 mL), and the mixture was stirred at room temperature for 16 h. Ether (15 mL) was then added, affording the desired compound after filtration.

Example 32

4-(2-(((2-Aminoquinolin-7-yl)methyl)amino)ethyl) benzonitrile Dihydrochloride (1)

Prepared from aldehyde 8 (0.070 g, 0.33 mmol) and 4-cyano-phenethylamine hydrochloride (9, 0.071 g, 0.39 mmol), using General Procedure, Step 1. After concentration, reduction with $NaBH_4$ (0.019 g, 0.50 mmol), and workup, the secondary amine was protected with $Boc_2O$ (0.078 g, 0.36 mmol), following General Procedure, Step 2. Workup and purification by flash column chromatography, eluting with a gradient of $CH_2Cl_2$ to 10% EtOAc in $CH_2Cl_2$, afforded the protected intermediate 11 (0.118 g, 79%). This was immediately reacted with $K_2CO_3$ (0.072 g, 0.52 mmol) following General Procedure, Step 3. Following workup, the protected amine was deprotected using General Procedure, Step 4, to give the title compound as a white solid (0.057 g, 57%): mp 292-294° C. $^1H$ NMR (500 MHz; DMSO-$d_6$): δ 14.57 (s, 1H), 9.85 (s, 2H), 9.36 (s, 1H), 8.38 (d, J=9.5 Hz, 1H), 8.33 (br s, 1H), 7.97 (d, J=8.0 Hz, 1H), 7.87 (s, 1H), 7.81 (d, J=8.0 Hz, 2H), 7.71 (d, J=9.5 Hz, 1H), 7.49 (d, J=8.0 Hz, 2H), 7.17 (d, J=8.0 Hz, 1H), 4.34 (s, 2H), 3.21 (t, J=5.0 Hz, 2H), 3.18-3.12 (m, 2H). $^{13}C$ NMR (126 MHz, DMSO-$d_6$) δ 159.9, 148.5, 147.9, 147.8, 141.7, 140.7, 137.8, 135.0, 134.3, 131.8, 126.1, 124.0, 119.7, 114.9, 54.7, 52.2, 36.6. ESIMS m/z (rel. intensity) 303 (MH$^+$, 100). FIRMS calcd for $C_{19}H_{19}N_4$, 303.1610. found, 303.1603.

Example 33

3-(2-(((2-Aminoquinolin-7-yl)methyl)amino)ethyl) benzonitrile Dihydrochloride (2)

Prepared from aldehyde 8 (0.065 g, 0.30 mmol) and phenethylamine 10 (0.061 g, 0.33 mmol), using General Procedure, Step 1. After concentration, reduction with $NaBH_4$ (0.016 g, 0.42 mmol), and workup, the secondary amine was protected with $Boc_2O$ (0.072 g, 0.33 mmol), following General Procedure, Step 2. Workup and purification by flash column chromatography, eluting with a gradient of 5% EtOAc in $CH_2Cl_2$ to 30% EtOAc in $CH_2Cl_2$, afforded the protected intermediate 12 (0.120 g, 89%). This was immediately reacted with $K_2CO_3$ (0.078 g, 0.54 mmol) following General Procedure, Step 3. Following workup and purification by flash column chromatography ($SiO_2$), eluting with a gradient of EtOAc to 5% MeOH in EtOAc, the protected amine was deprotected using General Procedure, Step 4, to give the title compound as a white solid (0.076 g, 75%): mp 268-269° C. (softens), 290-293° C. (melts). $^1H$ NMR (500 MHz; DMSO-$d_6$): δ 14.52 (s, 1H), 9.72 (s, 2H), 9.31 (br s, 1H), 8.38 (d, J=9.3 Hz, 1H), 8.30 (br s, 1H), 7.97 (d, J=8.2 Hz, 1H), 7.87 (s, 1H), 7.78 (s, 1H), 7.74 (dt, J=7.7, 1.3 Hz, 1H), 7.68 (dd, J=8.2, 1.0 Hz, 1H), 7.64 (d, J=8.0 Hz, 1H), 7.56 (t, J=7.7 Hz, 1H), 7.15 (d, J=9.3 Hz, 1H), 4.34 (s, 2H), 3.24-3.23 (m, 2H), 3.11 (t, J=7.9 Hz, 2H). $^{13}C$ NMR (126 MHz; DMSO-$d_6$): δ 154.7, 142.6, 138.9, 136.4, 133.9, 132.3, 130.7, 129.8, 129.1, 126.5, 120.9, 118.83, 118.74, 114.5, 111.5, 49.5, 47.1, 30.8; one of the quinoline carbons is not visible due to baseline broadening. ESIMS m/z (rel. intensity) 303 (MH$^+$, 100). HRMS calcd for $C_{19}H_{19}N_4$, 303.1610. found, 303.1602.

Example 34

7-(((3-(5-Fluoropyridin-3-yl)propyl)amino)methyl) quinolin-2-amine Trihydrochloride (3)

Prepared from aldehyde 8 (0.065 g, 0.30 mmol) and phenpropylamine 17 (0.082 g, 0.36 mmol), using General Procedure, Step 1. After concentration, reduction with $NaBH_4$ (0.017 g, 0.45 mmol), and workup, the secondary amine was protected with $Boc_2O$ (0.072 g, 0.33 mmol), following General Procedure, Step 2. Workup and purification by flash column chromatography, eluting with an isocratic gradient of EtOAc, afforded the protected intermediate 18 (0.108 g, 79%). This was immediately reacted with $K_2CO_3$ (0.066 g, 0.48 mmol) following General Procedure, Step 3. Following workup, the protected amine was deprotected using General Procedure, Step 4, to give the title compound as a white solid (0.039 g, 40%): mp 236-237° C. $^1H$ NMR (500 MHz; DMSO-$d_6$): δ 14.60 (s, 1H), 9.80 (s, 2H), 9.43 (s, 1H), 8.57 (s, 1H), 8.46 (s, 1H), 8.38 (d, J=9.5 Hz, 1H), 8.35 (br s, 1H), 7.96 (d, J=8.0 Hz, 1H), 7.87 (s, 1H), 7.85 (s, 1H), 7.73 (d, J=8.0 Hz, 1H), 7.19 (d, J=9.5 Hz, 1H), 4.30 (t, J=5.5 Hz, 2H), 2.97-2.87 (m, 2H), 2.80 (t, J=7.5 Hz, 2H), 2.10-2.04 (m, 2H); the pyridinium proton is broadened into residual water and appears as a broad hump at 5.29 ppm. $^{13}C$ NMR (126 MHz; DMSO-$d_6$): δ (160.7+158.7, 1C), 155.2, 144.9, 143.1, 140.0, 137.2, 135.8, (134.8+134.6, 1C), 129.5, 127.0, (125.4+125.3, 1C), 121.3, 119.1, 115.0, 49.8, 46.2, 28.9, 26.7. ESIMS m/z (rel. intensity) 311 (MH$^+$, 100). FIRMS calcd for $C_{18}H_{20}FN_4$, 311.1672. found, 311.1669.

Example 35

4-(2-(((2-Aminoquinolin-7-yl)methyl)amino)ethyl)-2-methylbenzonitrile Dihydrochloride (4)

Prepared from aldehyde 8 (0.037 g, 0.17 mmol) and phenethylamine 27 (0.040 g, 0.20 mmol), using General Procedure, Step 1. After concentration, reduction with $NaBH_4$ (0.010 g, 0.26 mmol), and workup, the secondary amine was protected with $Boc_2O$ (0.041 g, 0.19 mmol), following General Procedure, Step 2. Workup and purification by flash column chromatography, eluting with a gradient of $CH_2Cl_2$ to 15% EtOAc in $CH_2Cl_2$, afforded the protected intermediate 29 (0.043 g, 55%). This was immediately reacted with $K_2CO_3$ (0.026 g, 0.19 mmol) following General Procedure, Step 3. Following workup, the protected amine was deprotected using General Procedure, Step 4, to give the title compound as a white solid (0.019 g, 54%): mp 316-317° C. $^1H$ NMR (500 MHz; DMSO-$d_6$): δ 14.43 (s, 1H), 9.65 (s, 2H), 9.24 (s, 1H), 8.38 (d, J=9.0 Hz, 1H), 8.28 (br s, 1H), 7.98 (d, J=8.0 Hz, 1H), 7.86 (s, 1H), 7.74 (d, J=8.0 Hz, 1H), 7.65 (d, J=8.0 Hz, 1H), 7.37 (s, 1H), 7.29 (d, J=8.0 Hz, 1H), 7.14 (d, J=9.0 Hz, 1H), 4.35 (s, 2H), 3.26-3.17 (m, 2H), 3.12-3.08 (m, 2H), 2.47 (s, 3H). $^{13}C$ NMR (126 MHz; DMSO-$d_6$): δ 154.6, 152.5, 143.7, 137.7, 135.8, 133.0, 130.3, 126.8, 121.7, 119.6, 119.3, 113.7, 110.2, 49.8, 47.4, 31.9, 19.5; three of the aminoquinoline carbons are not visible due to baseline broadening. ESIMS m/z (rel. intensity) 317 (MH$^+$, 100). HRMS calcd for $C_{20}H_{21}N_4$, 317.1766. found, 317.1759.

Example 36

4-(2-(((2-Aminoquinolin-7-yl)methyl)amino)ethyl)-2-chlorobenzonitrile Dihydrochloride (5)

Prepared from aldehyde 8 (0.029 g, 0.13 mmol) and phenethylamine 28 (0.035 g, 0.16 mmol), using General Procedure, Step 1. After concentration, reduction with NaBH$_4$ (0.008 g, 0.20 mmol), and workup, the secondary amine was protected with Boc$_2$O (0.031 g, 0.14 mmol), following General Procedure, Step 2. Workup and purification by flash column chromatography, eluting with a gradient of 5% EtOAc in CH$_2$Cl$_2$ to 35% EtOAc in CH$_2$Cl$_2$, afforded the protected intermediate 30 (0.046 g, 72%). This was immediately reacted with K$_2$CO$_3$ (0.027 g, 0.19 mmol) following General Procedure, Step 3. Following workup, the protected amine was deprotected using General Procedure, Step 4, to give the title compound as a cream-colored solid (0.022 g, 56%): mp 309-311° C. $^1$H NMR (500 MHz; DMSO-d$_6$): δ 14.37 (s, 1H), 9.58 (s, 2H), 9.24 (br s, 1H), 8.38 (d, J=8.0 Hz, 1H), 8.24 (br s, 1H), 8.02-7.94 (m, 2H), 7.85 (s, 1H), 7.77 (s, 1H), 7.64 (d, J=8.0 Hz, 1H), 7.49 (dd, J=9.0 Hz, 1.5 Hz, 1H), 7.14 (d, J=9.0 Hz, 1H), 4.39-4.32 (m, 2H), 3.28 (s, 2H), 3.17-3.12 (m, 2H). $^{13}$C NMR (126 MHz; DMSO-d$_6$): δ 155.1, 145.9, 143.2, 135.9, 135.2, 130.8, 129.6, 129.2, 126.9, 121.5, 119.3, 116.5, 115.0, 110.8, 60.1, 47.1, 31.6; two of the aminoquinoline carbons are not visible due to baseline broadening. ESIMS m/z (rel. intensity) 337/339 (MH$^+$, 100/35). FIRMS calcd for C$_{19}$H$_{18}$ClN$_4$, 337.1220. found, 337.1218.

Example 37

4-(2-(((2-Amino-4-methylquinolin-7-yl)methyl)amino)ethyl)benzonitrile Dihydrochloride (6)

Prepared from aldehyde 36 (0.060 g, 0.26 mmol) and 4-cyano-phenethylamine hydrochloride (9, 0.058 g, 0.32 mmol), using General Procedure, Step 1. After concentration, reduction with NaBH$_4$ (0.015 g, 0.39 mmol), and workup, the secondary amine was protected with Boc$_2$O (0.063 g, 0.29 mmol), following General Procedure, Step 2. Workup and purification by flash column chromatography, eluting with a gradient of CH$_2$Cl$_2$ to 12% EtOAc in CH$_2$Cl$_2$, afforded the protected intermediate 37 (0.071 g, 62%). This was immediately reacted with K$_2$CO$_3$ (0.044 g, 0.32 mmol) following General Procedure, Step 3. Following workup, the protected amine was deprotected using General Procedure, Step 4, to give the title compound as a white solid (0.029 g, 47%): mp 304-306° C. $^1$H NMR (500 MHz; DMSO-d$_6$): δ 14.28 (s, 1H), 9.73 (s, 2H), 9.11 (br s, 1H), 8.18 (br s, 1H), 8.05 (d, J=8.0 Hz, 1H), 7.85 (s, 1H), 7.82 (d, J=8.0 Hz, 2H), 7.70 (d, J=8.0 Hz, 1H), 7.49 (d, J=8.0 Hz, 2H), 6.98 (s, 1H), 4.35 (s, 2H), 3.27-3.20 (m, 2H), 3.16-3.12 (m, 2H), 2.64 (s, 3H). $^{13}$C NMR (126 MHz; DMSO-d$_6$): δ 154.6, 152.5, 143.7, 136.7, 133.0, 130.3, 126.8, 126.4, 121.7, 119.5, 119.3, 113.7, 110.2, 49.8, 47.4, 31.9, 19.5; one of the aminoquinoline carbons is not visible due to baseline broadening. ESIMS m/z (rel. intensity) 317 (MH$^+$, 100). HRMS calcd for C$_{20}$H$_{21}$N$_4$, 317.1766. found, 317.1761.

Example 38

4-(2-(((2-Amino-4-methylquinolin-7-yl)methyl)amino)ethyl)-2-methylbenzonitrile Dihydrochloride (7)

Prepared from aldehyde 36 (0.059 g, 0.26 mmol) and phenethylamine 27 (0.043 g, 0.31 mmol), using General Procedure, Step 1. After concentration, reduction with NaBH$_4$ (0.015 g, 0.39 mmol), and workup, the secondary amine was protected with Boc$_2$O (0.063 g, 0.29 mmol), following General Procedure, Step 2. Workup and purification by flash column chromatography, eluting with a gradient of CH$_2$Cl$_2$ to 15% EtOAc in CH$_2$Cl$_2$, afforded the protected intermediate 38 (0.031 g, 25%). This was immediately reacted with K$_2$CO$_3$ (0.031 g, 0.13 mmol) following General Procedure, Step 3. Following workup, the protected amine was deprotected using General Procedure, Step 4, to give the title compound as a white solid (0.019 g, 86%): mp 300-301° C. $^1$H NMR (500 MHz; DMSO-d$_6$): δ 14.15 (s, 1H), 9.58 (s, 2H), 9.02 (br s, 1H), 8.20 (br s, 1H), 8.05 (d, J=7.5 Hz, 1H), 7.82 (s, 1H), 7.75 (d, J=8.0 Hz, 1H), 7.65 (br s, 1H), 7.37 (s, 1H), 7.29 (d, J=8.0 Hz, 1H), 6.95 (s, 1H), 4.35 (s, 2H), 3.26-3.15 (m, 2H), 3.07 (t, J=9.0 Hz, 2H), 2.63 (s, 3H), 2.47 (s, 3H). $^{13}$C NMR (126 MHz; DMSO-d$_6$): δ 143.4, 142.3, 133.3, 131.2, 127.5, 126.3, 121.9, 118.4, 113.7, 110.6, 49.9, 47.4, 31.8, 20.4, 19.4; four of the lepidine carbons and two of the aryl carbons are not visible due to baseline broadening. ESIMS m/z (rel. intensity) 331 (MH$^+$, 100). FIRMS calcd for C$_{21}$H$_{23}$N$_4$, 331.1922. found, 331.1924.

Example 39

3-(2-Aminoethyl)benzonitrile Hydrochloride (10)

A 5 mL sealable microwave vial was charged with compound 13 (0.300 g, 1 mmol), potassium ferricyanide (0.211 g, 0.66 mmol), Buchwald t-BuXPhos Pd G3 (28 mg, 3 mol %), and t-BuXPhos (12.7 mg, 3 mol %), the vial was sealed, evacuated, and backfilled with argon 3×, and 2.5 mL each anhydrous dioxane and 0.1 M KOAc in H$_2$O (degassed and purged with argon) were added. The reaction mixture was heated to 100° C. for 70 min and cooled, and the reaction mixture was partitioned between EtOAc and H$_2$O (10 mL each). (Senecal, T. D.; Shu, W.; and Buchwald, S. L. A general, practical palladium-catalyzed cyanation of (hetero) aryl chlorides and bromides. Angew. Chem. Int. Ed. 2013, 52, 10035-10039.) The aqueous layer was extracted with EtOAc (3×10 mL), and the organic layers were washed with H$_2$O and sat. aq. NaCl (30 mL each), dried over anhydrous sodium sulfate, and concentrated. The resulting oil was purified by flash column chromatography, eluting with a gradient of 5% EtOAc in hexanes to 50% EtOAc in hexanes to yield a clear syrup (14): $^1$H NMR (500 MHz; CDCl$_3$): δ 8.51 (s, 1H), 8.48 (d, J=6.2 Hz, 1H), 6.96 (d, J=6.2 Hz, 1H), 4.82 (br s, 1H), 4.22-4.21 (m, 2H), 4.02 (s, 3H), 1.47 (s, 9H). The syrup was taken up in ether (10 mL), and methanolic HCl (3 M, 1.5 mL, 4 mmol) wad added. The mixture was stirred 18 h at r.t., and a white solid was filtered from solution. Concentration of the filtrate and precipitation of the residue (from hot MeOH/ether) yielded additional product, and, in total, the desired compound was obtained as a white solid (0.149 g, 82%): mp 214-216.5° C. $^1$H NMR (500 MHz; DMSO-d6): δ 7.99 (br s, 3H), 7.78-7.77 (m, 1H), 7.74 (dt, J=7.7, 1.4 Hz, 1H), 7.64-7.62 (m, 1H), 7.55 (t, J=7.7 Hz, 1H), 3.11-3.06 (m, 2H), 2.95 (t, J=7.7 Hz, 2H). $^{13}$C NMR (126 MHz; DMSO): δ 139.0, 133.9, 132.4, 130.6, 129.7, 118.8, 111.5, 32.3; one methylene carbon is not visible due to overlap with the solvent peak.

Example 40

3-(5-Fluoropyridin-3-yl)propan-1-amine Dihydrochloride (17)

Prepared from 3-bromo-5-fluoropyridine (15, 0.352 g, 2.0 mmol), N-Boc-propargylamine (0.310, 2.0 mmol), triphenylphosphine (0.142 g, 0.54 mmol), CuI (0.0076 g, 2 mol %), and Pd(PPh$_3$)$_2$Cl$_2$ (0.0325, 2.5 mol %), using General Procedure, Step 1. After workup and concentration, purification by flash column chromatography (SiO$_2$), eluting with a gradient of hexanes to 20% EtOAc in hexanes yielded alkyne 16 as a yellow oil (0.317 g, 63%): $^1$H NMR (500 MHz; CDCl$_3$): δ 8.43 (s, 1H), 8.37 (s, 1H), 7.40-7.37 (m, 1H), 5.06 (s, 1H), 4.22-4.08 (m, 2H), 1.45 (s, 9H), 1.42-1.37 (m, 2H). This was immediately hydrogenated following General Procedure, Step 2. Filtration afforded the alkane, which was subsequently deprotected following General Procedure, Step 2 to afford the desired product as a brown solid (0.230 g, 80%): mp 86-88° C. $^1$H NMR (500 MHz; DMSO-d$_6$): δ 8.68 (s, 1H), 8.54 (s, 1H), 8.23 (s, 3H), 8.04 (d, J=10.0 Hz, 1H), 7.55 (br s, 1H), 2.84-2.73 (m, 4H), 1.97-1.91 (m, 2H). $^{13}$C NMR (126 MHz; DMSO-d$_6$): δ (165.5+163.5, 1C), (148.5+148.3, 1C), (145.65+145.62, 1C), (138.5+138.3, 1C), 131.8, 43.0, 33.5, 33.0. ESIMS m/z (rel. intensity) 155 (MH$^+$, 78).

Example 41

2-(4-Bromo-3-chlorophenyl)acetonitrile (22)

Compound 20 (1.85 g, 8.37 mmol) was diluted with CH$_2$Cl$_2$ (20 mL) and cooled to 0° C. Triphenylphosphine (2.41 g, 9.21 mmol) followed by CBr$_4$ (3.06 g, 9.21 mmol) were added to the solution while stirring. The mixture was warmed to room temperature and stirred for 6 h. The orange solution was concentrated and then diluted with CH$_2$Cl$_2$ (70 mL) and H$_2$O (70 mL). Tetrabutylammonium bromide (0.135 g, 0.42 mmol) and KCN (2.90 g, 44.6 mmol) were added while stirring. The biphasic solution was stirred at room temperature for 48 h, the phases were separated and the aqueous phase was extracted with CH$_2$Cl$_2$ (5×50 mL). (Brown, W.; Johnstone, S.; Larecque, D. Benzimidiazole Derivatives as Vanilloid Receptor Antagonists, Their Preparation, Pharmaceutical Compositions, and Use in Therapy. WO2008/018827, Feb. 14, 2008.) The organics were combined, dried with anhydrous sodium sulfate, concentrated, and purified by flash column chromatography (SiO$_2$), eluting with a gradient of 5% EtOAc in hexanes to 25% EtOAc in hexanes to yield the desired compound as an orange solid (1.48 g, 77%): mp 43-45° C. $^1$H NMR (500 MHz; CDCl$_3$): δ 7.63 (d, J=8.0 Hz, 1H), 7.44 (d, J=2.0 Hz, 1H), 7.11 (dd, J=8.0, 2.0 Hz, 1H), 3.71 (s, 2H). $^{13}$C NMR (126 MHz; CDCl$_3$): δ 135.4, 134.4, 130.7, 129.8, 127.4, 122.4, 116.7, 23.0. This intermediate does not ionize well under the described ESIMS conditions.

Example 42 tert-Butyl (4-bromo-3-methylphenethyl)carbamate (23)

Compound 21 (1.00 g, 4.78 mmol) was diluted in anhydrous THF (5 mL) and cooled to 0° C. (Compound 21 was prepared according to the procedure of Charrier, J.-D.; Binch, H. M., Hurley, D. J.; Cleveland, T.; Joshi, P.; Fanning, L. T. D.; Pinder, J.; O'Donnell, M.; Virani, A. N.; Knegtel, R. M. A.; Durrant, S. J.; Young, S. C.; Pierre-Henri; Kay, D. Reaper, P. M. Compounds Useful as Inhibitors of ATR Kinase. WO2011/143426, Nov. 17, 2011.) Borane-THF (1 M in THF, 14.3 mL) was added dropwise white stirring at 0° C. The mixture was heated to 75° C. for 8.5 h, cooled to room temperature and 10% NaOH (30 mL) was added. (Runyon, S. P.; Mosier, P. D.; Roth, B. L.; Glennon, R. A.; Westkaemper, R. B. Potential Modes of Interaction of 9-Aminomethyl-9,10-dihydroanthracene (AMDA) Derivatives with the 5-HT2A Receptor: A Ligand Structure-Affinity Relationship, Receptor Mutagenesis and Receptor Modeling Investigation. J. Med. Chem. 2008, 51, 6808-6828.) The solution was extracted with CH$_2$Cl$_2$ (3×40 mL), and the organics were combined, dried with anhydrous sodium sulfate, concentrated, and diluted in anhydrous THF (75 mL). Boc$_2$O (1.15 g, 5.26 mmol) was added and the mixture was stirred at room temperature for 16 h. The clear solution was concentrated and purified by flash column chromatography (SiO$_2$), eluting with a gradient of hexanes to 15% EtOAc in hexanes to yield the desired product as a white solid (0.902 g, 60%): mp 44-46° C. $^1$H NMR (500 MHz; CDCl$_3$): δ 7.44 (d, J=8.0 Hz, 1H), 7.06 (s, 1H), 6.87 (d, J=8.0 Hz, 1H), 4.52 (s, 1H), 3.34 (br s, 2H), 2.72 (br s, 2H), 2.37 (s, 3H), 1.44 (s, 9H). $^{13}$C NMR (126 MHz; CDCl$_3$): δ 155.8, 138.2, 137.9, 132.4, 131.4, 127.8, 122.7, 79.3, 41.6, 35.6, 28.4, 22.9. ESIMS m/z (rel. intensity) 336/338 (MNa$^+$, 46/46).

Example 43 tert-Butyl (4-bromo-3-chlorophenethyl)carbamate (24)

Compound 22 (1.00 g, 4.33 mmol) was diluted in anhydrous THF (5 mL) and cooled to 0° C. Borane-THF (1 M in THF, 13.0 mL) was added dropwise while stirring at 0° C. The mixture was heated to 75° C. for 16 h, cooled to room temperature and 10% NaOH (30 mL) was added. (See Runyon, supra.) The solution was extracted with CH$_2$Cl$_2$ (3×40 mL), and the organics were combined, dried with anhydrous sodium sulfate, concentrated, and diluted in anhydrous THF (5 mL). Boc$_2$O (1.04 g, 4.76 mmol) was added and the mixture was stirred at room temperature for 16 h. The clear solution was concentrated and purified by flash column chromatography (SiO$_2$), eluting with a gradient of hexanes to 20% EtOAc in hexanes to yield the desired product as a white solid (0.770 g, 53%): mp 97-99. $^1$H NMR (500 MHz; CDCl$_3$): δ 7.53 (d, J=8.0 Hz, 1H), 7.29 (d, J=2.0 Hz, 1H), 6.96 (dd, J=8.0, 2.0 Hz, 1H), 4.53 (br s, 1H), 3.37-3.29 (m, 2H), 2.75 (t, J=6.5 Hz, 2H), 1.44 (s, 9H). $^{13}$C NMR (126 MHz; CDCl$_3$): δ 155.8, 140.0, 134.4, 133.7, 130.7, 128.5, 120.2, 79.5, 41.4, 35.4, 28.4. ESIMS m/z (rel. intensity) 356/358 (MH$^+$, 19/24).

Example 44

4-(2-Aminoethyl)-2-methylbenzonitrile Hydrochloride (27)

Compound 23 (0.274 g, 0.87 mmol), potassium ferricyanide (0.184 g, 0.56 mmol), tBuXPhos (0.011 g, 0.026 mmol) and tBuXPhos Pd G3 (0.0024 g, 0.0035 mmol) were mixed, purged and degassed with argon, and diluted with a solution of anhydrous dioxane (0.75 mL) and KOAc (0.1 N, 0.75 mL) in a BioTage 5 mL microwave vial. The solution was heated at 100° C. for 24 h, cooled, diluted with H$_2$O (20 mL), and extracted with EtOAc (3×25 mL). (See Senecal, supra.) The combined organics were washed with H$_2$O (40 mL) and sat. aq. NaCl (40 mL), dried with anhydrous sodium sulfate, concentrated, and purified by flash column chromatography (SiO$_2$), eluting with a gradient of hexanes to 10% EtOAc in hexanes to yield a clear oil (25), which was immediately dissolved in ether (5 mL). Methanolic HCl (~3 N, 1.5 mL) was added, the solution was stirred at room temperature for 18 h and ether (12 mL) was added. Filtration afforded the desired salt as a white solid (0.070 g, 41%): mp 201-203° C. $^1$H NMR (500 MHz; DMSO-d$_6$): δ 7.93 (br s, 3H), 7.74 (d, J=7.5 Hz, 1H), 7.38 (s, 1H), 7.29 (d, J=7.5 Hz, 1H), 3.07 (t, J=8.5 Hz, 2H), 2.92 (t, J=8.5 Hz, 2H), 2.47 (s, 3H). $^{13}$C NMR (126 MHz; DMSO-d$_6$): δ 143.5, 142.2, 133.2, 131.3, 127.6, 118.5, 110.6, 33.4, 20.9; one methylene carbon is not visible due to overlap with the solvent peak. ESIMS m/z (rel. intensity) 161 (MH$^+$, 21).

Example 45

4-(2-Aminoethyl)-2-chlorobenzonitrile Hydrochloride (28)

Compound 24 (0.200 g, 0.60 mmol) and CuCN (0.106 g, 1.19 mmol) were diluted with DMF (2.5 mL). The resulting mixture was heated at 150° C. for 48 h, cooled to room temperature, diluted with EtOAc (20 mL), and filtered through Celite® S. The resulting filtrate was washed with sat. aq. NaCl (30 mL), the two phases were separated, and the aqueous phase was extracted with EtOAc (3×20 mL). (Baloglu, E.; Bohnert, G. J.; Ghosh, S.; Lobera, M.; Schmidt, D. R.; Sung, L. Isoxazolylmethybensofuranylphenylalkylacetamide Derivatives and Analogs for Use as Retinoid-Related Orphan Receptor Gamma Modulators. WO2013/019653, Feb. 7, 2013.) The organics were combined, dried with anhydrous sodium sulfate, concentrated, and purified by flash column chromatography (SiO$_2$), eluting with a gradient of hexanes to 40% EtOAc in hexanes to yield a white solid (26). This was immediately dissolved in ether (5 mL). Methanolic HCl (~3 N, 1.5 mL) was added, the solution was stirred at room temperature for 18 h and concentrated. The crude amine was confirmed by TLC and ninhydrin staining and used without further characterization.

Example 46

7-Bromo-4-methylquinoline (32)

Iron (III) chloride hexahydrate (11.4 g, 42 mmol) and 3-bromoaniline (31, 6.88 g, 40 mmol) were diluted with glacial AcOH (100 mL) and the mixture was heated to 60° C. until all the solids were dissolved (approximately 15 min). Methyl vinyl ketone (approximately 4 mL, 44 mmol) was added dropwise over 5 min, and the mixture was heated to reflux for 90 min, upon which a white solid formed. (Kawashima, K. et al. Preparation of novel cyclic compounds having a quinolinylalkylthio group. US Pat. Appl. Publ. 20080021064, 24 Jan. 2008.) The mixture was then cooled to r.t. and the solid was filtered from solution. The filtered solid was washed with EtOAc until the filtrate ran colorless and clear. The filtrate was discarded, and the solid was diluted in EtOAc (100 mL), and 1 M NaOH was added until the solids dissolved. The layers were separated, and the aqueous layer was extracted with EtOAc (3×100 mL). The organic phase was washed with H$_2$O (2×100 mL) and sat. aq. NaCl (100 mL). The combined organic layers were dried over anhydrous sodium sulfate and filtered through a pad of Celite to remove impurities. The solution was concentrated to $^1$/$_{10}$$^{th}$ of its original volume and re-filtered through Celite to yield a yellow solution. Concentration afforded the desired product as a grey-green crystalline solid (3.7 g, 42%). $^1$H NMR (500 MHz; DMSO-d$_6$): δ 8.78 (d, J=4.5 Hz, 1H), 8.33 (d, J=1.5 Hz, 1H), 7.88 (d, J=9.0 Hz, 1H), 7.67 (dd, J=9.0, 1.5 Hz, 1H), 7.28 (d, J=4.5 Hz, 1H), 2.72 (s, 3H).

Example 47

7-Bromo-4-methylquinoline N-Oxide (33)

Compound 32 (3.7 g, 16.7 mmol) was diluted in anhydrous CH$_2$Cl$_2$ (65 mL), and m-CPBA (4.03 g, 23.4 mmol) was added in small portions. The mixture was stirred at r.t. for 1 h, and then 1 M NaOH (60 mL) was added. The layers were separated, and the aqueous layer was extracted with CH$_2$Cl$_2$ (4×75 mL). The organic layers were washed with sat. aq. NaHCO$_3$ (100 mL) and sat. aq. NaCl (100 mL), dried over anhydrous sodium sulfate, and concentrated. The residue was diluted in minimal CH$_2$Cl$_2$ and excess hexane was added to precipitate the desired product as a yellow crystalline solid (3.7 g, 93%). $^1$H NMR (500 MHz; DMSO-d$_6$): δ 9.01 (d, J=2.0 Hz, 1H), 8.48 (d, J=6.0 Hz, 1H), 7.86 (d, J=9.0 Hz, 1H), 7.79 (dd, J=9.0, 2.0 Hz, 1H), 7.18 (d, J=6.0 Hz, 1H), 2.69 (s, 3H).

Example 48

2-Amino-7-bromo-4-methylquinoline (34)

Compound 33 (1.43 g, 6 mmol) was diluted in 2:1 PhCF$_3$:CH$_2$Cl$_2$ (45 mL), t-butylamine (3.15 mL, 30 mmol) was added, and the mixture was cooled to 0° C. Ts$_2$O (3.9 g, 12 mmol) was added in portions and the mixture was stirred for 10 min, upon which another 0.6 mL t-butylamine and ~1 g Ts$_2$O was added. After a total of 20 minutes, trifluoracetic acid (14 mL) was added, and the mixture was heated to 75° C. for 6 h. The mixture was cooled and concentrated to an oil, which was diluted with H$_2$O, and 1 N NaOH was added until the pH of the resulting suspension was approximately 10. The suspension was extracted with EtOAc (2×100 mL), and the organic layers were washed with H$_2$O and sat. aq. NaCl (100 mL each). (Yin, J.; Xiang, B.; Huffman, M. A.; Raab, C. E.; and Davies, I. W. A General and Efficient 2-Amination of Pyridines and Quinolines. *J. Org. Chem.* 2007, 72, 4554-4557.) The solution was dried over anhydrous sodium sulfate, concentrated, and the resulting residue was purified by flash column chromatography (SiO$_2$), eluting with a gradient of 50% EtOAc in CH$_2$Cl$_2$ to EtOAc to yield the product as a reddish-tan solid (0.932 g, 65%) after washing with hexanes and drying. The product was used crude without further purification.

Example 49

2-(Acetamido)-7-bromo-4-methylquinoline (35)

Compound 34 (0.932 g, 3.93 mmol) was diluted with anhydrous THF (25 mL) and N-acetylimidazole (0.562 g, 5.11 mmol) and a catalytic amount of DMAP were added. The mixture was heated at reflux for 18 h, cooled, and concentrated. The residue was partitioned between EtOAc (50 mL) and H$_2$O (50 mL), the layers were separated, and the aqueous layer was extracted with EtOAc (4×50 mL). The organic phase was washed with H$_2$O (50 mL) and sat. aq. NaCl (50 mL), dried over anhydrous sodium sulfate, and concentrated. The residue was diluted in hot EtOAc (~5 mL) and hexanes (100 mL) was added to precipitate a pale-blue microcrystalline solid. The product was used crude without further purification.

Example 50

2-(Acetamido)-7-formyl-4-methylquinoline (36)

An oven-dried microwave vial was charged with compound 35 (0.502 g, 1.8 mmol), Pd(OAc)$_2$ (0.012 g), dppb (0.036 g), N-formylsaccharin (0.570 g), and anhydrous Na$_2$CO$_3$ (0.288 g). The vial was sealed, vacuum evacuated, and backfilled with argon (5×). Degassed, anhydrous DMF (10 mL) containing Et$_3$SiH (372 µL) was added, and the mixture was heated to 75° C. for 18 h. The solution was cooled and diluted with 1:1 H$_2$O/sat. aq. NaCl (100 mL) and the suspension was extracted with EtOAc (3×70 mL). (Ueda, T.; Konishi, H.; and Manabe, K. Palladium-Catalyzed Reductive Carbonylation of Aryl Halides with N-Formylsaccharin as a CO Source. *Angew. Chem. Int. Ed.* 2013, 52, 8611-8615.) The organic layer was washed with 5% aq. NaCl (50 mL) and sat. aq. NaCl (50 mL) and dried over anhydrous sodium sulfate. The solution was concentrated and the residue was purified by flash column chromatography, eluting with a gradient of 5% EtOAc in CH$_2$Cl$_2$ to 40% EtOAc in CH$_2$Cl$_2$ to yield the product as a flocculent white solid after washing with hexanes and drying. The product was used crude without purification.

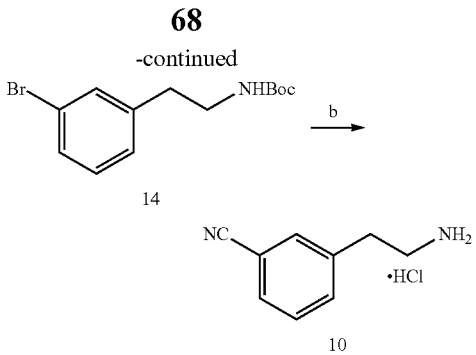

$^a$Reagents and conditions: (a) Boc$_2$O, THF, r.t.; (b) (i) Potassium Ferricyanide, Buchwald t-BuXPhos, Dioxane, KOAc (0.1M in H$_2$O), reflux, (ii) MeOH/HCl, r.t. (after isolation).

Scheme 15$^a$

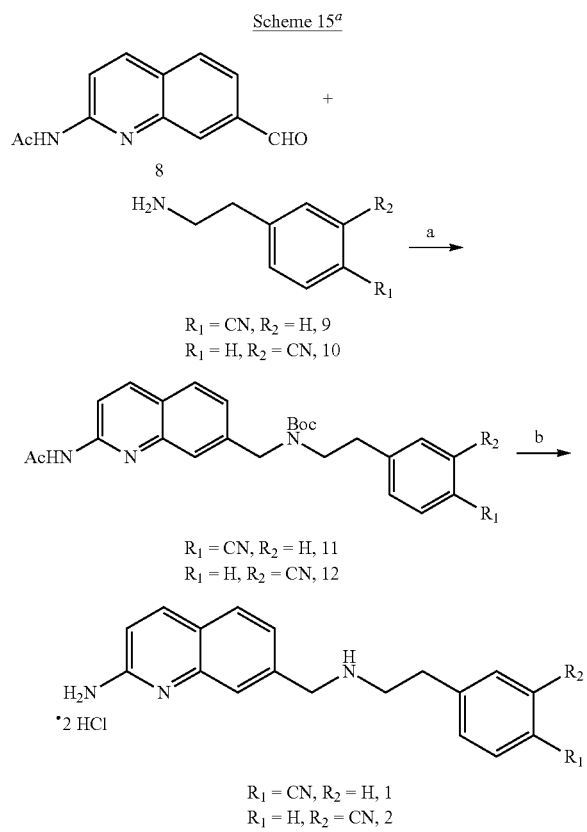

$^a$Reagents and conditions: (a) (i) AcOH, Na$_2$SO$_4$, CHCl$_3$, r.t., (ii) NaBH$_4$, MeOH, 0° C.->r.t., (iii) Boc$_2$O, THF, r.t.; (b) (i) K$_2$CO$_3$, MeOH, reflux, (ii) MeOH/HCl, r.t. (after isolation).

Scheme 16$^a$

Scheme 17$^a$ $^a$Reagents and conditions: (a) N-Boc-Propargylamine, CuI, PPh$_3$, Pd(PPh$_3$)$_2$Cl$_2$, Et$_3$N, 90° C.; (b) (i) H$_2$, Pd/C, MeOH, r.t., (ii) MeOH/HCl, r.t. (after isolation); (c) (i) 8, AcOH, Na$_2$SO$_4$, CHCl$_3$, r.t., (ii) NaBH$_4$, MeOH, 0° C.->r.t., (iii) Boc$_2$O, THF, r.t.; (d) (i) K$_2$CO$_3$, MeOH, reflux, (ii) MeOH/HCl, r.t. (after isolation).

Scheme 18$^a$

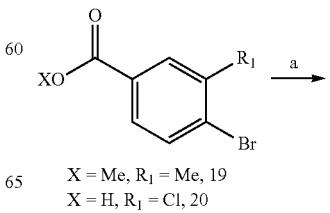

X = Me, R$_1$ = Me, 19
X = H, R$_1$ = Cl, 20

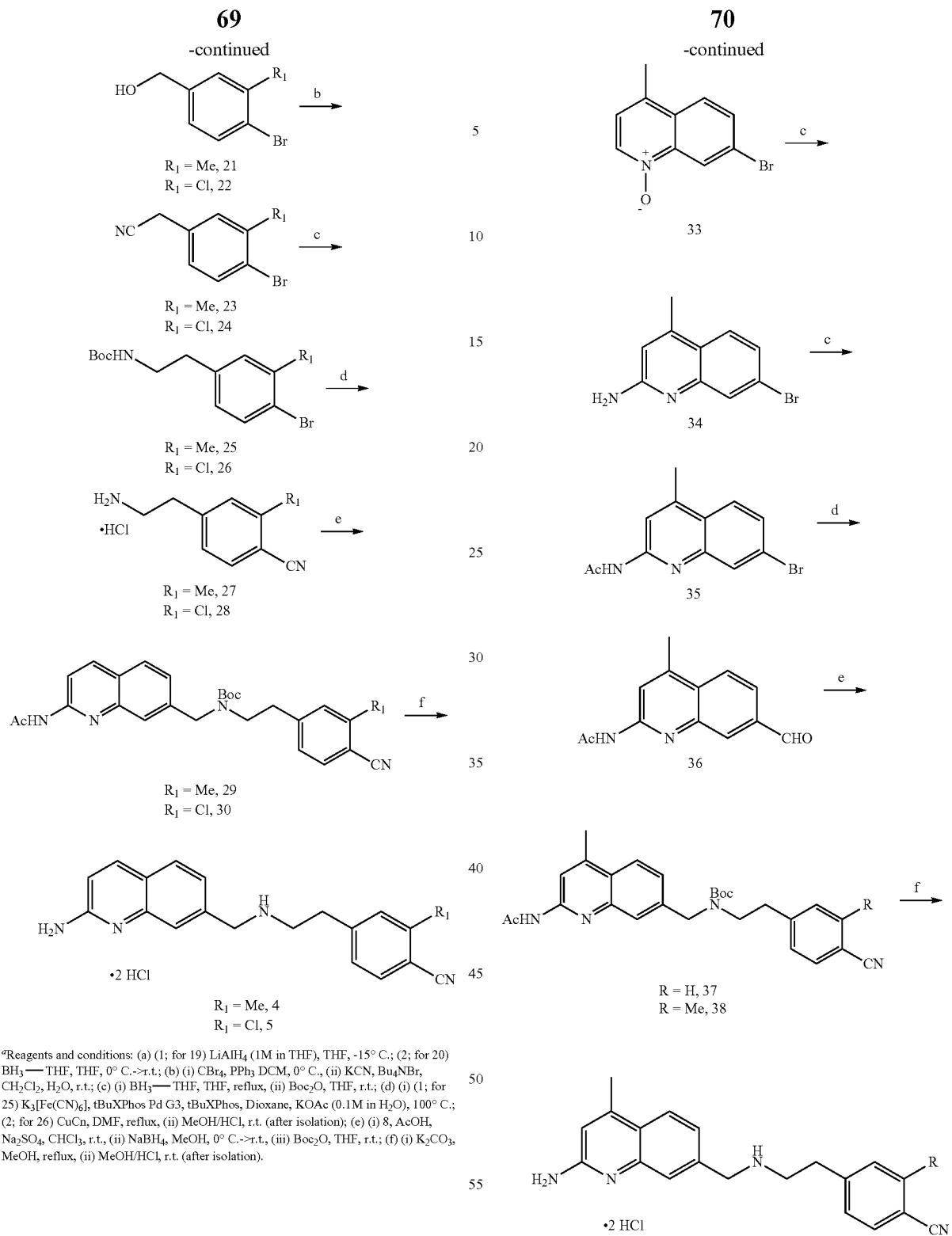
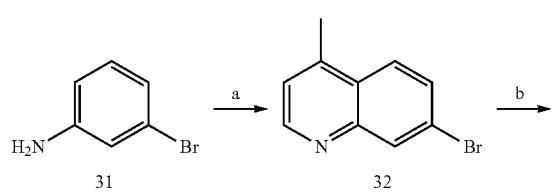
Scheme 19[a]

Inhibition Data,

TABLE 4

Inhibition of NOS enzymes by hydrophilic aminoquinoline analogues

| | $K_i$ (μM) | | | Selectivity | |
|---|---|---|---|---|---|
| Compound | nNOS | iNOS | eNOS | n/i | n/e |
| 1 (Ex. 32) | 0.037 | 21.3 | 0.581 | 575 | 16 |
| 2 (Ex. 33) | 0.041 | 25.0 | 0.273 | 609 | 7 |
| 3 (Ex. 34) | 0.216 | 84.2 | NA | 390 | NA |
| 4 (Ex. 35) | 0.021 | 10.3 | NA | 492 | NA |
| 5 (Ex. 36) | 0.031 | 5.15 | NA | 166 | NA |
| 6 (Ex. 37) | 0.019 | 4.70 | NA | 247 | NA |
| 7 (Ex. 38) | 0.025 | 4.83 | NA | 193 | NA |

TABLE 5

Inhibition of rat and human nNOS by novel analogues

| | $K_i$ (μM) | | Selectivity |
|---|---|---|---|
| Compound | Rat nNOS | Human nNOS | (Rat/Human) |
| 1 (Ex. 32) | 0.037 | 0.032 | 0.86 |
| 3 (Ex. 34) | 0.216 | 0.164 | 0.75 |
| 4 (Ex. 35) | 0.021 | 0.020 | 0.95 |
| 5 (Ex. 36) | 0.031 | 0.021 | 0.68 |
| 6 (Ex. 37) | 0.019 | 0.052 | 2.7 |
| 7 (Ex. 38) | 0.025 | 0.030 | 1.2 |

TABLE 6

Inhibition of human nNOS and eNOS by select compounds

| | $K_i$ (μM) | | Selectivity |
|---|---|---|---|
| Compound | Human nNOS | Human eNOS | (hn/he) |
| 4 (Ex. 35) | 0.020 | 2.08 | 104 |
| 6 (Ex. 37) | 0.052 | 5.79 | 111 |

Example 51

Purified NOS Enzyme Assays

Rat and human nNOS, murine macrophage iNOS, and bovine eNOS were recombinant enzymes, expressed in *E. coli* and purified as previously reported in the literature. To test for enzyme inhibition, the hemoglobin capture assay was used to measure nitric oxide production. The assay was performed at 37° C. in HEPES buffer (100 mM, with 10% glycerol, pH 7.4) in the presence of 10 μM L-arginine. Also included were 100 μM NADPH, 0.83 mM $CaCl_2$, approximately 320 units/mL of calmodulin, 10 μM tetrahydrobiopterin, and human oxyhemoglobin (3 μM). For iNOS, $CaCl_2$ and calmodulin were omitted and replaced with HEPES buffer (as neither are required for activation of iNOS). This assay was performed in 96-well plates using a Synergy 4 BioTek hybrid reader, and the dispensing of NOS enzyme and hemoglobin were automated; after 30 sec (maximum delay), NO production was read by monitoring the absorbance at 401 nm (resulting from the conversion of oxyhemoglobin to methemoglobin). Kinetic readouts were performed for 3 or 5 min. Each compound was assayed at least in duplicate, and nine concentrations (500 nM or 100 nM for eNOS and iNOS; 50 μM to 5 nM for nNOS) were used to construct dose-response curves. $IC_{50}$ values were calculated by non-linear regression using GraphPad Prism software, and $K_i$ values were obtained using the Cheng-Prusoff equation $[K_i=IC_{50}/(1+[S]/K_m)]$ using the following $K_m$ values: 1.3 (rat nNOS), 1.6 (human nNOS), 8.2 (murine macrophage iNOS) and 1.7 μM (bovine eNOS).

Example 52

Inhibitor Complex Crystal Preparation

The nNOS or eNOS heme domain proteins used for crystallographic studies were produced by limited trypsin digest from the corresponding full length enzymes and further purified through a Superdex 200 gel filtration column (GE Healthcare) as described previously. The nNOS heme domain (at 9 mg/mL containing 20 mM histidine), or the eNOS heme domain (at 12 mg/mL containing 2 mM imidazole) were used for the sitting drop vapor diffusion crystallization setup under conditions previously reported. Fresh crystals (1-2 days old) were first passed stepwise through cryoprotectant solutions and then soaked with 10 mM inhibitor for 4-6 h at 4° C. before being flash cooled with liquid nitrogen.

Example 53

X-Ray Diffraction Data Collection, Data Processing, and Structural Refinement

The cryogenic (100 K) X-ray diffraction data were collected remotely at the Stanford Synchrotron Radiation Lightsource (SSRL) or Advanced Light Source (ALS) through the data collection control software Blu-Ice and a crystal mounting robot. When a Q315r CCD detector was used, 90-100° of data were typically collected with 0.5° per frame. If a Pilatus pixel array detector was used, 120-130° of fine-sliced data were collected with 0.2° per frame. Raw CCD data frames were indexed, integrated, and scaled using HKL2000, but the pixel array data were processed with XDS and scaled with Scala. The binding of inhibitors was detected by the initial difference Fourier maps calculated with REFMAC. The inhibitor molecules were then modeled in COOT and refined using REFMAC. Disordering in portions of inhibitors bound in the NOS active sites was often observed, sometimes resulting in poor density quality. However, partial structural features usually could still be visible if the contour level of the sigmaA weighted 2 m|Fo|−D|Fc| map dropped to 0.5 σ, which afforded the building of reasonable models into the disordered regions. Water molecules were added in REFMAC and checked by COOT. The TLS protocol was implemented in the final stage of refinements with each subunit as one TLS group. The omit Fo-Fc density maps were calculated by repeating the last round of TLS refinement with inhibitor coordinate removed from the input PDB file to generate the map coefficients DELFWT and SIGDELFWT. The refined structures were validated in COOT before deposition in the RCSB protein data bank.

Example 54

Caco-2 Permeability Assay

Caco-2 monolayer assays were performed by Apredica, Inc (Watertown, Mass.) using the following standard procedure: Caco-2 cells, grown in tissue culture flasks, were trypsinized, re-suspended, and grown and differentiated in 96-well plates for three weeks; monolayer formation was determined by measuring transport of Lucifer yellow, an impermeable dye. All assays were performed at a concentration of 10 μM for 2 h. For apical to basolateral (A-->B) permeability, compounds were added on the apical side (A), with permeation determined at the receiving (basolateral, B) side, where the receiving buffer was removed for analysis by LC/MS/MS using an Agilent 6410 mass spectrometer (ESI, MRM mode) coupled with an Agilent 1200 HPLC. Buffers used were 100 μM Lucifer yellow in transport buffer (1.98 g/L glucose in 10 mM HEPES, 1×Hank's Balanced Salt Solution, pH 6.5) (apical side) and transport buffer, pH 7.4 (basolateral side). Apparent permeability ($P_{app}$) is expressed using the following equation: $P_{app}=(dQ/dt)/C_0A$, where the numerator is the rate of permeation, $C_0$ is initial concentration, and A is the monolayer area. For bidirectional permeability, the efflux ratio was defined as $P_{app}$ (B-->A)/$P_{app}$ (A-->B); high efflux ratio values (>3) indicate that a compound may be a substrate for P-gp or other active transport systems.

With reference to Schemes 20-27, Tables 7-8 and FIGS. 10-12, below, various other 2-aminoquinoline compounds can be prepared in accordance with procedures provided in Examples 55-126.

Example 55

General Procedures

Anhydrous solvents (THF, $CH_2Cl_2$, MeOH, $Et_3N$, MeCN, and DMF) were distilled prior to use. All other solvents, reactants, and reagents were purchased from commercial vendors and were used without further purification. Methanolic HCl (3 M, for ammonium hydrochloride salt formation and Boc-deprotection) was prepared fresh by the reaction of acetyl chloride and anhydrous MeOH at 0° C. Melting points were determined in capillary tubes using a Buchi melting point B-540 apparatus and are uncorrected. $^1$H-NMR spectra were recorded at 500 MHz, using a Bruker Avance III 500 (direct cryoprobe), and $^{13}$C-NMR spectra were obtained at 126 MHz using the same instrument. Low-resolution ESIMS were obtained on a Bruker AmaZon SL Ion Trap mass spectrometer system. High-resolution mass spectral data were obtained at the Integrated Molecular Structure Education and Research Center (IMSERC, Northwestern University) on an Agilent 6210A TOF mass spectrometer in positive ion mode using electrospray ionization with an Agilent G1312A HPLC pump and an Agilent G1367B autoinjector. Data were processed using MassHunter software version B.04.00. Flash column chromatography was performed using an Agilent 971-FP automated flash purification system with a Varian column station and SiliCycle cartridges (12-80 g, both normal and High Performance). Analytical HPLC was performed using an Agilent Infinity 1260 HPLC system and injection volumes of 5-10 μL. A Phenomenex Luna 5 μm C-8(2) 100 Å column, 50×4.60 mm, was used for all HPLC experiments, using a 10-minute gradient of 95% $H_2O$/5% acetonitrile+0.05% TFA to 95% acetonitrile/5% $H_2O$+0.05% TFA, at 1.5 mL/min. Chiral analytical HPLC was performed using a Chiralpak AD-H 5 μm column, 250×4.60 mm, using 25-min isocratic elution at 5% isopropanol in hexanes, at 1 mL/min. The purity of all final target compounds was found to be 95% by HPLC. Analytical thin-layer chromatography was performed on Silicycle extra-hard 250 μm TLC plates. Compounds were visualized with short-wavelength UV light, and with ninhydrin, $FeCl_3$, CAM, and $KMnO_4$ stains, where appropriate.

Compounds 30, 45, 46, and 51 were prepared by known literature procedures, and their spectral data are consistent with those data reported for them. The preparation of quinoline and lepidine precursors and assembly of final compounds is described in Examples 57-90, while the preparation of phenols and precursors 23-25, 26-29, 55-57, 59-62, 70-73 and 77-82 is described in Examples 91-126.

Abbreviations Used

NO, nitric oxide, nNOS, neuronal nitric oxide synthase; iNOS, inducible nitric oxide synthase; eNOS, endothelial nitric oxide synthase; rnNOS, rat neuronal nitric oxide synthase; hnNOS, human neuronal nitric oxide synthase; heNOS, human endothelial nitric oxide synthase; miNOS, murine inducible nitric oxide synthase, FMN, flavin mononucleotide; $H_4B$, (6R)-5,6,7,8-tetrahydrobiopterin; tPSA, total polar surface area; $P_{app}$, apparent permeability; HEPES, 4-(2-hydroxyethyl)-1-piperazineethanesulfonic acid.

Example 56

General Procedure for Synthesis and Deprotection of Phenyl Ether-Linked Aminoquinolines The procedure is similar to that discussed above and recently reported (Cinelli, M. A.; Li, H.; Pensa, A. V.; Kang, S.; Martásek, P.; Roman, L. J.; Poulos, T. L.; and Silverman, R. B. Phenyl Ether- and Aniline-Containing 2-Aminoquinolines as Potent and Selective Inhibitors of Neuronal Nitric Oxide Synthase. *J. Med. Chem.* 2015, 58 (21) 8694-8712.): sodium hydride (60% suspension in mineral oil, 1 eq.) was diluted with anhydrous DMF (1-2 mL) and cooled to 0° C. under argon. A solution of the required phenol (1 eq.) in anhydrous DMF (1-2 mL) was added slowly to the suspension and stirred at 0° C. for 10-30 min (typically ~25 min), following which bromides 30 or 43 (1 eq.) or chloride 44 (0.90-1 eq.) was added as a solution in anhydrous DMF. If 30 or 43 were employed, the reaction mixture was stirred at 0° C. for 40 min-1 h (typically ~50 min), and if 44 was employed, the reaction mixture was warmed to r.t. and then heated to 50° C. for 45 min-1 h. In both cases, the reaction mixture was then quenched at r.t. by addition of a 1:1 sat. aq. $NaCl/H_2O$ mixture (~15 mL) or a sat. aq. $NaHCO_3$ solution. The mixture was extracted with EtOAc (usually 3×20 mL was sufficient for these lipophilic carbamates) and the organic phase was washed with 5% aq. NaCl (3-4×30-80 mL) and sat aq. NaCl (30-50 mL). The organic layer was dried over anhydrous sodium sulfate, concentrated, and purified by flash column chromatography (12 g $SiO_2$ cartridge), using gradients as described for individual compounds below. The resulting intermediate acetamides were not characterized or purified further, but were diluted with anhydrous MeOH (5-10 mL), and anhydrous $K_2CO_3$ (~2 eq.) was added. The mixture was heated at reflux for 2-2.5, cooled, and concentrated. The resulting residue was partitioned between EtOAc and 1:1 $H_2O$/sat. aq. NaCl, and the aqueous layer was extracted with EtOAc (2-3×5-20 mL). The organic layers were washed with sat. aq. NaCl and dried over anhydrous sodium sulfate. Purification is detailed under subheadings for individual compounds. The free aminoquinoline was diluted in dry ether (or 10:1-4:1 ether/MeOH) or dichloromethane (for 31, 35, and 48) and filtered to remove any particulate matter. To the filtered solution, methanolic HCl (3 M, 1-2 mL) was added, (except for 31, 35, and 48, where 150-300 μL trifluoroacetic acid was added instead) and the mixture was stirred at room temperature either overnight or for 20-30 min (for 31, 35, and 48). The salts were isolated by filtration or precipitation, and the final purification was performed as described below for individual compounds.

Example 57

7-[(3-Chloro-5-((methylamino)methyl)phenoxy)methyl]quinolin-2-amine Dihydrochloride (5)

This compound was prepared from 30 (0.100 g, 0.358 mmol) and phenol 23 (0.097 g, 0.358 mmol). Workup and purification by flash column chromatography, eluting with a gradient of 2% EtOAc in $CH_2Cl_2$ to 35% EtOAc in $CH_2Cl_2$, afforded the intermediate acetamide 31 as a colorless foam (0.138 g, 82%), that was immediately deprotected using $K_2CO_3$ (0.081 g, 0.587 mmol) as described in the General Procedure. After workup, the resulting gum was purified by flash column chromatography, eluting with EtOAc to yield the free aminoquinoline as a semisolid residue that was diluted in 10:1 ether:MeOH (~12 mL) and treated with methanolic HCl (2 mL). After stirring overnight, filtration afforded 5 (0.081 g, 69% from 31) as a white flocculent solid, after precipitating from hot MeOH (1 mL) with ether (5 mL) and washing with ether: mp 298-299° C. $^1$H-NMR (500 MHz; DMSO-$d_6$): δ 14.36 (br s, 1H), 9.31 (br s, 2H), 9.20 (br s, 1H) 8.37 (d, J=9.3 Hz, 1H), 8.30 (br s, 1H), 7.96 (d, J=8.2 Hz, 1H), 7.76 (s, 1H), 7.53 (dd, J=8.2, 1.2 Hz, 1H), 7.30 (t, J=1.7 Hz, 1H), 7.25 (t, J=1.4 Hz, 1H), 7.22 (t, J=2.0 Hz, 1H), 7.10 (d, J=9.3 Hz, 1H), 5.38 (s, 2H), 4.09 (s, 2H), 2.55-2.50 (m, 3H, partially obscured by solvent peak). $^{13}$C-NMR (126 MHz; DMSO-$d_6$): δ 159.2, 154.8, 143.1, 141.7, 135.6, 134.3, 129.4, 124.2, 122.7, 120.8, 116.3, 115.7, 115.4, 114.2, 69.3, 50.7, 32.3; one of the quinoline carbons is not visible due to baseline broadening; ESIMS m/z (rel. intensity) 328/330 (MH$^+$, 100/33); HRMS calcd for $C_{18}H_{19}ClN_3O^+$: 328.1211. found, 328.1215.

Example 58

7-[(3-Bromo-5-((methylamino)methyl)phenoxy)methyl]quinolin-2-amine Dihydrochloride (6)

This compound was prepared from 30 (0.085 g, 0.305 mmol) and phenol 24 (0.096 g, 0.305 mmol). Workup and purification by flash column chromatography, eluting with a gradient of 2% EtOAc in $CH_2Cl_2$ to 35% EtOAc in $CH_2Cl_2$, afforded the intermediate acetamide 32 as an off-white foam (0.110 g, 70%), that was immediately deprotected using $K_2CO_3$ (0.059 g, 0.427 mmol) as described in the General Procedure. After workup, the free aminoquinoline was obtained as a gummy residue that was diluted in 4:1 ether:MeOH and treated with methanolic HCl (2 mL). After stirring overnight, filtration afforded 6 (0.081 g, 84% from 32) as a white flocculent solid, after precipitating from hot MeOH (2 mL) with ether (10 mL) and washing with ether: mp 286-287.5° C. $^1$H-NMR (500 MHz; DMSO-$d_6$): δ 14.32 (br s, 1H), 9.26 (br s, 2H), 9.20 (br s, 1H), 8.37 (d, J=9.3 Hz, 1H), 8.21 (br s, 1H), 7.96 (d, J=8.2 Hz, 1H), 7.76 (s, 1H), 7.53 (dd, J=8.2, 1.0 Hz, 1H), 7.37 (t, J=1.3 Hz, 1H), 7.35 (t, J=2.0 Hz, 1H), 7.34 (t J=1.3 Hz, 1H), 7.10 (d, J=9.3 Hz, 1H), 5.38 (s, 2H), 4.09 (t, J=4.7 Hz, 2H), 2.52-2.50 (m, 3H, partially obscured by solvent peak); $^{13}$C-NMR (126 MHz; DMSO-$d_6$): δ 158.88, 154.51, 142.59, 141.30, 135.56, 129.03, 125.19, 123.77, 122.22, 120.49, 117.81, 116.34, 115.51, 113.83, 68.97, 50.27, 32.00; one of the quinoline carbons is not visible due to baseline broadening; ESIMS m/z (rel. intensity) 372/374 (MH$^+$, 100/100); HRMS calcd for $C_{18}H_{19}BrN_3O^+$: 372.0706. found, 372.0709.

Example 59

7-[(3-Methoxy-5-((methylamino)methyl)phenoxy)methyl]quinolin-2-amine Ditrifluoroacetate (7)

This compound was prepared from 30 (0.054 g, 0.193 mmol) and phenol 25 (0.052 g, 0.193 mmol). Workup and purification by flash column chromatography, eluting with a gradient of 3% EtOAc in $CH_2Cl_2$ to 43% EtOAc in $CH_2Cl_2$, afforded the intermediate acetamide 33 as a pale-yellow foam (0.064 g, 71%), that was immediately deprotected using $K_2CO_3$ (0.038 g, 0.273 mmol) as described in the General Procedure. After workup, the free aminoquinoline was diluted with $CH_2Cl_2$, filtered, and concentrated. The residue was diluted with anhydrous $CH_2Cl_2$ mL) and trifluoroacetic acid (200 µL) was added. The mixture was stirred for 25 min and concentrated, and ether (10 mL) was added to the residue. The mixture was sonicated until a solid formed, which was collected to yield 7 (0.061 g, 81% from 33) as a white solid after precipitating from hot MeOH (1 mL) with ether (10 mL) and washing with ether: mp 130° C. (softens), 156-158° C. (melts). $^1$H-NMR (500 MHz; DMSO-$d_6$): δ 14.16 (br s, 1H), 8.79 (s, 2H), 8.23 (s, 1H), 7.87-7.82 (m, 1H), 7.64 (s, 1H), 7.43 (s, 1H), 6.98-6.97 (m, 1H), 6.76 (t, J=1.5 Hz, 1H), 6.69 (s, 1H), 6.68 (t, J=2.1 Hz, 1H), 5.29 (s, 2H), 4.05 (s, 2H), 3.76 (s, 3H), 2.55 (s, 3H); the aminoquinoline protons are not visible, but are broadened into the baseline and cause an overall broadening of the signals from 7-8 ppm; $^{13}$C-NMR (126 MHz; DMSO-$d_6$): δ 160.6, 159.4, (158.5+158.3+158.0+157.8, 1C), 134.1, 128.6, 121.0, (118.5+116.1, 1C), 113.5, 108.7, 107.9, 101.3, 68.9, 55.4, 51.3, 32.1; several of the aminoquinoline and trifloroacetate carbon signals are not visible due to baseline broadening; ESIMS m/z (rel. intensity) 324 (MH$^+$, 100); FIRMS calcd for $C_{19}H_{22}N_3O_2^+$: 3241707. found, 324.1711.

Example 60

3-[(2-Aminoquinolin-7-yl)methoxy]-5-((methylamino)methyl)benzonitrile Dihydrochloride (8)

This compound was prepared from 30 (0.085 g, 0.305 mmol) and phenol 26 (0.080 g, 0.305 mmol). Workup and purification by flash column chromatography, eluting with a gradient of 5% EtOAc in $CH_2Cl_2$ to 40% EtOAc in $CH_2Cl_2$, afforded the intermediate acetamide 34 as a yellow foam (0 127 g, 90%), that was immediately deprotected using $K_2CO_3$ (0.076 g, 0.551 mmol) as described in the General Procedure. After workup, the free aminoquinoline was purified by flash column chromatography (eluting with a gradient of EtOAc to 2% MeOH in EtOAc), and the resultant white solid was diluted in 4:1 ether:MeOH and treated with methanolic HCl (1.5 mL). After stirring overnight, filtration afforded 8 (0.073 g, 68% from 34) as a white flocculent solid, after precipitating from hot MeOH (2 mL) with ether (10 mL) and washing with ether: mp 304-305° C. (dec). $^1$H-NMR (500 MHz; DMSO-$d_6$): δ 14.24 (br s, 1H), 9.30 (br s, 2H), 9.20 (br s, 1H), 8.37 (d, J=9.2 Hz, 1H), 8.21 (br s, 1H), 7.96 (d, J=8.2 Hz, 1H), 7.76 (s, 1H), 7.67 (t, J=1.8 Hz, 1H), 7.64 (t, J=1.8 Hz, 1H), 7.61 (s, 1H), 7.54 (d, J=7.9 Hz, 1H), 7.09 (d, J=9.3 Hz, 1H), 5.42 (s, 2H), 4.15 (s, 2H), 2.53-2.50 (m, 3H); $^{13}$C-NMR (126 MHz; DMSO-$d_6$): δ $^{13}$C-NMR (126 MHz; DMSO): δ 158.2, 154.5, 142.7, 141.0, 135.3, 129.1, 126.3, 125.1, 123.9, 122.4, 120.6, 118.19, 118.00, 115.6, 113.9, 112.4, 69.2, 50.1, 32.0; ESIMS m/z (rel. intensity) 319 (MH+, 100); HRMS calcd for $C_{19}H_{19}N_4O$: 319.1553+. found, 319.1559.

Example 61

7-[(3-Ethyl-5-((methylamino)methyl)phenoxy)methyl]quinolin-2-amine Ditrifluoroacetate (9)

This compound was prepared from 30 (0.042 g, 0.152 mmol) and phenol 29 (0.041 g, 0.152 mmol). Workup and purification by flash column chromatography, eluting with a gradient of 5% EtOAc in $CH_2Cl_2$ to 30% EtOAc in $CH_2Cl_2$, afforded the intermediate acetamide 35 as a translucent, colorless gum (0.052 g, 74%), that was immediately deprotected using $K_2CO_3$ (0.031 g, 0.224 mmol) as described in the General Procedure. After workup, the free aminoquinoline was diluted with anhydrous $CH_2Cl_2$ (3 mL) and trifluoroacetic acid (150 μL) was added. The mixture was stirred for 15 min and concentrated, and ether (10 mL) was added to the residue. The mixture was stirred until a solid formed, which was collected to yield 9 (0 027 g, 67% from 35) as a white solid after washing with ether: mp 154-156° C. $^1$H-NMR (500 MHz; DMSO-$d_6$): δ 14.23 (br s, 1H), 8.81-8.70 (m, 4H), 8.36 (d, J=9.3 Hz, 1H), 7.95 (d, J=8.2 Hz, 1H), 7.70 (s, 1H), 7.53 (d, J=8.1 Hz, 1H), 7.06 (d, J=9.3 Hz, 1H), 7.00 (d, J=1.2 Hz, 1H), 6.98 (s, 1H), 6.94 (s, 1H), 5.31 (s, 2H), 4.07 (s, 2H), 2.61 (q, J=7.6 Hz, 2H), 2.56 (s, 3H), 1.19 (t, J=7.6 Hz, 3H); $^{13}$C-NMR (126 MHz; DMSO-$d_6$): δ (158.8+158.5+158.30+158.0, 1C), 158.27, 154.7, 146.1, 142.6, 142.0, 133.3, 129.0, 123.7, 121.8, 120.5, (118.3+115.9), 114.8, 113.8, 113.5, 68.5, 51.3, 32.2, 28.1, 15.3; the trifluoroacetate carbon signals are only partially visible; two of the aminoquinoline carbons are not visible due to baseline broadening; ESIMS m/z (rel. intensity) 322 (MH+, 100); HRMS calcd for $C_{20}H_{24}N_3O^+$: 322.1914. found, 322.1916.

Example 62

4-Methyl-7-[(3-((methylamino)methyl)phenoxy)methyl]quinolin-2-amine Dihydrochloride (10)

This compound was prepared from 43 (0.065 g, 0.221 mmol) and phenol 46 (0.052 g, 0.221 mmol). Workup and purification by flash column chromatography, eluting with a gradient of 5% EtOAc in $CH_2Cl_2$ to 30% EtOAc in $CH_2Cl_2$, afforded the intermediate acetamide 50 as a white solid (0 076 g, 77%), that was immediately deprotected using $K_2CO_3$ (0.047 g, 0.338 mmol) as described in the General Procedure. After workup, the free aminoquinoline was triturated with hexanes and filtered, and the resultant white solid was diluted in 10:1 ether:MeOH (8 mL) and treated with methanolic HCl (1.5 mL). After stirring overnight, filtration afforded 10 (0.051 g, 80% from 50) as a white flocculent solid, after precipitating from hot MeOH (0.5 mL) with ether (5 mL) and washing with ether: mp 249-251° C. $^1$H-NMR (500 MHz; DMSO-$d_6$): δ 14.12 (br s, 1H), 9.19 (br s, 2H), 9.00 (br s, 1H), 8.10 (br s, 1H), 8.03 (d, J=8.4 Hz, 1H), 7.78 (s, 1H), 7.57 (dd, J=8.4, 1.3 Hz, 1H), 7.39 (t, J=7.9 Hz, 1H), 7.32 (t, J=1.8 Hz, 1H), 7.12-7.09 (m, 2H), 6.94 (d, J=0.8 Hz, 1H), 5.37 (s, 2H), 4.09 (t, J=4.8 Hz, 2H), 2.65 (d, J=0.9 Hz, 3H), 2.54-2.50 (m, 3H, partially obscured by solvent peak); $^{13}$C-NMR (126 MHz; DMSO-$d_6$): δ 158.1, 153.8, 141.8, 133.6, 130.0, 125.8, 123.6, 122.4, 120.6, 116.6, 115.5, 115.1, 112.6, 68.4, 51.0, 32.0, 19.0; two of the aminoquinoline carbons are not visible due to baseline broadening; ESIMS m/z (rel. intensity) 308 (MH+, 100); FIRMS calcd for $C_{19}H_{22}N_3O^+$: 308.1757. found, 308.1757.

Example 63

3-[(2-Amino-4-methylquinolin-7-yl)methoxy]-5-((methylamino)methyl)benzonitrile Dihydrochloride (11)

This compound was prepared from 43 (0.065 g, 0.221 mmol) and phenol 26 (0.058 g, 0.221 mmol). Workup and purification by flash column chromatography, eluting with a gradient of 5% EtOAc in $CH_2Cl_2$ to 38% EtOAc in $CH_2Cl_2$, afforded the intermediate acetamide 47 as a yellow foam (0.043 g, 41%), that was immediately deprotected using $K_2CO_3$ (0.025 g, 0.181 mmol) as described in the General Procedure. After workup, the free aminoquinoline was purified by flash column chromatography (eluting with a gradient of EtOAc to 5% MeOH in EtOAc), and the resultant residue was diluted in 10:1 ether:MeOH and treated with methanolic HCl (1.5 mL). After stirring overnight, filtration afforded 8 (0.023 g, 68% from 47) as a pale yellow flocculent solid, after precipitating twice from hot MeOH (0.4 mL) with ether (10 mL) and washing with ether: mp 185-188° C. $^1$H-NMR (500 MHz; DMSO-$d_6$): δ 14.14 (br s, 1H), 9.38 (br s, 2H), 8.99 (br s, 1H), 8.10 (br s, 1H), 8.03 (d, J=8.4 Hz, 1H), 7.76 (s, 1H), 7.69 (d, J=1.4 Hz, 1H), 7.64-7.63 (m, 1H), 7.62 (s, 1H), 7.56 (dd, J=8.4, 1.2 Hz, 1H), 6.94 (s, 1H), 5.43 (s, 2H), 4.15 (s, 2H), 2.63 (d, J=0.7 Hz, 3H), 2.55-2.50 (m, 3H, partially obscured by solvent peak); $^{13}$C-NMR (126 MHz; DMSO-$d_6$): δ 158.2, 153.8, 152.2, 140.8, 135.8, 135.3, 126.3, 125.9, 123.8, 122.5, 120.8, 118.2, 118.0, 115.8, 112.7, 112.4, 69.0, 50.1, 32.0, 19.0; ESIMS m/z (rel. intensity) 333 (MH+, 100); HRMS calcd for $C_{20}H_{21}N_4O^+$: 333.1710. found, 333.1716.

Example 64

7-[(4-Chloro-3-((methylamino)methyl)phenoxy)methyl]-4-methylquinolin-2-amine Dihydrochloride (12)

This compound was prepared from 43 (0.065 g, 0.220 mmol) and phenol 45 (0.060 g, 0.220 mmol). Workup and purification by flash column chromatography, eluting with a gradient of 5% EtOAc in $CH_2Cl_2$ to 37% EtOAc in $CH_2Cl_2$, afforded the intermediate acetamide 49 as a white solid (0.084 g, 79%), that was immediately deprotected using $K_2CO_3$ (0.048 g, 0.347 mmol) as described in the General Procedure. After workup, the free aminoquinoline was diluted in ether (10 mL, with a few drops of MeOH added) and treated with methanolic HCl (1 mL). After stirring overnight, filtration afforded 12 (0.058 g, 81% from 49) as a white flocculent solid, after precipitating from hot MeOH (1 mL) with ether (10 mL) and washing with ether: mp 280-282° C. $^1$H-NMR (500 MHz; DMSO-d6): δ $^1$H-NMR (500 MHz; DMSO-$d_6$): δ 14.13 (s, 1H), 8.84-8.70 (s, 4H), 8.02 (d, J=8.4 Hz, 1H), 7.70 (s, 1H), 7.55 (d, J=8.3 Hz, 1H), 7.00 (s, 1H), 6.98 (s, 1H), 6.94 (s, 1H), 6.91 (s, 1H), 2.64-2.58 (m, 5H), 2.55 (s, 3H), 1.19 (t, J=7.5 Hz, 3H); $^{13}$C-NMR (126 MHz; DMSO-$d_6$): δ 156.9, 153.8, 152.3, 141.3, 135.7, 130.9, 130.5, 125.8, 124.9, 123.7, 120.7, 118.3, 117.0, 115.6, 112.6, 68.9, 48.3, 32.4, 19.0; ESIMS m/z (rel. intensity) 342/344 (MH+, 100/30); MS calcd for $C_{19}H_{21}ClN_3O^+$: 342.1368. found, 342.1371.

Example 65

7-((3-Ethyl-5-((methylamino)methyl)phenoxy) methyl)-4-methylquinolin-2-amine Ditrifluoroacetate (13)

This compound was prepared from 43 (0.065 g, 0.22 mmol) and phenol 29 (0.058 g, 0.22 mmol). Workup and purification by flash column chromatography, eluting with a gradient of 5% EtOAc in $CH_2Cl_2$ to 37% EtOAc in $CH_2Cl_2$, afforded the intermediate acetamide 48 as a white solid (0.076 g, 72%), that was immediately deprotected using $K_2CO_3$ (0.044 g, 0.318 mmol) as described in the General Procedure. After workup, the free aminoquinoline was diluted with anhydrous $CH_2Cl_2$ (6 mL) and trifluoroacetic acid (300 μL) was added. The mixture was stirred for 30 min and concentrated, and ether (10 mL) was added to the residue. The mixture was sonicated until a solid formed and filtered to yield 13 (0.079 g, 89% from 48) as a white solid after washing with ether: 199.5-201° C. $^1$H-NMR (500 MHz; DMSO-$d_6$): 14.13 (br s, 1H), 8.02 (d, J=8.4 Hz, 1H), 7.70 (s, 1H), 7.55 (d, J=8.3 Hz, 1H), 7.00 (s, 1H), 6.98 (s, 1H), 6.94 (s, 1H), 6.91 (s, 1H), 2.64-2.58 (m, 5H), 2.55 (s, 3H), 1.19 (t, J=7.5 Hz, 3H). $^{13}$C-NMR (126 MHz; DMSO-$d_6$): δ (158.9+158.7+158.43+158.19, 1C), 158.25, 154.1, 152.2, 146.0, 141.7, 136.2, 133.3, 125.7, 123.6, 121.9, 120.7, (118.3+115.9, 1C), 115.6, 114.8, 113.5, 112.7, 68.4, 51.3, 32.1, 28.1, 18.9, 15.3; the trifluoroacetate carbon signals are only partially visible; ESIMS m/z (rel. intensity) 336 (MH$^+$, 100); FIRMS calcd for $C_{21}H_{25}N_3O^+$: 336.2070. found, 336.2075.

Example 66

4-Methyl-7-[3-((methylamino)methyl)phenethyl] quinolin-2-amine dihydrochloride (14)

Compound 66 (0.058 g, 0.129 mmol) was deprotected using $K_2CO_3$ (0.036 g, 0.259 mmol) as described in the General Procedure. After workup, the free aminoquinoline was purified by flash column chromatography, eluting with a gradient of EtOAc to 7% MeOH in EtOAc, to yield a colorless gum that was diluted in 20:1 ether:MeOH (10 mL) and treated with methanolic HCl (0.7 mL). After stirring overnight, filtration afforded 14 (0.026 g, 54% from 66) as a white solid, after precipitating from hot MeOH (0.5 mL) with ether (3 mL) and washing with ether: 135-137° C.; $^1$H-NMR (500 MHz; DMSO-$d_6$): δ 14.05 (br s, 1H), 9.13-9.10 (br m, 3H), 9.00 (br s, 1H), 8.10 (br s, 1H), 7.90 (d, J=8.4 Hz, 1H), 7.50 (s, 1H), 7.47 (s, 1H), 7.41 (dd, J=8.4, 1.1 Hz, 1H), 7.35-7.31 (m, 2H), 7.28-7.26 (m, 1H), 6.87 (d, J=0.4 Hz, 1H), 4.08 (s, 2H), 3.10 (t, J=7.8 Hz, 2H), 2.98 (t, J=7.8 Hz, 2H), 2.60 (s, 3H), 2.55-2.50 (m, 3H, obscured by solvent peak); $^{13}$C-NMR (126 MHz; DMSO-$d_6$): δ 153.6, 152.3, 146.4, 141.3, 135.6, 132.0, 130.0, 129.0, 128.7, 127.5, 125.8, 125.4, 119.5, 116.6, 111.8, 51.2, 36.5, 36.2, 31.9, 18.9; ESIMS m/z (rel. intensity) 306 (MH$^+$, 100); HRMS calcd for $C_{20}H_{24}N_3^+$: 306.1965. found, 306.1969.

Example 67

3-[2-(2-Aminoquinolin-7-yl)ethyl]-5-((methylamino) methyl)benzonitrile Dihydrochloride (15)

Compound 67 (0.026 g, 0.057 mmol) was deprotected using $K_2CO_3$ (0.016 g, 0.114 mmol) as described in the General Procedure. After workup, the free aminoquinoline was passed through a short $SiO_2$ plug (eluting with EtOAc), to yield a colorless gum that was diluted in ether (10 mL) and treated with methanolic HCl (0.5 mL). After stirring 18 h, filtration afforded 15. The filtrate was concentrated and the residue re-suspended in ether and treated with methanolic HCl (0.5 mL), and after 24 h, additional 15 was obtained. The total obtained solid was precipitated from hot MeOH (0.5 mL) with ether (3 mL) and washed with ether to afford the title compound 15 as a cream-colored solid (0.014 g, 62% from 67): mp 260-261.5° C. $^1$H-NMR (500 MHz; DMSO-$d_6$): δ 14.01 (br s, 1H), 9.14-9.10 (br m, 3H), 8.32 (d, J=9.3 Hz, 1H), 8.10 (br s, 1H), 7.85-7.81 (m, 4H), 7.49 (s, 1H), 7.38 (d, J=8.3 Hz, 1H), 7.01 (d, J=9.3 Hz, 1H), 4.14 (s, 2H), 3.12 (dd, J=9.2, 6.2 Hz, 2H), 3.03 (dd, J=9.3, 6.3 Hz, 2H), 2.55-2.50 (m, 3H, obscured by solvent peak); $^{13}$C-NMR (126 MHz; DMSO-$d_6$): δ 31.93, 35.61, 36.13, 50.18, 111.38, 112.92, 116.36, 118.47, 119.33, 125.86, 128.75, 131.33, 132.46, 133.57, 135.22, 135.89, 142.84, 143.00, 146.24, 154.30; ESIMS m/z (rel. intensity) 317 (MH$^+$, 100); HRMS calcd for $C_{20}H_{21}N_4^+$: 317.1761. found, 317.1764.

Example 68

3-[2-(2-Amino-4-methylquinolin-7-yl)ethyl]-5-((methylamino)methyl)benzonitrile Dihydrochloride (16)

Compound 68 (0.045 g, 0.095 mmol) was deprotected using $K_2CO_3$ (0.026 g, 0.190 mmol) as described in the General Procedure. After workup, the free aminoquinoline was purified by flash column chromatography, eluting with a gradient of EtOAc to 3% MeOH in EtOAc, to yield a colorless gum that was diluted in 5:1 ether:MeOH (10 mL) and treated with methanolic HCl (1 mL). After stirring overnight, filtration afforded 16 (0.019 g, 50% from 68) as a white solid, after precipitating from hot MeOH (0.75 mL) with ether (13 mL) and washing with 30% MeOH in ether, with ether, and dried: mp 213-215° C. $^1$H-NMR (500 MHz; DMSO-$d_6$): δ 13.99 (s, 1H), 9.29 (s, 2H), 8.91 (br s, 1H), 7.91 (d, J=8.4 Hz, 1H), 7.85-7.82 (m, 2H), 7.83-7.81 (m, 1H), 7.49 (d, J=1.2 Hz, 1H), 7.41 (dd, J=8.4, 1.5 Hz, 1H), 6.87 (d, J=1.0 Hz, 1H), 4.14 (s, 2H), 3.13 (dd, J=9.1, 6.4 Hz, 2H), 3.03 (dd, J=9.2, 6.5 Hz, 2H), 2.61 (d, J=0.8 Hz, 3H), 2.55-2.50 (m, 3H, obscured by solvent peak). One of the aminoquinoline —NH protons is not visible due to baseline broadening; $^{13}$C-NMR (126 MHz; DMSO-$d_6$): δ 153.7, 152.3, 146.0, 143.0, 135.7, 135.2, 133.6, 132.4, 131.3, 125.7, 125.5, 119.6, 118.5, 116.6, 111.8, 111.4, 50.2, 35.9, 35.6, 31.9, 18.9; ESIMS m/z (rel. intensity) 331 (MH$^+$, 100); HRMS calcd for $C_{21}H_{23}N_4^+$: 331.1917. found, 331.1922.

Example 69

5-[(2-Amino-4-methylquinolin-7-yl)methoxy]-2-fluoro-3-((methylamino)methyl)benzonitrile Dihydrochloride (17)

This compound was prepared from 44 (0.050 g, 0.202 mmol) and phenol 73 (0.054 g, 0.192 mmol) at 50° C. Workup and purification by flash column chromatography, eluting with a gradient of 5% EtOAc in $CH_2Cl_2$ to 40% EtOAc in $CH_2Cl_2$, afforded the intermediate acetamide 74 as a colorless glass (0.072 g, 73%), that was immediately deprotected using $K_2CO_3$ (0.040 g, 0.291 mmol) as described in the General Procedure. After workup, the free aminoquinoline was purified by flash column chromatography, eluting with a gradient of EtOAc to 3% MeOH in EtOAc, and the obtained residue was diluted in 5:1 ether:MeOH (10 mL) and treated with methanolic HCl (1 mL). After stirring overnight, filtration afforded 17 (0.047 g, 77% from 74) as a white flocculent solid, after precipitating from hot MeOH (0.75 mL) with ether (10 mL) and washing with 30% MeOH in ether and ether: 279.5-281° C. (dec). $^1$H-NMR (500 MHz; DMSO-$d_6$): δ 14.15 (br s, 1H), 9.44 (br s, 2H), 9.00 (br s, 1H), 8.10 (br s, 1H), 8.03 (d, J=8.4 Hz, 1H), 7.85-7.84 (m, 1H), 7.76-7.74 (m, 2H), 7.56 (dd, J=8.4, 1.4 Hz, 1H), 6.94 (d, J=0.9 Hz, 1H), 5.40 (s, 2H), 4.21 (s, 2H), 2.63 (d, J=0.9 Hz, 3H), 2.59 (s, 3H); $^{13}$C-NMR (126 MHz; DMSO-$d_6$): δ (156.7+154.7, 1C), (153.92+153.90, 1C), 153.80, 152.2, 140.7, 135.7, 125.9, (124.92+124.89, 1C), 123.8, (121.92+121.80, 1C), 120.8, 119.2, 115.9, 113.6, 112.7, (100.83+100.69, 1C) 69.5, (43.84+43.82, 1C), 32.2, 19.0; ESIMS m/z (rel. intensity) 351 (MH$^+$, 100); FIRMS calcd for $C_{20}H_{20}FN_4O^+$: 351.1616. found, 351.1623.

Example 70

3-[(2-Amino-4-methylquinolin-7-yl)methoxy]-5-(2-(methylamino)ethyl)benzonitrile Dihydrochloride (18)

This compound was prepared from 44 (0.024 g, 0.0949 mmol) and phenol 81 (0.025 g, 0.0904 mmol). The reaction mixture was stirred at r.t. for four days. Workup and purification by flash column chromatography, eluting with a gradient of 5% EtOAc in $CH_2Cl_2$ to 35% EtOAc in $CH_2Cl_2$, afforded the intermediate acetamide 83 as a white semisolid (0.025 g, 57%), that was immediately deprotected using $K_2CO_3$ (0.014 g, 0.102 mmol) as described in the General Procedure. After workup, the free aminoquinoline was purified by flash column chromatography, eluting with a gradient of EtOAc to 7% MeOH in EtOAc, and the obtained clear gum was diluted in 10:1 ether:MeOH (10 mL) and treated with methanolic HCl (0.5 mL). After stirring overnight, filtration afforded 18 (0.010 g, 49% from 83) as a white flocculent solid, after precipitating from hot MeOH (1 mL) with ether (10 mL) and washing with ether: mp 213-215° C. $^1$H-NMR (500 MHz; DMSO-$d_6$): δ 14.07 (br s, 1H), 9.10-8.79 (br m, 3H), 8.10 (br m, 1H), 8.03 (d, J=8.4 Hz, 1H), 7.75 (s, 1H), 7.56 (dd, J=8.4, 1.1 Hz, 1H), 7.47 (dd, J=2.3, 1.3 Hz, 1H), 7.41-7.49 (m, 1H), 7.37 (t, J=1.8 Hz, 1H), 6.93 (s, 1H), 5.41 (s, 2H), 3.22-3.17 (m, 2H), 2.98 (t, J=7.7 Hz, 2H), 2.63 (d, J=0.8 Hz, 3H), 2.56 (t, J=5.3 Hz, 2H); $^{13}$C-NMR (126 MHz; DMSO-$d_6$): δ 158.3, 153.8, 141.1, 140.6, 125.8, 125.4, 123.7, 121.4, 120.8, 118.5, 116.0, 115.7, 112.7, 112.4, 68.8, 48.3, 32.5, 30.8, 19.0; ESIMS m/z (rel. intensity) 347 (MH$^+$, 100); HRMS caked for $C_{21}H_{23}N_4O^+$: 347.1866. found, 347.1872.

Example 71

(RS)-3-[(2-amino-4-methylquinolin-7-yl)methoxy]-5-(2-(methylamino)propyl)benzonitrile Dihydrochloride (RS-19)

This compound was prepared from 44 (0.054 g, 0.217 mmol) and phenol 82 (0.060 g, 0.206 mmol) at 50° C. Workup and purification by flash column chromatography, eluting with a gradient of 5% EtOAc in $CH_2Cl_2$ to 40% EtOAc in $CH_2Cl_2$, afforded the intermediate acetamide 84 as a yellow foam (0.063 g, 61%), that was immediately deprotected using $K_2CO_3$ (0.035 g, 0.251 mmol) as described in the General Procedure. After workup, the free aminoquinoline was purified by flash column chromatography, eluting with a gradient of EtOAc to 2% MeOH in EtOAc, and the obtained residue was diluted in 4:1 ether:MeOH (10 mL) and treated with methanolic HCl (0.5 mL). After stirring overnight, filtration afforded (RS)-19 (0.041 g, 76% from 84) as a white flocculent solid, after precipitating from hot MeOH (1 mL) with ether (10 mL) and washing with ether: 190-200° C. (softens); 246-250° C. (melts). $^1$H-NMR (500 MHz; DMSO-$d_6$): δ 14.10 (s, 1H), 9.00-8.90 (m, 3H), 8.10 (br s, 1H), 8.03 (d, J=8.4 Hz, 1H), 7.75 (d, J=0.8 Hz, 1H), 7.56 (dd, J=8.4, 1.4 Hz, 1H), 7.47 (dd, J=2.4, 1.3 Hz, 1H), 7.41 (s, 1H), 7.38 (dd, J=2.1, 1.6 Hz, 1H), 6.93 (d, J=0.8 Hz, 1H), 5.40 (s, 2H), 3.48-3.44 (m, 1H), 3.17 (dd, J=13.6, 4.5 Hz, 1H), 2.73 (dd, J=13.4, 9.4 Hz, 1H), 2.63 (d, J=0.9 Hz, 3H), 2.57 (t, J=5.4 Hz, 3H), 1.10 (d, J=6.5 Hz, 3H); $^{13}$C-NMR (126 MHz; DMSO-$d_6$): δ 158.3, 153.8, 141.1, 140.1, 125.88, 125.84, 123.8, 121.8, 120.7, 118.5, 116.2, 115.7, 112.7, 112.4, 68.8, 54.7, 37.6, 29.7, 19.0, 15.1; two of the aminoquinoline carbons are not visible due to baseline broadening; ESIMS m/z (rel. intensity) 361 (MH$^+$, 100); HRMS calcd for $C_{22}H_{25}N_4O^-$: 361.2023. found, 361.2028.

Example 72

(R)-3-[(2-amino-4-methylquinolin-7-yl)methoxy]-5-(2-(methylamino)propyl)benzonitrile Dihydrochloride ((R)-19)

This compound was prepared from 44 (0.057 g, 0.228 mmol) and phenol (R)-82 (0.070 g, 0.241 mmol) at 50° C. Workup and purification by flash column chromatography, eluting with a gradient of 5% EtOAc in $CH_2Cl_2$ to 40% EtOAc in $CH_2Cl_2$, afforded the intermediate acetamide (R)-84 as a white foam (0.079 g, 69%), that was immediately deprotected using $K_2CO_3$ (0.043 g, 0.312 mmol) as described in the General Procedure. After workup, the free aminoquinoline was purified by flash column chromatography, eluting with a gradient of EtOAc to 2% MeOH in EtOAc, and the obtained residue was diluted in 4:1 ether:MeOH (10 mL) and treated with methanolic HCl (0.75 mL). The mixture was stirred for 20 h at r.t., and concentrated. The residue was triturated with 5% MeOH in ether (10 mL) and collected by filtration. The precipitate was recrystallized from MeOH:ether (5:1, 15 mL) to yield (R)-19 as a white solid ((0.049 g, 72% from (R)-84)) after washing with ether: mp 146-148° C. (softens), 170-173° C. (melts). $^1$H-NMR (500 MHz; DMSO-$d_6$): δ 14.03 (s, 1H), 8.90-8.80 (m, 3H), 8.10 (br s, 1H), 8.03 (d, J=8.4 Hz, 2H), 7.75 (s, 1H), 7.56 (dd, J=8.4, 0.7 Hz, 1H), 7.48 (dd, J=2.3, 1.3 Hz, 1H), 7.41 (s, 1H), 7.38 (dd, J=2.0, 1.6 Hz, 1H), 6.93 (s, 1H), 5.40 (s, 2H), 3.48-3.44 (m, 1H), 3.17 (dd, J=13.4, 4.5 Hz, 1H), 2.73 (dd, J=13.4, 9.4 Hz, 1H), 2.63 (d, J=0.8 Hz, 3H), 2.57 (t, J=5.2 Hz, 3H), 1.10 (d, J=6.5 Hz, 3H); $^{13}$C NMR (126 MHz; DMSO-$d_6$): δ 158.3, 153.8, 141.0, 140.1, 125.88, 125.81, 123.7, 121.8, 120.8, 118.5, 116.2, 115.8, 112.7, 112.4, 68.8, 54.7, 37.6, 29.7, 19.0, 15.1; two of the aminoquinoline carbons are not visible due to baseline broadening; ESIMS m/z (rel. intensity) 361 (MH$^+$, 100); HRMS calcd for $C_{22}H_{25}N_4O^+$: 361.2023. found, 361.2030.

Example 73

(S)-3-[(2-amino-4-methylquinolin-7-yl)methoxy]-5-(2-(methylamino)propyl)benzonitrile Dihydrochloride ((S)-19)

This compound was prepared from 44 (0.047 g, 0.190 mmol) and phenol (S)-82 (0.058 g, 0.200 mmol) at 50° C.

Workup and purification by flash column chromatography, eluting with a gradient of 5% EtOAc in $CH_2Cl_2$ to 40% EtOAc in $CH_2Cl_2$, afforded the intermediate acetamide (S)-84 as a white foam (0.059 g, 62%), that was immediately deprotected using $K_2CO_3$ (0.033 g, 0.239 mmol) as described in the General Procedure. After workup, the free aminoquinoline was purified by flash column chromatography, eluting with a gradient of EtOAc to 2% MeOH in EtOAc, and the obtained residue was diluted in 6:1 ether:MeOH (7 mL) and treated with methanolic HCl (0.75 mL). The mixture was stirred for 20 h at r.t., ether (6 mL) was added, and the mixture was filtered. The precipitate was recrystallized from MeOH:ether (5:1, 10 mL) to yield (S)-19 as a white solid ((0.042 g, 83% from (S)-84)) after washing with ether: mp 146-148° C. (softens), 170-173° C. (melts); $^{13}C$ NMR (126 MHz; DMSO-$d_6$): δ 14.00 (br s, 1H), 8.90-8.80 (m, 3H), 8.10 (br s, 1H), 8.03 (d, J=8.4 Hz, 2H), 7.75 (s, 1H), 7.56 (dd, J=8.4, 0.6 Hz, 1H), 7.48 (dd, J=2.4, 1.3 Hz, 1H), 7.41 (s, 1H), 7.38 (t, J=1.8 Hz, 1H), 6.93 (s, 1H), 5.41 (s, 2H), 3.48-3.44 (m, 1H), 3.17 (dd, J=13.4, 4.6 Hz, 1H), 2.73 (dd, J=13.4, 9.4 Hz, 1H), 2.64 (d, J=0.8 Hz, 3H), 2.58 (t, J=5.3 Hz, 3H), 1.10 (d, J=6.5 Hz, 3H); $^{13}C$-NMR (126 MHz; DMSO-$d_6$): δ 158.8, 154.3, 141.5, 140.6, 126.37, 126.32, 124.3, 122.3, 121.3, 119.0, 116.6, 116.3, 113.2, 112.9, 69.3, 55.2, 38.0, 30.2, 19.4, 15.6; two of the aminoquinoline carbons are not visible due to baseline broadening; ESIMS m/z (rel. intensity) 361 ($MH^+$, 100); ESIMS m/z (rel. intensity) 361 ($MH^+$, 100); HRMS calcd for $C_{22}H_{25}N_4O^+$: 361.2023. found, 361.2033.

Example 74

7-Bromo-4-methylquinoline (37)

3-Bromoaniline (36, 13.8 g, 80 mmol) and $FeCl_3 \cdot 6H_2O$ (22.8 g, 84 mmol) were diluted with glacial acetic acid (200 mL). The mixture was heated to 60° C. to ensure dissolution of the solids (ca. 15 min) and then methyl vinyl ketone (8 mL, 88 mmol) was added slowly. The mixture was then heated at reflux (~140° C.) for 3 h, upon which a yellow precipitate formed. The mixture was then cooled to r.t., and the precipitate was filtered from the solution and washed with EtOAc the filtrate ran colorless (this filtrate was discarded). The filter cake was then diluted with EtOAc (400 mL), and 1 M NaOH was added until the pH of the resulting suspension was >9. The resulting emulsion was filtered through a coarse fritted funnel to remove iron salts, and the organic and aqueous layers were separated. The aqueous layer was extracted with EtOAc (4×400 mL). The combined organic layers (~1.5 L) were washed with $H_2O$ (2×400 mL) and sat. aq. NaCl (400 mL), dried over anhydrous sodium sulfate, and concentrated to $\frac{1}{10}^{th}$ of the original volume. The solution was filtered through a pad of Celite and re-concentrated to afford the title compound as a yellow-green solid (7.71 g, 44%). The analytical data for this compound are consistent with those previously reported.[26]

Example 75

7-Bromo-4-methylquinoline N-Oxide (38)

Compound 37 (7.71 g, 34.7 mmol) was diluted in anhydrous $CH_2Cl_2$, and m-chloroperoxybenzoic acid (8.39 g of 70% m-CPBA), 48.6 mmol) was added. The mixture was stirred at r.t. for 19 h, and 1 M NaOH (~100 mL) was added. The layers were separated and the aqueous layer was extracted exhaustively with $CH_2Cl_2$ (3×100 mL), following which the combined organic layers were washed with sat. aq. $NaHCO_3$ (100 mL) and sat. aq. NaCl (100 mL) and dried over anhydrous sodium sulfate. Concentration afforded a residue that was washed with 5% $CH_2Cl_2$ in hexanes to afford the desired compound (7.58 g, 92%) as a yellow crystalline solid after washing with hexanes and drying: mp 179-181° C. $^1H$ NMR (500 MHz; DMSO-$d_6$): δ 9.01 (d, J=2.0 Hz, 1H), 8.48 (d, J=6.0 Hz, 1H), 7.86 (d, J=9.0 Hz, 1H), 7.79 (dd, J=9.0, 2.0 Hz, 1H), 7.18 (d, J=6.0 Hz, 1H), 2.69 (s, 3H); $^{13}C$-NMR (126 MHz; DMSO-$d_6$): δ 140.8, 135.4, 133.5, 131.6, 128.4, 127.8, 123.7, 122.7, 121.7, 17.5; ESIMS m/z (rel. intensity) 260/262 ($MNa^+$, 13/13).

Example 76

7-Bromo-4-methylquinolin-2-amine (39)

N-oxide 38 (3.81 g, 16 mmol) was diluted in 2:1 trifluorotoluene:$CH_2Cl_2$ (120 mL) and cooled to 0° C. t-Butylamine (8.41 mL, 80 mmol) was added, followed by p-toluenesulfonic anhydride (10.4 g, 32 mmol) in small portions. After 10 min, an additional 1 mL t-$BuNH_2$ and 1.0 g $Ts_2O$ were added, and after a total of 20 minutes, TLC indicated the presence of a less polar product (intermediate t-butylaminoquinoline). The suspension was concentrated until the $CH_2Cl_2$ was removed, and trifluoroacetic acid (34 mL) was added, and the mixture was heated until the internal temp reached 80° C., where it was held for 5 h. The mixture was then cooled and stirred 17 h at r.t. The dark red mixture was concentrated and neutralized with 1 N NaOH until the pH was ~12. The suspension was extracted with EtOAc (3×150 mL), and the organic layers were washed with $H_2O$ and sat. aq. NaCl (100 mL each). The organic layers were dried over anhydrous sodium sulfate and concentrated to yield a residue that was adsorbed onto $SiO_2$ and purified by flash column chromatography, eluting with a gradient of 50% EtOAc in $CH_2Cl_2$ to EtOAc, to yield the desired product as a tan crystalline solid (2.26 g, 60%) after washing with hexanes: mp 180-182° C. $^1H$-NMR (500 MHz; DMSO-$d_6$): δ 7.68 (d, J=8.7 Hz, 1H), 7.57 (d, J=2.0 Hz, 1H), 7.27 (dd, J=8.7, 2.1 Hz, 1H), 6.62 (d, J=1.0 Hz, 1H), 6.53 (s, 2H), 2.46 (d, J=1.0 Hz, 3H); $^{13}C$-NMR (126 MHz; $CDCl_3$): δ 157.6, 148.5, 145.9, 128.5, 125.6, 125.1, 123.5, 122.6, 112.3, 18.7; ESIMS m/z (rel. intensity) 237/239 ($MNa^+$, 100/94).

Example 77

N-(7-Bromo-4-methylquinolin-2-yl)acetamide (40)

Compound 39 (2.20 g, 9.28 mmol) was diluted in anhydrous THF (50 mL), and N-acetylimidazole (1.53 g, 13.9 mmol) and a catalytic amount of DMAP (~20 mg) were added. The mixture was heated at reflux for 17 h. The mixture was cooled and concentrated, and the residue was dissolved in EtOAc (200 mL) and washed with $H_2O$ (100 mL). The aqueous layer was extracted with EtOAc (2×200 mL) and the organic layers were washed with $H_2O$ (200 mL) and sat. aq. NaCl (200 mL). The combined organic layers were dried over anhydrous sodium sulfate and concentrated, and the residue was suspended in EtOAc (5 mL) and precipitated by addition of hexanes (150 mL). The precipitate was collected and washed with hexanes to yield the product as an off-white iridescent solid (2.32 g, 90%): mp 246-248.5° C. $^1H$-NMR (500 MHz; $CDCl_3$): δ 8.75 (br s, 1H), 8.33 (s, 1H), 8.01 (d, J=1.9 Hz, 1H), 7.81 (d, J=8.8 Hz, 1H), 7.59 (dd, J=8.8, 1.5 Hz, 1H), 2.73 (s, 3H), 2.31 (s, 3H). $^{13}C$-NMR (126 MHz; $CDCl_3$): δ 169.9, 151.7, 147.9, 146.4, 129.4, 128.4, 125.4, 124.8, 124.0, 114.9, 24.8, 19.2; ESIMS m/z (rel. intensity) 301/303 (MNa$^+$, 20/19).

Example 78

N-(7-Formyl-4-methylquinolin-2-yl)acetamide (41)

Compound 40 (1.08 g, 3.6 mmol), Na$_2$CO$_3$ (0.576 g, 5.38 mmol), dppb (0.070 g, 0.164 mmol), Pd(OAc)$_2$ (0.024 g, 0.107 mmol), and N-formylsaccharin (1.15 g, 5.44 mmol) were placed in a sealable, heavy-walled glass tube, which was evacuated and backfilled with argon several times. To the tube was added anhydrous, degassed DMF (20 mL) containing Et$_3$SiH (0.744 mL, 4.66 mmol). The tube was sealed and the reaction mixture was allowed to stir at r.t. for 10 min before being heated to 70° C. for 22 h. The reaction mixture was cooled and quenched with 1:1 H$_2$O:sat. aq. NaCl (50 mL), and extracted with EtOAc (3×70 mL). The organic layer was washed with 5% aq. NaCl (3×100 mL) and sat. aq. NaCl (100 mL), dried over anhydrous sodium sulfate, and concentrated to yield a residue that was adsorbed onto SiO$_2$ and purified by flash column chromatography, eluting with a gradient of 5% EtOAc in CH$_2$Cl$_2$ to 40% EtOAc, to yield the desired product as a white flocculent solid (0.514 g, 63%) mp 209-211° C. (softens); 218-221° C. (melts). $^1$H-NMR (500 MHz; CDCl$_3$): δ 10.20 (d, J=0.5 Hz, 1H), 8.40 (s, 1H), 8.25 (d, J=1.3 Hz, 1H), 8.05 (d, J=8.6 Hz, 2H), 8.00 (br s, 1H), 7.95 (dd, J=8.6, 1.6 Hz, 1H), 2.76 (d, J=1.0 Hz, 3H), 2.29 (s, 3H). $^{13}$C-NMR (126 MHz; CDCl$_3$): δ 192.2, 169.3, 151.7, 147.7, 146.2, 137.3, 133.3, 130.1, 125.3, 122.1, 116.8, 25.2, 19.5; ESIMS m/z (rel. intensity) 229 (MH$^+$, 5).

Example 79

N-(7-(Hydroxymethyl)-4-methylquinolin-2-yl)acetamide (42)

Aldehyde 41 (0.514 g, 2.25 mmol) was diluted in MeOH (30 mL) and heated gently to 50° C. to effect solution. When the mixture was just dissolved, NaBH$_4$ (0.111 g, 2.92 mmol) was added in one portion, and the mixture was stirred for 20 minutes and concentrated. The residue was partitioned between EtOAc and 1:1 sat. aq. NaHCO$_3$:H$_2$O (30 mL each). The aqueous layer was extracted with EtOAc (3×30 mL) and the organic layers were washed with sat. aq. NaCl and dried over anhydrous sodium sulfate. Concentration afforded a residue that was partially dissolved in EtOAc (5 mL) and precipitated with hexanes (100 mL). Filtration afforded the title compound as a white crystalline powder (0.493 g, 95%) that was used without further purification. $^1$H-NMR (500 MHz; CDCl$_3$): δ 9.75 (br s, 1H), 8.22 (s, 1H), 7.89 (d, J=8.5 Hz, 1H), 7.78 (s, 1H), 7.49 (dd, J=8.5, 1.2 Hz, 1H), 4.83 (s, 2H), 3.50 (br s, 1H) 2.69 (s, 3H), 2.28 (s, 3H).

Example 80

N-(7-(Bromomethyl)-4-methylquinolin-2-yl)acetamide (43)

Alcohol 42 (0.147 g, 0.64 mmol) was diluted in anhydrous THF (5 mL) and cooled to 0° C. CBr$_4$ (0.255 g, 0.768 mmol) and PPh$_3$ (0.201 g, 0.768 mmol) were added. The mixture was stirred at 0° C. for 15 min and warmed to r.t., where it was stirred for 3.5 h. The mixture was then concentrated and diluted in CH$_2$Cl$_2$, and filtered to remove insoluble materials. The filtrate was concentrated and purified by flash column chromatography, eluting with a gradient of 3% EtOAc in CH$_2$Cl$_2$ to 30% EtOAc in CH$_2$Cl$_2$ to yield the product as a white solid (0.135 g, 72%). This crude product (containing some by-products arising from overbromination of the acetamide) was suitable for formation of phenyl ethers and was used without further purification or characterization; $^1$H-NMR (500 MHz; CDCl$_3$): δ 8.38 (s, 1H), 7.98 (d, J=8.6 Hz, 1H), 7.85 (d, J=1.4 Hz, 1H), 7.60 (dd, J=8.6, 1.4 Hz, 1H), 4.63 (s, 2H), 2.77 (d, J=0.4 Hz, 3H), 2.36 (s, 3H).

Example 81

N-(7-(Chloromethyl)-4-methylquinolin-2-yl)acetamide (44)

Alcohol 42 (0.500 g, 2.17 mmol) was cooled to 0° C. under argon. Chilled SOCl$_2$ (2.1 mL) was added, and the mixture was stirred at 0° C. for 1 h. The mixture was then concentrated, and the residue was azeotroped with toluene (2×5 mL) to remove traces of SOCl$_2$. The residue was suspended in H$_2$O and sat. aq. NaHCO$_3$ was added until a white solid precipitated (pH~8). The suspension was extracted with EtOAc (3×50 mL). Sat. aq. NaHCO$_3$ (50 mL) was added to the organic layer, and the mixture was sonicated vigorously until the EtOAc became cloudy, and the mixture was allowed to sit overnight for 17 h (this is to ensure hydrolysis of any by-products arising from overchlorination at the acetyl group). The layers were then separated, and the organic layer was washed with sat. aq. NaCl (100 mL), dried over anhydrous sodium sulfate, and concentrated. The resulting residue was washed with 1% EtOAc in hexanes to yield the title compound as a white iridescent solid (0.508 g, 94%): mp 211-212.5° C. $^1$H-NMR (500 MHz; CDCl$_3$): δ 8.28 (s, 1H), 8.15 (br s, 1H), 7.94 (d, J=8.6 Hz, 1H), 7.79 (d, J=1.4 Hz, 1H), 7.51 (dd, J=8.6, 1.8 Hz, 1H), 4.75 (s, 2H), 2.72 (d, J=0.9 Hz, 3H), 2.27 (s, 3H); $^{13}$C-NMR (126 MHz; CDCl$_3$): δ 169.4, 151.1, 148.1, 139.5, 127.0, 126.1, 125.5, 124.9, 114.9, 46.0, 25.2, 19.4; one of the quinoline carbons is not visible due to baseline broadening; ESIMS m/z (rel. intensity) 271/273 (MNa$^+$, 41/12).

Example 82

7-Bromoquinolin-2-amine (52)

Compound 51 (0.700 g, 2.89 mmol), anhydrous K$_2$CO$_3$ (1.99 g, 14.4 mmol) and acetamide (13.7 g, 231 mmol) were heated, under argon, to reflux (~230° C.) for 18 h. The mixture was cooled, diluted with H$_2$O (60 mL) and the resulting suspension was extracted with EtOAc (3×70 mL). The organic layers were washed with H$_2$O and sat. aq. NaCl (70 mL each), dried over anhydrous sodium sulfate, and concentrated. The resulting solid was dissolved in hot EtOAc (5 mL) and precipitated by the addition of hexanes (100 mL). The yellow solid was collected and dried to yield crude compound 52 (0.481 g, 75%) which was used without any further purification; analytical data for this compound are consistent with those previously reported (X)

Example 83

N-(7-Bromoquinolin-2-yl)acetamide (53)

Compound 52 (0.481 g, 2.15 mmol) was diluted in anhydrous THF (25 mL). N-acetylimidazole (0.284 g, 2.58 mmol) was added, and the mixture was heated to reflux under argon for 20 h, upon which additional N-acetylimidazole (0.284 g, 2.58 mmol) and a catalytic amount of DMAP (~20 mg) were added. After a total of 23 h at reflux, the mixture was cooled and concentrated, and the residue was partitioned between $H_2O$ and EtOAc (30 mL each). The aqueous layer was then extracted with EtOAc (3×30 mL), and the organic layers were washed with $H_2O$ and sat. aq. NaCl (100 mL each). The organic phase was dried over anhydrous sodium sulfate and concentrated, and the residue was purified by flash column chromatography, eluting with a gradient of 5% EtOAc in $CH_2Cl_2$ to 25% EtOAc in $CH_2Cl_2$ to yield the product as a flocculent, off-white solid (0.262 g, 46%) after washing with hexanes: mp 220-222° C. $^1$H-NMR (500 MHz; $CDCl_3$): δ 8.42 (br d, J=8.1 Hz, 1H), 8.20 (br s, 1H), 8.14 (d, J=9.1 Hz, 2H), 7.99 (s, 1H), 7.64 (d, J=8.6 Hz, 1H), 7.54 (d, J=8.7 Hz, 1H), 2.28 (s, 3H); $^{13}$C-NMR (126 MHz; $CDCl_3$): δ 169.3, 151.6, 147.0, 138.9, 129.6, 128.96, 128.94, 125.0, 124.5, 114.5, 25.1; 287/289 ($MNa^+$, 21/20).

Example 84

General Procedure for Sonogashira Coupling Between 7-Bromoquinolines and Phenylacetylenes A sealable vial or tube was charged with the requisite 7-bromoquinoline (1 eq.) and phenylacetylene (1.1-1.5 eq.), XPhos (6 mol %), $Pd(MeCN)_2Cl_2$ (3 mol %), and $Cs_2CO_3$ (1.5 eq.). The vial was evacuated and backfilled with argon several times, and then anhydrous MeCN (2 mL/100 mg bromoquinoline) was added, and the mixture was heated to 75-80° C. overnight (typically 16-18 h). The mixture was then cooled, diluted with water, and extracted with EtOAc (typically 3×30 mL is sufficient), and the organic layers were washed with 5% sat. aq. NaCl (3×50 mL) and sat. aq. NaCl (50 mL). The organic phases were dried over anhydrous sodium sulfate and concentrated to yield residues that were purified using flash column chromatography ($SiO_2$), using gradients as described for individual compounds below.

Example 85 tert-Butyl (3-((2-acetamido-4-methylquinolin-7-yl)ethynyl)benzyl)-(methyl)carbamate (63)

This compound was prepared from 40 (0.059 g, 0.179 mmol) and 57 (0.048 g, 0.197 mmol) at 75° C. Workup and purification by flash column chromatography, eluting with a gradient of 5% EtOAc in $CH_2Cl_2$ to 30% EtOAc in $CH_2Cl_2$ to yield the desired product as a yellow powder (0.058 g, 73%). The identity of the product was confirmed by NMR, and the product was carried on to the next step without further purification or characterization.

Example 86 tert-Butyl (3-((2-acetamidoquinolin-7-yl)ethynyl)-5-cyanobenzyl)-(methyl)carbamate (64)

This compound was prepared from 53 (0.071 g, 0.268 mmol) and 62 (0.083 g, 0.307 mmol) at 80° C. Workup and purification by flash column chromatography, eluting with a gradient of 5% EtOAc in $CH_2Cl_2$ to 30% EtOAc in $CH_2Cl_2$ to yield the desired product as a tan powder (0.031 g, 28%). The product was carried on to the next step without further purification or characterization.

Example 87 tert-Butyl (3-((2-acetamido-4-methylquinolin-7-yl)ethynyl)-5-cyanobenzyl)-(methyl)carbamate (65)

This compound was prepared from 40 (0.120 g, 0.430 mmol) and 62 (0.180 g, 0.665 mmol) at 80° C. Workup and purification by flash column chromatography, eluting with a gradient of 5% EtOAc in $CH_2Cl_2$ to 30% EtOAc in $CH_2Cl_2$ to yield the desired product as a brownish-yellow semisolid (0.191 g, 95%). The product was carried on to the next step without further purification or characterization.

Example 88 tert-Butyl (3-(2-(2-acetamido-4-methylquinolin-7-yl)ethyl)benzyl) (methyl)carbamate (66)

Compound 63 (0.385 g, 0.868 mmol) was diluted with MeOH (40 mL) and heated gently to affect solution. A catalytic amount of 10% Pd/C (~20 mg) was added, and the mixture was hydrogenated (using a balloon) for 20 h at r.t. The Pd/C was then removed via syringe filter, and the filtrate was concentrated. The residue was diluted in minimal $CH_2Cl_2$ (2 mL) and precipitated by the addition of hexanes (50 mL). The suspension was filtered to yield the title compound as a white solid (0.362 g, 93%) after washing with hexanes and drying in vacuo. This compound was deprotected immediately without further characterization or purification.

Example 89 tert-Butyl (3-(2-(2-acetamidoquinolin-7-yl)ethyl)-5-cyanobenzyl) (methyl)carbamate (67)

Compound 64 (0.035 g, 0.077 mmol) was diluted in THF (5 mL), and a catalytic amount of Pd/C(en) was added. The mixture was hydrogenated (using a balloon) for 66 h, with another equivalent of catalyst being added after 18 h. The Pd/C(en) was removed via filtration, and the filtrate was concentrated. The residue was purified by flash column chromatography, eluting with a gradient of 5% EtOAc in $CH_2Cl_2$ to 45% EtOAc in $CH_2Cl_2$ to yield the product as a yellow gum (0.026 g, 76%), which was deprotected immediately without further characterization or purification.

Example 90 tert-Butyl (3-(2-(2-acetamido-4-methylquinolin-7-yl)ethyl)-5-cyanobenzyl) (methyl)carbamate (68)

Compound 65 (0.100 g, 0.213 mmol) was diluted in THF (12 mL), and a catalytic amount of Pd/C(en) was added. The mixture was hydrogenated at 50 PSI on a Parr shaker for 48 h. The Pd/C(en) was removed via filtration, and the filtrate was concentrated. The residue was purified by flash column chromatography, eluting with a gradient of 5% EtOAc in $CH_2Cl_2$ to 40% EtOAc in $CH_2Cl_2$ to yield the product as a yellow gum (0.045 g, 45%), which was immediately deprotected without further purification or characterization.

Example 91

General Procedure for Synthesis of Phenols Containing Boc-Protected Methylamines (General Procedure 1)

This general procedure is similar to that previously reported. Step 1. Methylamine in THF (2 eq.) was diluted with CHCl$_3$ (5-10 mL), and the requisite hydroxybenzaldehyde (1 eq.) was added in a solution of CHCl$_3$/MeOH (typically 5:1-10:1). Anhydrous Na$_2$SO$_4$ (~2-3 g/mmol) was added, and the mixture was stirred rapidly under argon at room temp for 90 min. Glacial AcOH (10 μL/0.100 g starting material) and additional anhydrous Na$_2$SO$_4$ (~1 g/mmol) was added. The mixture was stirred for a total of 4-4.5, and the Na$_2$SO$_4$ was filtered from the mixture. The filtrate was concentrated, and the residue was diluted with MeOH (10 mL/mmol), and cooled to 0° C. NaBH$_4$ (1.4-1.5 eq.) was added, and the mixture was warmed to room temp and stirred for 20 min. The mixture was concentrated, and the residue was partitioned between EtOAc and sat. aq. NaHCO$_3$. The layers were separated and the aqueous layer was extracted with EtOAc until no residual amine was extracted (as measured by TLC, typically 3×). The organic layer was washed with sat. aq. NaCl and dried. Concentration afforded the intermediate secondary amine that was purified below as described for individual compounds. Step 2. The amine was immediately diluted in THF (10 mL/mmol) and Boc$_2$O (1.1-1.3 eq.) was added as a solution in minimal THF. The mixture was stirred until TLC indicated consumption of the starting amine (typically overnight), and then concentrated. The residue was partitioned between EtOAc and sat. aq. NaHCO$_3$ (or H$_2$O), and the aqueous layer was extracted with EtOAc. The combined organic layers were washed with water and sat. aq. NaCl, dried over anhydrous sodium sulfate, and evaporated. The desired Boc-protected amines were obtained after purification by flash column chromatography (described below for individual compounds) and drying in vacuo.

Example 92 tert-Butyl (3-Chloro-5-hydroxybenzyl)(methyl)carbamate (23)

This was prepared from aldehyde 20 (0.250 g, 1.60 mmol), methylamine (2 M in THF, 1.6 mL, 3.2 mmol) and NaBH$_4$ (0.083 g, 2.24 mmol), using General Procedure 1, Step 1. After workup and isolation, the crude intermediate amine was Boc-protected with Boc$_2$O (0.384 g, 1.76 mmol), using General Procedure 1, Step 2. Following workup and purification by flash column chromatography, eluting with a gradient of 5% EtOAc in hexanes to 35% EtOAc in hexanes, 23 was obtained as a chalky white wax (0.378 g, 87%): mp 107-108.5° C. $^1$H-NMR (500 MHz; CDCl$_3$, indicates mixture of rotamers due to Boc group): δ 7.52, 7.35 (2 s, 1H), 6.77 (d, J=7.3 Hz, 1H), 6.70 (s, 1H), 6.62 (d, J=9.0 Hz, 1H), 4.32 (s, 2H), 2.83, 2.79 (2 s, 2H), 1.49, 1.45 (2 s, 9H); $^{13}$C NMR (126 MHz; CDCl$_3$): δ 157.8, (156.7+156.2, 1C), (141.0+140.5, 1C), (135.08+134.93, 1C), (119.7+119.1, 1C), (115.4+115.0, 1C), (112.8+112.0, 1C), (80.85+80.83, 1C), (52.4+51.7, 1C), (34.4+34.2, 1C), 28.6; ESIMS m/z (rel. intensity) 270/272 (MH$^-$, 60/20), 306/308 (M+Cl$^-$, 100/60).

Example 93 tert-Butyl (3-Bromo-5-hydroxybenzyl)(methyl)carbamate (24)

This was prepared from aldehyde 21 (0.718 g, 3.57 mmol), methylamine (2 M in THF, 3.6 mL, 7.2 mmol) and NaBH$_4$ (0.203 g, 5.35 mmol), using General Procedure 1, Step 1. After workup and isolation, the residue was purified by flash column chromatography, eluting with a gradient of 3% MeOH in EtOAc to 30% MeOH in EtOAc to yield the crude intermediate amine (0.626 g) as a very pale tan solid. This material was Boc-protected with Boc$_2$O (0.695 g, 3.19 mmol), using General Procedure 1, Step 2. Following workup and purification by flash column chromatography, eluting with a gradient of 5% EtOAc in hexanes to 30% EtOAc in hexanes, 24 was obtained as a clear and colorless syrup that solidified upon standing (0.858 g, 76%): mp 114.5-116° C. $^1$H-NMR (500 MHz; CDCl$_3$, indicates mixture of rotamers due to Boc group): δ 7.00-6.75 (m, 3H), 6.67-6.64 (m, 1H), 4.32 (s, 2H), 2.84, 2.79 (2 s, 3H), 1.50, 1.56 (2 s, 9H); $^{13}$C-NMR (126 MHz; CDCl$_3$): δ 157.7, (156.6+156.1, 1C), (141.4+141.0, 1C), (122.96+122.91, 1C), (122.76+122.2, 1C), (118.3+117.9, 1C), (113.3+112.5, 1C), 80.7, (52.2+51.6, 1C), (34.4+34.2, 1C), 28.6; ESIMS m/z (rel. intensity) 314/316 (MH$^-$, 30/30), 350/352 (M+Cl$^-$, 80/100).

Example 94 tert-Butyl (3-Hydroxy-5-methoxybenzyl)(methyl)carbamate (25)

This was prepared from aldehyde 22 (0.152 g, 1.00 mmol), methylamine (2 M in THF, 1 mL, 1 mmol) and NaBH$_4$ (0.053 g, 1.4 mmol), using General Procedure 1, Step 1. After workup and isolation, the crude intermediate amine (0.103 g) was Boc-protected with Boc$_2$O (0.150 g, 0.688 mmol), using General Procedure 1, Step 2. Following workup and purification by flash column chromatography, eluting with a gradient of 5% EtOAc in hexanes to 35% EtOAc in hexanes, 24 was obtained as a clear, colorless syrup (0.125 g, 47%): $^1$H-NMR (500 MHz; CDCl$_3$, indicates mixture of rotamers due to Boc group): δ 7.30 (s, 1H), 6.35-7.30 (m, 2H), 6.29 (s, 1H), 4.31 (s, 2H), 3.73 (s, 3H), 2.80, 2.77 (2 s, 3H), 1.49, 1.46 (2 s, 9H); $^{13}$C-NMR (126 MHz; CDCl$_3$): δ (161.14+161.03, 1C), 158.1, (156.6+156.3, 1C), (140.5+140.1, 1C), (107.1+106.4, 1C), (105.9+105.0, 1C), 100.3, (80.47+80.35, 1C), 55.3, (52.7+52.1, 1C), (34.19+34.02), 28.6; ESIMS m/z (rel. intensity) 266 (MH$^-$, 33), 302 (M+Cl$^-$, 100).

Example 95

General Procedure for Cyanation of Aryl Bromides (General Procedure 2)

A sealable tube was charged with aryl bromide (1 eq), t-BuXPhos-Pd G3 (0.028 g/mmol), t-BuXPhos (0.0127 g/l mmol), and K$_4$Fe(CN)$_6$×3 H$_2$O (0.211 g/mmol). The tube was evacuated and backfilled with argon several times. Anhydrous dioxane (2.5 mL/mmol) and 0.1 M aqueous KOAc (degassed, 2.5 mL/mmol) were added, and the mixture was heated to 100° C. until TLC indicated consumption of the starting bromide (typically 1-3 h, sometimes overnight). The mixture was then cooled, and partitioned between EtOAc and H$_2$O (30 mL each). The aqueous layer was extracted with EtOAc (2×30 mL). The organic layers were washed with H$_2$O and sat. aq. NaCl (50 mL each), dried with anhydrous sodium sulfate, and concentrated. The obtained benzonitriles were purified by flash column chromatography as described below for individual compounds.

Example 96 tert-Butyl (3-Cyano-5-methoxybenzyl)(methyl)carbamate (26)

This compound was prepared from 24 (0.316 g, 1 mmol) according to General Procedure 2. After cyanation (80 min) and workup, the residue was purified by flash column chromatography, eluting with a gradient of 15% EtOAc in hexanes to 50% EtOAc in hexanes to yield 26 as a pale-pink foam that solidified to a white wax (0.261 g, 99%) upon standing: mp 81-83.3° C. $^1$H-NMR (500 MHz; CDCl$_3$, indicates mixture of rotamers due to Boc group): δ 7.79, 7.62 (2 s, 1H), 7.05-6.95 (m, 3H), 4.37 (s, 2H), 2.85, 2.83 (2 s, 3H), 1.51, 1.44 (2 s, 9H); $^{13}$C-NMR (126 MHz; CDCl$_3$): δ 157.6, (156.7+156.1, 1C), (141.3+140.9, 1C), (122.7+122.5, 1C), (119.2+118.53, 1C), 118.7, (118.34+118.1, 1C), (113.37+113.26, 1C), 81.2, (52.2+51.7, 1C), 34.6, 28.6. ESIMS m/z (rel. intensity) 262 (MH$^-$, 100).

Example 97 tert-Butyl [3-Hydroxy-5-((trimethylsilyl)ethynyl)benzyl](methyl)carbamate (27)

A sealable vial was charged with 24 (0.316 g, 1 mmol), CuI (0.010 g), and [(PPh$_3$)$_2$PdCl$_2$] (0.021 g). Anhydrous Et$_3$N (4 mL) was added, and the mixture was purged with argon for 10 min. Ethynyltrimethylsilane (0.22 mL, 1.5 mmol) was added, the vial was sealed, and the reaction mixture was heated at 70° C. for 19 h. The mixture was cooled, diluted with EtOAc, and filtered through Celite. The filtrate was concentrated, diluted with EtOAc (50 mL), and washed with 5% aq. NaCl (50 mL). The aqueous layer was extracted with EtOAc (50 mL), and the organic layer was washed with H$_2$O and sat. aq. NaCl (30 mL each), dried over anhydrous sodium sulfate, and dried. The residue was purified by flash column chromatography, eluting with a gradient of 5% EtOAc in hexanes to 20% EtOAc in hexanes to yield the product as a yellow syrup (0.174 g, 52%) that was desilylated immediately: $^1$H-NMR (500 MHz; CDCl$_3$): δ 6.89 (s, 1H), 6.84-6.80 (m, 1H), 6.69 (s, 1H), 4.33 (s, 2H), 2.80 (s, 3H), 1.48 (s, 9H), 0.24 (s, 9H); the phenol proton is not visible due to baseline broadening.

Example 98 tert-Butyl (3-Ethynyl-5-hydroxybenzyl)(methyl)carbamate (28)

Compound 27 (0.120 g, 0.360 mmol) was diluted in anhydrous THF (10 mL), and cooled to 0° C. under argon. TBAF in THF (0.396 mL, 0.396 mmol) was added dropwise, and after 5 min, the mixture was warmed to r.t. and quenched by the addition of 1:1 sat. aq. NaCl:H$_2$O (10 mL). The mixture was extracted with EtOAc (2×20 mL), and the organic layer was washed with 5% sat. aq. NaCl and sat. aq. NaCl, (30 mL each) dried over anhydrous sodium sulfate, and concentrated. The residue was filtered through a short SiO$_2$ plug, washing with EtOAc, and the filtrate was concentrated to afford the product as a brown syrup (0.100 mg, approx. quant.) that was used without any further characterization or purification.

Example 99 tert-Butyl (3-Ethyl-5-hydroxybenzyl)(methyl)carbamate (29)

Compound 28 (0.136 g, 0.52 mmol) was diluted with MeOH (10 mL), and a catalytic amount of 10% Pd/C (~0.010 g) was added. The mixture was hydrogenated with a balloon at room temperature for 18 h. The mixture was filtered through a small pad of Celite to remove the Pd/C and concentrated. The residue was purified by flash column chromatography, eluting with a gradient of 3% EtOAc in hexanes to 30% EtOAc in hexanes to yield the product as a colorless, clear syrup (0.129 g, 93%) after drying in vacuo; $^1$H-NMR (500 MHz; CDCl$_3$, indicates mixture of rotamers due to Boc group): 6.93 (br s, 1H), 6.62 (s, 1H), 6.56 (s, 2H), 4.33 (s, 2H), 2.83, 2.77 (2 s, 3H), 2.55 (q, J=7.4 Hz, 2H), 1.47 (s, 9H), 1.19 (t, J=7.4 Hz, 3H); $^{13}$C-NMR (126 MHz; CDCl$_3$): δ 156.8, (156.5+156.3, 1C), 146.3, (139.5+139.2, 1C), (119.5+118.7, 1C), (114.12+113.99, 1C), (111.9+111.2, 1C), 80.3, (52.7+52.0, 1C), (34.2+34.0, 1C), 28.8, 28.6, 15.5; ESIMS m/z (rel. intensity) 264 (MH$^-$, 5), 300 (M+Cl$^-$, 100).

Example 100 tert-Butyl (3-Iodobenzyl)(methyl)carbamate (55)

Methylamine in THF (2 M, 23.3 mL, 46.6 mmol) was added to anhydrous CH$_2$Cl$_2$ (45 mL). 3-Iodobenzyl bromide (54, 2.77 g, 9.32 mmol) in CH$_2$Cl$_2$ (10 mL) was added dropwise over 10 minutes, and the mixture was stirred at r.t. for 20 h. The formed precipitate was then filtered, and the filtrate concentrated to remove excess methylamine and THF. Anhydrous CH$_2$Cl$_2$ (60 mL) was added to the residue, Boc$_2$O (2.03 g, 9.32 mmol) in CH$_2$Cl$_2$ (10 mL) was added, and the mixture was stirred at room temperature. After 3 h, the mixture was concentrated, and the residue was partitioned between EtOAc and sat. aq. NaHCO$_3$ (50 mL each). The aqueous layer was extracted with EtOAc (2×50 mL) and the organic phase was washed with H$_2$O and sat. aq. NaCl (100 mL each), dried over anhydrous sodium sulfate, and concentrated. The residue was purified by flash column chromatography, eluting with a gradient of hexanes to 10% EtOAc in hexanes, to yield the product as a white solid (2.59 g, 80%): mp 58-60° C. $^1$H-NMR (500 MHz; CDCl$_3$): δ 7.60-7.58 (m, 2H), 7.18 (s, br 1H), 7.06 (t, J=7.7 Hz, 1H), 4.35 (s, 2H), 2.85-2.79 (m, 3H), 1.47 (s, 9H); $^{13}$C-NMR (126 MHz; CDCl$_3$, indicates mixture of rotamers due to Boc group): δ (156.2+155.7, 1C), 140.7, (136.62+136.46, 1C), 136.39, 130.4, (127.0+126.5, 1C), 94.6, 80.1, (52.2+51.5, 1C), 34.2, 28.6; ESIMS m/z (rel. intensity) 370 (M+Na$^+$, 50), 717 (2M+Na$^+$, 100).

Example 101 tert-Butyl Methyl (3-((trimethylsilyl)ethynyl)benzyl)carbamate (56)

A sealable vial was charged with 55 (1.39 g, 4 mmol), CuI (0.040 g), and [(PPh$_3$)$_2$PdCl$_2$] (0.084 g). Anhydrous Et$_3$N (15 mL) was added, and the mixture was purged with argon for 10 min. Ethynyltrimethylsilane (0.88 mL, 6 mmol) was added, the vial was sealed, and the reaction mixture was heated at 70° C. for 17 h. The mixture was cooled, diluted with EtOAc, and filtered through Celite. The filtrate was concentrated, diluted with EtOAc (50 mL), and washed with 5% aq. NaCl (50 mL). The aqueous layer was extracted with EtOAc (50 mL), and the organic layer was washed with $H_2O$ and sat. aq. NaCl (30 mL each), dried over anhydrous sodium sulfate, and dried. The residue was purified by flash column chromatography, eluting with a gradient of hexanes to 10% EtOAc in hexanes to yield the product as a clear syrup that was used in the next step without further characterization (1.24 g, 98%). $^1$H-NMR (500 MHz; $CDCl_3$): δ 7.36 (d, J=7.6 Hz, 1H), 7.33 (s, 1H), 7.27-7.24 (m, 1H, partially obscured by solvent peak), 7.18 (s, 1H), 4.38 (s, 2H), 2.83-2.77 (m, 3H), 1.48 (s, 9H), 0.25 (s, 9H).

Example 102 tert-Butyl (3-Ethynylbenzyl)(methyl)carbamate (57)

Compound 56 (1.24 g, 3.91 mmol) was diluted in anhydrous THF (50 mL), and cooled to 0° C. under argon. TBAF in THF (4.92 mL, 4.92 mmol) was added dropwise, and after 10 min, the mixture was warmed to r.t. and quenched by the addition of 1:1 sat. aq. $NaCl:H_2O$ (50 mL). The mixture was extracted with EtOAc (2×50 mL), and the organic layer was washed with 5% sat. aq. NaCl and sat. aq. NaCl (100 mL each), dried over anhydrous sodium sulfate, and concentrated. The residue was filtered through a short $SiO_2$ plug, washing with 4:1 hexanes/EtOAc, and the filtrate was concentrated to afford the product as a pale orange crystalline solid (0.914 g, 95%): mp 48-50° C. $^1$H-NMR (500 MHz; $CDCl_3$): δ 7.39 (d, J=7.6 Hz, 1H), 7.35 (s, 1H), 7.29 (t, J=7.6 Hz, 1H), 7.22 (br s, 1H), 4.39 (s, 2H), 3.07 (s, 1H), 2.84-2.79 (m, 3H), 1.48 (s, 9H); $^{13}$C-NMR (126 MHz; $CDCl_3$, indicates mixture of rotamers due to Boc group): δ (156.3+ 155.8, 1C), 138.6, 131.4, 131.1, 128.7, (128.3+127.8, 1C), 122.4, 83.6, 80.0, (52.4+51.7, 1C), 34.2, 28.6; one of the carbons is obscured by the solvent signal; ESIMS m/z (rel. intensity) 268 (M+Na$^+$, 50), 513 (2M+Na$^+$, 100).

Example 103

3-Bromo-5-(bromomethyl)benzonitrile (59)

Compound 58 (0.500 g, 2.55 mmol) was diluted in $CCl_4$ (12 mL). N-Bromosuccinimide (0.476 g, 2.67 mmol), and benzoyl peroxide (catalytic, ~0.020 g) were added, and the mixture was heated to reflux for 6 h, and then cooled to r.t. and stirred for 18 h. The mixture was filtered, and the filter cake was washed with 10% EtOAc in hexanes. The filtrate was concentrated and the residue was purified by flash column chromatography, eluting with a gradient of hexanes to 10% EtOAc in hexanes to yield the product as a white solid (0.327 g, 47%); the analytical data for this compound are constant with those previously reported. (X)

Example 104 tert-Butyl (3-bromo-5-cyanobenzyl)(methyl)carbamate (60)

Methylamine in THF (2 M, 3 mL, 6 mmol) was added to anhydrous $CH_2Cl_2$ (7 mL). Compound 59 (0.327 g, 1.20 mml) in $CH_2Cl_2$ (7 mL) was added dropwise over 10 minutes, and the mixture was stirred at r.t. for 90 min. The formed precipitate was then filtered, and the filtrate concentrated to remove excess methylamine and THF. Anhydrous $CH_2Cl_2$ (20 mL) was added to the residue, $Boc_2O$ (0.288 g, 1.32 mmol) in $CH_2Cl_2$ (3 mL) was added, and the mixture was stirred at room temperature. After 90 min, the mixture washed with sat. aq. $NaHCO_3$ (30 mL each). The aqueous layer was extracted with $CH_2Cl_2$ (20 mL) and the organic phase was washed with $H_2O$ and sat. aq. NaCl (30 mL each), dried over anhydrous sodium sulfate, and concentrated. The residue was purified by flash column chromatography, eluting with a gradient of 5% EtOAc hexanes to 25% EtOAc in hexanes, to yield the product as a clear, colorless syrup (0.307 g, 79%) that was immediately used in the next step without further characterization or purification.

Example 105 tert-Butyl [3-Cyano-5-((trimethylsilyl)ethynyl)benzyl](methyl)carbamate (61)

A sealable vial was charged with 60 (0.309 g, 0.944 mmol), CuI (0.0094 g), and [(PPh$_3$)$_2$PdCl$_2$] (0.021 g). Anhydrous $Et_3N$ (4 mL) was added, and the mixture was purged with argon for 10 min. Ethynyltrimethylsilane (0.22 mL, 1.5 mmol) was added, the vial was sealed, and the reaction mixture was heated at 70° C. for 17 h. The mixture was cooled, diluted with EtOAc (20 mL), and filtered through Celite. The filtrate was concentrated, and the residue was dried in vacuo and purified by flash column chromatography, eluting with a gradient of 5% EtOAc in hexanes to 20% EtOAc in hexanes to yield the product as a clear syrup (0.315 g, 98%) that was immediately used in the next step without further characterization or purification.

Example 106 tert-Butyl (3-Cyano-5-ethynylbenzyl)(methyl)carbamate (62)

Compound 61 (0.342 g, 1 mmol) was diluted in anhydrous THF (8 mL), and cooled to 0° C. under argon. TBAF in THF (1.1 mL, 1.1 mmol) was added dropwise, and after 10 min, the dark maroon mixture was warmed to r.t. and quenched by the addition of 1:1 sat. aq. $NaCl:H_2O$ (50 mL). The mixture was extracted with EtOAc (2×20 mL), and the organic layer was washed with 5% sat. aq. NaCl and sat. aq. NaCl (50 mL each), dried over anhydrous sodium sulfate, and concentrated. The residue was purified by flash column chromatography, eluting with a gradient of 5% EtOAc in hexanes to 30% EtOAc in hexanes to yield the product as a clear and colorless syrup (0.185 g, 69%). This alkyne is very sensitive to heat and light, and was used immediately without any further purification or characterization. $^1$H-NMR (500 MHz; $CDCl_3$): δ 7.66 (s, 1H), 7.55 (s, 1H), 7.48 (s, 1H), 4.42 (s, 2H), 3.18 (s, 1H), 2.88-2.83 (m, 3H), 1.49-1.47 (m, 9H).

Example 107

1-Bromo-3-(bromomethyl)-2-fluorobenzene (70)

Compound 69 (1.00 g, 5.29 mmol) was diluted in $CCl_4$ (10 mL). N-Bromosuccinimide (1.016 g, 5.71 mmol), and benzoyl peroxide (catalytic, ~0.030 g) were added, and the mixture was heated to reflux for 2.5 h, and then cooled to r.t. and stirred for 18 h. The mixture was filtered, and the filter cake was washed with hexanes. The filtrate was concentrated and the residue was purified by flash column chromatography, eluting with a gradient of 5% $CH_2Cl_2$ in hexanes to 10% $CH_2Cl_2$ in hexanes to yield the product as a white solid (0.908 g, 64%). The analytical data for this compound are constant with those previously reported. (X)

Example 108 tert-Butyl (3-bromo-2-fluorobenzyl)(methyl)carbamate (71)

Methylamine in THF (2 M, 8.47 mL, 16.9 mmol) was added to anhydrous $CH_2Cl_2$ (20 mL). Compound 70 (0.908 g, 3.39 mmol) in $CH_2Cl_2$ (10 mL) was added dropwise over 10 minutes, and the mixture was stirred at r.t. for 90 min. The formed precipitate was then filtered, and the filtrate concentrated to remove excess methylamine and THF. Anhydrous $CH_2Cl_2$ (30 mL) was added to the residue, $Boc_2O$ (0.739 g, 3.39 mmol) in $CH_2Cl_2$ (5 mL) was added, and the mixture was stirred at room temperature overnight, concentrated, and the residue was purified by flash column chromatography, eluting with a gradient of 5% EtOAc hexanes to 20% EtOAc in hexanes, to yield the product as a clear, colorless syrup (0.811 g, 75%); $^1$H-NMR (500 MHz; $CDCl_3$): δ 7.45 (t, J=6.9 Hz, 1H), 7.23-7.16 (m, 1H), 7.00 (t, J=7.8 Hz, 1H), 4.51-4.48 (m, 2H), 2.89-2.84 (m, 3H), 1.48-1.44 (m, 9H); $^{13}$C-NMR (126 MHz; $CDCl_3$, indicates mixture of rotamers due to Boc group): δ (158.23+158.12, 156.2, 1C,), (156.1+155.7, 1C), 132.5, (128.9+128.2, 1C), (127.05+126.93, 1C), (125.26+125.19, 1C), (109.32+109.15, 1C), (80.19+80.05, 1C), (46.7+45.9, 1C), 34.5, 28.5. ESIMS m/z (rel. intensity) 340/342 (M+Na$^+$, 95/100).

Example 109 tert-Butyl (3-cyano-2-fluorobenzyl)(methyl)carbamate (72)

This compound was prepared from 72 (0.636 g, 2 mmol) according to General Procedure 2. After cyanation (22 h) and workup, the residue was purified by flash column chromatography, eluting with a gradient of 5% EtOAc in hexanes to 45% EtOAc in hexanes to yield 73 as a clear, colorless syrup. (0.333 g, 63%); $^1$H-NMR (500 MHz; $CDCl_3$): δ 7.56-7.48 (m, 2H), 7.24 (t, J=7.7 Hz, 1H), 4.50 (s, 2H), 2.90-2.87 (m, 3H), 1.48-1.44 (m 9H). $^{13}$C-NMR (126 MHz; $CDCl_3$, indicates mixture of rotamers due to Boc group): δ (162.2+160.2, 1C), (156.0+155.4, 1C), (135.0+134.0, 1C), 132.4, 126.9, 124.9, 113.9, 101.6, (80.42+80.28, 1C), (46.1+45.3, 1C), 34.7, 28.4. ESIMS m/z (rel. intensity) 287 (M+Na$^+$, 40), 551 (2M+Na$^+$, 70).

Example 110 tert-Butyl (3-cyano-2-fluoro-5-hydroxybenzyl) (methyl)carbamate (73)

A sealable vial was charged with $Pin_2B_2$ (0.053 g, 0.208 mmol) dtbpy, (0.003 g, 3 mol %) and $[Ir(OMe)(COD)]_2$ (0.0037 g, 1.5 mol %), and the vial was flushed with argon for ~2 min and sealed. Anhydrous hexane (2 mL) was added and the mixture was heated to 50° C. for 10 min, upon which it became a dark red color, and following which compound 72 (0.100 g, 0.378 mmol) was added in anhydrous hexane (1 mL). The mixture was heated at 50° C. for 18 h and cooled. The mixture was concentrated, acetone (3 mL) was added to the residue, and the mixture was cooled to 0° C. Oxone (0.232 g, 0.754 mmol) in $H_2O$ (1 mL) was added dropwise, and the mixture was stirred at 0° C. for 10 min. The reaction was quenched by the addition of sat aq. $NaHCO_3$ until the pH was ~9, and the mixture was extracted with EtOAc (3×20 mL). The organic layers were washed with 5% aq. NaCl (2×30 mL) and sat aq. NaCl (30 mL) and dried over anhydrous sodium sulfate. Concentration afforded a residue that was purified by flash column chromatography to afford 73 as a cream-colored semisolid (0.054 g, 51%). $^1$H-NMR (500 MHz; $CDCl_3$): δ 7.05-6.92 (m, 3H), 4.44 (s, 2H), 2.89-2.86 (m, 3H), 1.48-1.43 (m, 9H).

Example 111 tert-Butyl (3-bromophenethyl)(methyl)carbamate (77)

3-Bromophenethylamine (75, 1.00 g, 5.00 mmol) was diluted in anhydrous THF (20 mL). $Boc_2O$ (1.14 g, 5.24 mmol) wad added as a solution in THF (5 mL) and the mixture was stirred at r.t. for 18 h and concentrated. The residue was diluted in anhydrous DMF (10 mL) and added slowly at 0° C. to NaH (0.200 g of a 60% dispersion, 5.00 mmol) in dry DMF (10 mL). The mixture was then warmed to r.t., and MeI (0.327 mL, 0.327 mL, 5.25 mmol) wad added. After 90 min, additional MeI (0.654 mL) was added, and the mixture was heated to 60° C. overnight. The mixture was cooled and quenched with 1:1 $H_2O$:sat. $NaHCO_3$, and extracted with EtOAc (3×50 mL). The organic layers were washed with 5% aq. NaCl (50 mL) and sat. aq. NaCl (50 mL), dried over anhydrous sodium sulfate, and concentrated. The residue was purified by flash column chromatography, eluting with a gradient of hexanes to 20% EtOAc in hexanes to yield the desired product as a colorless syrup (0.683 g, 44%). $^1$H-NMR (500 MHz; $CDCl_3$): δ 7.35-7.33 (m, 2H), 7.15 (t, J=7.8 Hz, 1H), 7.09 (br s, 1H), 3.42 (t, J=7.3 Hz, 2H), 2.83-2.77 (m, 5H), 1.43-1.38 (m, 9H). $^{13}$C-NMR (126 MHz; $CDCl_3$, indicates rotameric states due to the Boc group): δ 155.6, 141.7, 132.0, 130.1, 129.5, 127.7, 122.6, 79.5, 50.5, (35.0+33.9, 1C), 34.3, 28.5; ESIMS m/z (rel. intensity) 336/338 (M+Na$^+$, 100/98).

Example 112

(RS)-tert-Butyl (1-(3-bromophenyl)propan-2-yl) (methyl)carbamate (78)

Compound 76 (0.213 g, 1 mmol) was diluted in anhydrous $CH_2Cl_2$ (5 mL) and the solution was cooled to 0° C. Methylamine (2 M in THF, 2.25 mL, 4.5 mmol) was added, and the mixture was warmed to r.t. under argon. After 1 h, glacial AcOH (0.26 mL) was added, followed by $Na(OAc)_3BH$ (0.318 g, 1.5 mmol) in small portions. The mixture was stirred at r.t. for 18 h and concentrated. 2 M NaOH (30 mL) was added, and the suspension was extracted with EtOAc (3×30 mL). The organic phase was washed with sat. aq. NaCl (30 mL) and dried. Concentration afforded a residue that was diluted with anhydrous THF (25 mL), and Boc2O (0.218 g, 1 mmol) was added as a solution in THF (4 mL). The mixture was stirred at r.t. for 90 minutes, and the mixture was then concentrated and the residue was purified by flash column chromatography, eluting with a gradient of 5% EtOAc in hexanes to 30% EtOAc in hexanes to yield the desired product as a clear, colorless syrup (0.304 g, 93%) that was carried to the next step without further purification or characterization. $^1$H-NMR (500 MHz; $CDCl_3$, indicates rotameric states due to the Boc group): δ 7.34-7.30 (m, 2H), 7.13 (t, J=7.9 Hz, 1H), 7.10-7.04 (m, 1H), 4.51, 4.32 (2 br s, 1H), 2.71-2.60 (m, 5H), 1.36, 1.31 (2 s, 9H), 1.15-1.14 (m, 3H).

Example 113 tert-Butyl (3-cyanophenethyl)(methyl)carbamate (79)

This compound was prepared from 77 (0.314 g, 1 mmol) according to General Procedure 2. After cyanation (18 h) and workup, the residue was purified by flash column chromatography, eluting with a gradient of 10% EtOAc in hexanes to 45% EtOAc in hexanes to yield 79 as a pale yellow syrup (0.211 g, 81%); $^1$H-NMR (500 MHz; CDCl$_3$): δ 7.52-7.51 (m, 1H), 7.48 (s, 1H), 7.42-7.38 (m, 2H), 3.45 (t, J=7.2 Hz, 2H), 2.86-2.81 (m, 5H), 1.40 (s, 9H). 13C-NMR (126 MHz; CDCl$_3$, indicates rotameric states due to Boc group): δ 155.5, 140.9, 133.7, 132.5, 130.2, 129.4, 119.0, 112.7, 79.7, (50.3+50.0, 1C), 35.0, (34.3+33.8, 1C) 28.5; ESIMS m/z (rel. intensity) 283 (M+Na$^+$, 50).

Example 114

(RS)-tert-Butyl (1-(3-cyanophenyl)propan-2-yl)(methyl)carbamate (80)

This compound was prepared from 78 (0.304 g, 0.926 mmol) according to General Procedure 2. After cyanation (94 h) and workup, the residue was purified by flash column chromatography, eluting with a gradient of 5% EtOAc in hexanes to 30% EtOAc in hexanes to yield 26 as a clear, colorless syrup (0.166 g, 65%); $^1$H-NMR (500 MHz; CDCl$_3$): δ 7.50 (d, J=7.5 Hz, 1H), 7.45 (s, 1H), 7.43-7.36 (m, 2H), 4.45-4.44 (m, 1H), 2.78 (dd, J=13.9, 9.1 Hz, 1H), 2.71-2.68 (m, 4H), 1.33 (s, 9H), 1.17 (d, J=6.7 Hz, 3H); $^{13}$C-NMR (126 MHz; CDCl$_3$, indicates presence of rotamers due to Boc group): δ 155.4, 140.7, 133.7, 132.5, 130.1, 129.2, 118.9, 112.4, 79.5, (52.2+51.0, 1C), 40.1, 28.36, (28.19+27.5, 1C), (18.6+17.9, 1C); ESIMS m/z (rel. intensity) 297 (M+Na$^+$, 100).

Example 115 tert-Butyl (3-Cyano-5-hydroxyphenethyl)(methyl)carbamate (81)

A sealable vial was charged with Pin$_2$B$_2$ (0.049 g, 0.192 mmol) dtbpy, (0.006 g, 6 mol %) compound 79 (0.100 g, 0.384 mmol), and [Ir(OMe)(COD)]$_2$ (0.0076 g, 3 mol %). The vial was flushed with argon for ~2 min and sealed, and anhydrous hexane (1.5 mL) was added and the mixture was stirred at r.t. for 18 h. The mixture was concentrated, acetone (3 mL) was added to the residue, and Oxone (0.232 g, 754 mmol) in H$_2$O (2 mL) was added dropwise. The mixture was stirred at r.t. for 10 min, and the reaction was quenched by the addition of sat aq. NaHCO$_3$ until the pH was ~8, and the mixture was extracted with EtOAc (3×10 mL). The organic layers were washed with 5% aq. NaCl (20 mL) and sat aq. NaCl (20 mL) and dried over anhydrous sodium sulfate. Concentration afforded a residue that was purified by flash column chromatography, eluting with a gradient of 15% EtOAc in hexanes to 60% EtOAc in hexanes to afford 81 as a white solid (0.025 g, 24%) which was used crude in the next step without further purification or characterization. $^1$H-NMR (500 MHz; CDCl$_3$): δ 7.01 (s, 1H), 6.99 (s, 1H), 6.92-6.89 (m, 1H), 3.45 (t, J=7.1 Hz, 2H), 2.84 (s, 3H), 2.77 (t, J=7.0 Hz, 2H), 1.39 (s, 9H).

Example 116

(RS)-tert-Butyl (1-(3-Cyano-5-hydroxyphenyl)propan-2-yl)(methyl)carbamate (82)

A sealable vial was charged with Pin$_2$B$_2$ (0.053 g, 0.208 mmol) dtbpy, (0.003 g, 3 mol %) and [Ir(OMe)(COD)]$_2$ (0.0037 g, 1.5 mol %), and the vial was flushed with argon for ~2 min and sealed. Anhydrous hexane (0.5 mL) was added and the mixture was heated to 50° C. for 10 min, upon which it became a dark red color, and following which compound 80 (0.104 g, 0.378 mmol) was added in anhydrous hexane (1 mL). The mixture was heated at 50° C. for 19 h and cooled. The mixture was concentrated, acetone (3 mL) was added to the residue, and the mixture was cooled to 0° C. Oxone (0.232 g, 0.753 mmol) in H$_2$O (2 mL) was added dropwise, and the mixture was stirred at 0° C. for 10 min. The reaction was quenched by the addition of sat. aq. NaHCO$_3$ until the pH was ~8, and the mixture was extracted with EtOAc (3×20 mL). The organic layers were washed with 5% aq. NaCl (30 mL) and sat aq. NaCl (30 mL) and dried over anhydrous sodium sulfate. Concentration afforded a residue that was purified by flash column chromatography, eluting with a gradient of 10% EtOAc in hexanes to 40% ethyl EtOAc in hexanes to afford 82 as a yellow foamy semisolid (0.060 g, 55%) which was used crude in the next step without further purification or characterization. $^1$H-NMR (500 MHz; CDCl$_3$): δ 7.07-6.88 (m, 3H), 4.47-4.41 (m, 1H), 2.71-2.61 (m, 5H), 1.33 (s, 9H), 1.18 (d, J=6.6 Hz, 3H).

Example 117

(R,R)—N-(1-(3-bromophenyl)propan-2-yl)-2-methylpropane-2-sulfinamide (R,R-86)

Compound 76 (0.426 g, 2.00 mmol) was diluted in anhydrous THF (10 mL) and Ti(OEt)$_4$ (1.048 mL, 4 mmol) was added, followed by (R)-85 (0.242 g, 2.00 mmol), as a solution in 2 mL anhydrous THF. The reaction mixture was heated to 70° C. for 3 h, and was cooled to r.t. and then to 0° C. This solution was added dropwise to a stirring suspension of NaBH$_4$ (0.304 g, 8.00 mmol) in anhydrous THF (10 mL) at −48° C. After 45 min at −48° C., the reaction was quenched by addition of MeOH until gas evolution ceased. The mixture was then warmed to r.t. and an equal volume of sat. aq. NaCl was added to precipitate titanium salts. After stirring for 5 min, the suspension was filtered through celite and the filter cake was washed with EtOAc (100 mL). The organic layers were separated, and the aqueous layer was extracted with EtOAc (2×40 mL). The combined organic layers were dried over anhydrous sodium sulfate, and concentrated to yield a residue that was purified by flash column chromatography, eluting with a gradient of 30% EtOAc in hexanes to 70% EtOAc in hexanes to afford the title compound (major diastereomer) as a colorless, clear syrup (0.373 g, 59%). The compound was used crude in the next step without further purification. $^1$H-NMR (500 MHz; CDCl$_3$): δ 7.38-7.36 (m, 2H), 7.20-7.14 (m, 2H), 3.65 (sextet, J=6.4 Hz, 1H), 3.21-3.14 (m, 1H), 2.82 (qd, J=12.6, 6.6 Hz, 2H), 1.18-1.17 (m, 12H).

Example 118

(S,S)—N-(1-(3-bromophenyl)propan-2-yl)-2-methylpropane-2-sulfinamide (S,S-86)

Compound 76 (0.390 g, 1.83 mmol) was diluted in anhydrous THF (7 mL) and Ti(OEt)$_4$ (0.961 mL, 3.66 mmol)

was added, followed by (S)-85 (0.222 g, 1.93 mmol), as a solution in 2 mL anhydrous THF. The reaction mixture was heated to 70° C. for 3 h, and was cooled to r.t. and then to 0° C. This solution was added dropwise to a stirring suspension of $NaBH_4$ (0.279 g, 7.32 mmol) in anhydrous THF (10 mL) at −48° C. After 45 min at −48° C., the reaction was quenched by addition of MeOH until gas evolution ceased. The mixture was then warmed to r.t. and an equal volume of sat. aq. NaCl was added to precipitate titanium salts. After stirring for 5 min, the suspension was filtered through celite and the filter cake was washed with EtOAc (100 mL). The organic layers were separated, and the aqueous layer was extracted with EtOAc (2×40 mL). The combined organic layers were dried over anhydrous sodium sulfate, and concentrated to yield a residue that was purified by flash column chromatography, eluting with a gradient of 30% EtOAc in hexanes to 70% EtOAc in hexanes to afford the title compound (major diastereomer) as a colorless, clear syrup (0.341 g, 59%). The compound was used crude in the next step without further purification. $^1$H-NMR (500 MHz; $CDCl_3$): δ 7.38-7.36 (m, 2H), 7.21-7.14 (m, 2H), 3.65 (m, 1H), 3.23-3.17 (m, 1H), 2.82 (qd, J=12.9, 6.5 Hz, 2H), 1.18-1.17 (m, 12H).

Example 119

(R)-tert-Butyl (1-(3-bromophenyl)propan-2-yl)carbamate (R-87)

Compound (R,R)-86 (0.564 g, 1.77 mmol) was diluted in ether:MeOH (10:1, 11 mL) and methanolic HCl (3 M, 2.5 mL, 7.5 mmol) was added. The mixture was stirred at r.t. overnight and concentrated. Ether (10 mL) was added to precipitate a white crystalline solid that was diluted in minimal MeOH (2 mL). $Et_3N$ (0.323 mL, 2.44 mmol) was added, and after 5 min, the mixture was diluted with anhydrous THF (20 mL). $Boc_2O$ (0.391 g, 1.8 mmol) was then added as a solution in anhydrous THF (2 mL). The mixture was stirred at r.t. for 3 h and concentrated, and the residue was partitioned between 5% aq. NaCl and EtOAc (30 mL each). The layers were separated, and the aqueous layer was extracted with EtOAc (2×30 mL). The organic layer was washed with 5% aq. NaCl (2×30 mL), sat. aq. NaCl (30 mL) and dried over anhydrous sodium sulfate. Concentration afforded a residue that was purified by flash column chromatography, eluting with a gradient of 3% EtOAc in hexanes to 15% EtOAc in hexanes, to yield the title compound as a flocculent white solid ((0.506 g, 91% from (R,R-86)): mp 113-114.5° C. $^1$H-NMR (500 MHz; $CDCl_3$): δ 7.36-7.33 (m, 2H), 7.16 (t, J=7.7 Hz, 1H), 7.11 (d, J=7.6 Hz, 1H), 4.35 (br s, 1H), 3.88 (br s, 1H), 2.83-2.79 (m, 1H), 2.63 (dd, J=13.4, 7.3 Hz, 1H), 1.43 (s, 9H), 1.09 (d, J=6.7 Hz, 3H); $^{13}$C-NMR (126 MHz; $CDCl_3$): δ 155.2, 140.8, 132.6, 130.0, 129.6, 128.3, 122.5, 79.5, 47.5, 42.8, 28.5, 20.3; ESIMS m/z (rel. intensity) 336/338 ($MNa^+$, 41/46).

Example 120

(S)-tert-Butyl (1-(3-bromophenyl)propan-2-yl)carbamate (S-87)

Compound (S,S)-86 (0.341 g, 1.07 mmol) was diluted in ether:MeOH (10:1, 10 mL) and methanolic HCl (3 M, 1.43 mL, 4.28 mmol) was added. The mixture was stirred at r.t. overnight and concentrated. Ether (10 mL) was added to precipitate a white crystalline solid that was diluted in minimal MeOH (2 mL). $Et_3N$ (0.210 mL, 1.5 mmol) was added, and after 5 min, the mixture was diluted with anhydrous THF (20 mL). $Boc_2O$ (0.391 g, 1.8 mmol) was then added as a solution in anhydrous THF (2 mL). The mixture was stirred at r.t. for 3 h and concentrated, and the residue was partitioned between 5% aq. NaCl and EtOAc (30 mL each). The layers were separated, and the aqueous layer was extracted with EtOAc (2×30 mL). The organic layer was washed with 5% aq. NaCl (2×30 mL), sat. aq. NaCl (30 mL) and dried over anhydrous sodium sulfate. Concentration afforded a residue that was purified by flash column chromatography, eluting with a gradient of 3% EtOAc in hexanes to 15% EtOAc in hexanes, to yield the title compound as a flocculent white solid ((0.273 g, 81% from (S,S-86)): mp 113-114.5° C.; lit$^X$ mp 108-109° C. $^1$H-NMR (500 MHz; $CDCl_3$): δ 7.36-7.33 (m, 2H), 7.16 (t, J=7.7 Hz, 1H), 7.11 (d, J=7.6 Hz, 1H), 4.36 (br s, 1H), 3.88 (br s, 1H), 2.82-2.79 (m, 1H), 2.63 (dd, J=13.4, 7.3 Hz, 1H), 1.43 (s, 9H), 1.09 (d, J=6.7 Hz, 3H); $^{13}$C-NMR (126 MHz; $CDCl_3$): δ 155.2, 140.8, 132.6, 130.0, 129.6, 128.3, 122.5, 79.5, 47.5, 42.7, 28.5, 20.3; ESIMS m/z (rel. intensity) 336/338 ($MNa^+$, 23/20);

Example 121

(R)-tert-Butyl (1-(3-bromophenyl)propan-2-yl)(methyl)carbamate (R-78)

Compound (R)-87 (0.500 g, 1.59 mmol) was diluted in anhydrous THF (10 mL), and under argon, cooled to 0° C. NaH (0.076 g, 60% dispersion, 3.18 mmol) was added in one portion, and the mixture was stirred at r.t. for 20 min, and then cooled back to 0° C. Iodomethane (0.451 g, 3.18 mmol) was added dropwise, and the mixture was warmed to r.t. and stirred for 20 h, after which it was quenched by careful addition of 1:1 sat. aq. NaCl and sat. aq. $NaHCO_3$. The layers were separated and the aqueous layer was extracted with EtOAc (3×30 mL). The organic layers were washed with 5% aq. NaCl and sat. aq. NaCl (50 mL each), dried over anhydrous sodium sulfate, and concentrated. The residue was purified by flash column chromatography, eluting with a gradient of hexanes to 20% EtOAc in hexanes, to yield the title compound as a clear, colorless syrup (0.470 g, 90%). $^1$H-NMR (500 MHz; $CDCl_3$, indicates presence of rotamers due to Boc group): δ 7.32-7.30 (s, 2H), 7.13-7.00 (m, 2H), 4.48, 4.32 (2 br s, 1H), 2.71-2.59 (m, 5H), 1.36, 1.31 (2 s, 9H), 1.15-1.14 (m, 3H); $^{13}$C-NMR (126 MHz; $CDCl_3$): δ 155.4, 141.5, 132.0, 129.9, 129.3, 127.7, 122.4, 79.3, (52.3+51.1, 1C), 40.2, 28.34, (28.21+27.4, 1C), (18.5+17.6, 1C); ESIMS m/z (rel. intensity) 350/352 ($MNa^+$, 16/17), 679 (2$MNa^+$, 100).

Example 122

(S)-tert-Butyl (1-(3-bromophenyl)propan-2-yl)(methyl)carbamate (S-78)

Compound (S)-87 (0.267 g, 0.850 mmol) was diluted in anhydrous THF (5 mL), and under argon, was cooled to 0° C. NaH (0.042 g, 60% dispersion, 1.70 mmol) was added in one portion, and the mixture was stirred at r.t. for 20 min, and then cooled back to 0° C. Iodomethane (0.243 g, 1.70 mmol) was added dropwise, and the mixture was warmed to r.t. and stirred for 20 h, after which it was quenched by careful addition of 1:1 sat. aq. NaCl and sat. aq. $NaHCO_3$. The layers were separated and the aqueous layer was extracted with EtOAc (3×30 mL). The organic layers were washed with 5% aq. NaCl and sat. aq. NaCl (50 mL each), dried over anhydrous sodium sulfate, and concentrated. The residue was purified by flash column chromatography, eluting with a gradient of hexanes to 20% EtOAc in hexanes, to yield the title compound as a clear, colorless syrup (0.177 g, 63%). $^1$H-NMR (500 MHz; CDCl$_3$, indicates presence of rotamers due to Boc group): δ 7.32-7.30 (m, 2H), 7.15-7.03 (m, 2H), 4.50, 4.34 (2 br s, 1H), 2.73-2.60 (m, 5H), 1.39, 1.32 (2 s, 9H), 1.16-1.14 (m, 3H); $^{13}$C NMR (126 MHz; CDCl$_3$): δ 155.6, 141.6, 132.1, 129.4, 127.8, 122.5, 79.5, (52.5+51.3 1C), 40.3, 28.48, (28.30+27.5, 1C), (18.6+17.7, 1C); ESIMS m/z (rel. intensity) 350/352 (MNa$^+$, 74/71), 679 (2MNa$^+$, 100).

Example 123

(R)-tert-Butyl (1-(3-cyanophenyl)propan-2-yl)(methyl)carbamate (R-80)

This compound was prepared from (R)-78 (0.328 g, 1 mmol) according to General Procedure 2. After cyanation (19 h) and workup, the residue was purified by flash column chromatography, eluting with a gradient of 15% EtOAc in hexanes to 50% EtOAc in hexanes to yield (R)-80 as a clear, colorless syrup (0.268 g, 98%) after drying in vacuo. $^1$H-NMR (500 MHz; CDCl$_3$): δ 7.50 (d, J=7.5 Hz, 1H), 7.45 (s, 1H), 7.43-7.36 (m, 2H), 4.53-4.34 (m, 1H), 2.78 (dd, J=13.8, 9.2 Hz, 1H), 2.72-2.68 (m, 4H), 1.33 (s, 9H), 1.17 (d, J=5.4 Hz, 3H); $^{13}$C-NMR (126 MHz; CDCl$_3$, indicates presence of rotamers due to Boc group): δ 155.5, 140.7, 133.7, 132.6, 130.2, 129.2, 119.0, 112.4, 79.6, (52.3+51.1, 1C), 40.2, 28.45, (28.28+27.6, 1C), (18.7+18.0, 1C); ESIMS m/z (rel. intensity) 297 (MNa$^+$, 63), 571 (2MNa$^+$, 100).

Example 124

(S)-tert-Butyl (1-(3-cyanophenyl)propan-2-yl)(methyl)carbamate (S-80)

This compound was prepared from (S)-78 (0.164 g, 0.5 mmol) according to General Procedure 2. After cyanation (19 h) and workup, the residue was purified by flash column chromatography, eluting with a gradient of 15% EtOAc in hexanes to 50% EtOAc in hexanes to yield (S)-80 as a clear, colorless syrup (0.127 g, 93%) after drying in vacuo. $^1$H-NMR (500 MHz; CDCl$_3$, indicates presence of rotamers due to Boc group): δ 7.51-7.37 (m, 4H), 4.54-4.33 (m, 1H), 2.81-2.67 (m, 5H), 1.36, 1.32 (2 s, 9H), 1.18 (br s, 1H); $^{13}$C-NMR (126 MHz; CDCl$_3$): δ (155.6+155.4, 1C), (140.81+140.67, 1C), 133.7, 132.6, 130.2, 129.3, (119.07+119.02, 1C), (112.6+112.4, 1C), (79.63+79.57, 1C), (52.3+51.1, 1C), (40.26+40.11, 1C), 28.45, (28.33+27.5, 1C), (18.7+17.9, 1C); ESIMS m/z (rel. intensity) 297 (MNa$^+$, 95), 571 (2MNa$^+$, 100).

Example 125

(R)-tert-Butyl (1-(3-Cyano-5-hydroxyphenyl)propan-2-yl)(methyl)carbamate (R-82)

A sealable vial was charged with Pin$_2$B$_2$ (0.080 g, 0.312 mmol) dtbpy, (0.0045 g, 3 mol %) and [Ir(OMe)(COD)]$_2$ (0.0056 g, 1.5 mol %), and the vial was flushed with argon for ~2 min and sealed. Anhydrous hexane (0.5 mL) was added and the mixture was heated to 50° C. for 10 min, upon which it became a dark red color, and following which compound (R)-80 (0.156 g, 0.567 mmol) was added in anhydrous hexane (2 mL). The mixture was heated at 50° C. for 18 h and cooled. The mixture was concentrated, acetone (6 mL) was added to the residue, and the mixture was cooled to 0° C. Oxone (0.348 g, 1.13 mmol) in H$_2$O (4 mL) was added dropwise, and the mixture was stirred at 0° C. for 10 min. The reaction was quenched by the addition of sat aq. NaHCO$_3$ until the pH was ~8, and the mixture was extracted with EtOAc (3×20 mL). The organic layers were washed with 5% aq. NaCl (30 mL) and sat aq. NaCl (30 mL) and dried over anhydrous sodium sulfate. Concentration afforded a residue that was purified by flash column chromatography, eluting with a gradient of 10% EtOAc in hexanes to 40% EtOAc in hexanes to afford (R)-82 as a pale-orange waxy solid upon drying in vacuo (0.122 g, 74%): mp 105.5-107° C. $^1$H-NMR (500 MHz; CDCl$_3$, indicates presence of rotamers due to Boc group): δ 7.39 (br s, 1H), 7.01-6.82 (m, 3H), 4.52-4.32 (2 m, 1H), 2.75-2.64 (m, 5H), 1.39, 1.27 (2 s, 9H), 1.23, 1.16 (2 d, 6.0 Hz, 3H); $^{13}$C-NMR (126 MHz; CDCl$_3$): δ (157.05+157.00, 1C), (156.21+156.12, 1C), (142.4+141.8, 1C), (124.60+124.51, 1C), (121.32+121.13, 1C), (119.03+118.93, 1C), (117.4+116.9, 1C), 113.1+112.8, 1C), 80.4, (52.6+51.1, 1C), 40.0, (28.49+28.37, 3C), (28.1+27.6, 1C), (19.0+18.0, 1C); ESIMS m/z (rel. intensity) 289 (M$^-$, 94), 579 (2M$^-$, 100). Enantiomeric purity (HPLC, see General Procedures): >99%, retention time, 10.08 min.

Example 126

(S)-tert-Butyl (1-(3-Cyano-5-hydroxyphenyl)propan-2-yl)(methyl)carbamate (S-82)

A sealable vial was charged with Pin$_2$B$_2$ (0.058 g, 0.228 mmol) dtbpy, (0.0035 g, 3 mol %) and [Ir(OMe)(COD)]$_2$ (0.0041 g, 1.5 mol %), and the vial was flushed with argon for ~2 min and sealed. Anhydrous hexane (0.5 mL) was added and the mixture was heated to 50° C. for 10 min, upon which it became a dark red color, and following which compound (S)-80 (0.114 g, 0.416 mmol) was added in anhydrous hexane (2 mL). The mixture was heated at 50° C. for 18 h and cooled. The mixture was concentrated, acetone (6 mL) was added to the residue, and the mixture was cooled to 0° C. Oxone (0.348 g, 1.13 mmol) in H$_2$O (3 mL) was added dropwise, and the mixture was stirred at 0° C. for 10 min. The reaction was quenched by the addition of sat aq. NaHCO$_3$ until the pH was ~8, and the mixture was extracted with EtOAc (3×20 mL). The organic layers were washed with 5% aq. NaCl (30 mL) and sat aq. NaCl (30 mL) and dried over anhydrous sodium sulfate. Concentration afforded a residue that was purified by flash column chromatography, eluting with a gradient of 10% EtOAc in hexanes to 40% EtOAc in hexanes to afford (S)-82 as an off-white waxy solid upon drying in vacuo (0.060 g, 50%): mp 105.5-107° C. $^1$H-NMR (500 MHz; CDCl$_3$, indicates presence of rotamers due to Boc group): δ 7.31 (br s, 1H), 7.01-6.81 (m, 3H), 4.54-4.31 (m, 1H), 2.75-2.63 (m, 5H), 1.38, 1.27 (2 s, 9H), 1.23, 1.16 (2 d, 6.0 Hz, 3H); $^{13}$C-NMR (126 MHz; CDCl$_3$): δ 157.0, (156.17+156.10, 1C), (142.4+141.8, 1C), (124.62+124.56, 1C), (121.3+121.1, 1C) (119.02+118.92, 1C), (117.3+116.9, 1C), (113.1+112.9, 1C), 80.3, (52.5+51.0, 1C), 40.0, (28.49+28.37, 3C), (28.1+27.6, 1C), (19.0+18.0, 1C); ESIMS m/z (rel. intensity) 289 (M$^-$, 100). Enantiomeric purity (HPLC, see General Procedures): >99%, retention time, 11.62 min.

Example 127

Purified NOS Enzyme Assays

Rat and human nNOS, murine macrophage iNOS, and human eNOS were recombinant enzymes (expressed in *E. coli* and purified as reported previously in the literature). To test for NOS inhibition, the hemoglobin capture assay was used to measure nitric oxide production. The assay was performed at 37° C. in HEPES buffer (100 mM with 10% glycerol, pH 7.4) in the presence of 10 µM L-arginine. Also included were 100 µM NADPH, 0.83 mM $CaCl_2$, approximately 320 units/mL of calmodulin, 10 µM $H_4B$, and human oxyhemoglobin (3 µM). For iNOS, the $CaCl_2$ and calmodulin were omitted and replaced with HEPES buffer (neither are required for activation of iNOS). The assay was performed in 96-well plates using a Synergy 4 BioTek hybrid reader. The dispensing of NOS enzyme and hemoglobin were automated, and after 30 sec (maximum delay), NO production was read by monitoring the absorbance at 401 nm (resulting from conversion of oxyhemoglobin to methemoglobin). Kinetic readouts were performed for 5 min. Each compound was assayed at least in duplicate, and six to nine concentrations (500 µM-50 nM or 100 µM-10 nM for eNOS and iNOS; 50 µM to 5 nM for rat and human nNOS) were used to construct dose-response curves. $IC_{50}$ values were calculated by non-linear regression (variable slope, four parameters) using GraphPad Prism software, and $K_i$ values were obtained using the Cheng-Prusoff equation [$K_i=IC_{50}/(1+[S]/K_m)$] with the following $K_m$ values: 1.3 µM (rat nNOS), 1.6 µM (human nNOS), 8.2 µM (murine macrophage iNOS), and 3.9 (human eNOS).

Example 128

Inhibitor Complex Crystal Preparation

The sitting drop vapor diffusion methods were used to grow crystals at 4° C. for the heme domains of rat nNOS (9 mg/mL containing 20 mM histidine), the human nNOS K301R/R354A/G357D mutant (10 mg/mL), and human eNOS (7 mg/mL). The well solutions are: for rat nNOS, 20-24% PEG3350, 0.1 M MES, pH 5.8, 140-200 mM ammonium acetate, 10% ethylene glycol, 5 mM GSH, and 30 uM SDS; for human nNOS, 8% PEG3350, 35 mM citric acid, 65 mM Bis-Tris-Propane, pH 7.2, 10% glycerol, and 5 mM TCEP; for human eNOS, 12-15% PEG3350, 0.1 M Bis-Tris, pH 6.5, 200-300 mM Mg acetate, 100 mM $GdCl_3$, 10% glycerol, and 5 mM TCEP. Fresh crystals were first passed stepwise through cryoprotectant solutions and then soaked with 5-10 mM inhibitor for 3-4 h at 4° C. before being flash cooled with liquid nitrogen and stored until data collection.

Example 129

X-Ray Diffraction Data Collection, Data Processing, and Structural Refinement

The cryogenic (100 K) X-ray diffraction data were collected remotely at the Stanford Synchrotron Radiation Lightsource (SSRL) or Advanced Light Source (ALS) through the data collection control software Blu-Ice and a crystal mounting robot. When a Q315r CCD detector was used, 100-125° of data were typically collected with 0.5° per frame. If a Pilatus pixel array detector was used, 140-160° of fine-sliced data were collected with 0.2° per frame. Raw CCD data frames were indexed, integrated, and scaled using iMOSFLM, but the pixel array data were processed with XDS and scaled with Aimless. The binding of inhibitors was detected by initial difference Fourier maps calculated with REFMAC. The inhibitor molecules were then modeled in COOT and refined using REFMAC or PHENIX. Disordering in portions of inhibitors bound in the NOS active sites was often observed, sometimes resulting in poor density quality. However, partial structural features usually could still be visible if the contour level of the sigmaA weighted 2 m|Fo|–D|Fc| map dropped to 0.5 sigma, which afforded the building of reasonable models into the disordered regions. Water molecules were added in PHENIX and checked by COOT. The TLS protocol was implemented in the final stage of refinements with each subunit as one TLS group. The omit Fo-Fc density maps were calculated by removing inhibitor coordinates from the input PDB file before running one more round of TLS refinement in PHENIX (simulated annealing protocol with a 2000 K initial temperature). The resulting map coefficients DELFWT and PHDELWT were used to generate maps. The refined structures were validated in COOT before deposition in the RCSB protein data bank.

Example 130

Caco-2 Permeability Assay

Caco-2 monolayer assays were performed by Cyprotex US, LLC (Watertown, Mass.) using standard procedure as previously reported for compound 4. (Cinelli, M. A.; Li, H.; Pensa, A. V.; Kang, S.; Martásek, P.; Roman, L. J.; Poulos, T. L.; and Silverman, R. B. Phenyl Ether- and Aniline-Containing 2-Aminoquinolines as Potent and Selective Inhibitors of Neuronal Nitric Oxide Synthase. *J. Med. Chem.* 2015, 58 (21) 8694-8712.)

Example 131

Preparation of the 7-Bromo-2-Chloro Quinoline (51)

Cyclization of the precursory E-(N)-(3-substituted phenyl)-3-ethoxypropenamides was effected in concentrated $H_2$—$SO_4$, to give a mixture of isomeric 2-quinolinols. Treatment of the crude mixture with $POCl_3$ provided a mixture of the 2-chloroquinolines. The 7-bromo-2-chloro quinoline was obtained after removal of dark polar contaminants by filtering the latter, dissolved in $CHCl_3$ through silica gel. Fractional crystallization of the mixture of solids from 2-propanaol removed the 5-substituted isomer, providing 51 as white crystals. (See, Horwitz et al, Synthesis and Biological Evaluation of Some Bioisosteres and Congeners of the Antitumor Agent, 2-{4-[(7-Chloro-2-quinoxalinyl)oxy]phenoxy}propionic Acid (XK469). *J. Med. Chem.* 2002, 45, 3130-3137), the entirety of which is incorporated herein by reference.)

TABLE 7

Inhibition of NOS enzymes by synthesized compounds.

| Compound | $K_i$ (µM)[a] | | | | Selectivity | |
| --- | --- | --- | --- | --- | --- | --- |
| | rnNOS | hnNOS | miNOS | heNOS | rn/mi | hn/he |
| 1 | 0.049 | 0.318 | 44.0 | 9.49 | 899 | 30 |
| 2 | 0.066 | 0.440 | 28.4 | 11.8 | 431 | 27 |
| 3 | 0.142 | 0.911 | 33.2 | 17.3 | 237 | 19 |
| 4 | 0.058 | 0.295 | 27.7 | 7.41 | 478 | 25 |
| 5 | 0.079 | NT | 16.8 | NT | 213 | ND |
| 6 | 0.071 | NT | 15.2 | NT | 215 | ND |
| 7 | 0.082 | 0.135 | 32.7 | NT | 399 | ND |
| 8 | 0.035 | 0.036 | 12.5 | 12.2 | 357 | 339 |
| 9 | 0.054 | 0.125 | 40.5 | 43.0 | 754 | 344 |
| 10 | 0.039 | 0.033 | 5.75 | 6.66 | 147 | 202 |
| 11 | 0.024 | 0.031 | 6.7 | 5.61 | 279 | 181 |
| 12 | 0.028 | 0.052 | 7.44 | 4.19 | 266 | 81 |
| 13 | 0.037 | 0.078 | 13.0 | 21.0 | 350 | 269 |

TABLE 7-continued

Inhibition of NOS enzymes by synthesized compounds.

| | $K_i$ (µM)[a] | | | | Selectivity | |
|---|---|---|---|---|---|---|
| Compound | rnNOS | hnNOS | miNOS | heNOS | rn/mi | hn/he |
| 14 | 0.033 | 0.051 | 5.44 | 6.09 | 138 | 119 |
| 15 | 0.063 | NT | 19.9 | NT | 333 | ND |
| 16 | 0.036 | 0.056 | 3.42 | 5.04 | 95 | 90 |
| 17 | 0.032 | 0.054 | 3.34 | 6.08 | 105 | 113 |
| 18 | 0.042 | 0.060 | 25.7 | 18.9 | 611 | 315 |
| rac-19 | 0.050 | 0.074 | 10.8 | 15.0 | 216 | 203 |
| (R)-19 | 0.061 | 0.065 | 7.35 | 16.1 | 120 | 247 |
| (S)-19 | 0.050 | 0.046 | 25.6 | 22.1 | 512 | 482 |

[a]The compounds were assayed for in vitro inhibition against four purified NOS isoforms: rat nNOS (rnNOS), human nNOS (hnNOS), murine iNOS (miNOS), and human eNOS (heNOS) using known literature methods (see Experimental Section for details), and $K_i$ values are calculated directly from $IC_{50}$ values. $IC_{50}$ values are the average of at least two replicates from 6-9 data points; all experimental standard error values are less than 12%, and all correlation coefficients are good ($R2 > 0.85$). Selectivity values are ratios of respective $K_i$ values.

NT = not tested;

ND = not determined.

TABLE 8

Caco-2 permeability summary for select compounds.

| | Apparent Permeability ($P_{app}$, $10^{-6}$ cm s$^{-1}$)[b] | | | Recovery | |
|---|---|---|---|---|---|
| | Mean | Mean | Efflux | | |
| Compound | A-->B | B-->A | ratio[f] | A-->B | B-->A |
| 8 | 9.2 | 32.1 | 3.5 | 63% | 89% |
| 10 | 7.1 | 34.4 | 4.8 | 70% | 100% |
| Warfarin[c] | 26.0 | 17.7 | 0.68 | — | — |

TABLE 8-continued

Caco-2 permeability summary for select compounds.

| | Apparent Permeability ($P_{app}$, $10^{-6}$ cm s$^{-1}$)[b] | | | Recovery | |
|---|---|---|---|---|---|
| | Mean | Mean | Efflux | | |
| Compound | A-->B | B-->A | ratio[f] | A-->B | B-->A |
| Ranitidine[d] | 0.33 | 2.4 | 7.3 | — | — |
| Talinolol[e] | 0.12 | 8.2 | 68.3 | — | — |

[a]All assays were performed over 2 h at a concentration of 10 µM. See Experimental Section for details.

[b]Apparent permeability value.

[c]High permeability control;

[d]low permeability control;

[e]high efflux control.

[f]Efflux ratio is defined as $P_{app}$ (B-->A)/$P_{app}$ (A-->B); efflux ratio values >3 indicate that a compound may be a substrate for P-gp or other active transport systems.

TABLE 9

Caco-2 permeability data for select compounds

| | Apparent Permeability ($P_{app}$, $10^{-6}$ cm s$^{-1}$)[b] | | | Recovery | |
|---|---|---|---|---|---|
| | Mean | Mean | Efflux | | |
| Compound | A-->B | B-->A | ratio[c] | A-->B | B-->A |
| 7 | 20.8 | 20.1 | 0.97 | 58.5% | 83.0% |
| Warfarin[d] | 23.2 | 22.5 | 0.97 | — | — |
| Ranitidine[e] | 0.15 | 1.2 | 8.0 | — | — |
| Talinolol[f] | 0.066 | 3.4 | 51.5 | — | — |

[a]All assays were performed over 2 h at a concentration of 10 µM. See Experimental Section for details.

[b]$P_{app}$: apparent permeability rate value.

[c]Efflux ratio: $P_{app}$ B→A)/$P_{app}$ (A→B).

[d]High permeability control.

[e]Low permeability control.

[f]high efflux control.

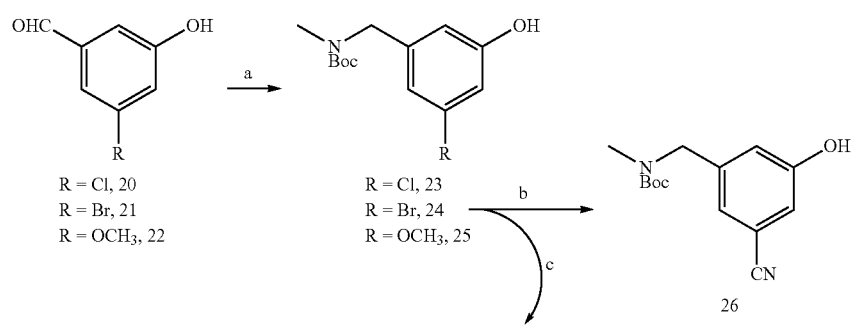

Scheme 20[a]

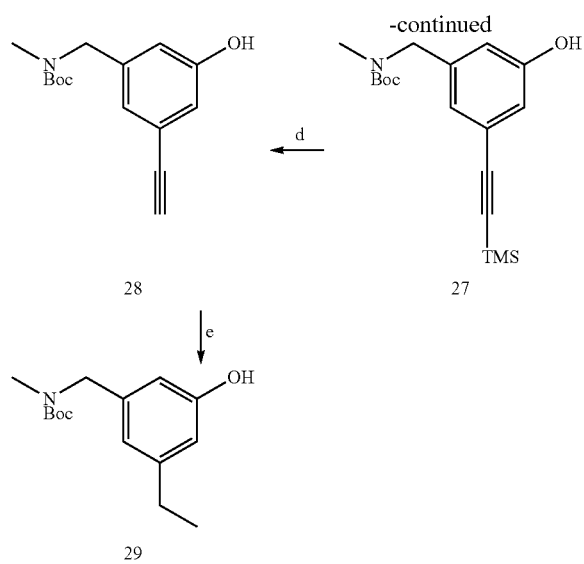

<sup>a</sup>Reagents and condition: (a) i. MeNH₂ in THF, cat. AcOH, CHCl₃/MeOH, Na₂SO₄, r.t., ii. NaBH₄, MeOH, 0° C.-r.t., iii. Boc₂O, THF, r.t.; (b) K₄Fe(CN)₆ x 3 H₂O, t-BuXPhos, t-BuXPhos G3, KOAc, H₂O/dioxane, 100° C.; (c) [(PPh₃)₂PdCl₂], CuI, Et₃N, 70° C.; (d) TBAF in THF, THF, 0° C.; (e) H₂, Pd/C, MeOH, r.t.

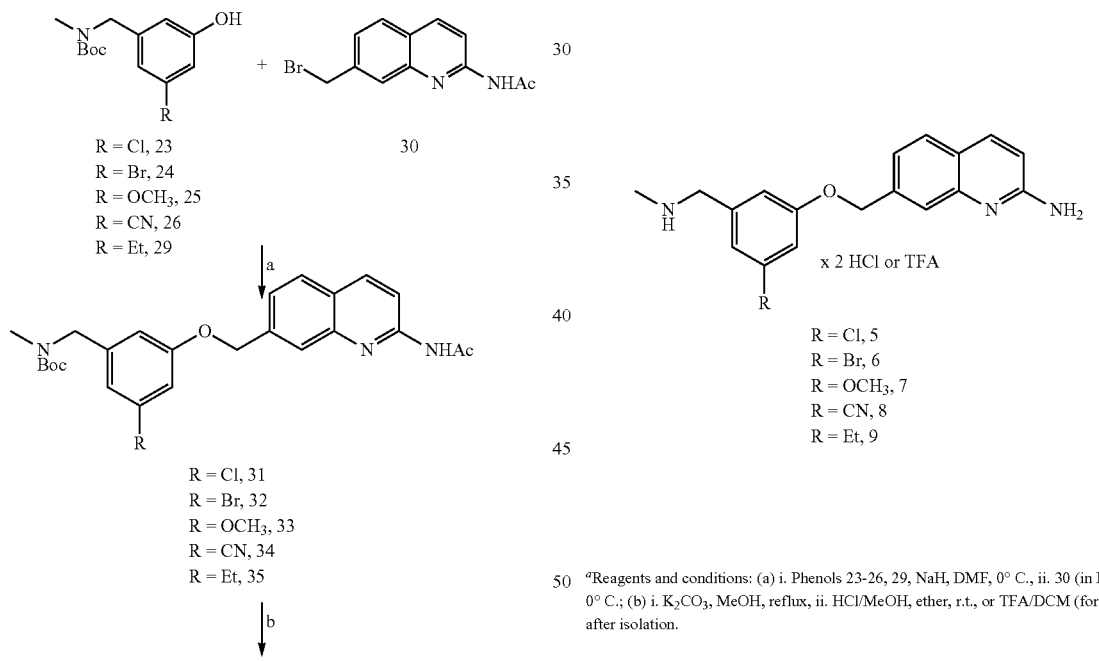

<sup>a</sup>Reagents and conditions: (a) i. Phenols 23-26, 29, NaH, DMF, 0° C., ii. 30 (in DMF), 0° C.; (b) i. K₂CO₃, MeOH, reflux, ii. HCl/MeOH, ether, r.t., or TFA/DCM (for 35), after isolation.

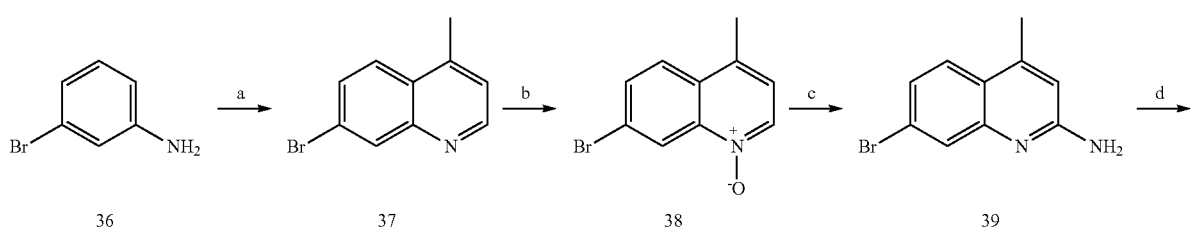

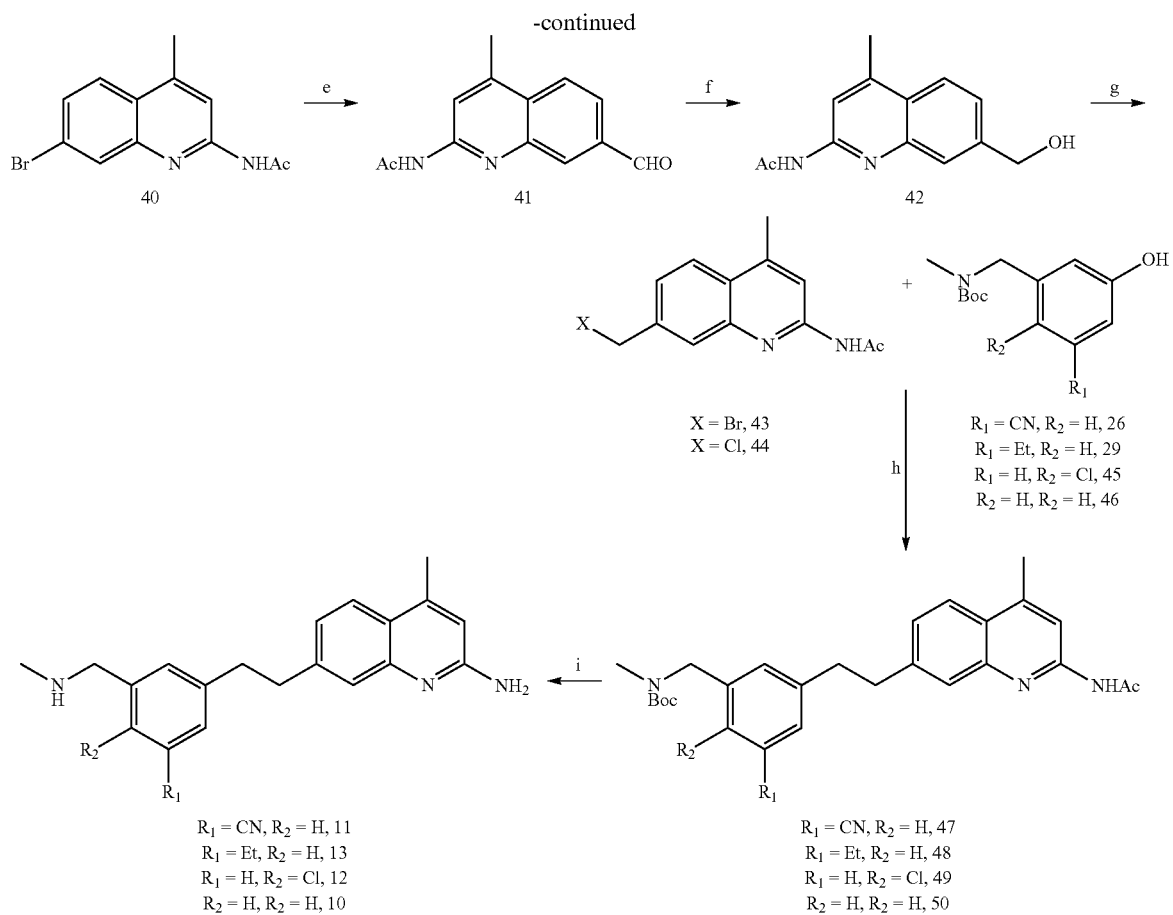
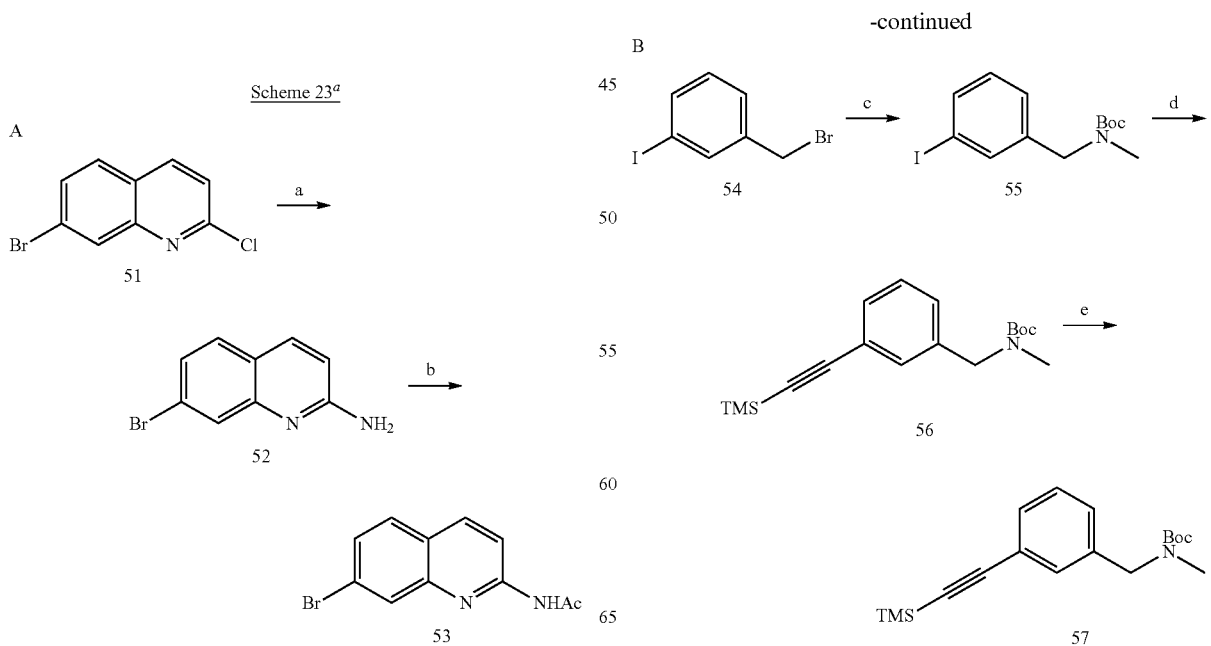
Scheme 23[a]

111
-continued

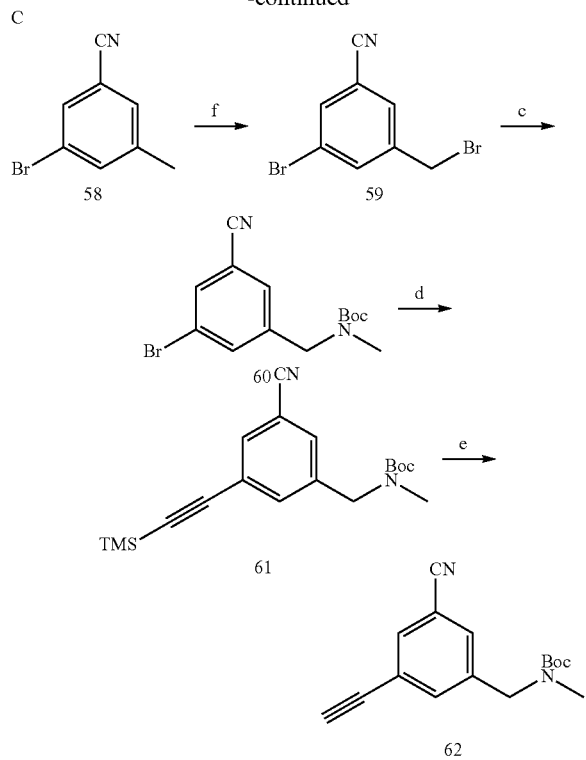

<sup>a</sup>Reagents and conditions:
(a) AcNH₂, K₂CO₃, reflux (230° C.);
(b) N-acetylimidazole, DMAP, THF, reflux;
(c) i. MeNH₂ in THF, CH₂Cl₂, r.t., ii. Boc₂O, CH₂Cl₂, r.t.;
(d) [(PPh₃)₂PdCl₂], CuI, Et₃N, 70° C.;
(e) TBAF in THF, THF, 0° C.;
(f) NBS, (PhCO₂)₂, CCl₄, relfux.

112
-continued

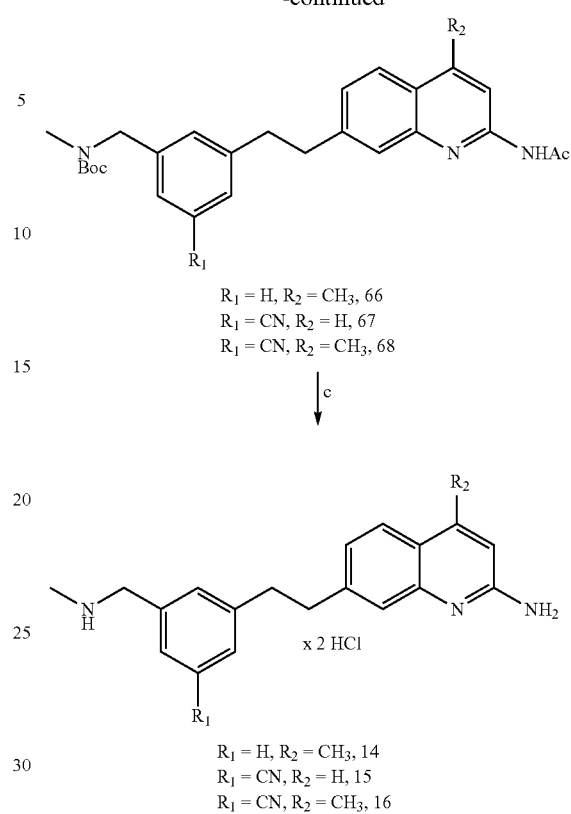

R₁ = H, R₂ = CH₃, 66
R₁ = CN, R₂ = H, 67
R₁ = CN, R₂ = CH₃, 68

R₁ = H, R₂ = CH₃, 14
R₁ = CN, R₂ = H, 15
R₁ = CN, R₂ = CH₃, 16

<sup>a</sup>Reagents and conditions: (a) XPhos, Pd(MeCN)₂Cl₂, Cs₂CO₃, MeCN, 80° C.;
(b) H₂, Pd/C, MeOH, r.t. (for 66), H₂, Pd/C(en), THF, atmospheric pressure or 50 PSI (for 67 and 68); (c) i. K₂CO₃, MeOH, reflux, ii. HCl/MeOH, ether, r.t., after isolation.

Scheme 24<sup>a</sup>

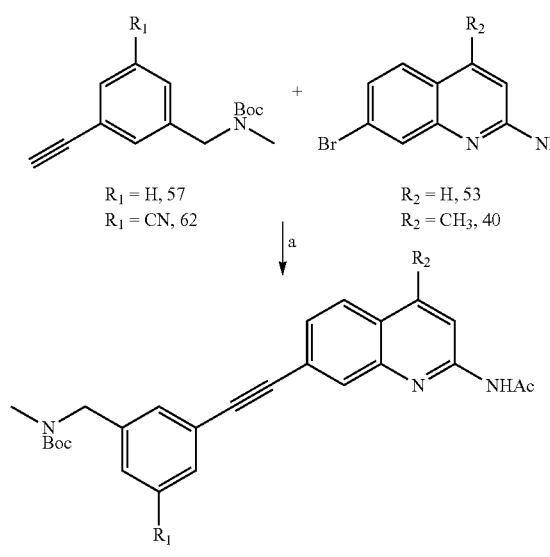

R₁ = H, 57
R₁ = CN, 62

R₂ = H, 53
R₂ = CH₃, 40

R₁ = H, R₂ = CH₃, 63
R₁ = CN, R₂ = H, 64
R₁ = CN, R₂ = CH₃, 65

Scheme 25<sup>a</sup>

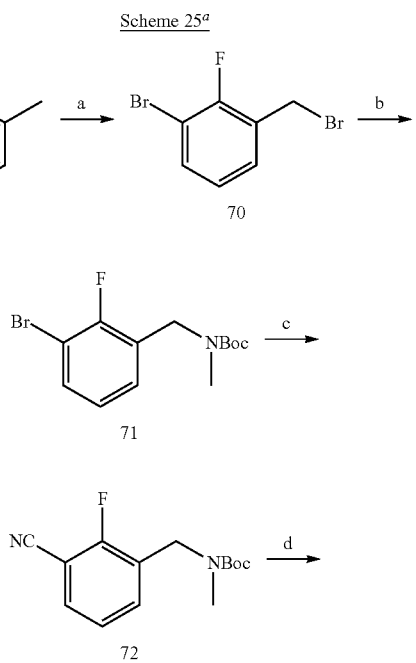

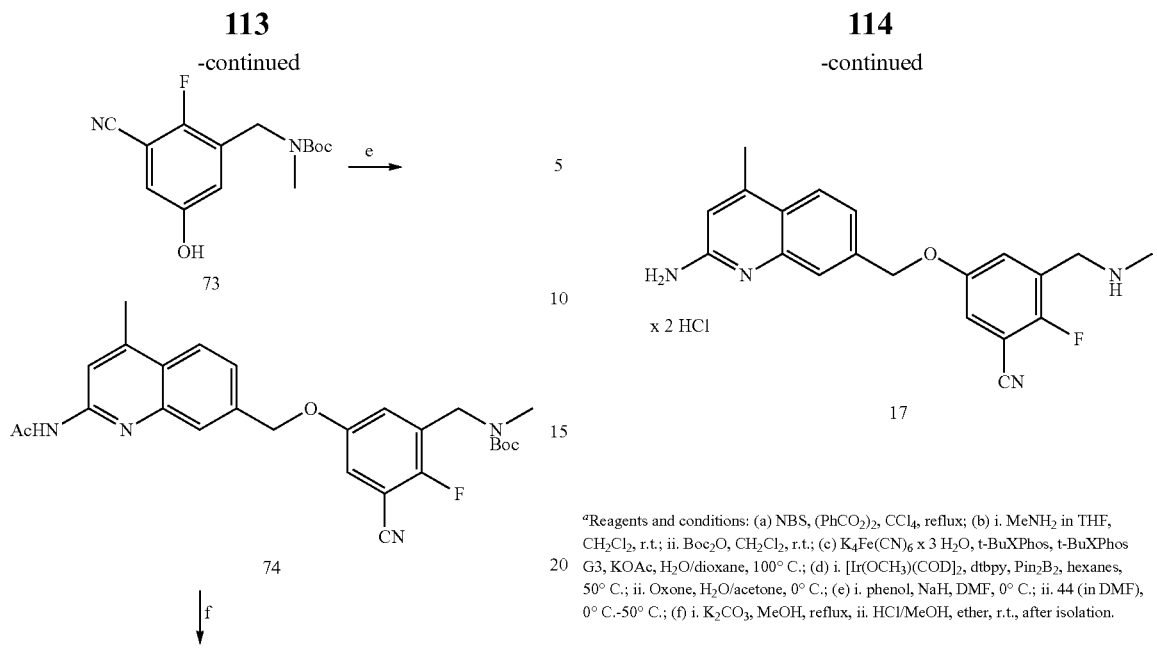
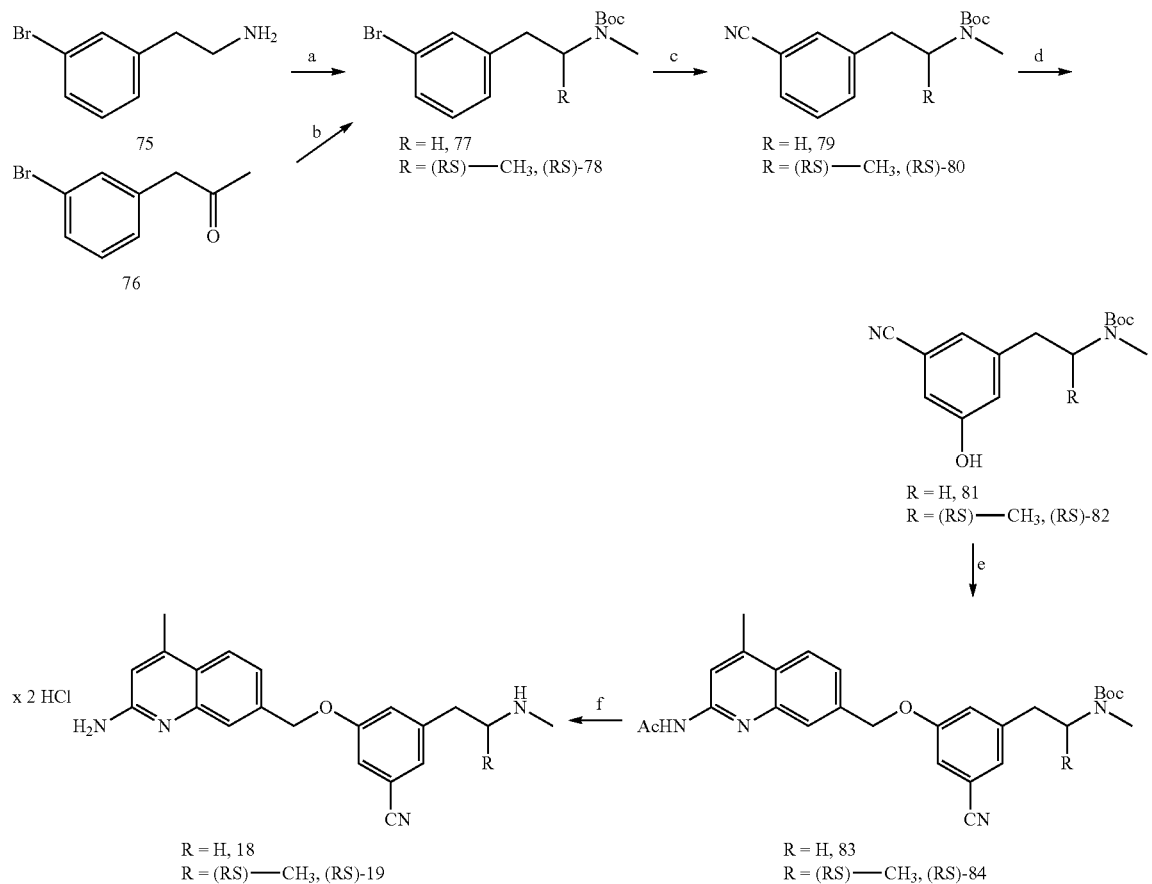
Scheme 26[a]
[a]Reagents and conditions: (a) i. Boc₂O, THF, r.t., ii. NaH, DMF, then MeI, 0° C.-60° C.; (b) i. Na(OAc)₃BH, AcOH, CH₂Cl₂, ii. Boc₂O, THF, r.t.; (c) K₄Fe(CN)₆ x 3 H₂O, t-BuXPhos, t-BuXPhos, 1:1 KOAc, H₂O: dioxane, 100° C.; (d) i. [Ir(OCH₃)(COD)]₂, dtbpy, Pin₂B₂, hexanes, r.t. or 50° C.; ii. Oxone, H₂O/acetone, 0° C.-r.t. or r.t.; (e) i. NaH, DMF, 0° C.; ii. 44 (in DMF), 0° C.-50° C.; (f) i. K₂CO₃, MeOH, reflux, ii. HCl/MeOH, ether, r.t.

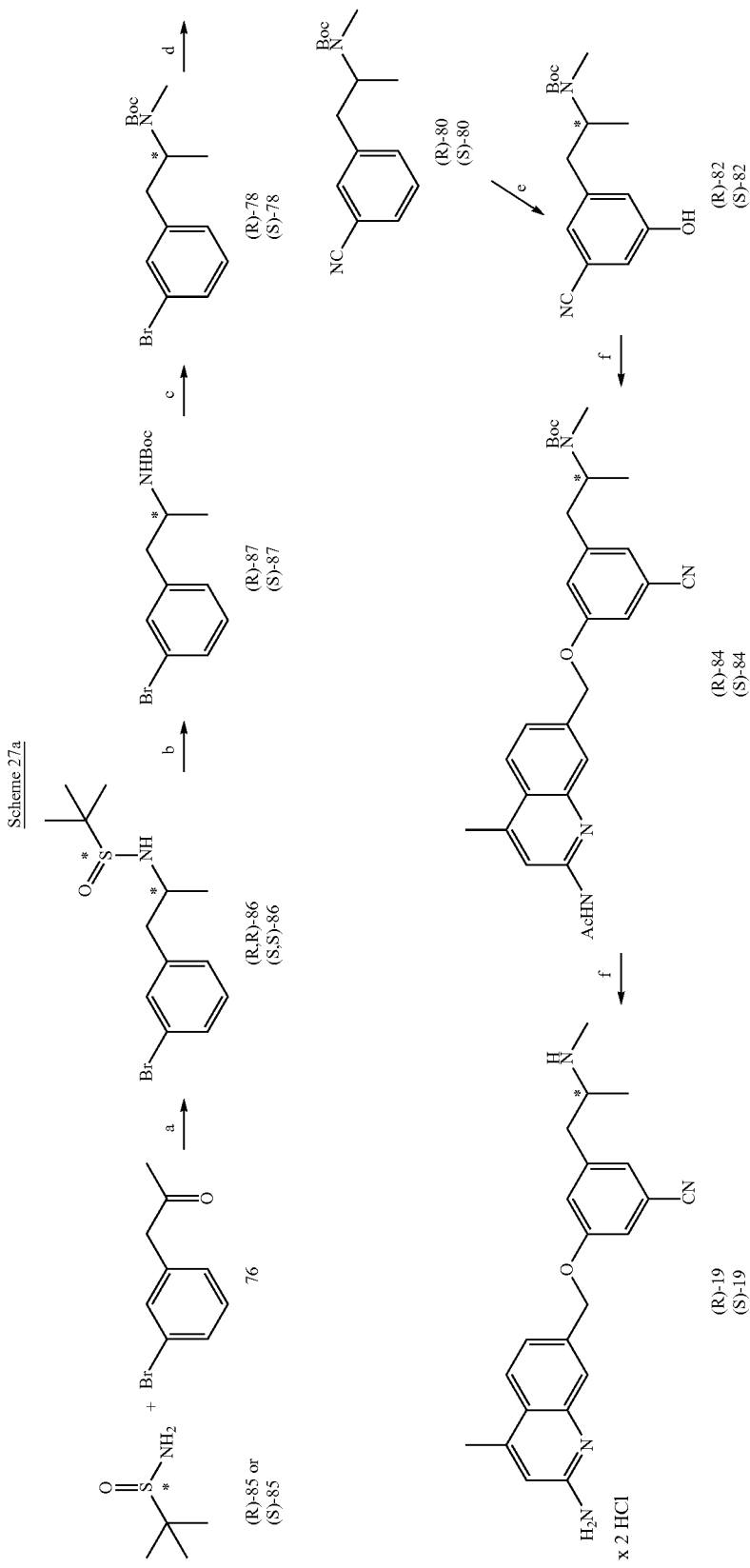

While the principles of this invention have been described in connection with specific embodiments, it should be understood that these descriptions are added only by way of example and are not intended to limit, in any way, the scope of this application. For instance, the present invention can include compounds with one or more substituents (e.g., alkyl, haloalkyl, etc.) on the quinoline ring (e.g., at the 4-position, etc.) and/or on the phenyl tail moiety, such compounds as would be understood by those skilled in the art made aware of this invention and prepared using synthetic techniques of the sort described herein or straightforward modifications thereof. Regardless, compounds of this invention can be utilized as described herein and as probes for further study of nNOS or pathways dependent upon nNOS or modulated or otherwise affected by nNOS inhibition.

We claim:

1. A compound of a formula

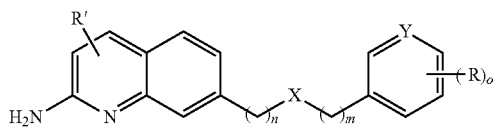

wherein X is selected from O and $CH_2$; Y is selected from CH and N; n is an integer selected from 1-2; m is an integer selected from 0-2; o is an integer selected from 0-3; and each R is independently selected from H, halo, alkyl, haloalkyl, alkoxy, cyano, amino, N-alkylamino, N,N-dialkylamino, aminealkyl, N-alkylaminealkyl, and N,N-dialkylaminealkyl; and R' is selected from H, halo, alkyl, haloalkyl and cyano moieties, or a salt thereof.

2. The compound of claim 1 wherein X is O and Y is CH.

3. The compound of claim 2 wherein n is 1 and m is 0.

4. The compound of claim 3 wherein o is 1-3 and each R is independently select from H, halo, cyano and N-alkylaminealkyl moieties.

5. The compound of claim 4 wherein one R is cyano and said phenyl moiety is substituted at the 5-position thereof.

6. The compound of claim 5 wherein R' is methyl and said quinoline moiety is substituted at the 4-position thereof.

7. The compound of claim 1 wherein X is $CH_2$ and Y is CH.

8. The compound of claim 7 wherein n is 1 and m is 0.

9. The compound of claim 8 wherein o is 1-3 and each R is independently selected from H, halo, cyano and N-alkylaminealkyl moieties.

10. The compound of claim 9 wherein one R is cyano and said phenyl moiety is substituted at the 5-position thereof.

11. The compound of claim 1 wherein said compound is an ammonium salt.

12. The compound of claim 11 wherein said salt has a counter ion that is the conjugate base of a protic acid.

13. A compound of a formula

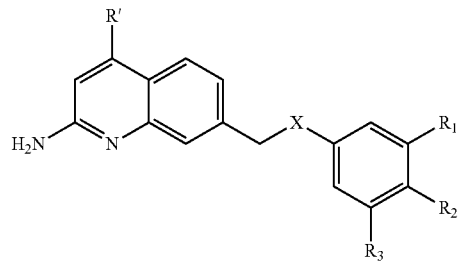

wherein X is selected from O and $CH_2$; each of $R_1$-$R_3$ is independently selected from H, halo, alkyl, haloalkyl, alkoxy, cyano and N-alkylaminealkyl moieties and R' is selected from H, alkyl and haloalkyl moieties, or a salt thereof.

14. The compound of claim 13 wherein X is O and $R_1$ is an N-methylaminealkyl moiety.

15. The compound of claim 14 wherein $R_2$ is selected from H and a halo moiety; and $R_3$ is selected from H and a cyano moiety.

16. The compound of claim 15 wherein $R_2$ is H and $R_3$ is cyano.

17. The compound of claim 13 wherein R' is methyl.

18. The compound of claim 13 wherein said compound is an ammonium salt.

19. The compound of claim 18 wherein said salt has a counter ion that is the conjugate base of a protic acid.

20. A compound of a formula

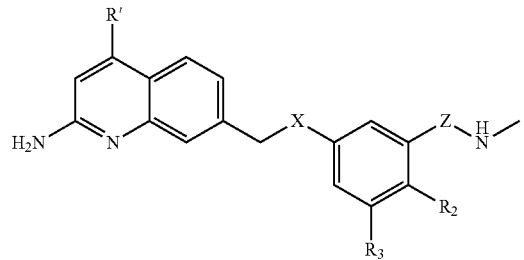

wherein X is selected from O and $CH_2$; Z is select from methylene, ethylene and methyl-substituted ethylene moieties; each of $R_2$-$R_3$ is independently selected from H, halo, alkyl and cyano moieties and R' is selected from H and a methyl moiety, or a salt thereof.

21. The compound of claim 20 wherein X is O and Z is a methyl-substituted ethylene moiety.

22. The compound of claim 21 wherein said phenyl is substituted with a 2-(methylamino) propyl moiety.

23. The compound of claim 22 wherein said moiety has an (S)-configuration.

24. The compound of claim 23 wherein $R_2$ is selected from H and a halo moiety; and $R_3$ is selected from H and a cyano moiety.

25. The compound of claim 24 wherein $R_2$ is H and $R_3$ is cyano.

26. The compound of claim 20 wherein said compound is an ammonium salt.

27. The compound of claim 26 wherein said salt has a counter ion that is the conjugate base of a protic acid.

28. A method of modulating nitric oxide synthase activity, said method comprising contacting a nitric oxide synthase with an effective amount of a compound of claim 1.

29. The method of claim 28 wherein the sum of n and m is 1.

30. The method of claim 29 wherein o is 2-3, and R is selected from a combination of halo, alkyl, cyano and N-alkylaminealkyl moieties.

31. The method of claim 25 wherein o is 2, said phenyl substituted at the 3-position with an N-alkylaminealkyl moiety and at the 5-position with a cyano moiety.

32. A method of inhibiting a nitric oxide synthase, said method comprising:
    providing a compound of claim 20; and
    contacting said compound with a nitric oxide synthase, said compound in an amount effective to inhibit nitric oxide synthase activity, thereby reducing nitric oxide production.

33. The method of claim 32 wherein X is O.

34. The method of claim 32 selective for inhibition of neuronal nitric oxide synthase.

35. The method of claim 34 selective for inhibition of human neuronal nitric oxide synthase.

36. The method of claim 32 wherein said compound is provided in a pharmaceutical composition.

* * * * *